(12) United States Patent
Schunk et al.

(10) Patent No.: US 9,926,302 B2
(45) Date of Patent: Mar. 27, 2018

(54) HETEROARYL SUBSTITUTED HETEROCYCLYL SULFONES

(71) Applicant: GRÜNENTHAL GMBH, Aachen (DE)

(72) Inventors: Stefan Schunk, Aachen (DE); Melanie Reich, Aachen (DE); Florian Jakob, Aachen (DE); Nils Damann, Hürth (DE); Michael Haurand, Aachen (DE); Achim Kless, Aachen (DE); Marc Rogers, Cambridgeshire (GB); Kathy Mackenzie, Hertfordshire (GB)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 15/404,758

(22) Filed: Jan. 12, 2017

(65) Prior Publication Data

US 2017/0121314 A1 May 4, 2017

Related U.S. Application Data

(62) Division of application No. 14/685,732, filed on Apr. 14, 2015.

(30) Foreign Application Priority Data

Apr. 14, 2014 (EP) .................... 14001346

(51) Int. Cl.
| | |
|---|---|
| C07D 405/04 | (2006.01) |
| A61K 31/435 | (2006.01) |
| C07D 413/04 | (2006.01) |
| C07D 309/08 | (2006.01) |
| C07D 405/12 | (2006.01) |

(52) U.S. Cl.
CPC ......... C07D 405/04 (2013.01); C07D 309/08 (2013.01); C07D 405/12 (2013.01); C07D 413/04 (2013.01)

(58) Field of Classification Search
CPC ... C07D 405/04; C07D 413/04; A61K 31/435
See application file for complete search history.

(56) References Cited

FOREIGN PATENT DOCUMENTS

| WO | 2007/125398 A2 | 11/2007 |
| WO | 2010-007072 A1 | 1/2010 |
| WO | 2011-035159 A1 | 3/2011 |

OTHER PUBLICATIONS

Maakosza et al (2009):STN International HCAPLUS database, Columbus (OH), Accession No. 2009:371746.*
Craig et al., "Stereoselective Synthesis of 3-(Phenylsulphonyl)-2,5 Disubstituted Tetrahydrofurans via 5-Endo-trig Ring-Closure Reactions"; Tetrahedron Letters, vol. 33, No. 5, pp. 695-698, 1992.
Makosza et al., "New Reactions of y-Halocarbanions: Simple Synthesis of Substituted Tetrahydrofurans"; Chem. Eur. J., vol. 8, No. 18, pp. 4234-4240, 2002.
Makosza et al., "Diastereoselective Synthesis of Tetrahydrofurans via Reaction of y,6-Eposycarbanions with Aldehydes", Organic Letters, vol. 7, No. 14, pp. 2945-2948, 2005.
Craig, et al., "Stereoselective Synthesis of Substituted Tetrahydrofurans Using 5-Endo-trig Cyclisation Reactions"; Tetrahedron 55, pp. 13471-13494, 1999.
Barbasiewicz, et al., "New reactions of y-halocarbanions: underestimated reactive intermediates in organic synthesis"; Russian Chemical Bulletin, International Edition, vol. 53, No. 9, pp. 1846-1858, Sep. 2004.
Brandt, et al., "Synthesis of substituted tetrahydrofurans via intermolecular reactions of y-chlorocarbanions of 3- substituted 3-chloro-propylphenyl sulfones with aldehydes", Tetrahedron 66, pp. 3378-3385, 2010.
Maakosza et al. (2009): Stn International Hcaplus database, Columbus (Oh), Accession number: 2009:371746.
Bennett et al., "A Peripheral Mononeuropathy in rat that produces disorders of pain sensation like those seen in man": Pain, Elsevier Sciences Publishers B.V., No. 33, pgs. 87-107, 1998.
Craig et al., "Stereoselective Synthesis of 2,5-Dialky-3-(phenylsulfonyl) Tetrahydrofurans via Cyclisation of Z-Sulfonyl-substituted Homoallylic Alcohols", Tetrahedron Letters, vol. 36, No. 4, pp/ 7531-7534, 1995.
D'Amour et al., "A Method for Determining Loss of Pain Sensation", the Biologic Research Laboratory, University of Denver, pp. 74-79, Jan. 27, 1941.
Dubuisson et al., "The Formalin Test: a Quantitative Study of the Analgesic Effects of Morphine, Meperidine, and Brain Stem Stimulation in Rats and Cat"; Elsevier/North-Holland Biomedical Press, Pain, No. 4 pp. 161-174, 1977.
Kim et al., "An Experimental Model for Peripheral Neuropathy Produced by Segmental Spinal Nerve Ligation in the Rat", Pain, Elsevier Sciences Publishers B.V., No. 50, pp. 355-363, 1992.
Staats et al., "Intrathecal Ziconotide in the Treatment of Refractory Pain in Patients With Cancer or Aids a Randomized Controlled Trial", American Medical Association, vol. 291, no. 1, pp. 63-70, 2004.
Makosza et al., "y-Diphenylphosphinoxy Carbanions: Slow Reacting Analogues of y-Halocarbanions", Phosphorus, Sulfur, and Silicon, No. 184, pp. 857-864, 2009.
G.P. Miljanich,"Ziconotide: Neuronal Calcium Channel Blocker for Treating Severe Chronic Pain", Current Medicinal Chemistry, No. 11, pp. 3029-3040, 2004.
Rauck et al., "Intrathecal Ziconotide for Neuropathic Pain: a Review", Pain Practice, vol. 9, Issue 5, pp. 327-337, 2009.
Yamamoto, et al; "Recent Updates of N-Type Calcium Channel Blockers with Therapeutic Potential for Neuropathic Pain.." Current Topics in Medicinal Chemistry, 2009, 9, 377-395.

* cited by examiner

*Primary Examiner* — Golam M M Shameem
(74) *Attorney, Agent, or Firm* — Norris McLaughlin & Marcus, P.A.

(57) ABSTRACT

The invention relates to aryl substituted heterocyclyl sulfones as voltage gated calcium channel blockers, to pharmaceutical compositions containing these compounds and also to these compounds for use in the treatment and/or prophylaxis of pain and further diseases and/or disorders.

13 Claims, No Drawings

HETEROARYL SUBSTITUTED HETEROCYCLYL SULFONES

This application is a division of U.S. patent application Ser. No. 14/685,732, filed Apr. 14, 2015, which claims priority of European Patent Application No. 14001346.7, filed Apr. 14, 2014, the entire contents of which are incorporated herein by reference.

FIELD OF THE INVENTION

The invention relates to heteroaryl-substituted heterocycl sulfones as voltage gated Ca-channel (CaV) blockers, to pharmaceutical compositions containing these compounds and also to these compounds for use in the treatment and/or prophylaxis of pain and further diseases and/or disorders.

BACKGROUND OF THE INVENTION

Ion channels are proteins that form pores in membranes of biological cells and control the flow of ions down their electrochemical gradient. They are involved in the regulation of a wide range of cellular functions in both excitable and nonexcitable cells and provide attractive therapeutic targets for the treatment of various diseases.

In the somatosensory context, CaV2.2 channels, specific cellular plasma membrane calcium channels that belong to a diverse superfamily of voltage-gated calcium channels (VGCCs), were demonstrated to play an important role in spinal nociceptive processing.

The critical role of CaV2.2 in pain processing was underlined by the clinical efficacy of the intrathecally delivered, selective CaV2.2 channel antagonist Ziconotide (SNX-111; Prialt™), a synthetic peptide derived from a ω-(omega)-conotoxin peptide (Miljanich, 2004, Curr. Med. Chem., 11(23), p. 3029-40; Staats et al., 2004, JAMA, 291(1), p. 63-70). Inthrathecal administration of Ziconotide is required in order to reach the ion channel in presynaptic terminals of sensory neurons in the spinal cord. Common side effects of Ziconotide include memory impairment, dizziness, nystagmus, speech disorder, nervousness, somnolence and abnormal gait (Rauck et al., 2009, Pain Pract., 9, p. 327-37), which have been attributed to the inhibition of CaV2.2 channels in the brain by Ziconotide.

Therefore, a demand remains for the development of orally available CaV2.2 calcium channel blockers that show the desired qualities and effectively block CaV2.2 calcium channels in the nociceptive signaling pathway.

SUMMARY OF THE INVENTION

The present invention describes small molecule CaV2.2 channel blockers. Sulfonamide based CaV2.2 channel modulators are known from WO 2007/125398.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CaV2.2 calcium channels.

This object is achieved by the subject matter described herein.

The present invention therefore relates to a compound of general formula (I),

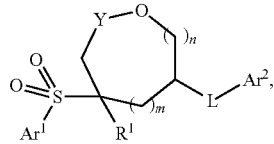

wherein
m represents 0, 1 or 2;
n denotes 0 or 1;
Y is selected from the group consisting of bond and —C(R$^3$)$_2$—;
 wherein each R$^3$ is independently selected from the group consisting of H and C$_{1-6}$-alkyl, or two R$^3$ form together with the C-atom connecting them a C$_{3-10}$-cycloalkyl or a 3 to 7 membered heterocyclyl;
L is —[C(R$^4$)$_2$]$_x$—(X)$_y$—[C(R$^4$)$_2$]$_z$—,
 wherein x is 0, 1 or 2, y is 0 or 1 and z is 0 or 1, with the proviso that x≥y;
 each R$^4$ is independently selected from the group consisting of H and C$_{1-6}$-alkyl,
 or two R$^4$ form together with the C-atom connecting them a C$_{3-10}$-cycloalkyl or a 3 to 7 membered heterocyclyl or two R$^4$ form together with two adjacent C-atoms connecting them a C$_{3-10}$-cycloalkyl or a 3 to 7 membered heterocyclyl,
X is selected from the group consisting of O, S, S(O)$_2$, N(H) or N(C$_{1-6}$-alkyl);
R$^1$ is selected from the group consisting of H; F; Cl; CN; C$_{1-6}$-alkyl; C$_{1-6}$-alkyl-O(R$^5$) and C$_{1-6}$-alkyl-N(R$^5$)$_2$;
 wherein each R$^5$ is independently selected from H or C$_{1-6}$-alkyl or two R$^5$ form together with the N-atom connecting them a 3 to 7 membered heterocyclyl;
R$^2$ is selected from the group consisting of H; F; Cl; CN; C$_{1-6}$-alkyl; C$_{1-6}$-alkyl-O(R$^6$) and C$_{1-6}$-alkyl-N(R$^6$)$_2$;
 wherein each R$^6$ is independently selected from H or C$_{1-6}$-alkyl or two R$^6$ form together with the N-atom connecting them a 3 to 7 membered heterocyclyl;
Ar$^1$ represents aryl or heteroaryl, wherein said aryl or said heteroaryl is substituted by zero or one or two or three substituents R$^7$,
Ar$^2$ represents heteroaryl, substituted by zero or one or two or three substituents R$^8$, wherein each R$^7$ and each R$^8$ is independently selected from the group consisting of F; Cl; Br; I; NO$_2$; CN; C$_{1-6}$-alkyl; CF$_3$; CF$_2$H; CFH$_2$; CF$_2$Cl; CFCl$_2$; C(═O)—H; C(═O)—C$_{1-6}$-alkyl; C(═O)—OH; C(═O)—O—C$_{1-6}$-alkyl; C(═O)—N(H)(OH); C(═O)—NH$_2$; C(═O)—N(H)(C$_{1-6}$-alkyl); C(═O)—N(C$_{1-6}$-alkyl)$_2$; C(═N—OH)—H; C(═N—OH)—C$_{1-6}$-alkyl; C(═N—O—C$_{1-6}$-alkyl)-H; C(═N—O—C$_{1-6}$-alkyl)-C$_{1-6}$-alkyl; OH; OCF$_3$; OCF$_2$H; OCFH$_2$; OCF$_2$Cl; OCFCl$_2$; O—C$_{1-6}$-alkyl; O—C(═O)—C$_{1-6}$-alkyl; O—C(═O)—O—C$_{1-6}$-alkyl; O—(C═O)—N(H)(C$_{1-6}$-alkyl); O—C(═O)—N(C$_{1-6}$-alkyl)$_2$; O—S(═O)$_2$—C$_{1-6}$-alkyl; O—S(═O)$_2$—OH; O—S(═O)$_2$—O—C$_{1-6}$-alkyl; O—S(═O)$_2$—NH$_2$; O—S(═O)$_2$—N(H)(C$_{1-6}$-alkyl); O—S(═O)$_2$—N(C$_{1-6}$-alkyl)$_2$; NH$_2$; N(H)(C$_{1-6}$-alkyl); N(C$_{1-6}$-alkyl)$_2$; N(H)—C(═O)—C$_{1-6}$-alkyl; N(H)—C(═O)—O—C$_{1-6}$-alkyl; N(H)—C(═O)—NH$_2$; N(H)—C(═O)—N(H)(C$_{1-6}$-alkyl); N(H)—C(═O)—N(C$_{1-6}$-alkyl)$_2$; N(C$_{1-6}$-alkyl)-C(═O)—C$_{1-6}$-alkyl; N(C$_{1-6}$-alkyl)-C(═O)—O—C$_{1-6}$-alkyl; N(C$_{1-6}$-alkyl)-C(═O)—NH$_2$; N(C$_{1-6}$-alkyl)-C(═O)—N(H)(C$_{1-6}$-alkyl); N(C$_{1-6}$-alkyl)-C(═O)—N(C$_{1-6}$-alkyl)$_2$; N(H)—S(═O)$_2$OH; N(H)—S(═O)$_2$—C$_{1-6}$-alkyl; N(H)—S(═O)$_2$—O—C$_{1-6}$-alkyl; N(H)—S(═O)$_2$—NH$_2$; N(H)—S(═O)$_2$—N(H)(C$_{1-6}$-alkyl); N(H)—S(═O)$_2$N(C$_{1-6}$-alkyl)$_2$; N(C$_{1-6}$-alkyl)-S(═O)$_2$—OH; N(C$_{1-6}$-alkyl)-S(═O)$_2$—C$_{1-6}$-alkyl; N(C$_{1-6}$-alkyl)-S(═O)$_2$—O—C$_{1-6}$-alkyl; N(C$_{1-6}$-alkyl)-S (=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; SCF$_2$H; SCFH$_2$; SCF$_2$Cl; SCFCl$_2$; S—C$_{1-6}$-alkyl; S(=O)—C$_{1-6}$-alkyl; S(=O)$_2$—C$_{1-6}$-alkyl; S(=O)$_2$—OH; S(=O)$_2$—O—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-10}$-cycloalkyl; 3 to 7 membered heterocyclyl; aryl; heteroaryl; O—C$_{3-10}$-cycloalkyl; O-(3 to 7 membered heterocyclyl); O-aryl; O-heteroaryl; N(H)—C$_{3-10}$-cycloalkyl; N(H)-(3 to 7 membered heterocyclyl); N(H)-aryl; N(H)-heteroaryl; N(C$_{1-6}$-alkyl)-C$_{3-10}$-cycloalkyl; N(C$_{1-6}$-alkyl)-(3 to 7 membered heterocyclyl); N(C$_{1-6}$-alkyl)-aryl; N(C$_{1-6}$-alkyl)-heteroaryl; C(=O)—C$_{3-10}$-cycloalkyl; C(=O)-(3 to 7 membered heterocyclyl); C(=O)-aryl; C(=O)-heteroaryl; S(=O)$_2$—C$_{3-10}$-cycloalkyl; S(=O)$_2$-(3 to 7 membered heterocyclyl); S(=O)$_2$-aryl; S(=O)$_2$-heteroaryl; S(=O)(=NR$^{13}$)—C$_{3-10}$-cycloalkyl; S(=O)(=NR$^{13}$)-(3 to 7 membered heterocyclyl); S(=O)(=NR$^{13}$)-aryl and S(=O)(=NR$^{13}$)-heteroaryl, wherein R$^{13}$ represents H or C$_{1-6}$-alkyl;

wherein in each case said C$_{1-6}$-alkyl may be branched or unbranched; unsubstituted or mono- or polysubstituted; and wherein in each case said C$_{3-10}$-cycloalkyl, 3 to 7 membered heterocyclyl aryl and heteroaryl may be unsubstituted or mono- or polysubstituted;

optionally in the form of an individual stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The compounds according to general formula (I) possess at least 2 stereogenic carbon atoms: the carbon atom bearing R$^1$ and the carbon atom bearing R$^2$.

The compounds according to formula (I) may be stereochemically differentiated according to their relative structural orientation. The compounds wherein the residues R$^1$ and R$^2$ have the same relative orientation, for instance both up ("bold wedge") or both down ("broken wedge") are referred within the scope of the present invention as the "cis" diastereomer (scheme 1). The compounds wherein the residues R$^1$ and R$^2$ have a differented relative orientation, for instance R$^1$ up ("bold wedge") and R$^2$ down ("broken wedge") or vice versa are referred within the scope of the present invention as the "trans" diastereomer (scheme 2).

Diastereoisomers differ with respect to their physical and chemical properties. Methods to determine the diatstereomeric ratio (dr) are well known to the person skilled in the art and include, but are not limited to, NMR-methods.

A diastereomerically pure compound or a diastereomer according to the present invention refers to a stereoisomer, having a diastereomeric ratio of >90:10, particularly >92:8, preferably >95:5, more preferably >98:2 and even more preferably >99:1.

For both diastereomers, two enantiomers are possible.

An enantiomerically pure compound or an enantiomer according to the present invention refers to a stereoisomer, having an enantiomeric excess of >90% ee, particularly >92% ee, preferably >95% ee, more preferably >98% ee and even more preferably >98% ee. A racemic mixture or a racemate refers to an equal mixture of two corresponding enantiomers.

Methods to determine the enantiomeric excess are well known to the person skilled in the art and include, but are not limited to, optical rotary dispersion, circular dichroism, NMR-methods using chiral auxiliaries ("shift reagents") or separation via chiral HPLC (high performance liquid chromatography, using a chiral stationary phase), chiral GLC (gas-liquid chromatography, using a chiral stationary phase) or chiral SFC (supercritical fluid chromatography using a chiral stationary phase).

Determination of the absolute stereochemical structure is well known to the person skilled in the art and includes, but are not limited to, x-ray diffractometry.

The stereogenic information of the compounds of the present invention is described according to their relative chemical structure as as detailed below:

1) A cis racemic compound (cis-rac) refers to a racemic mixture of two enantiomers as depicted in scheme 1.

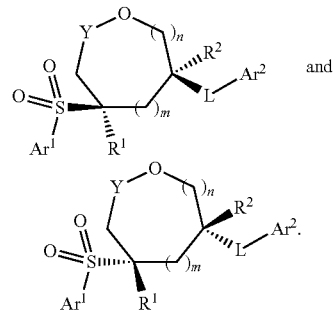

(Scheme 1)

2) A trans racemic compound (trans-rac) refers to a racemic mixture of two enantiomers as depicted in scheme 2.

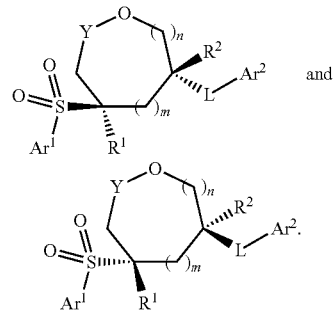

(Scheme 2)

3) A cis enantiomer 1 compound (cis-EN1) refers to one single enantiomer as depicted in scheme 3.

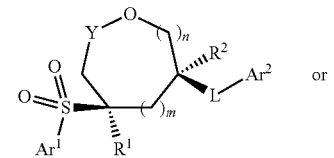

(Scheme 3)

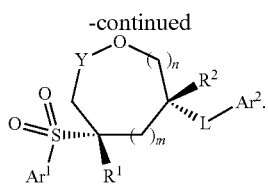

4) A cis enantiomer 2 compound (cis-EN2) refers to the other single enantiomer, which is not cis-EN1 as depicted in scheme 3.

(Scheme 3)

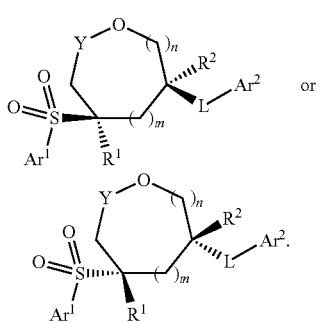

5) A trans enantiomer 1 compound (trans-EN1) refers to one single enantiomer as depicted in scheme 4.

(Scheme 4)

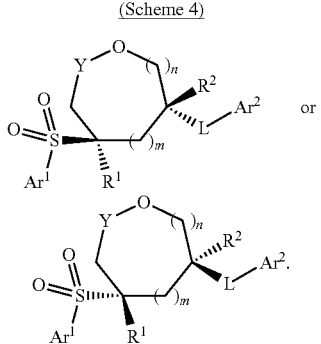

6) A trans enantiomer 2 compound (trans-EN2) refers to the other single enantiomer, which is not trans-EN1 as depicted in scheme 4.

(Scheme 4)

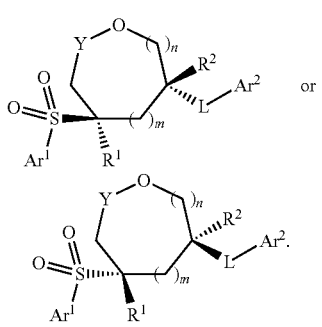

The term "physiologically acceptable salt" preferably comprises in the sense of this invention a salt of at least one compound according to the present invention and at least one physiologically acceptable acid or base.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The term "$C_{1-6}$-alkyl" comprise in the sense of this invention acyclic sat. aliphatic hydrocarbon residues, which can be respectively branched or unbranched and can be unsubstituted or can be mono- or polysubstituted, e.g. mono-, di- or trisubstituted, and which contain 1 to 6 carbon atoms, i.e. 1, 2, 3, 4, 5 or 6 carbon atoms. Preferred $C_{1-6}$-alkyl groups are selected from the group consisting of methyl, ethyl, n-propyl, 2-propyl, n-butyl, isobutyl, sec.-butyl, tert.-butyl, n-pentyl, isopentyl, neopentyl, and n-hexyl.

In relation to the term "$C_{1-6}$-alkyl" the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of $CF_3$ or $CH_2CF_3$ or at various points, as in the case of $CH(OH)CH_2CH_2CHCl_2$. The multiple substitution can be carried out using the same or using different substituents.

The term "$C_{3-10}$-cycloalkyl" mean for the purposes of this invention cyclic aliphatic hydrocarbons containing 3, 4, 5, 6, 7, 8, 9 or 10 carbon atoms, respectively, wherein the hydrocarbons in each case can be sat. or unsat. (but not aromatic), unsubstituted or mono- or polysubstituted. The cycloalkyl group can be bound to the respective superordinate general structure via any desired and possible ring member of the cycloalkyl group. The cycloalkyl group can also be condensed with further sat., (partially) unsat., (hetero)cyclic, aromatic or heteroaromatic ring systems, i.e. with cycloalkyl, heterocyclyl, aryl or heteroaryl residues, which in each case can in turn be unsubstituted or mono- or polysubstituted. $C_{3-10}$-cycloalkyls can furthermore be singly or multiply bridged such as, for example, in the case of adamantyl, bicyclo[2.2.1]heptyl or bicyclo[2.2.2]octyl. Preferred $C_{3-10}$-cycloalkyl groups are selected from the group consisting of cyclopropyl, cyclobutyl, cyclopentyl, cyclohexyl, cycloheptyl, cyclooctyl, cyclononyl, cyclodecyl, adamantly, cyclopentenyl, cyclohexenyl, cycloheptenyl, cyclooctenyl,

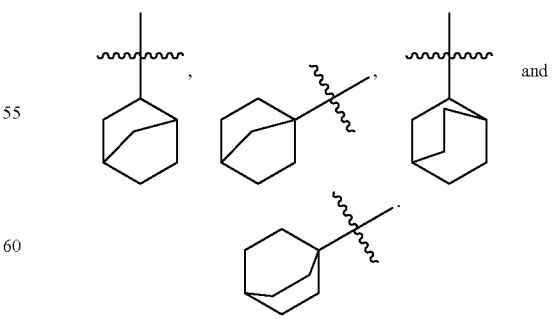

Particularly preferred $C_{3-10}$-cycloalkyl groups are $C_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" mean for the purposes of this invention heterocycloaliphatic sat. or unsat. (but not aromatic) residues having 3 to 7, i.e. 3, 4, 5, 6 or 7 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N($C_{1-6}$-alkyl) such as N(CH$_3$), wherein the ring members can be unsubstituted or mono- or polysubstituted. The cycloalkyl groups can also be condensed with further sat. or (partially) unsat. cycloalkyl or heterocyclyl, aromatic or heteroaromatic ring systems, which in each case can in turn be unsubstituted or mono- or polysubstituted. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further sat. or (partially) unsat. cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further sat. or (partially) unsat. cycloalkyl or heterocyclyl, aromatic or heteroaromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

In relation to the terms "$C_{1-6}$-alkyl", "$C_{3-10}$-cycloalkyl", "3 to 7-membered heterocyclyl" and "3 to 10-membered heterocyclyl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; NO$_2$; CN; =O; =NH; =N(OH); =N(O—$C_{1-6}$-alkyl); CF$_3$; CF$_2$H; CFH$_2$; CF$_2$Cl; CFCl$_2$; $C_{1-6}$-alkyl; C(=O)—H; C(=O)—$C_{1-6}$-alkyl; C(=O)—OH; C(=O)—O—$C_{1-6}$-alkyl; C(=O)—N(H)(OH); C(=O)—NH$_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; OCF$_3$; OCF$_2$H; OCFH$_2$; OCF$_2$Cl; OCFCl$_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—NH$_2$; O—S(=O)$_2$—N(H)($C_{1-6}$-alkyl); O—S(=O)$_2$—N($C_{1-6}$-alkyl)$_2$; NH$_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—NH$_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—NH$_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$—OH; N(H)—S(=O)$_2$—$C_{1-6}$-alkyl; N(H)—S(=O)$_2$—O—$C_{1-6}$-alkyl; N(H)—S(=O)$_2$—NH$_2$; N(H)—S(=O)$_2$—N(H)($C_{1-6}$-alkyl); N(H)—S(=O)$_2$—N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); S(=O)$_2$—N($C_{1-6}$-alkyl)$_2$; $C_{3-6}$-cycloalkyl; 3 to 7 membered heterocyclyl; aryl or heteroaryl. The term "polysubstituted" with respect to polysubstituted residues and groups includes the polysubstitution of these residues and groups either on different or on the same atoms, for example trisubstituted on the same carbon atom, as in the case of CF$_3$, CH$_2$CF$_3$ or 1,1-difluorocyclohexyl, or at various points, as in the case of CH(OH)—CHCl$_2$ or 1-chloro-3-fluorocyclohexyl. A substituent can if appropriate for its part in turn be mono- or polysubstituted. The multiple substitution can be carried out using the same or using different substituents.

Preferred substituents of "$C_{1-6}$-alkyl" are selected from the group consisting of F; Cl; Br; CF$_3$; C(=O)—NH$_2$; C(=O)—N(H)($C_{1-6}$-alkyl); C(=O)—N($C_{1-6}$-alkyl)$_2$; $C_{3-6}$-cycloalkyl or 3 to 7 membered heterocyclyl; OH; O—$C_{1-6}$-alkyl; NH$_2$; N(H)($C_{1-6}$-alkyl); N($C_{1-6}$-alkyl)$_2$; N(H)—C(=O)—$C_{1-6}$-alkyl; N(H)—S(=O)$_2$—$C_{1-6}$-alkyl; N($C_{1-6}$-alkyl)-S(=O)$_2$—$C_{1-6}$-alkyl; N(H)—S(=O)$_2$—NH$_2$; SH; S—$C_{1-6}$-alkyl; S(=O)$_2$ $C_{1-6}$-alkyl and S(=O)$_2$—N(H)($C_{1-6}$-alkyl).

Preferred substituents of "$C_{3-6}$-cycloalkyl" and "3 to 7-membered heterocyclyl" are selected from the group consisting of F; Cl; Br; CF$_3$; CN; =O; $C_{1-6}$-alkyl; $C_{3-6}$-cycloalkyl or 3 to 7 membered heterocyclyl; CHO; C(=O)—$C_{1-6}$-alkyl; CO$_2$H; C(=O)O—$C_{1-6}$-alkyl; CONH$_2$; C(=O)NH—$C_{1-6}$-alkyl; C(=O)N($C_{1-6}$-alkyl)$_2$; OH; O—$C_{1-6}$-alkyl; OCF$_3$; O—C(=O)—$C_{1-6}$-alkyl; NH$_2$; NH—$C_{1-6}$-alkyl; N($C_{1-6}$-alkyl)$_2$; NH—C(=O)—$C_{1-6}$-alkyl; SH; S—$C_{1-6}$-alkyl; SCF$_3$; S(=O)$_2$—$C_{1-6}$-alkyl; S(=O)$_2$OH; S(=O)$_2$O—$C_{1-6}$-alkyl and S(=O)$_2$—NH—$C_{1-6}$-alkyl.

In relation to the terms "aryl" and "heteroaryl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; $NO_2$; CN; $CF_3$; $CF_2H$; $CFH_2$; $CF_2Cl$; $CFCl_2$; $C_{1-6}$-alkyl; $C_{3-6}$-cycloalkyl; 3 to 7 membered heterocyclyl; aryl; heteroaryl; aryl, heteroaryl, $C_{3-6}$-cycloalkyl or 3 to 7 membered heterocyclyl, each connected via a $C_{1-8}$-alkylene; C(=O)H; C(=O)—($C_{1-6}$-alkyl); C(=O)—($C_{3-6}$-cycloalkyl); C(=O)-(3 to 7 membered heterocyclyl); C(=O)-(aryl); C(=O)-(heteroaryl); C(=O)OH; C(=O)—O($C_{1-6}$-alkyl); C(=O)—O($C_{3-6}$-cycloalkyl); C(=O)—O(3 to 7 membered heterocyclyl); C(=O)—O(aryl); C(=O)—O(heteroaryl); C(=O)—$NH_2$; C(=O)—N(H)($C_{1-6}$-alkyl); C(=O)—N(H)($C_{3-6}$-cycloalkyl); C(=O)—N(H)(3 to 7 membered heterocycloalkyl); C(=O)—N(H)(aryl); C(=O)—N(H)(heteroaryl); C(=O)—N($C_{1-6}$-alkyl)$_2$; C(=O)—N($C_{1-6}$-alkyl)($C_{3-6}$-cycloalkyl); C(=O)—N($C_{1-6}$-alkyl)(3 to 7 membered heterocyclyl); C(=O)—N($C_{1-6}$-alkyl)(aryl); C(=O)—N($C_{1-6}$-alkyl)(heteroaryl); OH; =O; O—($C_{1-6}$-alkyl); O—($C_{3-6}$-cycloalkyl); O-(3 to 7 membered heterocyclyl); O-(aryl); O-(heteroaryl); $OCF_3$; $OCF_2H$; $OCFH_2$; $OCF_2Cl$; $OCFCl_2$; O—C(=O)—($C_{1-6}$-alkyl); O—C(=O)—($C_{3-6}$-cycloalkyl); O—C(=O)-(3 to 7 membered heterocyclyl); O—C(=O)-(aryl); C(=O)-(heteroaryl); O—C(=O)—$NH_2$; O—C(=O)—N(H)($C_{1-6}$-alkyl); O—C(=O)—N(H)($C_{3-6}$-cycloalkyl); O—C(=O)—N(H)(3 to 7 membered heterocyclyl); O—C(=O)—N(H)(aryl); O—C(=O)—N(H)(heteroaryl); O—C(=O)—N($C_{1-6}$-alkyl)$_2$; O—C(=O)—N($C_{1-6}$-alkyl)($C_{3-6}$-cycloalkyl); O—C(=O)—N($C_{1-6}$-alkyl)(3 to 7 membered heterocyclyl); O—C(=O)—N($C_{1-6}$-alkyl)(aryl); O—C(=O)—N($C_{1-6}$-alkyl)(heteroaryl); $NH_2$; N(H)($C_{1-6}$-alkyl); N(H)($C_{3-6}$-cycloalkyl); N(H)(3 to 7 membered heterocyclyl); N(H)(aryl); N(H)(heteroaryl); N($C_{1-6}$-alkyl)$_2$; N($C_{1-6}$-alkyl)($C_{3-6}$-cycloalkyl); N($C_{1-6}$-alkyl)(3 to 7 membered heterocyclyl); N($C_{1-6}$-alkyl) (aryl); N($C_{1-6}$-alkyl)(heteroaryl); N(H)—C(=O)—($C_{1-6}$-alkyl); N(H)—C(=O)—($C_{3-6}$-cycloalkyl); N(H)—C(=O)-(3 to 7 membered heterocyclyl); N(H)—C(=O)-(aryl); N(H)—C(=O)-(heteroaryl); N($C_{1-6}$-alkyl)-C(=O)—($C_{1-6}$-alkyl); N($C_{1-6}$-alkyl)-C(=O)—($C_{3-6}$-cycloalkyl); N($C_{1-6}$-alkyl)-C(=O)-(3 to 7 membered heterocyclyl); N($C_{1-6}$-alkyl)-C(=O)-(aryl); N($C_{1-6}$-alkyl)-C(=O)-(heteroaryl); N(H)—S(=O)$_2$—($C_{1-6}$-alkyl); N(H)—S(=O)$_2$—($C_{3-6}$-cycloalkyl); N(H)—S(=O)$_2$-(3 to 7 membered heterocyclyl); N(H)—S(=O)$_2$-(aryl); N(H)—S(=O)$_2$-(heteroaryl); N($C_{1-4}$-alkyl)-S(=O)$_2$—($C_{1-6}$-alkyl); N($C_{1-6}$-alkyl)-S(=O)$_2$—($C_{3-6}$-cycloalkyl); N($C_{1-6}$-alkyl)-S(=O)$_2$-(3 to 7 membered heterocyclyl); N($C_{1-6}$-alkyl)-S(=O)$_2$-(aryl); N($C_{1-6}$-alkyl)-S(=O)$_2$-(heteroaryl); N(H)—C(=O)—O($C_{1-6}$-alkyl); N(H)—C(=O)—O($C_{3-6}$-cycloalkyl); N(H)—C(=O)—O(3 to 7 membered heterocyclyl); N(H)—C(=O)—O(aryl); N(H)—C(=O)—O(heteroaryl); N($C_{1-6}$-alkyl)-C(=O)—O($C_{1-6}$-alkyl); N($C_{1-6}$-alkyl)-C(=O)—O($C_{3-6}$-cycloalkyl); N($C_{1-6}$-alkyl)-C(=O)—O(3 to 7 membered heterocyclyl); N($C_{1-6}$-alkyl)-C(=O)—O(aryl); N($C_{1-6}$-alkyl)-C(=O)—O(heteroaryl); N(H)—C(=O)—$NH_2$; N(H)—C(=O)—N(H)($C_{1-6}$-alkyl); N(H)—C(=O)—N(H)($C_{3-6}$-cycloalkyl); N(H)—C(=O)—N(H)(3 to 7 membered heterocyclyl); N(H)—C(=O)—N(H)(aryl); N(H)—C(=O)—N(H)(heteroaryl); N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N(H)($C_{3-6}$-cycloalkyl); N($C_{1-6}$-alkyl)-C(=O)—N(H)(3 to 7 membered heterocyclyl); N($C_{1-6}$-alkyl)-C(=O)—N(H)(aryl); N($C_{1-6}$-alkyl)-C(=O)—N(H)(heteroaryl); N(H)—C(=O)—N($C_{1-6}$-alkyl)$_2$; N(H)—C(=O)—N($C_{1-6}$-alkyl)($C_{3-6}$-cycloalkyl); N(H)—C(=O)—N($C_{1-6}$-alkyl)(3 to 7 membered heterocyclyl); N(H)—C(=O)—N($C_{1-6}$-alkyl)(aryl); N(H)—C(=O)—N($C_{1-6}$-alkyl)(heteroaryl); N($C_{1-6}$-alkyl)-C(=O)—N($C_{1-6}$-alkyl)$_2$; N($C_{1-6}$-alkyl)-C(=O)—N($C_{1-6}$-alkyl)($C_{3-6}$-cycloalkyl); N($C_{1-6}$-alkyl)-C(=O)—N($C_{1-6}$-alkyl)(3 to 7 membered heterocyclyl); N($C_{1-6}$-alkyl)-C(=O)—N($C_{1-6}$-alkyl)(aryl); N($C_{1-6}$-alkyl)-C(=O)—N($C_{1-6}$-alkyl) heteroaryl); SH; S—($C_{1-6}$-alkyl); S—($C_{3-6}$-cycloalkyl); S-(3 to 7 membered heterocyclyl); S-(aryl); S-(heteroaryl); $SCF_3$; $S(=O)_2OH$; S(=O)—($C_{1-6}$-alkyl); S(=O)—($C_{3-6}$-cycloalkyl); S(=O)-(3 to 7 membered heterocyclyl); S(=O)-(aryl); S(=O)-(heteroaryl); $S(=O)_2$—($C_{1-6}$-alkyl); $S(=O)_2$—($C_{3-6}$-cycloalkyl); $S(=O)_2$-(3 to 7 membered heterocyclyl); $S(=O)_2$-(aryl); $S(=O)_2$-(heteroaryl); $S(=O)_2$—O($C_{1-6}$-alkyl); $S(=O)_2$—O($C_{3-6}$-cycloalkyl); $S(=O)_2$—O(3 to 7 membered heterocyclyl); $S(=O)_2$—O(aryl); $S(=O)_2$—O(heteroaryl); $S(=O)_2$—N(H)($C_{1-6}$-alkyl); $S(=O)_2$—N(H)($C_{3-6}$-cycloalkyl); $S(=O)_2$—N(H)(3 to 7 membered heterocyclyl); $S(=O)_2$—N(H)(aryl); $S(=O)_2$—N(H)(heteroaryl); $S(=O)_2$—N($C_{1-6}$-alkyl)$_2$; $S(=O)_2$—N($C_{1-6}$-alkyl)($C_{3-6}$-cycloalkyl); $S(=O)_2$—N($C_{1-6}$-alkyl)(3 to 7 membered heterocyclyl); $S(=O)_2$—N($C_{1-6}$-alkyl)(aryl); $S(=O)_2$—N($C_{1-6}$-alkyl)(heteroaryl); S(=O)(=$NR^{13}$)—$C_{3-10}$-cycloalkyl; S(=O)(=$NR^{13}$)-(3 to 7 membered heterocyclyl); S(=O)(=$NR^{13}$)-aryl and S(=O)(=$NR^{13}$)-heteroaryl, wherein $R^{13}$ represents H or $C_{1-6}$-alkyl.

Preferred substituents of "aryl" and "heteroaryl" are selected from the group consisting of F; Cl; $CF_3$; CN; $C_{1-6}$-alkyl; C(=O)—OH; C(=O)—O—$C_{1-6}$-alkyl; CO—$NH_2$; C(=O)—N(H)$C_{1-6}$-alkyl; C(=O)—N($C_{1-6}$-alkyl)$_2$; OH; O—$C_{1-6}$-alkyl; O—C(=O)—$C_{1-6}$-alkyl; $OCF_3$; $OCHF_2$; $OCH_2F$; $NH_2$; N(H)$C_{1-6}$-alkyl; N($C_{1-6}$-alkyl)$_2$; N(H)—C(=O)—$C_{1-6}$-alkyl; N($C_{1-6}$-alkyl)-C(=O)$C_{1-6}$-alkyl; N(H)—S(=O)$_2$—$C_{1-6}$-alkyl; N($C_{1-6}$-alkyl)-S(=O)$_2$ ($C_{1-6}$-alkyl); N(H)C(=O)$NH_2$; N(H)—C(=O)—N(H)$C_{1-6}$-alkyl; N(H)—C(=O)—N($C_{1-6}$-alkyl)$_2$; N($C_{1-6}$-alkyl)-C(=O)—$NH_2$; N($C_{1-6}$-alkyl)-C(=O)—N(H)$C_{1-6}$-alkyl; N($C_{1-6}$-alkyl)-C(=O)—N($C_{1-6}$-alkyl)$_2$; $S(=O)_2C_{1-6}$-alkyl; $S(=O)_2$—$NH_2$; $S(=O)_2$—N(H)$C_{1-6}$-alkyl and $S(=O)_2$—N($C_{1-6}$-alkyl)$_2$.

The compounds according to the invention are defined by substituents, for example by $R^1$, $R^2$ and $R^3$ ($1^{st}$ generation substituents) which are for their part if appropriate themselves substituted ($2^{nd}$ generation substituents). Depending on the definition, these substituents of the substituents can for their part be resubstituted ($3^{rd}$ generation substituents). If, for example, $R^1$=a $C_{1-6}$-alkyl ($1^{st}$ generation substituent), then the $C_{1-6}$-alkyl can for its part be substituted, for example with a NH—$C_{1-6}$-alkyl ($2^{nd}$ generation substituent). This produces the functional group $R^1$=($C_{1-6}$-alkyl-NH—$C_{1-6}$-alkyl). The NH—$C_{1-6}$-alkyl can then for its part be resubstituted, for example with Cl ($3^{rd}$ generation substituent). Overall, this produces the functional group $R^1$=$C_{1-6}$-alkyl-NH—$C_{1-6}$-alkyl, wherein the $C_{1-6}$-alkyl of the NH—$C_{1-6}$-alkyl is substituted by Cl. However, in a preferred embodiment, the $3^{rd}$ generation substituents may not be resubstituted, i.e. there are then no $4^{th}$ generation substituents. If a residue occurs multiply within a molecule, then this residue can have respectively different meanings for various substituents: if, for example, both $R^1$ and $R^2$ denote a 3 to 10 membered heterocyclyl, then the 3 to 10 membered heterocyclyl can e.g. represent morpholinyl for $R^1$ and can represent piperazinyl for $R^2$.

Within the scope of the present invention, the symbols

used in the formulae denotes a link of a corresponding residue to the respective superordinate general structure.

In one embodiment of the first aspect of the invention, the compound according to general formula (I) is characterized in that m represents 0 or 1. Preferably, m represents 1.

In another embodiment of the first aspect of the invention, the compound according to general formula (I) is characterized in that n represents 0.

In yet another embodiment of the first aspect of the invention, the compound according to general formula (I) is characterized in that m represents 1 and n represents 0, so the compound is represented by general formula (II),

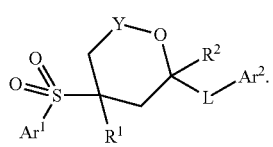

(II)

In a preferred embodiment of the of the first aspect of the invention, the compound according to general formula (I) is characterized in that m represents 1, n represents 0, and Y is bond, $CH_2$ or $C(CH_3)_2$.

In a particularly preferred embodiment of the of the first aspect of the invention, the compound according to general formula (I) is characterized in that m represents 1, n represents 0 and Y is $CH_2$,
so the compound is represented by general formula (IIa),

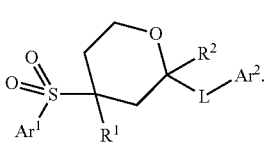

(IIa)

In another particularly preferred embodiment of the first aspect of the invention, the compound according to general formula (I) is characterized in that m represents 1, n represents 0 and Y is bond,
so the compound is represented by general formula (IIb),

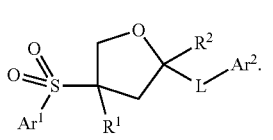

(IIb)

In another embodiment of the first aspect of the invention, the compound according to the invention is one diastereomer. Preferably, the compound according to the invention is the cis-diastereomer. Still preferably, the compound according to the invention is the trans-diastereomer.

Thus, one preferred embodiment of the first aspect of the invention is characterized in that the compound of general formula (I), (II), (IIa) or (IIb) is one diastereomer.

The cis-diastereomer or the trans-diastereomer may be in the form of a single enantiomer or in the form of an enantiomeric mixture, preferably of a racemate.

In yet another embodiment of the first aspect of the invention, the compound according to the invention is in only one enantiomeric form. Preferably, the compound according to the invention is the racemate of the cis-diastereomer (cis-rac) or a single enantiomer of the cis-diastereomer (cis-EN1 or cis-EN2). Still preferably, the compound according to the invention is the racemate of the trans-diastereomer (trans-rac) or a single enantiomer of the trans-diastereomer (trans-EN1 or trans-EN2).

Thus, one preferred embodiment of the first aspect of the invention is characterized in that the compound of general formula (I), (II), (IIa) or (IIb) is one enantiomer.

In one preferred embodiment of the first aspect of the invention is characterized in that the compound of general formula (I), (II), (IIa) or (IIb) is the enantiomer, which exhibits at room temperature and a wavelength of 589 nm (Na-D-line) a positive optical rotation in dichloromethane or methanol.

In another preferred embodiment of the first aspect of the invention is characterized in that the compound of general formula (I), (II), (IIa) or (IIb) is the enantiomer, which exhibits at room temperature and a wavelength of 589 nm (Na-D-line) a negative optical rotation in dichloromethane or methanol.

In another embodiment of the first aspect of the invention, the compound according to general formula (I) is characterized in that $R^2$ represents H, $CH_3$, $C_2H_5$, $CH_2CH_2CH_3$, $CH(CH_3)_2$, $CH_2OH$, $CH_2OCH_3$, $CH_2NH_2$, $CH_2N(H)CH_3$ or $CH_2N(CH_3)_2$.

Preferably, $R^2$ represents H, $CH_3$ or $C_2H_5$.

In a preferred embodiment, the compound according to formula (I) is characterized in that m represents 1, n represents 0, Y is $CH_2$, and $R^2$ represents H, $CH_3$ or $C_2H_5$.

In another preferred embodiment, the compound according to formula (I) is characterized in that m represents 1, n represents 0, Y is bond, and $R^2$ represents H, $CH_3$ or $C_2H_5$.

In another embodiment of the first aspect of the invention, the compound according to general formula (I) is characterized in that $R^1$ represents H, $CH_3$, $C_2H_5$, $CH_2CH_2CH_3$, $CH_2OCH_3$ or $CH_2N(CH_3)_2$.

Preferably, $R^1$ represents H, $CH_3$, $C_2H_5$ or $CH_2OCH_3$. Particularly preferred are compounds wherein $R^1$ represents $CH_3$.

In a preferred embodiment, the compound according to formula (I) is characterized in that m represents 1, n represents 0, Y is $CH_2$, and $R^1$ represents H, $CH_3$, $C_2H_5$ or $CH_2OCH_3$.

In another preferred embodiment, the compound according to formula (I) is characterized in that m represents 1, n represents 0, Y is bond, and $R^1$ represents H, $CH_3$, $C_2H_5$ or $CH_2OCH_3$.

In another embodiment of the first aspect of the invention, the compound according to general formula (I) is characterized in that $Ar^1$ represents phenyl or pyridinyl, substituted by zero or one or two or three substituents $R^7$.

In preferred embodiment of the first aspect of the invention, the compound according to general formula (I) is characterized in that $Ar^1$ represents phenyl or pyridinyl, substituted by one or two substituents $R^7$.

Preferably, $R^7$ is independently selected from the group consisting of F; Cl; CN; $C_{1-6}$-alkyl; $CF_3$; $CF_2H$; $CFH_2$; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; OH; $OCF_3$; $OCF_2H$; $OCFH_2$; $OCF_2Cl$; $OCFCl_2$; O—$C_{1-6}$-alkyl; $NH_2$; N(H)($C_{1-6}$-alkyl); N($C_{1-6}$-alkyl)$_2$; N(H)—C(=O)—$C_{1-6}$-alkyl; N($C_{1-6}$-alkyl)-C(=O)—$C_{1-6}$-alkyl; N(H)—S(=O)$_2$—$C_{1-6}$-alkyl; $SCF_3$; S—$C_{1-6}$-alkyl; S(=O)—$C_{1-6}$-alkyl; S(=O)$_2$—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$; $C_{3-10}$-cycloalkyl; 3 to 7 membered heterocyclyl; O—$C_{3-10}$-cycloalkyl and O-(3 to 7 membered heterocyclyl).

In yet another embodiment of the first aspect of the invention, the compound according to general formula (I) is characterized in that $Ar^1$ represents phenyl or pyridinyl, substituted by zero or one or two or three substituents $R^7$, wherein each $R^7$ is independently selected from the group consisting of F; Cl; CN; $C_{1-6}$-alkyl; $CF_3$; $CF_2H$; $CFH_2$; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; OH; $OCF_3$; $OCF_2H$; $OCFH_2$; $OCF_2Cl$; $OCFCl_2$; O—$C_{1-6}$-alkyl; $NH_2$; N(H)($C_{1-6}$-alkyl); N($C_{1-6}$-alkyl)$_2$; N(H)—C(=O)—$C_{1-6}$-alkyl; N($C_{1-6}$-alkyl)-C(=O)—$C_{1-6}$-alkyl; N(H)—S(=O)$_2$—$C_{1-6}$-alkyl; $SCF_3$; S—$C_{1-6}$-alkyl; S(=O)—$C_{1-6}$-alkyl; S(=O)$_2$—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$; $C_{3-10}$-cycloalkyl; 3 to 7 membered heterocyclyl; O—$C_{3-10}$-cycloalkyl and O-(3 to 7 membered heterocyclyl).

Preferably, $Ar^1$ represents phenyl or 2-pyridinyl.

In another preferred embodiment of the first aspect of the invention, the compound according to general formula (I) is characterized in that $Ar^1$ represents subformula SF-I

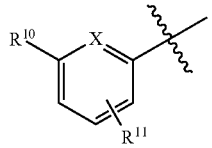

(SF-I)

wherein X is CH or N,
$R^{10}$ is selected from the group consisting of $CF_3$; $CF_2H$; $CFH_2$; $OCF_3$; $OCF_2H$; $OCFH_2$; cyclopropyl; Ocyclopropyl; $CH(CH_3)_2$; $OCH(CH_3)_2$; $C(CH_3)_3$ and $OC(CH_3)_3$; and
$R^{11}$ is selected from the group consisting of H; F; Cl; CN; $CH_3$; $CH_2CH_3$; $CH_2CH_2CH_3$; $CH(CH_3)_2$; $CH(CH_3)CH_2CH_3$; $CH_2CH_2CH_2CH_3$; $CH_2CH(CH_3)_2$; $C(CH_3)_3$; $CF_3$; $CF_2H$; $CFH_2$; $OCF_3$; $OCH_3$; $OCH_2CH_3$; $OCH(CH_3)_2$; S(=O)—$CH_3$ and S(=O)$_2$—$CH_3$.

More preferably, $R^{10}$ is $CF_3$; $CF_2H$; $CFH_2$; $OCF_3$; $OCF_2H$ or $OCFH_2$. Even more preferably, $R^{10}$ is $CF_3$ or $OCF_3$.

In yet another embodiment of the first aspect of the invention, the compound according to general formula (I) is characterized in that L is —[C($R^4$)$_2$]$_x$—(X)$_y$—[C($R^4$)$_2$]$_z$—,
wherein x is 0, 1 or 2, y is 0 or 1 and z is 0, with the proviso that x≥y;
each $R^4$ is independently selected from the group consisting of H and $C_{1-6}$-alkyl,
or two $R^4$ form together with the C-atom connecting them a $C_{3-10}$-cycloalkyl or a 3 to 7 membered heterocyclyl or two $R^4$ form together with two adjacent C-atoms connecting them a $C_{3-10}$-cycloalkyl or a 3 to 7 membered heterocyclyl, X is selected from the group consisting of O, S, S(O)$_2$, N(H) or N($C_{1-6}$-alkyl).

In a preferred embodiment of the first aspect of the invention, the compound according to general formula (I) is characterized in that L is —[C($R^4$)$_2$]$_x$—(X)$_y$—[C($R^4$)$_2$]$_z$—, wherein z is 0 and the sum (x+y) is 0 or 2.

Preferably, the compound according to general formula (I) is characterized in that L is —[C($R^4$)$_2$]$_x$—(X)$_y$—[C($R^4$)$_2$]$_z$—,
wherein x is 0, 1 or 2, y is 0 or 1 and z is 0, with the proviso that x≥y;
each $R^4$ is independently selected from the group consisting of H and $C_{1-6}$-alkyl, or two $R^4$ form together with the C-atom connecting them a $C_{3-10}$-cycloalkyl, and
X is O.

More preferably, the compound according to general formula (I) is characterized in that L is —[C($R^4$)$_2$]$_x$—(X)$_y$—[C($R^4$)$_2$]$_z$—,
wherein x is 0 or 1, y is 0 or 1 and z is 0, with the proviso that x≥y;
each $R^4$ is independently selected from the group consisting of H and $C_{1-6}$-alkyl, or two $R^4$ form together with the C-atom connecting them a $C_{3-10}$-cycloalkyl, and
X is O.

In a preferred embodiment of the first aspect of the invention, the compound according to general formula (I) is characterized in that
L is bond (x=y=z=0); $CH_2$ (x=1; each $R^4$=H; y=z=0); $CH_2CH_2$ (x=2; each $R^4$=H; y=z=0); $C(CH_3)_2$ (x=2; $R^4$=H and $R^4$=$CH_3$; y=z=0); $CH_2C(CH_3)_2$ (x=2; $R^4$=H and $R^4$=$CH_3$; y=z=0); $C(CH_3)_2CH_2$ (x=1; each $R^4$=$CH_3$; y=z=0); $CH(CH_3)$ (x=1; $R^4$=H and $R^4$=$CH_3$; y=z=0); $CH_2O$ (x=1; each $R^4$=H; y=1; X=O; z=0); $C(CH_3)_2O$ (x=1; each $R^4$=$CH_3$; y=1; X=O; z=0); $CH(CH_3)O$ (x=1; $R^4$=H and $R^4$=$CH_3$; y=1; X=O; z=0);

(x=1; two $R^4$ form together with the C-atom connecting them a $C_3$-cycloalkyl; y=z=0); or

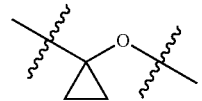 [SMILES: *OC1(*)CC1]

(x=1; two $R^4$ form together with the C-atom connecting them a $C_3$-cycloalkyl; y=1; X=O; z=0).

In case, L contains an oxygen atom, the compound according to the invention characterized in that the oxygen atom is directly bond to $Ar^2$. Therefore, the structural element -L-$Ar^2$ is represented by —$Ar^2$ (L=bond); —$CH_2$—$Ar^2$; —C($CH_3$)$_2$—$Ar^2$; —CH($CH_3$)—$Ar^2$; —$CH_2$O—$Ar^2$; —C($CH_3$)$_2$O—$Ar^2$; —CH($CH_3$)O—$Ar^2$;

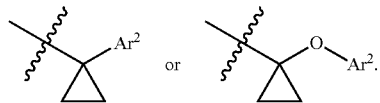

Preferably L is bond, $CH_2$; C($CH_3$)$_2$; $CH_2CH_2$; $CH_2$C($CH_3$)$_2$; C($CH_3$)$_2$$CH_2$; $CH_2$O or C($CH_3$)$_2$O,
more preferably L is bond or $CH_2$O.

It has been surprisingly found that compounds with $Ar^2$ being a heteroaryl moiety have advantageous properties, in particular with respect to their pharmacokinetic and pharmacodynamics properties.

In another embodiment of the first aspect of the invention, the compound according to general formula (I) is characterized in that $Ar^2$ is selected from the group consisting of pyridinyl, pyrazinyl, pyridazinyl, pyrimidinyl, pyrazolyl, oxazolyl, isoxazolyl and oxadiazolyl.

Preferably, $Ar^2$ is selected from the group consisting of 2-pyridinyl, 3-pyridinyl, 4-pyridinyl, 2-pyrazinyl, 3-pyrazinyl, 3-pyridazinyl, 4-pyridazinyl, 2-pyrimidinyl, 4-pyrimidinyl, 5-pyrimidinyl, 1-methyl-pyrazol-5-yl, 1,3-oxazol-2-yl, 1,3-oxazol-4-yl, 1,3-oxazol-5-yl, 1,2-oxazol-3-yl, 1,2-oxazol-4-yl, 1,2-oxazoyl-5-yl, 1,2,4-oxadiazol-3-yl, 1,2,4-oxadiazol-5-yl and 1,3,4-oxadiazol-2-yl.

Preferably, $Ar^2$ is selected from the group consisting of 2-pyridinyl, 3-pyridinyl, 2-pyrazinyl, 5-pyrimidinyl, 1,2,4-oxadiazol-5-yl and 1,3,4-oxadiazol-2-yl.

In another embodiment of the first aspect of the invention, the compound according to general formula (I) is characterized in that $Ar^2$ is selected from the group consisting of pyridinyl, pyrazinyl, pyridazinyl, pyrimidinyl, pyrazolyl, oxazolyl, isoxazolyl and oxadiazolyl, each substituted by zero or one or two substituents $R^8$,
wherein each $R^8$ is independently selected from the group consisting of F; Cl; CN; $C_{1-6}$-alkyl; $CF_3$; $CF_2H$; $CFH_2$; $OCF_3$; $OCF_2H$; $OCFH_2$; O—$C_{1-6}$-alkyl; S—$C_{1-6}$-alkyl; S(=O)—$C_{1-6}$-alkyl; S(=O)$_2$—$C_{1-6}$-alkyl; $C_{3-10}$-cycloalkyl; 3 to 7 membered heterocyclyl; aryl; heteroaryl; O—$C_{3-10}$-cycloalkyl; O-(3 to 7 membered heterocyclyl); O-aryl; O-heteroaryl; C(=O)—$C_{3-10}$-cycloalkyl; C(=O)-(3 to 7 membered heterocyclyl); C(=O)-aryl; C(=O)-heteroaryl; S(=O)$_2$—$C_{3-10}$-cycloalkyl; S(=O)$_2$-(3 to 7 membered heterocyclyl); S(=O)$_2$-aryl; S(=O)$_2$-heteroaryl; S(=O)(=$NR^{13}$)—$C_{3-10}$-cycloalkyl; S(=O)(=$NR^{13}$)-(3 to 7 membered heterocyclyl); S(=O)(=$NR^{13}$)-aryl and S(=O)(=$NR^{13}$)-heteroaryl, wherein $R^{13}$ represents H or $C_{1-6}$-alkyl.

Preferably, $R^8$ is selected from the group consisting of F; Cl; CN; $CH_3$; $CH_2CH_3$; $CH_2CH_2CH_3$; $CH(CH_3)_2$; $CH(CH_3)CH_2CH_3$; $CH_2CH_2CH_2CH_3$; $CF_3$; $CF_2H$; $CFH_2$; $OCF_3$; $OCF_2H$; $OCFH_2$; $OCH_3$; $OCH_2CH_3$; $OCH_2CH_2CH_3$; $OCH(CH_3)_2$; S(=O)$CH_3$; S(=O)$CH_2CH_3$; S(=O)$_2CH_3$; S(=O)$_2CH_2CH_3$; cyclopropyl; O-cyclopropyl; oxetanyl; 1,1-dioxidothietanyl; (oxetanyl)oxy; (1,1-dioxidothietanyl) oxy; 2-oxopyrrolidin-1-yl; 2-oxopiperidin-1-yl; azetidine-1-carbonyl; pyrrolidine-1-carbonyl; piperidine-1-carbonyl; pyridinyl; pyrimidinyl; (pyridinyl)oxy, (pyrimidinyl)oxy; imidazolyl; triazinyl; pyrazolyl; N-methyl-pyrazolyl; methoxypyridinyl; hydroxypyridinyl; 2-oxopyridinyl; 3-oxo-2,3-dihydro-1H-1,2,4-triazol-1-yl.

In yet another embodiment of the first aspect of the invention, the compound according to general formula (I) is characterized in that $Ar^2$ is selected from the group consisting of pyridinyl, pyrazinyl, pyrimidinyl, pyrazolyl, oxazolyl, isoxazolyl and oxadiazolyl, each substituted by zero, one or two substituents $R^8$,
wherein each $R^8$ is selected from the group consisting of F; Cl; CN; $CH_3$; $CH_2CH_3$; $CH_2CH_2CH_3$; $CH(CH_3)_2$; $CF_3$; $CF_2H$; $CFH_2$; $OCF_3$; $OCF_2H$; $OCFH_2$; $OCH_3$; $OCH_2CH_3$; $OCH(CH_3)_2$; S(=O)$CH_3$; S(=O)$CH_2CH_3$; S(=O)$_2CH_3$; S(=O)$_2CH_2CH_3$; cyclopropyl and O-cyclopropyl.

In yet another embodiment of the first aspect of the invention, the compound according to general formula (I) is characterized in that $Ar^2$ is selected from the group consisting of 2-pyridinyl, 3-pyridinyl, 3-pyrazinyl, 4-pyrimidinyl, 1-methyl-pyrazol-5-yl, 1,3-oxazol-2-yl, 1,3-oxazol-4-yl, 1,3-oxazol-5-yl, 1,2-oxazol-3-yl, 1,2-oxazol-4-yl, 1,2-oxazoyl-5-yl, 1,2,4-oxadiazol-3-yl, 1,2,4-oxadiazol-5-yl and 1,3,4-oxadiazol-2-yl, each substituted by zero, one or two substituents $R^8$,
wherein each $R^8$ is selected from the group consisting of F; Cl; CN; $CH_3$; $CH_2CH_3$; $CH_2CH_2CH_3$; $CH(CH_3)_2$; $CF_3$; $CF_2H$; $CFH_2$; $OCF_3$; $OCF_2H$; $OCFH_2$; $OCH_3$; $OCH_2CH_3$; $OCH(CH_3)_2$; S(=O)$CH_3$; S(=O)$CH_2CH_3$; S(=O)$_2CH_3$; S(=O)$_2CH_2CH_3$; cyclopropyl and O-cyclopropyl.

In another particularly preferred embodiment of the first aspect of the invention, the compound according to general formula (I) is characterized in that m represents 1, n represents 0, Y is $CH_2$;

$R^1$ represents H, $CH_3$, $C_2H_5$ or $CH_2OCH_3$;

$R^2$ represents H, $CH_3$ or $C_2H_5$;

$Ar^1$ represents subformula SF-I,

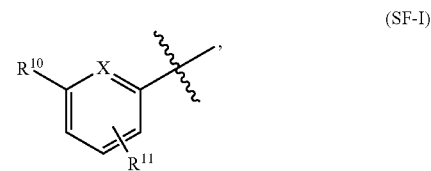

(SF-I)

wherein X is CH or N, $R^{10}$ is selected from the group consisting of $CF_3$; $CF_2H$; $CFH_2$; $OCF_3$; $OCF_2H$ and $OCFH_2$; and $R^{11}$ is selected from the group consisting of H; F; Cl; CN; $CH_3$; $CH_2CH_3$; $CH_2CH_2CH_3$; $CH(CH_3)_2$; $CH(CH_3)CH_2CH_3$; $CH_2CH_2CH_2CH_3$; $CH_2CH(CH_3)_2$; $C(CH_3)_3$; $CF_3$; $CF_2H$; $CFH_2$; $OCF_3$; $OCH_3$; $OCH_2CH_3$; $OCH(CH_3)_2$; S(=O)—$CH_3$ and S(=O)$_2$—$CH_3$;

L is bond; and $Ar^2$ is selected from the group consisting of pyridinyl, pyrazinyl, pyridazinyl, pyrimidinyl, pyrazolyl, oxazolyl, isoxazolyl and oxadiazolyl, each substituted by zero or one or two substituents $R^8$, wherein each $R^8$ is independently selected from the group consisting of F; Cl; CN; $C_{1-6}$-alkyl; $CF_3$; $CF_2H$; $CFH_2$; $OCF_3$; $OCF_2H$; $OCFH_2$; O—$C_{1-6}$-alkyl; S—$C_{1-6}$-alkyl; S(=O)—$C_{1-6}$-alkyl; S(=O)$_2$—$C_{1-6}$-alkyl; $C_{3-10}$-cycloalkyl; 3 to 7 membered heterocyclyl; aryl; heteroaryl; O—$C_{3-10}$-cycloalkyl; O-(3 to 7 membered heterocyclyl); O-aryl; O-heteroaryl; C(=O)—$C_{3-10}$-cycloalkyl; C(=O)-(3 to 7 membered heterocyclyl); C(=O)-aryl; C(=O)-heteroaryl; S(=O)$_2$—$C_{3-10}$-cycloalkyl; S(=O)$_2$-(3 to 7 membered heterocyclyl); S(=O)$_2$-aryl; S(=O)$_2$-heteroaryl; S(=O)(=$NR^{13}$)—$C_{3-10}$-cycloalkyl; S(=O)(=$NR^{13}$)-(3 to 7 membered heterocyclyl); S(=O)(=$NR^{13}$)-aryl and S(=O)(=$NR^{13}$)-heteroaryl, wherein $R^{13}$ represents H or $C_{1-6}$-alkyl.

In another particularly preferred embodiment of the first aspect of the invention, the compound according to general formula (I) is characterized in that m represents 1, n represents 0, Y is bond;

$R^1$ represents H, $CH_3$, $C_2H_5$ or $CH_2OCH_3$;

$R^2$ represents H, $CH_3$ or $C_2H_5$;

$Ar^1$ represents subformula SF-I,

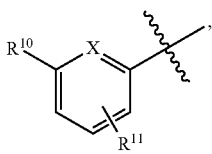

(SF-I)

wherein X is CH or N,
R$^{10}$ is selected from the group consisting of CF$_3$; CF$_2$H; CFH$_2$; OCF$_3$; OCF$_2$H and OCFH$_2$; and
R$^{11}$ is selected from the group consisting of H; F; Cl; CN; CH$_3$; CH$_2$CH$_3$; CH$_2$CH$_2$CH$_3$; CH(CH$_3$)$_2$; CH(CH$_3$)CH$_2$CH$_3$; CH$_2$CH$_2$CH$_2$CH$_3$; CH$_2$CH(CH$_3$)$_2$; C(CH$_3$)$_3$; CF$_3$; CF$_2$H; CFH$_2$; OCF$_3$; OCH$_3$; OCH$_2$CH$_3$; OCH(CH$_3$)$_2$; S(=O)—CH$_3$ and S(=O)$_2$—CH$_3$;
L is bond; and
Ar$^2$ is selected from the group consisting of pyridinyl, pyrazinyl, pyridazinyl, pyrimidinyl, pyrazolyl, oxazolyl, isoxazolyl and oxadiazolyl, each substituted by zero or one or two substituents R$^8$,
wherein each R$^8$ is independently selected from the group consisting of F; Cl; CN; C$_{1-6}$-alkyl; CF$_3$; CF$_2$H; CFH$_2$; OCF$_3$; OCF$_2$H; OCFH$_2$; O—C$_{1-6}$-alkyl; S—C$_{1-6}$-alkyl; S(=O)—C$_{1-6}$-alkyl; S(=O)$_2$—C$_{1-6}$-alkyl; C$_{3-10}$-cycloalkyl; 3 to 7 membered heterocyclyl; aryl; heteroaryl; O—C$_{3-10}$-cycloalkyl; O-(3 to 7 membered heterocyclyl); O-aryl; O-heteroaryl; C(=O)—C$_{3-10}$-cycloalkyl; C(=O)-(3 to 7 membered heterocyclyl); C(=O)-aryl; C(=O)-heteroaryl; S(=O)$_2$—C$_{3-10}$-cycloalkyl; S(=O)$_2$-(3 to 7 membered heterocyclyl); S(=O)$_2$-aryl; S(=O)$_2$-heteroaryl; S(=O)(=NR$^{13}$)—C$_{3-10}$-cycloalkyl; S(=O)(=NR$^{13}$)-(3 to 7 membered heterocyclyl); S(=O)(=NR$^{13}$)-aryl and S(=O)(=NR$^{13}$)-heteroaryl, wherein R$^{13}$ represents H or C$_{1-6}$-alkyl.

In yet another particularly preferred embodiment of the first aspect of the invention, the compound according to general formula (I) is characterized in that
m represents 1, n represents 0, Y is bond or CH$_2$;
R$^1$ represents H, CH$_3$, C$_2$H$_5$ or CH$_2$OCH$_3$;
R$^2$ represents H, CH$_3$ or C$_2$H$_5$;
Ar$^1$ represents subformula SF-I,

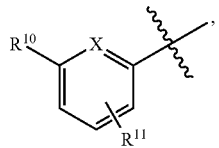

(SF-I)

wherein X is CH or N,
R$^{10}$ is selected from the group consisting of CF$_3$; CF$_2$H; CFH$_2$; OCF$_3$; OCF$_2$H and OCFH$_2$; and
R$^{11}$ is selected from the group consisting of H; F; Cl; CN; CH$_3$; CH$_2$CH$_3$; CH$_2$CH$_2$CH$_3$; CH(CH$_3$)$_2$; CH(CH$_3$)CH$_2$CH$_3$; CH$_2$CH$_2$CH$_2$CH$_3$; CH$_2$CH(CH$_3$)$_2$; C(CH$_3$)$_3$; CF$_3$; CF$_2$H; CFH$_2$; OCF$_3$; OCH$_3$; OCH$_2$CH$_3$; OCH(CH$_3$)$_2$; S(=O)—CH$_3$ and S(=O)$_2$—CH$_3$;
L is bond; and
Ar$^2$ is selected from the group consisting of pyridinyl, pyrazinyl, pyrimidinyl, pyrazolyl, oxazolyl, isoxazolyl and oxadiazolyl, each substituted by zero, one or two substituents R$^8$,
wherein each R$^8$ is selected from the group consisting of F; Cl; CN; CH$_3$; CH$_2$CH$_3$; CH$_2$CH$_2$CH$_3$; CH(CH$_3$)$_2$; CF$_3$; CF$_2$H; CFH$_2$; OCF$_3$; OCF$_2$H; OCFH$_2$; OCH$_3$; OCH$_2$CH$_3$; OCH(CH$_3$)$_2$; S(=O)CH$_3$; S(=O)CH$_2$CH$_3$; S(=O)$_2$CH$_3$; S(=O)$_2$CH$_2$CH$_3$; cyclopropyl and O-cyclopropyl.

Particularly preferred compounds according to the invention are selected from the group consisting of 1  3-Methylsulfonyl-5-[4-methyl-4-[[3-(trifluoromethyl)phenyl]sulfonyl]-tetrahydro-pyran-2-yl]-pyridine
2  5-Cyclopropyl-2-[4-methyl-4-[[3-(trifluoromethyl)phenyl]sulfonyl]-tetrahydro-pyran-2-yl]-pyridine
3  5-Methylsulfonyl-2-[4-methyl-4-[[3-(trifluoromethyl)phenyl]sulfonyl]-tetrahydro-pyran-2-yl]-pyridine
4  2-[4-Ethyl-4-[[3-(trifluoromethyl)phenyl]sulfonyl]-tetrahydro-pyran-2-yl]-5-(trifluoro-methyl)-pyridine
5  5-[4-Ethyl-4-[[3-(trifluoromethyl)phenyl]sulfonyl]-tetrahydro-pyran-2-yl]-3-(trifluoro-methyl)-[1,2,4]oxadiazole
6  3-Cyclopropyl-5-[4-ethyl-4-[[3-(trifluoromethyl)phenyl]sulfonyl]-tetrahydro-pyran-2-yl]-[1,2,4]oxadiazole
7  2-Cyclopropyl-5-[4-methyl-4-[[3-(trifluoromethyl)phenyl]sulfonyl]-tetrahydro-pyran-2-yl]-pyrimidine
8  2-Cyclopropyl-5-[4-ethyl-4-[[3-(trifluoromethyl)phenyl]sulfonyl]-tetrahydro-pyran-2-yl]-[1,3,4]oxadiazole
9  2-Isopropoxy-5-[4-methyl-4-[[3-(trifluoromethyl)phenyl]sulfonyl]-tetrahydro-pyran-2-yl]-pyridine
10  2-[4-Ethyl-4-[[3-(trifluoromethyl)phenyl]sulfonyl]-tetrahydro-pyran-2-yl]-6-methyl-pyridine
11  5-[4-Methyl-4-[[3-(trifluoromethyl)phenyl]sulfonyl]-tetrahydro-pyran-2-yl]-2-(trifluoromethyl)-pyrimidine
12  2-[4-Methyl-4-[[3-(trifluoromethyl)phenyl]sulfonyl]-tetrahydro-pyran-2-yl]-5-(trifluoromethyl)-pyridine
13  3-[4-Ethyl-4-[[3-(trifluoromethyl)phenyl]sulfonyl]-tetrahydro-pyran-2-yl]-2-methyl-pyridine
14  5-[4-Methyl-4-[[3-(trifluoromethyl)phenyl]sulfonyl]-tetrahydro-pyran-2-yl]-2-(trifluoromethyl)-pyridine
15  3-[4-Ethyl-4-[[3-(trifluoromethyl)phenyl]sulfonyl]-tetrahydro-pyran-2-yl]-2,6-dimethyl-pyridine
16  2-[4-Ethyl-4-[[3-(trifluoromethyl)phenyl]sulfonyl]-tetrahydro-pyran-2-yl]-6-methyl-pyridine
17  3-Cyclopropyl-5-[4-methyl-4-[[3-(trifluoromethyl)phenyl]sulfonyl]-tetrahydro-pyran-2-yl]-pyridine
18  2-Cyclopropyl-5-[4-methyl-4-[[3-(trifluoromethyl)phenyl]sulfonyl]-tetrahydro-pyran-2-yl]-pyrazine
19  5-Cyclopropyl-3-[4-methyl-4-[[3-(trifluoromethyl)phenyl]sulfonyl]-tetrahydro-pyran-2-yl]-[1,2,4]oxadiazole
20  2-Methyl-5-[[4-methyl-4-[[3-(trifluoromethyl)phenyl]sulfonyl]-tetrahydro-pyran-2-yl]-methoxy]-pyridine
21  3-[4-Methyl-4-[[3-(trifluoromethyl)phenyl]sulfonyl]-tetrahydro-pyran-2-yl]-5-(trifluoromethyl)-pyridine
22  2-Cyclopropyl-5-[[4-methyl-4-[[3-(trifluoromethyl)phenyl]sulfonyl]-tetrahydro-pyran-2-yl]-methoxy]-pyridine
23  3-Fluoro-5-methylsulfonyl-2-[4-methyl-4-[[3-(trifluoromethyl)phenyl]sulfonyl]-tetra-hydro-pyran-2-yl]-pyridine
24  2-[4-Methyl-4-[[3-(trifluoromethyl)phenyl]sulfonyl]-tetrahydro-pyran-2-yl]-5-(trifluoromethyl)-[1,3,4]oxadiazole
25  2-(Difluoro-methyl)-5-[4-methyl-4-[[3-(trifluoromethyl)phenyl]sulfonyl]-tetrahydro-pyran-2-yl]-[1,3,4]oxadiazole
26  2-Isopropyl-5-[4-methyl-4-[[3-(trifluoromethyl)phenyl]sulfonyl]-tetrahydro-pyran-2-yl]-[1,3,4]oxadiazole
27  2-Cyclopropyl-5-[4-methyl-4-[[3-(trifluoromethyl)phenyl]sulfonyl]-tetrahydro-pyran-2-yl]-[1,3,4]oxadiazole 28 3-Chloro-5-methylsulfonyl-2-[4-methyl-4-[[3-(trifluoromethyl)phenyl]sulfonyl]-tetrahydro-pyran-2-yl]-pyridine
29 2-Cyclopropyl-5-[[4-methyl-4-[[3-(trifluoromethyl)phenyl]sulfonyl]-tetrahydro-pyran-2-yl]-methoxy]-pyrazine
30 3-Chloro-2-(4-methyl-4-((3-(trifluoromethyl)phenyl)sulfonyl)tetrahydrofuran-2-yl)-5-(methylsulfonyl)pyridine
31 3-Methyl-2-(4-methyl-4-((3-(trifluoromethyl)phenyl)sulfonyl)tetrahydrofuran-2-yl)-5-(methylsulfonyl)pyridine
32 4-Cyclopropyl-2-[4-methyl-4-[[3-(trifluoromethyl)phenyl]sulfonyl]-tetrahydro-pyran-2-yl]-oxazole
33 5-[[4-Methyl-4-[[3-(trifluoromethyl)phenyl]sulfonyl]-tetrahydro-pyran-2-yl]-methoxy]-2-(trifluoromethyl)-pyridine
34 2-[4-Methyl-4-[(3-methylsulfonyl-phenyl)sulfonyl]-tetrahydro-pyran-2-yl]-3-methyl-sulfonyl-5-(trifluoromethyl)-pyridine
35 2-[4-[[3-(Difluoro-methyl)-phenyl]sulfonyl]-4-methyl-tetrahydro-pyran-2-yl]-3-methylsulfonyl-5-(trifluoromethyl)-pyridine
36 3-Chloro-2-[4-[[3-fluoro-5-(trifluoromethyl)phenyl]sulfonyl]-4-methyl-tetrahydro-pyran-2-yl]-5-methylsulfonyl-pyridine
37 3-Chloro-2-[4-[[3-(difluoro-methyl)-5-fluoro-phenyl]sulfonyl]-4-methyl-tetrahydro-pyran-2-yl]-5-methylsulfonyl-pyridine
38 3-Chloro-5-methylsulfonyl-2-[4-methyl-4-[[3-(trifluoromethyloxy)-phenyl]sulfonyl]-tetrahydro-pyran-2-yl]-pyridine
39 3-Methylsulfonyl-2-[4-methyl-4-[[3-(trifluoromethyloxy)-phenyl]sulfonyl]-tetrahydro-pyran-2-yl]-5-(trifluoromethyl)-pyridine
40 5-Methylsulfonyl-2-[4-methyl-4-[[3-(trifluoromethyl)phenyl]sulfonyl]-tetrahydro-pyran-2-yl]-3-(trifluoromethyl)-pyridine
41 3-Methoxy-5-methylsulfonyl-2-[4-methyl-4-[[3-(trifluoromethyl)phenyl]sulfonyl]-tetrahydro-pyran-2-yl]-pyridine
42 5-Chloro-3-methylsulfonyl-2-[4-methyl-4-[[3-(trifluoromethyl)phenyl]sulfonyl]-tetra-hydro-pyran-2-yl]-pyridine
43 3-(Methylsulfinyl)-2-[4-methyl-4-[[3-(trifluoromethyl)phenyl]sulfonyl]-tetrahydro-pyran-2-yl]-5-(trifluoromethyl)-pyridine
44 3-Chloro-5-(methylsulfinyl)-2-[4-methyl-4-[[3-(trifluoromethyl)phenyl]sulfonyl]-tetrahydro-pyran-2-yl]-pyridine
45 3-Chloro-5-(difluoro-methyl)-2-[4-methyl-4-[[3-(trifluoromethyl)phenyl]sulfonyl]-tetrahydro-pyran-2-yl]-pyridine
46 5-Cyclopropyl-3-[4-ethyl-4-[[3-(trifluoromethyl)phenyl]sulfonyl]-tetrahydro-pyran-2-yl]-[1,2,4]oxadiazole
47 2-[4-Ethyl-4-[[3-(trifluoromethyl)phenyl]sulfonyl]-tetrahydro-pyran-2-yl]-5-(trifluoro-methyl)-[1,3,4]oxadiazole
48 5-Chloro-2-[4-methyl-4-[[3-(trifluoromethyl)phenyl]sulfonyl]-tetrahydro-pyran-2-yl]-pyridine
49 2,4-Dimethoxy-5-[4-methyl-4-[[3-(trifluoromethyl)phenyl]sulfonyl]-tetrahydro-pyran-2-yl]-pyridine
50 2-Methoxy-4-methyl-5-[4-methyl-4-[[3-(trifluoromethyl)phenyl]sulfonyl]-tetrahydro-pyran-2-yl]-pyridine
51 2-Methoxy-5-[4-methyl-4-[[3-(trifluoromethyl)phenyl]sulfonyl]-tetrahydro-pyran-2-yl]-pyridin-4-ol
52 4-(Difluoro-methoxy)-2-methoxy-5-[4-methyl-4-[[3-(trifluoromethyl)phenyl]sulfonyl]-tetrahydro-pyran-2-yl]-pyridine
53 3-Fluoro-2-methoxy-5-[4-methyl-4-[[3-(trifluoromethyl)phenyl]sulfonyl]-tetrahydro-pyran-2-yl]-pyridine
54 4-Fluoro-2-methoxy-5-[4-methyl-4-[[3-(trifluoromethyl)phenyl]sulfonyl]-tetrahydro-pyran-2-yl]-pyridine
55 2-Methoxy-5-[4-methyl-4-[[3-(trifluoromethyl)phenyl]sulfonyl]-tetrahydro-pyran-2-yl]-isonicotinonitrile
56 3-Methyl-5-methylsulfonyl-2-[4-methyl-4-[[3-(trifluoromethyl)phenyl]sulfonyl]-tetrahydro-pyran-2-yl]-pyridine
57 3-Chloro-2-[4-[[3-(difluoro-methyl)-phenyl]sulfonyl]-4-methyl-tetrahydro-pyran-2-yl]-5-methylsulfonyl-pyridine
58 5-(difluoromethoxy)-2-(4-methyl-4-((3-(trifluoromethyl)phenyl)sulfonyl)tetrahydro-2H-pyran-2-yl)-3-(methylsulfonyl)pyridine
59 3-(difluoromethoxy)-2-(4-methyl-4-((3-(trifluoromethyl)phenyl)sulfonyl)tetrahydro-2H-pyran-2-yl)-5-(methylsulfonyl)pyridine
60 3-cyclopropyl-2-(4-methyl-4-(3-(trifluoromethyl)phenylsulfonyl)tetrahydro-2H-pyran-2-yl)-5-(methylsulfonyl)pyridine
61 Dimethyl-[5-[4-methyl-4-[[3-(trifluoromethyl)phenyl]sulfonyl]-tetrahydro-pyran-2-yl]-pyridin-2-yl]-amine
62 2-Cyclopropyl-5-[4-ethyl-4-[[3-(trifluoromethyl)phenyl]sulfonyl]-tetrahydro-pyran-2-yl]-pyrazine
63 2,6-Dimethyl-3-[4-[[3-(trifluoromethyl)phenyl]sulfonyl]-tetrahydro-pyran-2-yl]-pyridine
64 2-Methylsulfonyl-5-[4-methyl-4-[[3-(trifluoromethyl)phenyl]sulfonyl]-tetrahydro-pyran-2-yl]-pyridine
65 2-Bromo-5-[4-methyl-4-[[3-(trifluoromethyl)phenyl]sulfonyl]-tetrahydro-pyran-2-yl]-pyridine
67 2-Isopropoxy-5-[4-[[3-(trifluoromethyl)phenyl]sulfonyl]-tetrahydro-pyran-2-yl]-pyridine
68 3-Chloro-2-[4-methyl-4-[[3-(trifluoromethyl)phenyl]sulfonyl]-tetrahydro-pyran-2-yl]-5-(trifluoromethyl)-pyridine
69 2-Methyl-6-[4-[[3-(trifluoromethyl)phenyl]sulfonyl]-tetrahydro-pyran-2-yl]-pyridine
70 2-(Trifluoromethyl)-5-[4-[[3-(trifluoromethyl)phenyl]sulfonyl]-tetrahydro-pyran-2-yl]-pyridine
71 1-Methyl-5-[4-methyl-4-[[3-(trifluoromethyl)phenyl]sulfonyl]-tetrahydro-pyran-2-yl]-3-(trifluoromethyl)-1H-pyrazole
72 2-Cyclopropyl-5-[4-methyl-4-[[3-(trifluoromethyl)phenyl]sulfonyl]-tetrahydro-pyran-2-yl]-pyridine
74 2-(Trifluoromethyl)-6-[4-[[3-(trifluoromethyl)phenyl]sulfonyl]-tetrahydro-pyran-2-yl]-pyridine
75 2-[4-Methyl-4-[[3-(trifluoromethyl)phenyl]sulfonyl]-tetrahydro-pyran-2-yl]-6-(trifluoromethyl)-pyridine
76 2-Methoxy-5-[4-methyl-4-[[3-(trifluoromethyl)phenyl]sulfonyl]-tetrahydro-pyran-2-yl]-pyridine
77 3-Methylsulfonyl-2-[4-methyl-4-[[3-(trifluoromethyl)phenyl]sulfonyl]-tetrahydro-pyran-2-yl]-5-(trifluoromethyl)-pyridine
78 5-[4-Methyl-4-[[3-(trifluoromethyl)phenyl]sulfonyl]-tetrahydro-pyran-2-yl]-2-pyrrolidin-1-yl-pyridine
79 5-[4-Methyl-4-[[3-(trifluoromethyl)phenyl]sulfonyl]-tetrahydro-pyran-2-yl]-2-(1H-[1,2,4]triazol-1-yl)-pyridine
80 2-(2-Methoxy-ethoxy)-5-[4-methyl-4-[[3-(trifluoromethyl)phenyl]sulfonyl]-tetrahydro-pyran-2-yl]-pyridine
81 Methyl-[5-[4-methyl-4-[[3-(trifluoromethyl)phenyl]sulfonyl]-tetrahydro-pyran-2-yl]-pyridin-2-yl]-amine
82 2-Methoxy-5-[4-methyl-4-[[3-(trifluoromethyl)phenyl]sulfonyl]-tetrahydro-pyran-2-yl]-pyrimidine
83 Dimethyl-[5-[4-methyl-4-[[3-(trifluoromethyl)phenyl]sulfonyl]-tetrahydro-pyran-2-yl]-pyrimidin-2-yl]-amine
84 2-Methoxy-5-[4-methyl-4-[[3-(trifluoromethyl)phenyl]sulfonyl]-tetrahydro-pyran-2-yl]-pyrazine 85  2-(Difluoro-methoxy)-5-[4-methyl-4-[[3-(trifluoromethyl)phenyl]sulfonyl]-tetrahydro-pyran-2-yl]-pyridine
86  Dimethyl-[5-[4-methyl-4-[[3-(trifluoromethyl)phenyl]sulfonyl]-tetrahydro-pyran-2-yl]-pyrazin-2-yl]-amine
87  5-Methoxy-2-[4-methyl-4-[[3-(trifluoromethyl)phenyl]sulfonyl]-tetrahydro-pyran-2-yl]-pyrimidine
88  3-Chloro-5-cyclopropyl-2-[4-methyl-4-[[3-(trifluoromethyl)phenyl]sulfonyl]-tetrahydro-pyran-2-yl]-pyridine
89  3-Chloro-5-(difluoro-methoxy)-2-[4-methyl-4-[[3-(trifluoromethyl)phenyl]sulfonyl]-tetrahydro-pyran-2-yl]-pyridine
90  1-Methyl-3-methylsulfonyl-5-[4-methyl-4-[[3-(trifluoromethyl)phenyl]sulfonyl]-tetra-hydro-pyran-2-yl]-1H-pyrazole
91  3-Cyclopropyl-1-methyl-5-[4-methyl-4-[[3-(trifluoromethyl)phenyl]sulfonyl]-tetrahydro-pyran-2-yl]-1H-pyrazole
92  3-Chloro-2-[4-[[3-(difluoro-methoxy)-phenyl]sulfonyl]-4-methyl-tetrahydro-pyran-2-yl]-5-methylsulfonyl-pyridine
93  3-Chloro-2-[4-[(3-chlorophenyl)sulfonyl]-4-methyl-tetrahydro-pyran-2-yl]-5-methyl-sulfonyl-pyridine
94  3-Methyl-5-methylsulfonyl-2-[4-methyl-4-[[3-(trifluoromethyl)phenyl]sulfonyl]-tetrahydro-pyran-2-yl]-pyridine
95  2-[4-[[3-(Difluoro-methyl)-5-fluoro-phenyl]sulfonyl]-4-methyl-tetrahydro-pyran-2-yl]-3-methyl-5-methylsulfonyl-pyridine
96  2-[4-[[3-Fluoro-5-(trifluoromethyl)-phenyl]sulfonyl]-4-methyl-tetrahydro-pyran-2-yl]-3-methyl-5-methylsulfonyl-pyridine
97  3-Chloro-2-[4-[(3-isopropyl-phenyl)sulfonyl]-4-methyl-tetrahydro-pyran-2-yl]-5-methylsulfonyl-pyridine
98  3-Methyl-5-methylsulfonyl-2-[4-methyl-4-[[3-(trifluoromethyloxy)-phenyl]sulfonyl]-tetrahydro-pyran-2-yl]-pyridine
99  3-[[2-(3-Chloro-5-methylsulfonyl-pyridin-2-yl)-4-methyl-tetrahydro-pyran-4-yl]sulfonyl]-benzonitrile
100  [(5-Methyl-isoxazol-3-yl)-methyl]-[5-[4-methyl-4-[[3-(trifluoromethyl)phenyl]sulfonyl]-tetrahydro-pyran-2-yl]-pyridin-2-yl]-amine
101  7-[5-[4-Methyl-4-[[3-(trifluoromethyl)phenyl]sulfonyl]-tetrahydro-pyran-2-yl]-pyridin-2-yl]-2-oxa-7-azaspiro[3.5]nonane
102  2-[Methyl-[5-[4-methyl-4-[[3-(trifluoromethyl)phenyl]sulfonyl]-tetrahydro-pyran-2-yl]-pyridin-2-yl]-amino]-ethanol
103  [(5-Methyl-isoxazol-3-yl)-methyl]-[6-[4-methyl-4-[[3-(trifluoromethyl)phenyl]sulfonyl]-tetrahydro-pyran-2-yl]-pyridin-2-yl]-amine
104  7-[6-[4-Methyl-4-[[3-(trifluoromethyl)phenyl]sulfonyl]-tetrahydro-pyran-2-yl]-pyridin-2-yl]-2-oxa-7-azaspiro[3.5]nonane
105  [6-[4-Methyl-4-[[3-(trifluoromethyl)phenyl]sulfonyl]-tetrahydro-pyran-2-yl]-pyridin-2-yl]-tetrahydro-pyran-4-yl-amine
106  2-[Methyl-[6-[4-methyl-4-[[3-(trifluoromethyl)phenyl]sulfonyl]-tetrahydro-pyran-2-yl]-pyridin-2-yl]-amino]-ethanol
107  2-[Methyl-[5-[4-methyl-4-[[3-(trifluoromethyl)phenyl]sulfonyl]-tetrahydro-pyran-2-yl]-pyridin-2-yl]-amino]-ethanol
108  Cyclopropyl-[6-[4-methyl-4-[[3-(trifluoromethyl)phenyl]sulfonyl]-tetrahydro-pyran-2-yl]-pyridin-2-yl]-amine
109  1-Ethyl-3-methylsulfonyl-5-[4-methyl-4-[[3-(trifluoromethyl)phenyl]sulfonyl]-tetrahydro-pyran-2-yl]-1H-pyrazole
110  3-(Difluoro-methoxy)-1-methyl-5-[4-methyl-4-[[3-(trifluoromethyl)phenyl]sulfonyl]-tetrahydro-pyran-2-yl]-1H-pyrazole optionally in the form of a single stereoisomer or a mixture of stereoisomers, in the form of the free compound and/or a physiologically acceptable salt or solvate thereof.

Further preferred compounds of the first aspect of the invention are compounds according to formula (IIc),

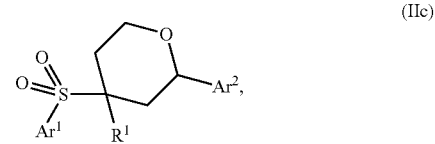

(IIc)

wherein $R^1$, $Ar^1$ and $Ar^2$ are defined as above. The preferred embodiments for $R^1$, $Ar^1$ and $Ar^2$ apply mutatis mutandis.

Further preferred compounds of the invention have formula (IIc), wherein $R^1$, $Ar^1$ and $Ar^2$ are represented as in the table given below:

| Example No | $Ar^1$ | $R^1$ | $Ar^2$ |
|---|---|---|---|
| 111 | 3-(trifluoromethyl)phenyl | $CH_3$ | 3-ethyl-5-(methylsulfonyl)pyridin-2-yl |
| 112 | 3-(3,3-difluoroazetidin-1-yl)phenyl | $CH_3$ | 3-chloro-5-(methylsulfonyl)pyridin-2-yl |
| 113 | 3-(trifluoromethyl)phenyl | $CH_3$ | 1-methyl-3-(difluoromethylsulfonyl)pyrazol-5-yl |

-continued

| Example No | Ar¹ | R¹ | Ar² |
|---|---|---|---|
| 114 | 3-(trifluoromethyl)phenyl | CH₃ | 1-methyl-3-(cyclopropylsulfonyl)pyrazol-5-yl |
| 115 | 3-(trifluoromethyl)phenyl | CH₃ | 3-chloro-5-(1-hydroxycyclopropyl)pyridin-2-yl |
| 116 | 3-(trifluoromethyl)phenyl | CH₃ | 3-chloro-5-(2-hydroxypropan-2-yl)pyridin-2-yl |
| 117 | 3-(trifluoromethyl)phenyl | CH₃ | 1-methyl-3-(difluoromethyl)pyrazol-5-yl |
| 118 | 3-(trifluoromethyl)phenyl | CH₃ | 1-methyl-3-(3,3-difluoroazetidin-1-yl)pyrazol-5-yl |
| 119 | 3-(trifluoromethyl)phenyl | CH₃ | 1-(2-methoxyethyl)-3-(trifluoromethyl)pyrazol-5-yl |
| 120 | 3-(trifluoromethyl)phenyl | CH₃ | 1-methyl-4-bromopyrazol-5-yl |
| 121 | 3-(trifluoromethyl)phenyl | CH₃ | 1-methyl-3-chloropyrazol-5-yl |

-continued

| Example No | Ar¹ | R¹ | Ar² |
|---|---|---|---|
| 122 | 3-(trifluoromethyl)phenyl | CH₃ | 3-(3,3-difluoroazetidin-1-yl)-5-(methylsulfonyl)pyridin-2-yl |
| 123 | 3-(trifluoromethyl)phenyl | CH₃ | 5-(trifluoromethyl)-1H-pyrazol-3-yl |
| 124 | 3-(trifluoromethyl)phenyl | CH₃ | 3-chloro-5-(difluoromethyl)pyridin-2-yl |
| 125 | 3-(trifluoromethyl)phenyl | CH₃ | 3-chloro-5-(1,1-difluoroethyl)pyridin-2-yl |
| 126 | 3-(trifluoromethyl)phenyl | CH₃ | 3-cyano-5-(methylsulfonyl)pyridin-2-yl |
| 127 | 3-(trifluoromethyl)phenyl | CH₃ | 5-cyclopropyl-3-(methylsulfonyl)pyridin-2-yl |
| 128 | 3-(trifluoromethyl)phenyl | CH₃ | 3-chloro-5-(3-methyloxetan-3-yl)pyridin-2-yl |
| 129 | 3-(trifluoromethyl)phenyl | CH₃ | 3-chloro-5-(cyclopropylsulfonyl)pyridin-2-yl |

-continued

| Example No | Ar¹ | R¹ | Ar² |
|---|---|---|---|
| 130 | 3-(F₃C)-C₆H₄- | CH₃ | 3-OEt, 5-SO₂Me-pyridin-2-yl |
| 131 | 3,5-(Cl)(F₃C)-C₆H₃- | CH₃ | 3-Cl, 5-SO₂Me-pyridin-2-yl |
| 132 | 3-(F₃C)-C₆H₄- | CH₃ | 4-cyclopropyl-isothiazol-5-yl 1,1-dioxide |
| 133 | 3-(F₂HC)-C₆H₄- | CH₃ | 3-SO₂Me, 5-OCF₂H-pyridin-2-yl |
| 134 | 3-(F₃C)-C₆H₄- | CH₃ | 3-SO₂Me, 5-CF₂H-pyridin-2-yl |
| 135 | 3-(F₃C)-C₆H₄- | CH₃ | 3-CHF₂, 5-SO₂Me-pyridin-2-yl |
| 136 | 3-(F₃C)-C₆H₄- | CH₃ | 4-SO₂Me, 1-cyclopropyl-pyrazol-3-yl |
| 137 | 3-(F₃C)-C₆H₄- | CH₃ | 4-SO₂Me, 1-methyl-pyrazol-3-yl |
| 138 | 3-(F₃C)-C₆H₄- | CH₃ | 4-SO₂Me, 1H-pyrazol-3-yl |

Within the scope of the invention, it is understood that the compounds according the aforesaid list may be in the form of a single stereoisomer or any mixture of stereoisomers.

For instance, the given compound 3-methylsulfonyl-5-[4-methyl-4-[[3-(trifluoromethyl)phenyl]sulfonyl]-tetrahydro-pyran-2-yl]-pyridine (Example 1),

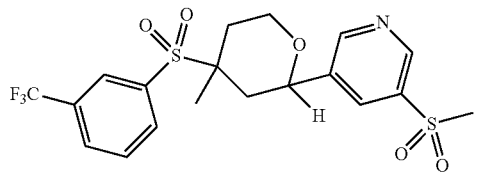 [SMILES: CC1(S(=O)(=O)c2cccc(C(F)(F)F)c2)CCOC(c2cncc(S(C)(=O)=O)c2)C1]

represents cis-rac-3-methylsulfonyl-5-[4-methyl-4-[[3-(trifluoromethyl)phenyl]sulfonyl]-tetrahydro-pyran-2-yl]-pyridine,

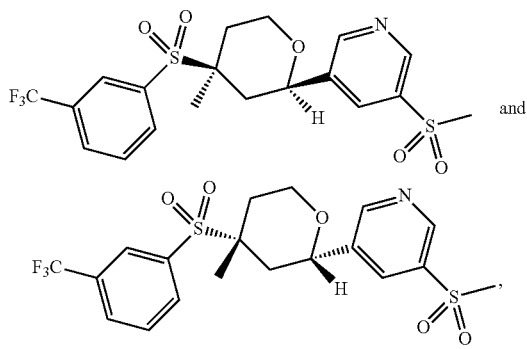

[(2R,4S) and (2S,4R)-3-methylsulfonyl-5-[4-methyl-4-[[3-(trifluoromethyl)phenyl]sulfonyl]-tetrahydro-pyran-2-yl]-pyridine],
and
trans-rac-3-methylsulfonyl-5-[4-methyl-4-[[3-(trifluoromethyl)phenyl]sulfonyl]-tetrahydro-pyran-2-yl]-pyridine,

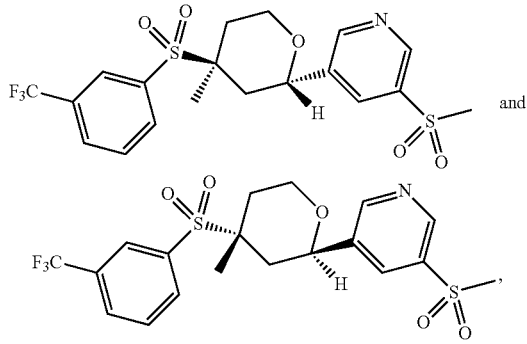

[(2S,4S) and (2R,4R)-3-methylsulfonyl-5-[4-methyl-4-[[3-(trifluoromethyl)phenyl]sulfonyl]-tetrahydro-pyran-2-yl]-pyridine], as well as each individual stereoisomer or any other mixture thereof.

Furthermore, preference may be given to compounds according to the invention that cause at least a 50% inhibition, which is present at a concentration of 3 µM, in a fluorescent assay for CaV2.2 channels with HEK293 cells in which human CaV2.2 channels were stably expressed at a concentration of less 3 µM, preferably less than 1000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR 3, Molecular Devices, Sunnyvale, USA), as described hereinafter.

The present invention further relates to a compound according to the present invention for CaV2.2 calcium channel regulation, preferably for use in CaV2.2 calcium channel blockage. The present invention therefore further relates to a compound according to the present invention for the prophylaxis and/or treatment of disorders and/or diseases which are mediated, at least in part, at least in part, by CaV2.2 channels. The term "disorders and/or diseases which are mediated, at least in part, by CaV2.2 channels", is intended to include each of or all of the disease states.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CaV2.2 channels are believed to be involved in a variety of diseases or disorders in mammals such as humans. These include pain (e.g.; acute pain, chronic pain, visceral pain, headache pain, inflammatory pain, mixed pain), stroke (the neuronal damage resulting from head trauma), epilepsy, mood disorders, schizophrenia, neurodegenerative disorders.

Another embodiment of the present invention is at least one compound according the present invention for the treatment and/or prophylaxis of one or more disorders selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Another embodiment of the present invention is at least one compound according to the present invention for the treatment and/or prophylaxis of pain, in particular acute pain and/or chronic pain and/or visceral pain and/or headache pain and/or inflammatory pain and/or mixed pain. Acute pain according to the invention might include nociceptive pain and post-operative or surgical pain. Chronic pain according to the invention might include peripheral neuropathic pain such as post-herpetic neuralgia, traumatic nerve injury, nerve compression or entrapment, small fibre neuropathy, diabetic neuropathy, neuropathic cancer pain, failed back surgery Syndrome, trigeminal neuralgia, phantom limb pain; neuroma pain, complex regional pain syndrome, chronic arthritic pain and related neuralgias, and pain associated with cancer, chemotherapy, HIV and HIV treatment-induced neuropathy; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome. In treating osteoarthritic pain, joint mobility will also improve as the underlying chronic pain is reduced. Thus, at least one compound for treatment of osteoarthritic pain inherently will also improve joint mobility in patients suffering from osteoarthritis. Visceral pain according to the invention might include interstitial cystitis, irritable bowel syndrome, Crohn's disease and chronic pelvic pain syndrome. Inflammatory pain according to the invention might include rheumatoid arthritis and endometriosis. Headache pain according to the invention might include migraine, cluster headache, tension headache syndrome, facial pain and headache caused by other diseases. Mixed pain according to the invention might include lower back pain, neck and shoulder pain, burning mouth syndrome and complex regional pain syndrome.

In another embodiment of the invention, at least one compound according to the present invention is particularly suitable for the treatment and/or prophylaxis of mood disorders. Mood disorders according to the invention might include anxiety disorder, social anxiety disorder, panic disorder, specific phobias, for example, specific animal phobias, social phobias, obsessive-compulsive disorder, agoraphobia, post-traumatic stress syndrome, addiction (including dependence, withdrawal and/or relapse of medication, including opioids, but also drugs such as cocaine, opioids, alcohol and nicotine), generalised anxiety disorders, single episodic or recurrent major depressive disorders and dysthymic disorders, or bipolar disorders, for example, bipolar I disorder, bipolar II disorder and cyclothymic disorder.

In another embodiment of the invention, at least one compound according to the present invention is particularly suitable for the treatment and/or prophylaxis of epilepsy. Epilepsy according to the invention might include partial seizures such as temporal lobe epilepsy, absence seizures generalized seizures, and tonic/clonic seizures.

In yet another embodiment of the invention, at least one compound according to the present invention is particularly suitable for the treatment and/or prophylaxis of neurodegenerative disorders. Neurodegenerative disorders according to the invention might include Parkinson's disease, Alzheimer's disease, multiple sclerosis, neuropathies, Huntington's disease, presbycusis and amyotrophic lateral sclerosis (ALS).

Particularly preferably, at least one compound according to the present invention is suitable for the treatment and/or prophylaxis of one or more disorders and/or diseases selected from the group consisting of pain, preferably of pain selected from the group consisting of acute pain, chronic pain, visceral pain, headache pain, inflammatory pain and mixed pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Another embodiment of the present invention therefore relates to use of at least one compound according to the present invention for the preparation of a pharmaceutical composition for the treatment and/or prophylaxis of one or more disorders or diseases, particularly selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders.

Another aspect of the present invention is a method of treatment and/or prophylaxis of disorders and/or diseases in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

All preferred embodiments of the first aspect of the invention are preferred vice versa for the other aspects and embodiments.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour und Smith (J. Pharm. Exp. Ther. 72, 74-79 (1941)) or by the formalin test (e.g. according to D. Dubuisson et al., Pain 1977, 4, 161-174).

EXAMPLES

The compounds according to the invention can be prepared in the manner described below. The following examples further illustrate the invention but are not to be construed as limiting its scope.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The reactions were, if necessary, carried out under an inert atmosphere (mostly $N_2$). The number of equivalents of reagents and the amounts of solvents employed as well as the reaction temperatures and times can vary slightly between different reactions carried out by analogous methods. The work-up and purification methods were adapted according to the characteristic properties of each compound and can vary slightly for analogous methods. The yields of the compounds prepared are not optimized.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

The indication "equivalents" ("eq." or "eq" or "equiv.") means molar equivalents, "RT" or "rt" means room temperature T (23±7° C.), "M" are indications of concentration in mol/l, "aq." means aq., "sat." means sat., "sol." means solution, "conc." means concentrated and "anhydr." means anhydr. The mixing ratios of solvents are usually stated in the volume/volume ratio.

Further abbreviations:
CC=column chromatography; COSY=correlation spectroscopy; d=day(s); DCE=1,2-dichloroethane; DCM=dichloromethane; DIPEA=N,N-diisopropylethylamine; DMF=N,N-dimethylformamide; EDC•HCl=1-ethyl-3-(3-dimethylaminopropyl)carbodiimide hydrochloride; ee=enantiomeric excess; Et$_2$O=diethyl ether; EtOAc=ethyl acetate; EtOH=ethanol; h=hour(s); HMBC=heteronuclear multiple-bond correlation spectroscopy; HMQC=heteronuclear multiple quantum coherence spectroscopy; HOBt=1-hydroxybenzotriazole; KOt-Bu=potassium tert-butoxide; LiHMDS=Lithium hexymethyldisilazide; min=minute(s); MeCN=acetonitrile; MeOH=methanol; MS=methanesulfonyl; NOE=Nuclear Overhauser Effect; NOESY=Nuclear Overhauser effect spectroscopy; PE=petroleum ether; RM=reaction mixture; TEA=triethylamine; TFA=trifluoroacetic acid; THF=tetrahydrofuran.

Instruments:
$^1$H-NMR-spectra (including NOESYs) were recorded at 400 MHz on a Bruker Avance-400 spectrometer or on Agilent 300 & 400 MHz spectrometer.

Analytical chiral HPLCs were measured on:
Agilent 1260 Quart. Pump: G1311C, autosampler, Col-Com, DAD: Agilent G4212B or Waters 2695 separation module Detector 2996 & Agilent 1200 series with G 1315B detector Preparative HPLC were performed on:
Waters 2545 Quaternary gradient module with Autosampler 2707 & Waters 2545
Quaternary gradient module with Manual mode.
Analytical SFC were performed on Thar SFC analytical.
Preparative SFC were performed THAR-SFC 80.
Instruments employed for chiral separations:
Fraction Collector: Gilson 215 Liquid Handler; HPLC instrument modules: Shimadzu LC8-A preparative pumps, Shimadzu SCL-10 Avp system controller, Shimadzu SPD-10 Avp UV-VIS detector.

Synthesis of Example Compounds

2-[4-Ethyl-4-[[3-(trifluoromethyl)phenyl]sulfonyl]-tetrahydro-pyran-2-yl]-5-(trifluoromethyl)-pyridine (Example 4)

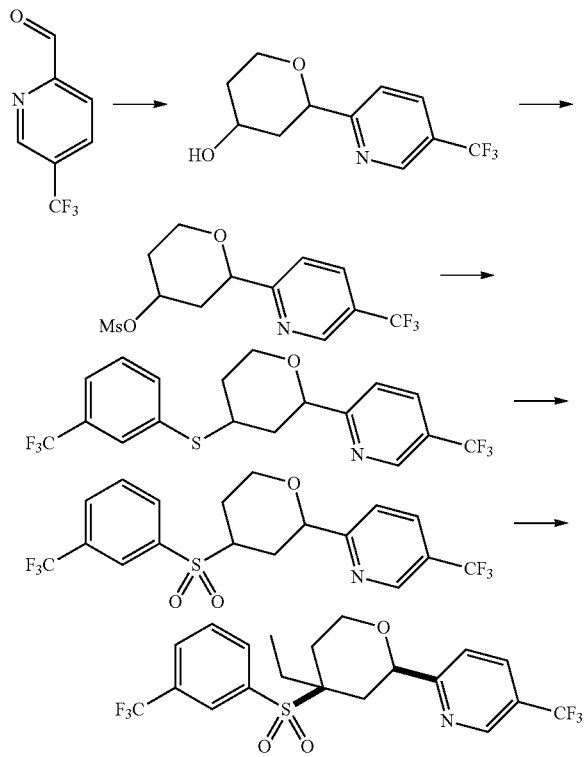

2-(5-(Trifluoromethyl)pyridin-2-yl)tetrahydro-2H-pyran-4-ol

To a stirred solution of but-3-en-1-ol (1.2 g, 17.1 mmol, 1.0 eq) in DCE (80 mL) and TFA (24 mL, 308 mmol, 18 eq), 5-(trifluoromethyl)picolinaldehyde (3.0 g, 17.1 mmol, 1 eq) was added and the mixture was stirred for 72 h. After completion of the reaction it was quenched with ice water, basified with NaOH and extracted with DCM. The organic layer was dried over anhydr. $Na_2SO_4$, filtered and evaporated under reduced pressure to give yellow oil. The residue was dissolved in MeOH (50 mL) and LiOH (1.2 g, 51.3 mmol, 3.0 eq) was added at RT and the mixture was stirred for 2 h until no evidence of the ester remained. The RM was evaporated to dryness and dissolved in DCM and dried over anhydr. $Na_2SO_4$ to give crude product which was further purified by CC to afford 2-(5-(trifluoromethyl)pyridin-2-yl) tetrahydro-2H-pyran-4-ol (1.5 g, 36%).

2-(5-(Trifluoromethyl)pyridin-2-yl)tetrahydro-2H-pyran-4-yl Methanesulfonate Methanesulfonyl chloride (1.76 mlL 18.21 mmol, 1.5 eq) was added to an ice-cold solution of 2-(5-(trifluoromethyl) pyridin-2-yl)tetrahydro-2H-pyran-4-ol (3.0 g, 12.1 mmol, 1.0 eq) and TEA (5.0 mL, 3.5 mmol, 3.0 eq) in DCM (50 mL) and the RM was stirred at the same temperature for 2 h. The RM was quenched with $H_2O$. The aq. layer was extracted with DCM (2×50 mL), combined organic layer was dried over anhydr. $Na_2SO_4$, filtered and concentrated under reduced pressure to yield crude product which was purified by CC to afford 2-(5-(trifluoromethyl)pyridin-2-yl) tetrahydro-2H-pyran-4-yl methanesulfonate (3.0 g, 76%).

5-(Trifluoromethyl)-2-(4-((3-(trifluoromethyl)phenyl)thio)tetrahydro-2H-pyran-2-yl)pyridine $K_2CO_3$ (2.5 g, 18.5 mmol, 2.0 eq) was added to the solution of 2-(5-(trifluoromethyl)pyridin-2-yl)tetrahydro-2H-pyran-4-yl methanesulfonate (3.0 g, 9.2 mmol, 1.0 eq) and 3-(trifluoromethyl)benzenethiol (3.3 g, 18.5 mmol, 2.0 eq) in DMF (30 mL). The RM was stirred at 60° C. for 12 h. Then the RM was cooled to RT and then quenched with ice. The aq. layer was extracted with EtOAc (2×150 mL). Combined organic layer was dried over anhydr. $Na_2SO_4$, filtered and concentrated under reduced pressure to yield crude mass which was then purified by CC to afford 5-(trifluoromethyl)-2-(4-((3-(trifluoromethyl)phenyl)thio)tetrahydro-2H-pyran-2-yl)pyridine (3.0 g, 80%).

5-(Trifluoromethyl)-2-(4-((3-(trifluoromethyl)phenyl)sulfonyl)tetrahydro-2H-pyran-2-yl)pyridine To a stirred ice cold solution of 5-(trifluoromethyl)-2-(4-((3-(trifluoromethyl)phenyl)thio)-tetrahydro-2H-pyran-2-yl)pyridine (3.0 g, 7.4 mmol, 1.0 eq) in THF:$H_2O$ (3:1), oxone (13.5 g, 22.1 mmol, 3.0 eq) was added and RM was stirred at RT for 4 h. After completion of the reaction it was diluted with water and the crude product was extracted with EtOAc. The combined organic layer was washed with water, sat. brine and dried over anhydr. $Na_2SO_4$, filtered and evaporated under reduced pressure to get crude product which was further purified by CC to afford 5-(trifluoromethyl)-2-(4-((3-(trifluoro-methyl)phenyl)sulfonyl)tetrahydro-2H-pyran-2-yl)pyridine (3.0 g, 92%) as a white solid).

2-[4-Ethyl-4-[[3-(trifluoromethyl)phenyl]sulfonyl]-tetrahydro-pyran-2-yl]-5-(trifluoromethyl)-pyridine To a stirred solution of 5-(trifluoromethyl)-2-(4-((3-(trifluoromethyl)phenyl)sulfonyl)tetrahydro-2H-pyran-2-yl) pyridine (1.0 g, 2.3 mmol, 1.0 eq) in dry THF (30 mL), LiHMDS (1M) (4.55 mL, 4.6 mmol, 2.0 eq) was added at −78° C. under Ar and stirred for 30 min. Ethyl iodide (0.7 g, 4.6 mmol, 2.0 eq) was added at the same temperature and the mixture was stirred for 30 min. The RM was allowed to stir for 1 h at RT. The RM was quenched with water and extracted with EtOAc (3×50 mL). The combined organic layer was washed with sat. brine and finally dried over anhydr. $Na_2SO_4$, filtered and the solvent was evaporated under reduced pressure to get crude product which was further purified by CC to afford cis (0.5 g, 47%, yellow solid) and trans isomer (0.45 g, 42%, off white solid) as two diastereomers. The relative configuration (cis or trans) was determined by $^1$H-NMR and NOE experiments.

cis-isomer (SC-106, SC-108): 1H NMR (400 MHz, DMSO-$d_6$, δ ppm): 1.01-1.06 (3H), 1.64-1.68 (1H), 1.79-1.85 (1H), 1.99-2.09 (3H), 2.16-2.20 (1H), 3.74-3.80 (1H), 4.06-4.10 (1H), 4.69-4.72 (1H), 7.63-7.65 (1H), 7.92-7.96 (1H), 8.02 (s, 1H), 8.14-8.16 (1H), 8.21-8.23 (1H), 8.93 (s, 1H).

On irradiating OCH proton "positive" NOE was observed with ethyl protons —$CH_2CH_3$. trans-isomer (SC-107, SC-109): 1H NMR (400 MHz, DMSO-$d_6$, δ ppm): 0.79-0.85 (3H), 1.43-1.49 (2H), 1.71-1.77 (1H), 1.95-1.99 (1H), 2.04-2.08 (1H), 2.42-2.49 (1H), 4.06-4.10 (1H), 4.28-4.33 (1H), 5.26-5.29 (1H), 7.70-7.72 (1H), 7.97-8.01 (1H), 8.13 (s, 1H), 8.23-26 (3H), 8.91 (s, 1H).

On irradiating OCH proton "no" NOE was observed with ethyl protons —$CH_2CH_3$. Enantiomers of cis and trans diastereomers were separated by chiral HPLC using chiral pack AD-H column and Ethanol/DEA: (100/0.1) as mobile phase to obtain two desired cis enantiomers (SC-106 and SC-108) and two trans enantiomers (SC-107 and SC-109).

[cis-EN1] SC-106: (0.186 g, 17.5%, off white solid, cis-EN1)

[cis-EN2] SC-108: (0.164 g, 15.4%, yellow solid, cis-EN2)

[trans-EN1] SC-107: (0.079 g, 7.5%, gummy liquid, trans-EN1)

[trans-EN2] SC-109: (0.148 g, 14.0%, gummy liquid, trans-EN2)

3-Methylsulfonyl-5-[4-methyl-4-[[3-(trifluoromethyl)phenyl]sulfonyl]-tetrahydro-pyran-2-yl]-pyridine (Example 1)

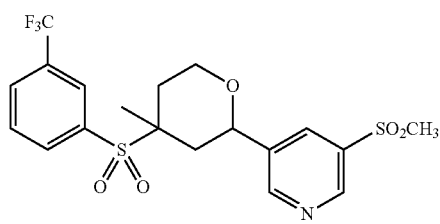 [SMILES: CC1(S(=O)(=O)c2cccc(C(F)(F)F)c2)CCOC(c2cncc(S(C)(=O)=O)c2)C1]

Two enantiomers of cis racemic were separated by chiral HPLC, using chiral pack 1A column and Methanol/DEA: (100/0.1) as mobile phase to obtain two desired cis enantiomers (SC-100 and SC-101).

[cis-EN1] SC-100: 1$^{st}$ eluted enantiomer

[cis-EN2] SC-101: 2$^{nd}$ eluted enantiomer

5-Cyclopropyl-2-[4-methyl-4-[[3-(trifluoromethyl)phenyl]sulfonyl]-tetrahydro-pyran-2-yl]-pyridine (Example 2)

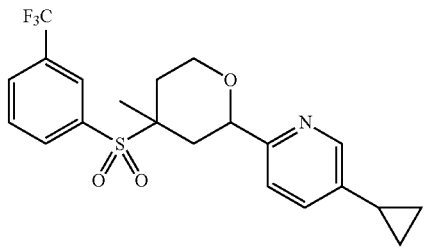 [SMILES: CC1(S(=O)(=O)c2cccc(C(F)(F)F)c2)CCOC(c2ccc(C3CC3)cn2)C1]

Two enantiomers of cis racemic were separated by SFC using on a chiral pack OJ-H column to obtain two desired cis enantiomers (SC-102 and SC-103).
[cis-EN1] SC-102: $1^{st}$ eluted enantiomer
[cis-EN2] SC-103: $2^{nd}$ eluted enantiomer

5-Methylsulfonyl-2-[4-methyl-4-[[3-(trifluoromethyl)phenyl]sulfonyl]-tetrahydro-pyran-2-yl]-pyridine (Example 3)

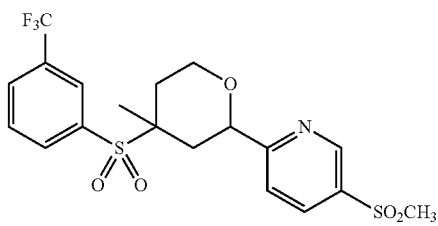 [SMILES: CC1(S(=O)(=O)c2cccc(C(F)(F)F)c2)CCOC(c2ccc(S(C)(=O)=O)cn2)C1]

Two enantiomers of cis racemic were separated by chiral HPLC, using chiral pack-1A column and Hexane/EtOAc/Ethanol/DEA: (50/25/25/0.1) as mobile phase to obtain two desired cis enantiomers (SC-104 and SC-105).
[cis-EN1] SC-104: $1^{st}$ eluted enantiomer
[cis-EN2] SC-105: $2^{nd}$ eluted enantiomer

4-Ethyl-4-[[3-(trifluoromethyl)phenyl]sulfonyl]-tetrahydro-pyran-2-carboxylic Acid

Step 1: 4-Oxo-pyran-2-carboxylic Acid Methyl Ester

Comanic acid (50 g, 0.357 mol) was dissolved in MeOH (1 L) and cooled to <10° C. Conc. $H_2SO_4$ (10 mL) was added dropwise and then the whole refluxed overnight. The volatiles were concentrated in vacuo and the residue poured into excess iced water. The mixture was extracted with DCM (3×250 mL). The combined organic layer was washed with $NaHCO_3$ solution, brine, dried ($Na_2SO_4$) and concentrated in vacuo to yield crude, which was triturated with hexane to give 4-oxo-pyran-2-carboxylic acid methyl ester (50 g, 97%) as solid.

Step 2: 4-Hydroxy-tetrahydro-pyran-2-carboxylic Acid Methyl Ester

A solution of 4-oxo-pyran-2-carboxylic acid methyl ester (25 g, 0.162 mol) in MeOH (500 mL) was hydrogenated over 10% Pd—C (8 g) overnight at 40-50 psi. Filtration and concentration in vacuo gave residue. This was purified by flash CC (silica gel) by eluting with 0-20% EtOAc in hexane (to remove non-polar impurities) and then with 3-5% MeOH in $CHCl_3$ to yield 4-hydroxy-tetrahydro-pyran-2-carboxylic acid methyl ester (12.5 g, 48%) as an oil.

Step 3: 4-Methylsulfonyloxy-tetrahydro-pyran-2-carboxylic Acid Methyl Ester

DIPEA (64 mL, 0.37 mol) was added to a solution of 4-Hydroxy-tetrahydro-pyran-2-carboxylic acid methyl ester (24 g, 0.15 mol) in DCM (240 mL) at 0° C. and MSCl (17.27 g, 0.22 mol) was added dropwise. The mixture was warmed to RT and stirred overnight. The RM was diluted with DCM and washed with iced-water, $NaHCO_3$ solution, brine, dried ($Na_2SO_4$) and concentrated in vacuo to yield crude 4-methylsulfonyloxy-tetrahydro-pyran-2-carboxylic acid methyl ester (34 g) which was taken as such to the next step.

Step 4: 4-[[3-(Trifluoromethyl)phenyl]sulfanyl]-tetrahydro-pyran-2-carboxylic Acid Methyl Ester A solution of 4-methylsulfonyloxy-tetrahydro-pyran-2-carboxylic acid methyl ester (34 g 0.147 mol) in DMF (340

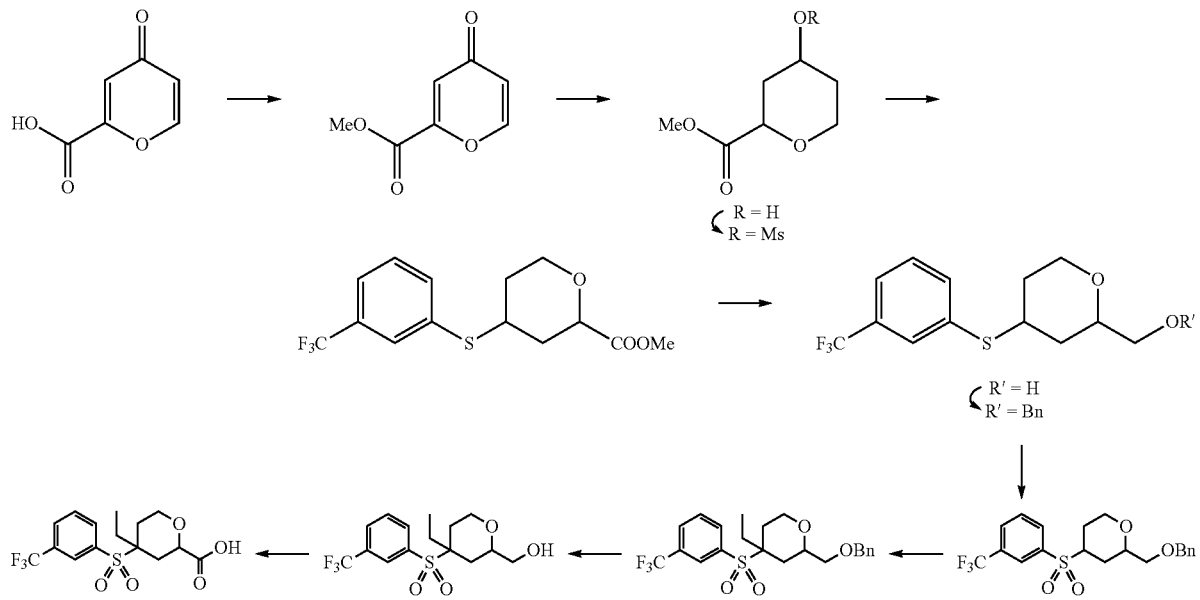

mL) was treated with 3-trifluoromethyl benzene thiol (40 mL, 0.294 mol) and $K_2CO_3$ (40 g, 0.294 mol) at 0° C. The whole was then heated at 50-55° C. for 6 h. The mixture was quenched into iced-water and extracted with EtOAc (5×100 mL). The combined filtrate was washed with brine (4×100 mL), dried ($Na_2SO_4$) and evaporated to dryness. The crude was purified over flash CC (silica gel) by eluting with EtOAc in hexane (10-20%) to afford 4-[[3-(trifluoromethyl)phenyl]sulfanyl]tetra-hydro-pyran-2-carboxylic acid methyl ester (21 g, 42.8% over 2 steps).

Step 5: [4-[[3-(Trifluoromethyl)phenyl]sulfanyl]-tetrahydro-pyran-2-yl]-methanol A suspension of $LiAlH_4$ (0.47 g, 0.012 mol) in dry THF (40 mL) was cooled to <10° C. and a solution of 4-[[3-(trifluoromethyl)phenyl]sulfanyl]tetrahydro-pyran-2-carboxylic acid methyl ester (4 g, 0.12 mol) in dry THF (40 mL) was added dropwise. The mixture was stirred at same temperature for 2 h and then quenched with sat. $NH_4Cl$ solution. The mixture was then filtered over celite, washed with EtOAc and filtrate was washed with brine, dried ($Na_2SO_4$) and concentrated in vacuo to give [4-[[3-(trifluoromethyl)-phenyl]sulfanyl]tetrahydro-pyran-2-yl]-methanol (3.3 g, 90.4%) as oil.

Step 6: 2-(Phenylmethoxy-methyl)-4-[[3-(trifluoromethyl)phenyl]sulfanyl]-tetrahydro-pyran A solution of give [4-[[3-(Trifluoromethyl)phenyl]sulfanyl]-tetrahydro-pyran-2-yl]-methanol (3.3 g, 0.011 mol) in dry THF (33 mL) was added dropwise to a suspension of NaH (60% in mineral oil; 0.9 g, 0.022 mol) was added to dry THF (33 mL) at 0° C. and stirred at same temperature for 30 min. Benzyl bromide (1.34 mL, 0.011 mol) was added and the whole heated at reflux for 4 h. The mixture was cooled to RT, quenched with $NH_4Cl$ solution and extracted with EtOAc (3×25 mL). The combined organic layer was washed with brine, dried ($Na_2SO_4$) and concentrated in vacuo to give crude. Purification (silica gel) using 10-15% EtOAc in hexane afforded 2-(phenylmethoxy-methyl)-4-[[3-(trifluoromethyl)phenyl]sulfanyl]-tetrahydro-pyran (4.5 g, 96%) as an oil.

Step 7: 2-(Phenylmethoxy-methyl)-4-[[3-(trifluoromethyl)phenyl]sulfonyl]-tetrahydro-pyran A solution of oxone (21.7 g, 0.035 mol) in water (110 mL) was added dropwise to a solution of 2-(phenylmethoxymethyl)-4-[[3-(trifluoromethyl)phenyl]sulfanyl]-tetrahydro-pyran (4.5 g, 0.011 mol) in MeOH (135 mL) at <10° C. and stirred overnight at RT. The RM was concentrated to remove MeOH and diluted with iced-water. Extracted with DCM (3×30 mL); the combined organic layer washed with brine, dried ($Na_2SO_4$) and concentrated in vacuo. The crude was purified (silica gel) and compound eluted with 18-22% EtOAc in hexane. Evaporation gave 2-(Phenylmethoxymethyl)-4-[[3-(trifluoro-methyl)phenyl]sulfonyl]-tetrahydro-pyran (3.7 g, 78%) as an oil.

Step 8: 4-Ethyl-2-(phenylmethoxy-methyl)-4-[[3-(trifluoromethyl)phenyl]sulfonyl]-tetrahydro-pyran A solution of KOt-Bu (1 M in THF, 17.8 mL, 0.017 mol) was added dropwise to a solution of 2-(phenylmethoxymethyl)-4-[[3-(trifluoromethyl)phenyl]sulfonyl]-tetrahydropyran (3.7 g, 0.009 mol) in dry THF (74 mL) at −78° C. and stirred at same temperature for 15 min. Ethyl iodide (1.78 mL, 0.022 mol) was added and the RM stirred at RT for 24 h. The mixture was poured into iced-water, extracted with EtOAc (3×100 mL). The combined organic layer was washed with water, brine, dried ($Na_2SO_4$) and concentrated in vacuo to crude. Purification (silica gel) by eluting with 16% EtOAc in hexane gave 4-ethyl-2-(phenylmethoxymethyl)-4-[[3-(trifluoromethyl)phenyl]sulfonyl]-tetrahydropyran (1.2 g, 30%) as oil.

Step 9: [4-Ethyl-4-[[3-(trifluoromethyl)phenyl]sulfonyl]-tetrahydro-pyran-2-yl]-methanol A solution of $BBr_3$ (1 M in DCM; 0.0054 mol, 5.4 mL) was added dropwise into a solution of 4-ethyl-2-(phenylmethoxy-methyl)-4-[[3-(trifluoromethyl)phenyl]sulfonyl]-tetrahydro-pyran (1.2 g, 0.0027 mol) in DCM (24 mL) at −78° C. and stirred for 3 h at same temperature. The RM was quenched with MeOH (3 mL) and poured into iced-water. The organic layer was separated, washed with $NaHCO_3$ solution, water, brine, dried ($Na_2SO_4$) and concentrated in vacuo to crude. Purification (silica gel) by eluting with 18% EtOAc in hexane gave [4-ethyl-4-[[3-(trifluoromethyl)phenyl]sulfonyl]-tetrahydro-pyran-2-yl]-methanol (750 mg, 79%) as an oil.

Step 10: 4-Ethyl-4-[[3-(trifluoromethyl)phenyl]sulfonyl]-tetrahydro-pyran-2-carboxylic Acid Jones' reagent [0.63 g (0.0063 mol) $CrO_3$ in $H_2SO_4$ (1.72 mL) and water (5.6 mL)] was added to a solution of [4-ethyl-4-[[3-(trifluoromethyl)phenyl]sulfonyl]-tetrahydro-pyran-2-yl]-methanol (750 mg, 0.0021 mol) in acetone (13 mL) and the whole stirred at 0-5° C. for 6-7 h. Excess reagent was quenched with isopropanol (3 mL) and the mixture concentrated in vacuo and residue added to iced-water. Basified with $NaHCO_3$ solution and filtered. The filtrate was washed with EtOAc and aq. layer acidified with 6 N HCl to pH~2. Extracted with EtOAc (5×25 mL), washed with brine, dried ($Na_2SO_4$) and concentrated to give 4-ethyl-4-[[3-(trifluoromethyl)phenyl]sulfonyl]-tetrahydro-pyran-2-carboxylic acid (400 mg, 51%) as an oil.

5-[4-Ethyl-4-[[3-(trifluoromethyl)phenyl]sulfonyl]-tetrahydro-pyran-2-yl]-3-(trifluoromethyl)-[1,2,4]oxadiazole (Example 5)

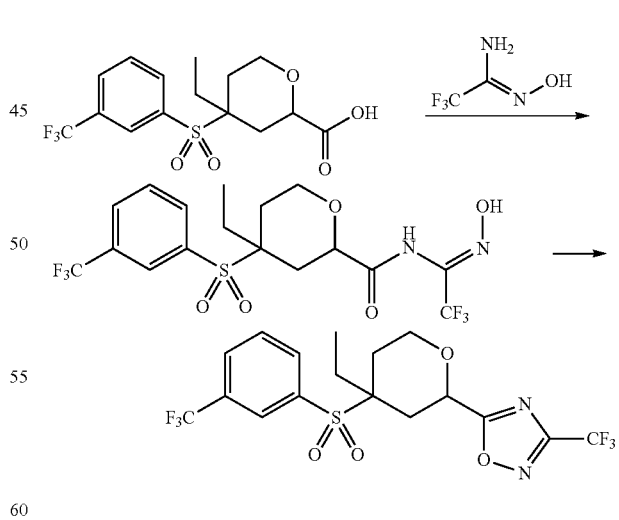

Step 1: 4-ethyl-N-(2,2,2-trifluoro-1-(hydroxyimino)ethyl)4-ethyl-4-((3-(trifluoromethyl)phenyl)sulfonyl)tetrahydro-2H-pyran-2-carboxamide EDC·HCl (1.04 g, 5.46 mmol) and HOBt (0.73 g, 5.46 mmol) were added to a stirred solution of 4-ethyl-4-[[3-

(trifluoromethyl)phenyl]sulfonyl]-tetrahydro-pyran-2-carboxylic acid (1 g, 2.73 mmol) in THF (20 mL) at 0° C., stirred for 15 min and added TEA (0.76 mL, 5.46 mmol) followed by 2,2,2-trifluoro-N'-hydroxyacetimidamide (0.35 g, 2.73 mmol). The resulting RM was allowed to warm to RT and stirred for 16 h. RM was diluted with chilled water (40 ml) and extracted with EtOAc (2×100 mL). Combined organic extract was washed with brine solution (50 mL), dried ($Na_2SO_4$) and concentrated under reduced pressure to get crude 4-ethyl-N-(2,2,2-trifluoro-1-(hydroxyimino)ethyl) 4-ethyl-4-((3-(trifluoromethyl)phenyl)sulfonyl)tetrahydro-2H-pyran-2-carboxamide (1.2 g, crude) as a thick liquid. Crude was used as such in next step without purification.

Step 2: 5-[4-Ethyl-4-[[3-(trifluoromethyl)phenyl]sulfonyl]-tetrahydro-pyran-2-yl]-3-(trifluoromethyl)-[1,2,4]oxadiazole Sodium acetate (0.56 g, 6.89 mmol) was added to a solution of 4-ethyl-N-(2,2,2-trifluoro-1-(hydroxyimino) ethyl)4-ethyl-4-((3-(trifluoromethyl)phenyl)sulfonyl)tetrahydro-2H-pyran-2-carboxamide (1.2 g, 3.44 mmol) in EtOH (12 mL) and water (9.5 mL) mixture and stirred at 80° C. for 16 h. RM mass was concentrated and the residue was diluted with DCM (150 mL) and water (50 mL). Organic layer was separated and washed with brine solution (50 mL), dried ($Na_2SO_4$) and concentrated under reduced pressure to get crude. The crude upon purification by CC (silica gel, 0-13% EtOAc in PE) gave 5-(4-ethyl-4-((3-(trifluoromethyl)phenyl)sulfonyl)tetrahydro-2H-pyran-2-yl)-3-(trifluoromethyl)-1,2,4-oxadiazole (racemic) (0.50 g) as a white solid.
$^1$H-NMR (600 MHz, [$d_6$]-DMSO): δ=8.24-8.25 (1H), 8.19-8.20 (1H), 8.06 (1H), 7.97-8.00 (1H), 5.16-5.19 (1H), 4.02-4.06 (1H), 3.76-3.81 (1H), 2.16-2.27 (2H), 1.94-2.07 (3H), 1.68-1.72 (1H), 1.00-1.02 (3H) ppm.
NOE: C-2 proton & ethyl=cis

Chiral Resolution of [Cis-rac] 5-[4-Ethyl-4-[[3-(trifluoromethyl)phenyl]sulfonyl]-tetrahydro-pyran-2-yl]-3-(trifluoromethyl)-[1,2,4]oxadiazole

[Cis-rac] 5-[4-Ethyl-4-[[3-(trifluoromethyl)phenyl]sulfonyl]-tetrahydro-pyran-2-yl]-3-(trifluoromethyl)-[1,2,4]oxadiazole (500 mg) was subjected to preparative chiral-LC (OJ-H-column, 0.1% diethylamine in hexane/EtOH, 9:1). The products were dried to give 105 mg of [cis-EN1] SC-200 and 96 mg of [cis-EN2] SC-201.
[cis-EN1] SC-200—analytical chiral HPLC: chiralpak IC (250×4.6 mm 5μ), 1 ml/min, RT, 0.1% isopropylamine in hexane/EtOH 70/30, Ret. Time 6.08; ee >95%
[cis-EN2] SC-201—analytical chiral HPLC: chiralpak IC (250×4.6 mm 5μ), 1 ml/min, RT, 0.1% isopropylamine in hexane/EtOH 70/30, Ret. Time 7.31; ee >95%

3-Cyclopropyl-5-[4-ethyl-4-[[3-(trifluoromethyl)phenyl]sulfonyl]-tetrahydro-pyran-2-yl]-[1,2,4]oxadiazole (Example 6)

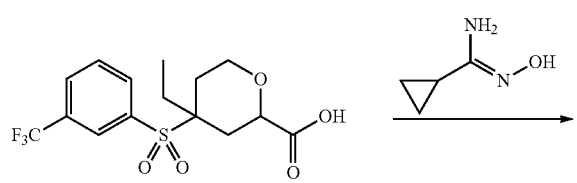

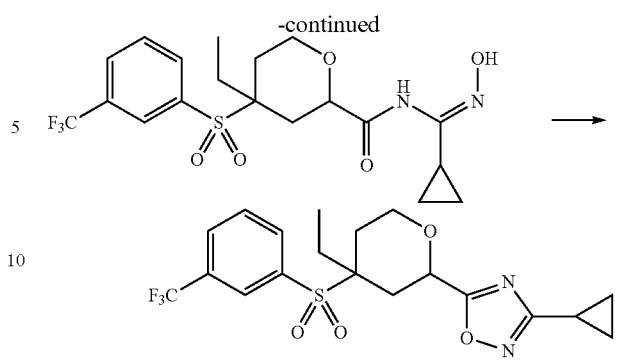

Step 1: N-(cyclopropyl(hydroxyimino)methyl)4-ethyl-4-((3-(trifluoromethyl)phenyl)sulfonyl)tetrahydro-2H-pyran-2-carboxamide EDC•HCl (1.04 g, 5.46 mmol) and HOBt (0.73 g, 5.46 mmol) were added to a stirred solution of 4-ethyl-4-[[3-(trifluoromethyl)phenyl]sulfonyl]-tetrahydro-pyran-2-carboxylic acid (1 g, 2.73 mmol) in THF (20 mL) at 0° C., stirred for 10 min and added TEA (0.76 mL, 5.46 mmol) followed by (Z)—N'-hydroxycyclopropanecarboximidamide (0.27 g, 2.73 mmol). The resulting mixture was allowed to RT and stirred for 16 h. RM was diluted with chilled water (40 ml) and extracted with EtOAc (2×100 mL). Combined organic extract was washed with brine solution (50 mL), dried ($Na_2SO_4$) and concentrated under reduced pressure to get crude N-(cyclopropyl(hydroxyimino) methyl)4-ethyl-4-((3-(trifluoromethyl)-phenyl)sulfonyl)tetrahydro-2H-pyran-2-carboxamide (0.9 g, crude) as a thick liquid.

Step 2: 3-Cyclopropyl-5-[4-ethyl-4-[[3-(trifluoromethyl)phenyl]sulfonyl]-tetrahydro-pyran-2-yl]-[1,2,4] oxadiazole Sodium acetate (0.32 g, 4.01 mmol) was added to a solution of N-(cyclopropyl(hydroxyimino)methyl)-4-ethyl-4-((3-(trifluoromethyl)phenyl)sulfonyl)tetrahydro-2H-pyran-2-carboxamide (0.9 g, 2.00 mmol) in EtOH (10 mL) and water (8 mL) mixture and stirred at 80° C. for 16 h. RM was concentrated and the residue was diluted with DCM (150 mL) and water (50 mL). Organic layer was separated and washed with brine solution (50 mL), dried ($Na_2SO_4$) and concentrated under reduced pressure to get crude. The crude upon purification by CC (silica gel, 0-9% EtOAc in PE) gave 3-cyclopropyl-5-[4-ethyl-4-[[3-(trifluoro-methyl)phenyl] sulfonyl]-tetrahydro-pyran-2-yl]-[1,2,4]oxadiazole (0.38 g, 44%) as a thick liquid.
$^1$H-NMR (600 MHz, [$d_6$]-DMSO): δ=8.23-8.25 (1H), 8.18-8.19 (1H), 8.04 (1H), 7.96-7.98 (1H), 4.93-4.95 (1H), 3.96-3.98 (1H), 3.69-3.73 (1H), 2.03-2.16 (3H), 1.94-2.02 (3H), 1.66-1.69 (1H), 1.05-1.09 (2H), 0.97-1.00 (3H), 0.87-0.90 (2H) ppm.
NOE: C-2 proton & ethyl=cis

Chiral Resolution of [Cis-rac] 3-Cyclopropyl-5-[4-ethyl-4-[[3-(trifluoromethyl)phenyl]sulfonyl]-tetrahydro-pyran-2-yl-]-[1,2,4]oxadiazole

[Cis-rac] 3-Cyclopropyl-5-[4-ethyl-4-[[3-(trifluoromethyl)phenyl]sulfonyl]-tetrahydro-pyran-2-yl]-[1,2,4]oxadiazole (380 mg) was subjected to preparative chiral-SFC. The products were dried to give 86 mg of [cis-EN1] SC-202 and 94 mg of [cis-EN2] SC-203.

[cis-EN1] SC-202—analytical chiral SFC: LUX Amylose-2 (250×4.6 mm 5μ), 3 g/min, 100 bar, RT, co-solvent: 20% of 0.5% diethylamine in MeOH, Ret. Time 2.12; ee >95%

[cis-EN2] SC-203—analytical chiral SFC: LUX Amylose-2 (250×4.6 mm 5μ), 3 g/min, 100 bar, RT, co-solvent: 20% of 0.5% diethylamine in MeOH, Ret. Time 2.72; ee >95%

2-Cyclopropyl-5-[4-methyl-4-[[3-(trifluoromethyl) phenyl]sulfonyl]-tetrahydro-pyran-2-yl]-pyrimidine (Example 7)

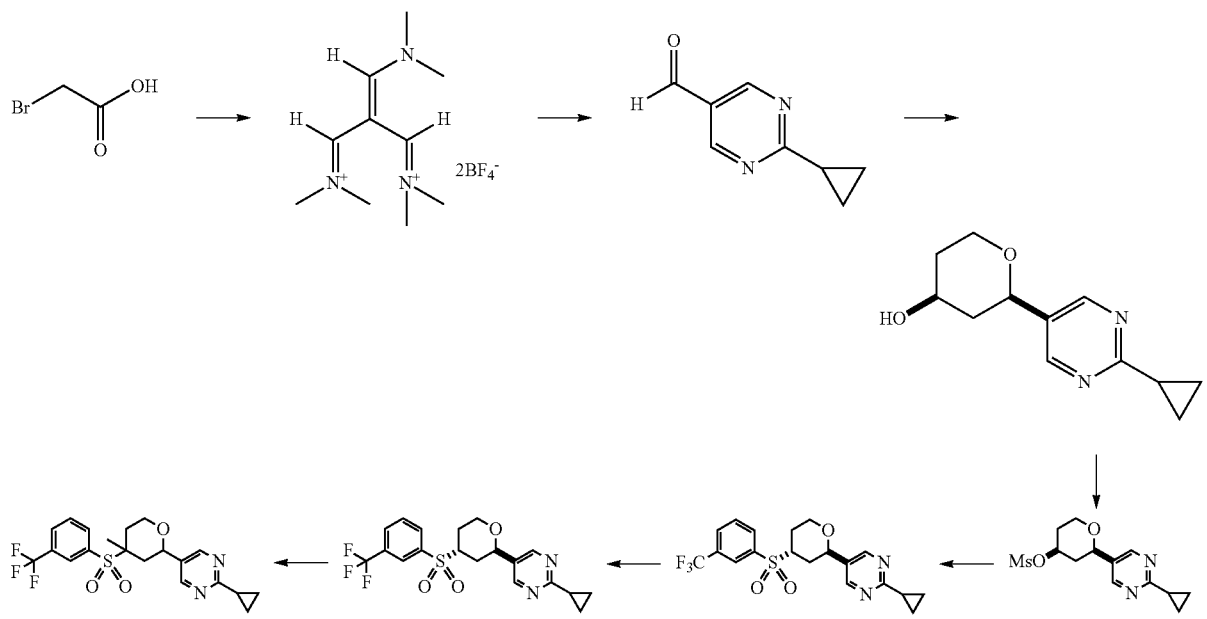

Step 1: N, N'-(2-(1-dimethylamino)methylidine)-propane-1,3-diylidene)-bis-(N-methylmethan-aminium) Bis Tetrafluoroborate POCl₃ (27 mL, 345 mmol) was added drop-wise over a period of 90 min to DMF (122 mL, 1.57 mol) at 0° C., and then Bromoacetic acid (15 g, 107 mmol) was added and heated to 90° C. for 6 h. DMF was distilled off in vacuo and crushed ice was added to the residue. A solution of NaBF₄ (23.7 g, 215.8 mmol) in H₂O (60 mL) was then added to the mixture and cooled to −40° C. for 2 h. The precipitated solid was filtered and washed with EtOAc, then recrystallized in hot MeCN (3 Vol) thrice and the resulting solid was dried in suction to get crude N, N'-(2-(1-dimethylamino) methylidine)-propane-1,3-diylidene)-bis-(N-methylmethan-aminium) bis tetrafluoroborate (14 g, 36%).

Step 2: 2-cyclopropylpyrimidine-5-carbaldehyde

Sodium methoxide (16.74 g, 310 mmol) was added to a solution of cyclopropane carboxamidine HCl (12 g, 124 mmol) in MeOH (150 mL) at −20° C., stirred for 30 min and added N, N'-(2-(1-dimethylamino) methylidine)-propane-1,3-diylidene)-bis-(N-methylmethanaminium) bis tetrafluoroborate (25 g, 105 mmol) at same temperature and then warmed to RT and stirred for 16 h. Solvent was concentrated and the residue was diluted with chilled water (100 mL) and extracted with DCM (2×150 mL). Combined organic layer was washed with brine (100 mL), dried (Na₂SO₄) and concentrated in vacuo to get crude. Purification by CC (silica gel, 0-30% EtOAc in PE) gave 2-cyclopropylpyrimidine-5-carbaldehyde (3 g; 29%) as a solid.

Step 3: 2-(2-cyclopropylpyrimidin-5-yl)tetrahydro-2H-pyran-4-ol(4-chloro-2-methylphenyl)tetrahydro-2H-pyran-4-ol 2-cyclopropylpyrimidine-5-carbaldehyde (8 g, 54.05 mmol) was dissolved in DCE (160 mL), cooled in an ice bath and TFA (64 mL) followed by 3-butenol (4.68 mL, 54.05 mmol) were added and stirred at RT for 72 h. The mixture was concentrated in vacuo and the residue diluted with water (100 mL), basified with 6 M NaOH (aq) and extracted with DCM (3×200 mL). Organic layer was separated and washed with brine (50 mL), dried (Na₂SO₄) and concentrated under reduced pressure to get crude. The crude product was dissolved in MeOH (200 mL) and LiOH (6.64 g, 158.22 mmol) was added. The reaction was stirred at RT for 16 h. MeOH was concentrated under reduced pressure and the residue was diluted with DCM (200 mL) and washed with water (50 mL), brine (50 mL), dried (Na₂SO₄) and concentrated in vacuo to get crude. Purification by CC (silica gel, 0-50% EtOAc in PE) gave 2-(2-cyclopropylpyrimidin-5-yl)tetrahydro-2H-pyran-4-ol(4-chloro-2-methylphenyl) tetrahydro-2H-pyran-4-ol (8 g; 67%) as a solid.

Step 4: 2-(2-cyclopropylpyrimidin-5-yl)tetrahydro-2H-pyran-4-ylmethanesulfonate Methanesulphonyl chloride (4.26 mL, 54.79 mmol) was added to a solution of 2-(2-cyclopropylpyrimidin-5-yl)tetrahydro-2H-pyran-4-ol(4-chloro-2-methylphenyl)tetrahydro-2H-pyran-4-ol (8 g, 36.52 mmol) and DIPEA (15.97 mL, 91.30 mmol) in DCM (70 mL) at 0° C. and allowed to RT and stirred for 16 h. The RM was diluted with DCM (500 mL) and washed sequentially with sat. NaHCO₃ solution (50 mL), water (50 mL), and brine (50 mL), dried (Na₂SO₄) and concentrated under reduced pressure to get crude 2-(2-cyclopropylpyrimidin-5-yl)tetrahydro-2H-pyran-4-ylmethanesulfonate (10 g) as a thick liquid.

Step 5: 2-cyclopropyl-5-(4-(3-(trifluoromethyl)phenylthio)tetrahydro-2H-pyran-2yl)pyrimidine 3-Trifluoromethyl thiophenol (13.79 mL, 100.67 mmol) was added to a suspension of 2-(2-cyclopropylpyrimidin-5-yl)tetrahydro-2H-pyran-4-ylmethanesulfonate (10 g, 33.55 mmol) and K₂CO₃ (9.25 g, 67.10 mmol) in DMF (100 mL) and the RM was heated to 50° C. for 5 h and continued at RT for 16 h. After completion of reaction, the RM was diluted with water (100 mL) and extracted with EtOAc (3×250 mL). Combined organic extract was washed with water (100 mL), brine (100 mL), dried (Na₂SO₄) and concentrated under reduced pressure to get crude compound. The crude compound was purified by CC (silica gel, 0-15% EtOAc in PE) to obtain 2-cyclopropyl-5-(4-(3-(trifluoromethyl)phenylthio)tetrahydro-2H-pyran-2yl)pyrimidine (6 g, 44%) as a solid.

Step 6: 2-cyclopropyl-5-(4-(3-(trifluoromethyl)phenylsulfonyl)tetrahydro-2H-pyran-2-yl)pyrimidine 2-Cyclopropyl-5-(4-(3-(trifluoromethyl)phenylthio)tetrahydro-2H-pyran-2yl)pyrimidine (4 g, 10.52 mmol) was dissolved in MeOH (120 mL) and a solution of OXONE (9.69 g, 15.78 mmol) in water (100 mL) was added and stirred at RT for 16 h. MeOH was concentrated in vacuo; the residue was diluted with water (50 mL) and extracted with EtOAc (3×150 mL). The organic extract was washed with brine (50 mL), dried (Na₂SO₄) and concentrated to get crude. The crude compound was purified by CC (silica gel, 0-15% EtOAc in PE) to obtain 2-cyclopropyl-5-(4-(3-(trifluoromethyl)phenylsulfonyl)tetra-hydro-2H-pyran-2-yl)pyrimidine (3 g, 69%) as a solid.

Step 7: 2-cyclopropyl-5-4-methyl-4-(3-(trifluoromethyl)phenylsulfonyl)tetrahydro-2H-pyran-2-yl)pyrimidine A solution of 2-cyclopropyl-5-(4-(3-(trifluoromethyl)phenylsulfonyl)tetrahydro-2H-pyran-2-yl)pyrimidine (2 g, 4.85 mmol) in THF (40 mL) was cooled to −78° C. and KOt-Bu (1 M solution in THF; 9.70 mL, 9.70 mmol) was added drop-wise, stirred for 30 min, then added methyl iodide (0.75 mL, 12.12 mmol) and the RM was allowed to RT and stirred for 16 h. The RM was diluted with EtOAc (200 mL) and washed with water (50 mL), brine (50 mL), dried over (Na₂SO₄) and concentrated under reduced pressure to get crude compound. The crude compound was purified by CC (Neutral alumina, 0-15% EtOAc in PE) to obtain 2-cyclopropyl-5-4-methyl-4-(3-(trifluoromethyl)phenylsulfonyl)tetrahydro-2H-pyran-2-yl)pyrimidine (1 g, 48%) as a white solid.

¹H-NMR (600 MHz, [d₆]-DMSO): δ=8.56 (2H), 8.17-8.22 (2H), 8.06 (1H), 7.92-7.96 (1H), 4.59-4.62 (1H), 4.04-4.07 (1H), 3.69-3.73 (1H), 2.10-2.22 (2H), 1.94-1.97 (1H), 1.76-1.77 (1H), 1.48-1.52 (4H), 0.96-1.05 (4H) ppm.

NOE: C-2 proton & methyl=cis

Chiral Resolution of [Cis-rac] 2-cyclopropyl-5-4-methyl-4-(3-(trifluoromethyl)phenyl sulfonyl)tetrahydro-2H-pyran-2-yl)pyrimidine

[Cis-rac] 2-[4-methyl-4-[[3-(trifluoromethyl)phenyl]sulfonyl]-tetrahydro-pyran-2-yl]-5-(trifluoromethyl)-pyridine (900 mg) was subjected to preparative chiral-LC (IC-column, hexane/EtOH, 7:3). The products were dried to give 113 mg of [cis-EN1] SC-204 and 113 mg of [cis-EN2] SC-205.

[cis-EN1] SC-204—analytical chiral HPLC: chiralpak IC (250×4.6 mm 5μ), 1 ml/min, RT, 0.1% diethylamine in hexane/EtOH 60/40, Ret. Time 6.64; ee >95%

[cis-EN2] SC-205—analytical chiral HPLC: chiralpak IC (250×4.6 mm 5μ), 1 ml/min, RT, 0.1% diethylamine in hexane/EtOH 60/40, Ret. Time 8.20; ee >95%

2-Cyclopropyl-5-[4-ethyl-4-[[3-(trifluoromethyl)phenyl]sulfonyl]-tetrahydro-pyran-2-yl]-[1,3,4]oxadiazole (Example 8)

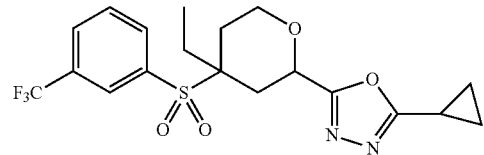 [SMILES: CCC1(S(=O)(=O)c2cccc(C(F)(F)F)c2)CCOC(c2nnc(C3CC3)o2)C1]

Chiral Resolution of [Cis Racemic] 2-Cyclopropyl-5-[4-ethyl-4-[[3-(trifluoromethyl)phenyl]sulfonyl]-tetrahydro-pyran-2-yl]-[1,3,4]oxadiazole

[Cis-rac] 2-Cyclopropyl-5-[4-ethyl-4-[[3-(trifluoromethyl)phenyl]sulfonyl]-tetrahydro-pyran-2-yl]-[1,3,4]oxadiazole was subjected to preparative chiral-SFC (LUX Cellulose-column, 35% MeOH, 100 bar, 100 g/min) to give [cis-EN1] SC-206 and [cis-EN2] SC-207.

[cis-EN1] SC-206—analytical chiral SFC: LUX Cellulose (250×4.6 mm 5μ), 3 g/min, RT, MeOH 30%, Ret. Time 2.56; ee >95%

[cis-EN2] SC-207—analytical chiral SFC: LUX Cellulose (250×4.6 mm 5μ), 3 g/min, RT, MeOH 30%, Ret. Time 3.42; ee >95%

General Reaction Scheme for the Preparation of Examples 9 to 18

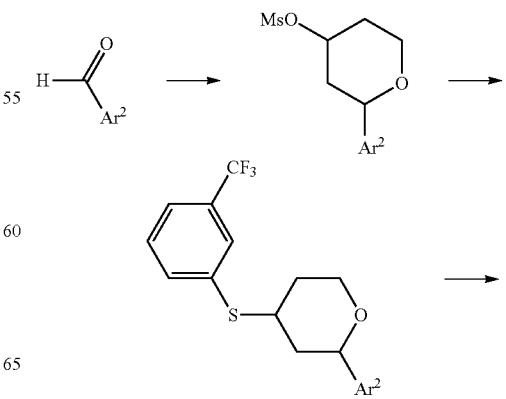

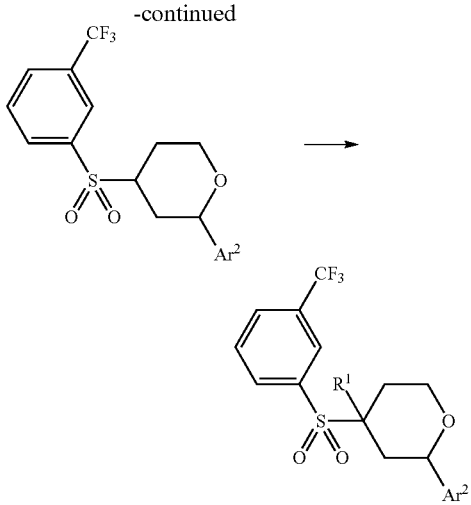

2-Isopropoxy-5-[4-methyl-4-[[3-(trifluoromethyl)phenyl]sulfonyl]-tetrahydro-pyran-2-yl]-pyridine
(Example 9)

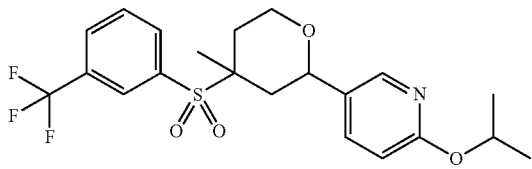 [SMILES: CC(C)Oc1ccc(C2CC(C)(S(=O)(=O)c3cccc(C(F)(F)F)c3)CCO2)cn1]

Step 1: 2-(6-Isopropoxypyridin-3-yl)tetrahydro-2H-pyran-4-yl Methanesulfonate MsOH (19.18 mL, 295 mmol) was added dropwise by syringe to a cooled (0° C.) solution of 6-isopropoxynicotinaldehyde (4.88 g, 29.5 mmol) and but-3-en-1-ol (2.54 mL, 29.5 mmol) in DCM (40 mL). The RM was stirred at 0° C. for 3 h. The RM was diluted with DCM (60 mL) and, while stirring vigorously, sat. aq. NaHCO₃ (350 mL) was added. The organics were separated and the aq. layer was extracted with DCM (2×100 mL). The combined organics were dried over Na₂SO₄ and the solvent was removed under reduced pressure to afford a yellow oil. The product was coated onto hydromatrix and purified using CC (silica, gradient, heptane/EtOAc, 9:1 to 1:1) to give 8.02 g (82%) of the desired product as a pale yellow oil.

Step 2: 2-Isopropoxy-5-(4-((3-(trifluoromethyl)phenyl)thio)tetrahydro-2H-pyran-2-yl)pyridine 3-(Trifluoromethyl)benzenethiol (2.403 mL, 18.07 mmol) and K₂CO₃ (2.498 g, 18.07 mmol) were added to a N₂ degassed solution of 2-(6-isopropoxypyridin-3-yl)tetrahydro-2H-pyran-4-yl methanesulfonate (3 g, 9.04 mmol) in MeCN (60 mL) and the RM was stirred for 3 h at 50° C., more 3-(trifluoromethyl)benzenethiol (1.202 mL, 9.04 mmol), K₂CO₃ (1.249 g, 9.04 mmol) and MeCN (40 mL) were added and the RM was stirred at 50° C. for 64 h. The RM was allowed to cool to RT and the solvent was removed under reduced pressure. The residue was partitioned between H₂O (150 mL) and EtOAc (150 mL). The aq. layer was extracted with EtOAc (2×100 mL) and the combined organics were washed with brine (100 mL) and dried over Na₂SO₄. The solvent was removed under reduced pressure and the residue which was coated onto silica and purified using flash chromatography (silica, gradient heptane/i-Pr₂O, 1:0-2:1) to give 3.16 g (88%) of the desired product as a yellow oil.

Step 3: 2-Isopropoxy-5-(4-((3-(trifluoromethyl)phenyl)sulfonyl)tetrahydro-2H-pyran-2-yl)pyridine A solution of oxone (9.78 g, min. 27.5 mmol) in H₂O (70 mL) was added dropwise to a cooled (0° C.) solution of 2-isopropoxy-5-(4-((3-(trifluoromethyl)phenyl)thio)tetrahydro-2H-pyran-2-yl)pyridine (3.16 g, 7.95 mmol) in MeOH (100 mL) while keeping the internal temperature below 5° C. The RM was stirred at 0° C. for 1 h and subsequently for 18 h at RT. The majority of the MeOH was removed under reduced pressure and the residue partitioned between sat. aq. NaHCO₃ (100 mL) and EtOAc (100 mL). The aq. layer was extracted with EtOAc (2×50 mL). The organics were combined and washed with brine (100 mL), dried over Na₂SO₄ and concentrated under reduced pressure to afford a pale yellow oil that slowly partially crystallised. The product was diluted with DCM (10 mL) and purified using flash chromatography (silica, gradient heptane/EtOAc, 1:0-3:1) to afford a colorless oil which was co-evaporated with DCM (50 mL) and heptane (50 mL). The resulting oil slowly solidified into a white solid over the course of 72 h. The solids were dried further under reduced pressure to give 3.22 g (94%) of the desired product as a white solid.

Step 4: 2-Isopropoxy-5-[4-methyl-4-[[3-(trifluoromethyl)phenyl]sulfonyl]-tetrahydro-pyran-2-yl]-pyridine The glassware was dried under N₂ using a heatgun. 1 M KOt-Bu in THF (3.49 mL, 3.49 mmol) was added dropwise by syringe to a cooled (−78° C.) solution of 2-isopropoxy-5-(4-((3-(trifluoromethyl)phenyl)sulfonyl)tetrahydro-2H-pyran-2-yl)pyridine (1 g, 2.329 mmol) in dry THF (10 mL). The RM was stirred for 10 min at −78° C. MeI (0.728 mL, 11.64 mmol) was added dropwise by syringe and the RM was stirred for 30 min at −78° C. The RM was quenched by adding sat. aq. NH₄Cl (10 mL) and most of the solvent was removed under reduced pressure. The residue was partitioned between DCM (100 mL) and H₂O (100 mL). The aq. layer was extracted with DCM (3×50 mL) and the combined organics were concentrated under reduced pressure to give a yellow oil which was purified using flash chromatography (silica, gradient heptane/EtOAc, 1:0-7:3) to give 892 mg (86%) of [cis-rac] 2-isopropoxy-5-[4-methyl-4-[[3-(trifluoromethyl)phenyl]sulfonyl]-tetrahydro-pyran-2-yl]-pyridine as a colorless oil that slowly crystallised into a white solid. [Trans-rac] 2-isopropoxy-5-[4-methyl-4-[[3-(trifluoromethyl)phenyl]sulfonyl]-tetrahydro-pyran-2-yl]-pyridine SC-302 was also obtained and lyophilised using MeCN/H₂O (1/1, v/v, 2 mL) to give 101 mg (10%).

¹H-NMR (400 MHz, CDCl₃) of [cis-rac] 2-isopropoxy-5-[4-methyl-4-[[3-(trifluoromethyl)phenyl]sulfonyl]-tetrahydro-pyran-2-yl]-pyridine: δ=8.14 (s, 1H), 8.09-8.00 (m, 2H), 7.95 (d, J=7.8 Hz, 1H), 7.74 (t, J=7.8 Hz, 1H), 7.55 (dd, J=8.6, 2.5 Hz, 1H), 6.68 (d, J=8.6 Hz, 1H), 5.27 (hept, J=6.2 Hz, 1H), 4.39 (dd, J=11.5, 1.9 Hz, 1H), 4.14 (dd, J=12.1, 4.2 Hz, 1H), 3.70 (td, J=12.4, 2.1 Hz, 1H), 2.36 (td, J=12.7, 5.3

Hz, 1H), 2.22 (t, J=12.3 Hz, 1H), 1.70 (d, J=13.0 Hz, 1H), 1.56-1.51 (m, 5H) [overlap with H₂O signal], 1.33 (d, J=6.2 Hz, 6H).

¹H-NMR (400 MHz, CDCl₃) of [trans-rac] 2-isopropoxy-5-[4-methyl-4-[[3-(trifluoromethyl)phenyl]sulfonyl]-tetrahydro-pyran-2-yl]-pyridine SC-302: δ=8.19-8.06 (m, 3H), 7.96 (d, J=7.8 Hz, 1H), 7.77 (d, J=7.8 Hz, 1H), 7.57 (dd, J=8.6, 2.5 Hz, 1H), 6.67 (d, J=8.6 Hz, 1H), 5.29 (hept, J=6.2 Hz, 1H), 5.17 (dd, J=11.7, 2.2 Hz, 1H), 4.41 (td, J=12.4, 2.4 Hz, 1H), 4.04 (dd, J=11.9, 4.4 Hz, 1H), 2.39 (d, J=15.3 Hz, 1H), 2.33-2.24 (m, 1H), 1.83 (ddd, J=15.4, 12.8, 5.7 Hz, 1H), 1.67 (dd, J=15.3, 11.8 Hz, 1H), 1.34 (d, J=6.2 Hz, 6H), 1.24 (s, 3H).

The relative stereochemistry was assigned by comparing the central ring signals in the ¹H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 2-isopropoxy-5-[4-methyl-4-[[3-(trifluoromethyl)phenyl]sulfonyl]-tetrahydro-pyran-2-yl]-pyridine

[Cis-rac] 2-isopropoxy-5-[4-methyl-4-[[3-(trifluoromethyl)phenyl]sulfonyl]-tetrahydro-pyran-2-yl]-pyridine (300 mg, 0.676 mmol) was subjected to preparative chiral-LC (IC-column, heptane/EtOH 9:1) and the products were lyophilised using MeCN/H₂O (3/1, v/v, 2 mL) to give 131 mg (44%) of [cis-EN1] SC-300 and 128 mg (43%) of [cis-EN2] SC-301 as white solids.

[cis-EN1] SC-300—analytical chiral HPLC: chiralpak IC (250×4.6 mm 5µ), 1 ml/min, 35° C., heptane/EtOH 80/20, Ret. Time 8.337; ee >95%/specific rotation [α]$_D^{23.4}$ −14.1° (c 0.94; DCM).

[cis-EN2] SC-301—analytical chiral HPLC: chiralpak IC (250×4.6 mm 5µ), 1 ml/min, 35° C., heptane/EtOH 80/20, Ret. Time 12.064; ee >95%/specific rotation [α]$_D^{23.5}$ +12.7° (c 0.87; DCM).

2-[4-Ethyl-4-[[3-(trifluoromethyl)phenyl]sulfonyl]-tetrahydro-pyran-2-yl]-6-methyl-pyridine (Example 10)

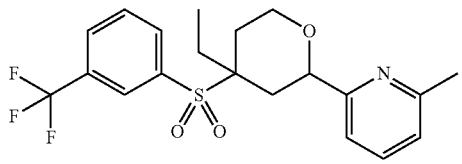 [SMILES: CCC1(S(=O)(=O)c2cccc(C(F)(F)F)c2)CCOC(c2cccc(C)n2)C1]

The first 3 steps were carried out in analogy to the synthesis of 2-isopropoxy-5-[4-methyl-4-[[3-(trifluoromethyl)phenyl]sulfonyl]-tetrahydro-pyran-2-yl]-pyridine (steps 1-3).

Step 4: 2-[4-Ethyl-4-[[3-(trifluoromethyl)phenyl]sulfonyl]-tetrahydro-pyran-2-yl]-6-methyl-pyridine 1M KOt-Bu in THF (11.68 mmol, 11.68 mL) was added dropwise by syringe over the course of 1 h to a cooled (−78° C.) solution of 2-methyl-6-(4-((3-(trifluoromethyl)phenyl)sulfonyl)tetrahydro-2H-pyran-2-yl)pyridine (1.5 g, 3.89 mmol) in dry THF (15 mL) under N₂. After stirring for 10 min at −78° C., EtI (1.573 mL, 19.46 mmol) was added dropwise by syringe and the RM was stirred for 1 h at −78° C. under N₂. The RM was quenched with sat. aq. NH₄Cl (20 mL) and allowed to warm to RT. The solvent was removed under reduced pressure and the residue was stored at −20° C. for 18 h. H₂O (100 mL), brine (50 mL) and EtOAc (200 mL) were added. The organic layer was separated and washed with brine (100 mL) and dried over Na₂SO₄. The solvent was removed under reduced pressure to give a brown oil. The crude product was subjected to flash chromatography (silica, gradient heptane/EtOAc, 1:0 to 2:1). Impure [cis-rac] 2-methyl-6-(4-((3-(trifluoromethyl)phenyl)sulfonyl)tetrahydro-2H-pyran-2-yl)pyridine was dissolved in EtOAc (50 mL) and washed with aq. 1M K₂S₂O₃ (50 mL). The organic layer was dried over Na₂SO₄ and concentrated under reduced pressure. The product was purified further using flash chromatography (silica, gradient heptane/EtOAc, 1:0 to 2:1) to give 0.76 g (47%) of [cis-rac] 2-methyl-6-(4-((3-(trifluoro-methyl)phenyl)sulfonyl)tetrahydro-2H-pyran-2-yl)pyridine as a colorless oil. Impure [trans-rac] 2-methyl-6-(4-((3-(trifluoromethyl)phenyl)sulfonyl)tetrahydro-2H-pyran-2-yl)pyridine SC-303, obtained from the first CC, was also dissolved in EtOAc (50 mL) and washed with aq. 1M K₂S₂O₃ (50 mL) and brine (50 mL). The organic layer was dried over Na₂SO₄ and concentrated under reduced pressure to give a colorless oil. This product was then lyophilised using MeCN/H₂O (3/1, v/v, 3 mL) to give 0.55 g (34%) of pure [trans-rac] 2-methyl-6-(4-((3-(trifluoromethyl)phenyl)sulfonyl)tetrahydro-2H-pyran-2-yl)pyridine SC-303.

¹H-NMR (400 MHz, CDCl₃) of [cis-rac] 2-methyl-6-(4-((3-(trifluoromethyl)phenyl)sulfonyl)tetrahydro-2H-pyran-2-yl)pyridine: δ=8.12 (s, 1H), 8.05 (d, J=7.9 Hz, 1H), 7.93 (d, J=7.8 Hz, 1H), 7.72 (t, J=7.8 Hz, 1H), 7.58 (t, J=7.7 Hz, 1H), 7.19 (d, J=7.7 Hz, 1H), 7.06 (d, J=7.7 Hz, 1H), 4.50 (dd, J=11.3, 2.1 Hz, 1H), 4.14 (m, 1H), 3.71 (td, J=12.2, 1.8 Hz, 1H), 2.51 (s, 3H), 2.28-1.99 (m, 1H), 1.84-1.75 (m, 1H), 1.19 (t, J=7.5 Hz, 3H).

¹H-NMR (400 MHz, CDCl₃) of [trans-rac] 2-methyl-6-(4-((3-(trifluoromethyl)phenyl)sulfonyl)tetrahydro-2H-pyran-2-yl)pyridine SC-303: δ=8.25 (s, 1H), 8.18 (d, J=7.9 Hz, 1H), 7.95 (d, J=7.8 Hz, 1H), 7.76 (t, J=7.8 Hz, 1H), 7.57 (t, J=7.7 Hz, 1H), 7.23 (d, J=7.7 Hz, 1H), 7.04 (d, J=7.6 Hz, 1H), 5.36 (dd, J=11.6, 2.4 Hz, 1H), 4.50 (td, J=12.2, 2.7 Hz, 1H), 4.13 (dd, J=11.7, 4.7 Hz, 1H), 2.54 (s, 3H), 2.40-2.30 (m, 1H), 2.27-2.17 (m, 1H), 2.12-1.98 (m, 1H), 1.88 (dd, J=15.5, 11.6 Hz, 1H), 1.65 (dq, J=14.8, 7.4 Hz, 1H), 1.44 (dq, J=14.7, 7.4 Hz, 1H), 0.95 (t, J=7.5 Hz, 3H).

The relative stereochemistry was assigned by comparing the central ring signals in the ¹H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

5-[4-Methyl-4-[[3-(trifluoromethyl)phenyl]sulfonyl]-tetrahydro-pyran-2-yl]-2-(trifluoromethyl)-pyrimidine (Example 11)

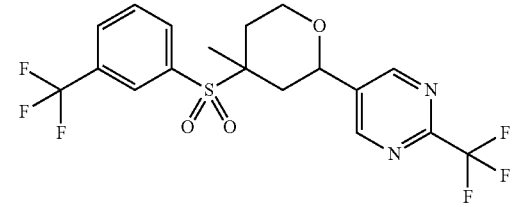 [SMILES: CC1(S(=O)(=O)c2cccc(C(F)(F)F)c2)CCOC(c2cnc(C(F)(F)F)nc2)C1]

Step 1: 2-(2-(Trifluoromethyl)pyrimidin-5-yl)tetrahydro-2H-pyran-4-yl Methanesulfonate A solution of 2-(trifluoromethyl)pyrimidine-5-carbaldehyde (860 mg, 4.88 mmol) and but-3-en-1-ol (0.420 mL, 4.88 mmol) in DCM (5.2 mL) was cooled to 0° C. MsOH (3.17 mL, 48.8 mmol) was added dropwise and the RM was stirred at RT for 90 min. DCM (30 mL) was added, followed by the careful addition of sat. aq. $NaHCO_3$ (30 mL). The organic layer was washed with sat. aq. $NaHCO_3$ (2×30 mL), dried ($Na_2SO_4$) and evaporated under reduced pressure. The product was purified by flash chromatography (silica, gradient heptane/EtOAc, 1:0 to 1:1), to give 1.24 g (78%) of the desired product.

Step 2: 2-(Trifluoromethyl)-5-(4-((3-(trifluoromethyl)phenyl)thio)tetrahydro-2H-pyran-2-yl)pyrimidine This reaction was performed in a three-necked flask under Ar. To a solution of 2-(2-(trifluoromethyl)pyrimidin-5-yl)tetrahydro-2H-pyran-4-yl methanesulfonate (1.23 g, 3.77 mmol) in dry DMF (25 mL) was added $K_2CO_3$ (1.042 g, 7.54 mmol). The RM was put under Ar/vacuum 5× in ca. 10 min, 3-(trifluoromethyl)benzenethiol (2.56 mL, 18.85 mmol) was added and the mixture was purged with Ar for 1 h. The RM was stirred at 50° C. overnight (hot-start). EtOAc (250 mL), brine (250 mL) and $H_2O$ (250 mL) were added. The aq. layer was extracted with EtOAc (250 mL). Organic layers were combined, washed with $H_2O$ (250 mL) and brine (250 mL), dried ($Na_2SO_4$) and evaporated under reduced pressure. The product was purified by flash chromatography (silica, gradient heptane/EtOAc, 1:0 to 3:1), to furnish 1.38 g (90%) of the desired product.

Step 3: 2-(Trifluoromethyl)-5-(4-((3-(trifluoromethyl)phenyl)sulfonyl)tetrahydro-2H-pyran-2-yl)pyrimidine To a solution of 2-(trifluoromethyl)-5-(4-((3-(trifluoromethyl)phenyl)thio)tetrahydro-2H-pyran-2-yl)pyrimidine (1.33 g, 3.26 mmol) in MeOH (10 mL) was dropwise added oxone (2.89 g, min. 8.14 mmol) in $H_2O$ (10 mL). The RM was stirred at RT overnight. More MeOH (10 mL) was added followed by the dropwise addition of oxone (2.89 g, min. 8.14 mmol) in $H_2O$ (10 mL). Stirring at RT was continued overnight. The mixture was concentrated to evaporate most of the MeOH. EtOAc (100 mL) and $H_2O$ (100 mL) were added. The organic layer was washed with sat. aq. $NaHCO_3$ (100 mL), dried ($Na_2SO_4$) and evaporated under reduced pressure. The product was purified by flash chromatography (silica, gradient heptane/EtOAc, 1:0 to 1:1), to give 1.33 g (93%) of the desired product.

Step 4 was carried out in 3 batches as described below: The reaction vials were dried (heat-gun) before use.

Step 4 (Batch 1): 5-[4-Methyl-4-[[3-(trifluoromethyl)phenyl]sulfonyl]-tetrahydro-pyran-2-yl]-2-(trifluoromethyl)-pyrimidine A solution of 2-(trifluoromethyl)-5-(4-((3-(trifluoromethyl)phenyl)sulfonyl)tetrahydro-2H-pyran-2-yl)pyrimidine (250 mg, 0.568 mmol) in dry THF (3.5 mL) was cooled to −78° C., 1 M KOt-Bu in THF (0.852 mL, 0.852 mmol) was added dropwise and 10 min later, MeI (0.177 mL, 2.84 mmol) was added dropwise. The RM was stirred at −78° C. for 3.5 h. Half sat. aq. $NH_4Cl$ (ca. 5 drops) was added and the cooling bath was removed after 2 min. At RT, DCM (25 mL) and half sat. aq. $NH_4Cl$ (25 mL) were added. The aq. layer was extracted with DCM (2×25 mL). Organic layers were combined, dried ($Na_2SO_4$) and evaporated under reduced pressure.

Step 4 (Batch 2): 5-[4-Methyl-4-[[3-(trifluoromethyl)phenyl]sulfonyl]-tetrahydro-pyran-2-yl]-2-(trifluoromethyl)-pyrimidine A solution of 2-(trifluoromethyl)-5-(4-((3-(trifluoromethyl)phenyl)sulfonyl)tetrahydro-2H-pyran-2-yl)pyrimidine (250 mg, 0.568 mmol) in dry THF (3.5 mL) was cooled to −78° C., 1 M KOt-Bu in THF (0.852 mL, 0.852 mmol) was added dropwise and 10 min later, MeI (0.177 mL, 2.84 mmol) was added dropwise. The RM was stirred at −78° C. for 3.5 h. Half sat. aq. $NH_4Cl$ (ca. 5 drops) was added and the cooling bath was removed after 2 min. At RT, DCM (25 mL) and half sat. aq. $NH_4Cl$ (25 mL) were added. The aq. layer was extracted with DCM (2×25 mL). Organic layers were combined, dried ($Na_2SO_4$) and evaporated under reduced pressure.

Step 4 (Batch 3): 5-[4-Methyl-4-[[3-(trifluoromethyl)phenyl]sulfonyl]-tetrahydro-pyran-2-yl]-2-(trifluoromethyl)-pyrimidine A solution of 2-(trifluoromethyl)-5-(4-((3-(trifluoromethyl)phenyl)sulfonyl)tetrahydro-2H-pyran-2-yl)pyrimidine (384 mg, 0.872 mmol) in dry THF (5 mL) was cooled to −78° C., 1 M KOt-Bu in THF (1.308 mL, 1.308 mmol) added dropwise and 10 min later, MeI (0.273 mL, 4.36 mmol) was added dropwise. The RM was stirred at −78° C. for 3.5 h. Half sat. aq. $NH_4Cl$ (ca. 5 drops) was added and the cooling bath was removed after 2 min. At RT, DCM (50 mL) and half sat. aq. $NH_4Cl$ (50 mL) were added. The aq. layer was extracted with DCM (2×50 mL). Organic layers were combined, dried ($Na_2SO_4$) and evaporated under reduced pressure.

The batches were combined and purified by flash chromatography (silica, gradient heptane/EtOAc, 1:0 to 2:1), to afford 380 mg (42%) of [cis-rac] 5-[4-methyl-4-[[3-(trifluoromethyl)phenyl]sulfonyl]-tetrahydro-pyran-2-yl]-2-(trifluoromethyl)-pyrimidine. $^1$H-NMR (400 MHz, $CDCl_3$) of [cis-rac] 5-[4-methyl-4-[[3-(trifluoromethyl)phenyl]sulfonyl]-tetrahydro-pyran-2-yl]-2-(trifluoromethyl)-pyrimidine: δ=8.85 (s, 2H), 8.14 (s, 1H), 8.06 (d, J=7.9 Hz, 1H), 7.98 (d, J=7.8 Hz, 1H), 7.77 (t, J=7.8 Hz, 1H), 4.62 (dd, J=11.6, 1.8 Hz, 1H), 4.24 (dd, J=12.2, 4.3 Hz, 1H), 3.73 (td, J=12.4, 2.1 Hz, 1H), 2.41 (td, J=12.9, 5.4 Hz, 1H), 2.18 (t, J=12.4 Hz, 1H), 1.86 (dt, J=13.0, 2.1 Hz, 1H), 1.60 (s, 3H), 1.62-1.53 (m, 1.6H) [overlap with $H_2O$ signal].

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis Racemic] 5-[4-methyl-4-[[3-(trifluoromethyl)phenyl]sulfonyl]-tetrahydro-pyran-2-yl]-2-(trifluoromethyl)-pyrimidine

[Cis-rac] 5-[4-methyl-4-[[3-(trifluoromethyl)phenyl]sulfonyl]-tetrahydro-pyran-2-yl]-2-(trifluoromethyl)-pyrimidine (444 mg) was separated on a Jasco SFC (Chiralcel OJ-H, MeOH/EtOH 1:1; $CO_2$) to give 160 mg of [cis-EN1] SC-304 and 145 mg of [cis-EN2] SC-305.

[cis-EN1] SC-304—analytical chiral SFC: Jasco SFC, Chiralcel OJ, 5 um, 250×4.6 mm, 40° C., 2 ml/Min $CO_2$/10% MeOH:EtOH (1:1), Ret. Time 4.52; ee >95%

[cis-EN2] SC-305—analytical chiral SFC: Jasco SFC, Chiralcel OJ, 5 um, 250×4.6 mm, 40° C., 2 ml/Min $CO_2$/10% MeOH:EtOH (1:1), Ret. Time 5.19; ee >95%

2-[4-Methyl-4-[[3-(trifluoromethyl)phenyl]sulfonyl]-tetrahydro-pyran-2-yl]-5-(trifluoromethyl)-pyridine (Example 12)

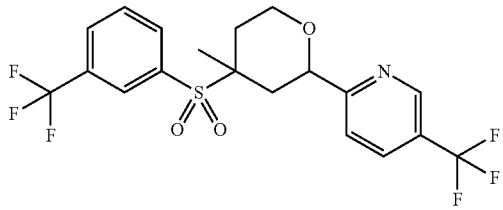 [SMILES: CC1(S(=O)(=O)c2cccc(C(F)(F)F)c2)CCOC(c2ccc(C(F)(F)F)cn2)C1]

Step 1: 2-(5-(Trifluoromethyl)pyridin-2-yl)tetrahydro-2H-pyran-4-yl Methanesulfonate A solution of 5-(trifluoromethyl)picolinaldehyde (3.82 g, 21.82 mmol) in DCM (20 mL) was prepared, followed by applying an ice/water bath and dropwise addition of methanesulfonic acid (14.1 mL, 218 mmol). Subsequently, 3-buten-1-ol (2.25 mL, 26.2 mmol) was added. The RM was stirred at RT for 3 h and poured out in 10% aq. $K_3PO_4$ (300 mL). Addition of some ice and DCM (300 mL) resulted in a clear two phase system. The phases were separated, the aq. layer was extracted with DCM (50 mL). The combination of organic layers was dried (brine & $Na_2SO_4$) and concentrated in vacuo. The residue was dissolved in DCM (5 mL), addition of heptane (200 mL) was followed by evaporation of the DCM in vacuo. Trituration, followed by air-drying provided 5.25 g (59%, purity 80%) of the desired product as an off-white solid.

Step 2: 5-(Trifluoromethyl)-2-(4-((3-(trifluoromethyl)phenyl)thio)tetrahydro-2H-pyran-2-yl)pyridine 2-(5-(Trifluoromethyl)pyridin-2-yl)tetrahydro-2H-pyran-4-yl methanesulfonate (5.10 g, 12.5 mmol) was dissolved in dry MeCN (125 mL), the solution was degassed by $N_2$ purging for 30 min. $K_2CO_3$ (4.33 g, 31.4 mmol) was added, followed by 3-(trifluoromethyl)benzenethiol (4.17 mL, 31.4 mmol). The RM was stirred vigorously at 50° C. overnight. Subsequently, the RM was mixed with EtOAc (125 mL) and silica (5 g). Filtration over a cotton plug and washing of the residue with EtOAc (3×30 mL) was followed by concentration in vacuo. The residue of the concentration was mixed with DCM (100 mL). Silica (20 g) was added, the mixture was concentrated in vacuo. The residue was placed on top of a silica column and used for flash chromatography (silica, gradient heptane/EtOAc, 95:5 to 7:3) to result in 4.98 g (97%) of the desired product as a clear oil.

Step 3: 5-(Trifluoromethyl)-2-(4-((3-(trifluoromethyl)phenyl)sulfonyl)tetrahydro-2H-pyran-2-yl)pyridine 5-(Trifluoromethyl)-2-(4-((3-(trifluoromethyl)phenyl)thio)tetrahydro-2H-pyran-2-yl)pyridine (4.90 g, 12.0 mmol) was dissolved in MeOH (120 mL). A water bath was applied. Oxone (18.5 g, min. 52.0 mmol) was almost completely dissolved in $H_2O$ (70 mL), the turbid solution was added portionwise. The RM was stirred vigorously at RT for 3 h. A turbid solution of oxone (4.55 g, min. 12.8 mmol) in $H_2O$ (20 mL) was prepared and added to the RM, followed by MeOH (15 mL). The RM was stirred vigorously at RT for 1 h. The major part of the MeOH was removed from the RM by rotary evaporation. The resulting suspension was mixed with $H_2O$ (350 mL) and EtOAc (350 mL) to result in a clear two phase system. The layers were separated, the aq. layer was extracted with EtOAc (50 mL). The combination of organic layers was washed with sat. aq. $NaHCO_3$ (100 mL) and dried (brine and $Na_2SO_4$). Concentration in vacuo was followed by trituration with heptane (100 mL). Filtration and air-drying was followed by crystallisation from hot MeOH (25 mL) to provide 3.04 g (57%) of the desired product as a white solid.

Step 4: 2-[4-Methyl-4-[[3-(trifluoromethyl)phenyl]sulfonyl]-tetrahydro-pyran-2-yl]-5-(trifluoromethyl)-pyridine A solution of 5-(trifluoromethyl)-2-(4-((3-(trifluoromethyl)phenyl)sulfonyl)tetrahydro-2H-pyran-2-yl)pyridine (2.00 g, 4.55 mmol) in dry THF (25 mL) was prepared, the temperature was lowered to −78° C. A solution of 1M LiHMDS in THF (6.83 mL, 6.83 mmol) was added dropwise and the RM was stirred at −78° C. for 10 min. Dropwise addition of MeI (0.569 mL, 9.10 mmol) was followed by stirring the RM at −78° C. for 1 h. The RM was left in the cooling bath. Consequently, the temperature was kept at −78° C. for a few hours, followed by a slow raise of temperature to RT overnight. Subsequently, the RM was combined with aq. 1M $KHSO_4$ (150 mL), some ice and EtOAc (200 mL) to result in a two phase system. The layers were separated, the aq. layer was extracted with EtOAc (50 mL). The combination of organic layers was washed with sat. aq. $NaHCO_3$ (100 mL) and dried (brine and $Na_2SO_4$). Concentration in vacuo was followed by flash chromatography (silica, gradient heptane/EtOAc, 1:0 to 3:1) to give 1.55 g (75%) of [cis-rac] 2-[4-methyl-4-[[3-(trifluoromethyl)phenyl]sulfonyl]-tetrahydro-pyran-2-yl]-5-(trifluoromethyl)-pyridine and 0.4 g (19%) of [trans-rac] 2-[4-methyl-4-[[3-(trifluoromethyl)phenyl]sulfonyl]-tetrahydro-pyran-2-yl]-5-(trifluoromethyl)-pyridine. $^1$H-NMR (400 MHz, $CDCl_3$) of [cis-rac] 2-[4-methyl-4-[[3-(trifluoromethyl)phenyl]sulfonyl]-tetrahydro-pyran-2-yl]-5-(trifluoromethyl)-pyridine: δ=8.80-8.72 (m, 1H), 8.12 (s, 1H), 8.05 (d, J=7.9 Hz, 1H), 8.00-7.92 (m, 2H), 7.74 (t, J=7.8 Hz, 1H), 7.64 (d, J=8.2 Hz, 1H), 4.60 (dd, J=9.5, 4.5 Hz, 1H), 4.25 (ddd, J=11.9, 5.3, 1.2 Hz, 1H), 3.77 (td, J=12.4, 2.2 Hz, 1H), 2.40 (td, J=12.9, 5.4 Hz, 1H), 2.13-2.00 (m, 2H), 1.66-1.60 (m, 1H), 1.59 (s, 3H).

$^1$H-NMR (400 MHz, $CDCl_3$) of [trans-rac] 2-[4-methyl-4-[[3-(trifluoromethyl)phenyl]sulfonyl]-tetrahydro-pyran-2-yl]-5-(trifluoromethyl)-pyridine: δ=8.82 (s, 1H), 8.23 (s, 1H), 8.17 (d, J=7.9 Hz, 1H), 8.01-7.91 (m, 2H), 7.79 (t, J=7.8 Hz, 1H), 7.62 (d, J=8.2 Hz, 1H), 5.42 (dd, J=11.4, 2.2 Hz, 1H), 4.47 (td, J=12.2, 2.6 Hz, 1H), 4.11 (ddd, J=11.8, 5.6, 1.5 Hz, 1H), 2.66 (dt, J=15.3, 2.2 Hz, 1H), 2.43 (dq, J=15.3, 2.0 Hz, 1H), 1.87 (ddd, J=15.4, 12.5, 5.7 Hz, 1H), 1.70 (dd, J=15.4, 11.5 Hz, 1H), 1.23 (s, 3H).

The relative stereochemistry was assigned by 2D-NMR. For [cis-rac] 2-[4-methyl-4-[[3-(trifluoromethyl)phenyl]sulfonyl]-tetrahydro-pyran-2-yl]-5-(trifluoromethyl)-pyridine a NOE was observed for the Me-group with $H4_{ax}$. For [trans-rac] 2-[4-methyl-4-[[3-(trifluoromethyl)phenyl]sulfonyl]-tetrahydro-pyran-2-yl]-5-(trifluoromethyl)-pyridine a NOE was observed for the sulfone aromate with $H4_{ax}$.

Chiral Resolution of [Cis-rac] 2-[4-methyl-4-[[3-(trifluoromethyl)phenyl]sulfonyl]-tetrahydro-pyran-2-yl]-5-(trifluoromethyl)-pyridine

[Cis-rac] 2-[4-methyl-4-[[3-(trifluoromethyl)phenyl]sulfonyl]-tetrahydro-pyran-2-yl]-5-(trifluoromethyl)-pyridine (600 mg, 1.323 mmol) was subjected to preparative chiral-LC (IC-column, heptane/i-PrOH, 9:1). The products were dried to give 225 mg (38%) of

[cis-EN1] SC-308 and 215 mg (36%) of [cis-EN2] SC-309.

[cis-EN1] SC-308—analytical chiral HPLC: chiralpak IC (250×4.6 mm 5μ), 1 ml/min, 35° C., heptane/iPrOH 95/5, Ret. Time 14.847; ee >95%/specific rotation $[\alpha]_D^{27.6}$ −35.5° (c 0.96; MeOH).

[cis-EN2] SC-309—analytical chiral HPLC: chiralpak IC (250×4.6 mm 5μ), 1 ml/min, 35° C., heptane/iPrOH 95/5, Ret. Time 26.630; ee >95%/specific rotation $[\alpha]_D^{27.7}$ +34.8° (c 0.91; MeOH).

Chiral Resolution of [Trans-rac] 2-[4-methyl-4-[[3-(trifluoromethyl)phenyl]sulfonyl]-tetrahydro-pyran-2-yl]-5-(trifluoromethyl)-pyridine

[Trans-rac] 2-[4-methyl-4-[[3-(trifluoromethyl)phenyl]sulfonyl]-tetrahydro-pyran-2-yl]-5-(trifluoromethyl)-pyridine (0.4 g, 0.882 mmol) was subjected to preparative chiral-LC (IC-column, heptane/i-PrOH, 9:1) to afford 142 mg (36%) of [trans-EN1] SC-310 and 144 mg (36%) of [trans-EN2] SC-311.

[trans-EN1] SC-310—analytical chiral HPLC: chiralpak IC (250×4.6 mm 5μ), 1 ml/min, 35° C., heptane/iPrOH 95/5, Ret. Time 8.776; ee >95%

[trans-EN2] SC-311—analytical chiral HPLC: chiralpak IC (250×4.6 mm 5μ), 1 ml/min, 35° C., heptane/iPrOH 95/5, Ret. Time 13.639; ee >95%

3-[4-Ethyl-4-[[3-(trifluoromethyl)phenyl]sulfonyl]-tetrahydro-pyran-2-yl]-2-methyl-pyridine (Example 13)

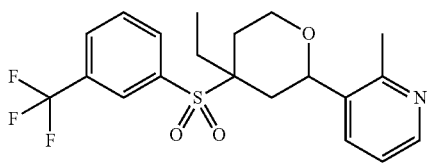 [SMILES: CCC1(S(=O)(=O)c2cccc(C(F)(F)F)c2)CCOC(c2cccnc2C)C1]

The synthesis was carried out in analogy to 2-[4-ethyl-4-[[3-(trifluoromethyl)phenyl]sulfonyl]-tetrahydro-pyran-2-yl]-6-methyl-pyridine (see above). The crude product obtained in the last step was subjected to flash chromatography (silica, gradient heptane/EtOAc, 84:16 to 0:1) to yield [cis-rac] 3-[4-ethyl-4-[[3-(trifluoromethyl)phenyl]sulfonyl]-tetrahydro-pyran-2-yl]-2-methyl-pyridine (172 mg, 17%). [Trans-rac] 3-[4-ethyl-4-[[3-(trifluoromethyl)phenyl]sulfonyl]-tetrahydro-pyran-2-yl]-2-methyl-pyridine SC-314 (126 mg, 12%) was also obtained.

$^1$H-NMR (400 MHz, CDCl$_3$) of [cis-rac] 3-[4-ethyl-4-[[3-(trifluoromethyl)phenyl]sulfonyl]-tetrahydro-pyran-2-yl]-2-methyl-pyridine: δ=8.44 (d, J=4.8 Hz, 1H), 8.12 (s, 1H), 8.04 (d, J=7.9 Hz, 1H), 7.96 (d, J=7.7 Hz, 1H), 7.78-7.68 (m, 2H), 7.18 (dd, J=7.8, 4.8 Hz, 1H), 4.61 (m, 1H), 4.15 (dd, J=12.0, 5.2 Hz, 1H), 3.71 (t, J=12.3 Hz, 1H), 2.52 (s, 3H), 2.28 (td, J=12.8, 5.2 Hz, 1H), 2.18-1.95 (m, 5H), 1.71 (d, J=13.1 Hz, 1H), 1.19 (t, J=7.5 Hz, 3H).

$^1$H-NMR (400 MHz, CDCl$_3$) of [trans-rac] 3-[4-ethyl-4-[[3-(trifluoromethyl)phenyl]sulfonyl]-tetrahydro-pyran-2-yl]-2-methyl-pyridine SC-314: δ=8.44 (dd, J=4.8, 1.7 Hz, 1H), 8.18 (s, 1H), 8.11 (d, J=7.9 Hz, 1H), 7.96 (d, J=7.8 Hz, 1H), 7.82-7.72 (m, 2H), 7.17 (dd, J=7.8, 4.8 Hz, 1H), 5.50 (dd, J=11.6, 2.1 Hz, 1H), 4.49 (td, J=12.2, 2.8 Hz, 1H), 4.12 (dd, J=11.8, 4.7 Hz, 1H), 2.69 (s, 3H), 2.34 (d, J=15.4 Hz, 1H), 2.17-1.93 (m, 2H), 1.67-1.41 (m, 3H), 0.94 (t, J=7.4 Hz, 3H).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 3-[4-ethyl-4-[[3-(trifluoromethyl)phenyl]sulfonyl]-tetrahydro-pyran-2-yl]-2-methyl-pyridine

[Cis-rac] 3-[4-ethyl-4-[[3-(trifluoromethyl)phenyl]sulfonyl]-tetrahydro-pyran-2-yl]-2-methyl-pyridine (172 mg, 0.416 mmol) was subjected to preparative chiral-LC (IC-column, heptane/EtOH, 90:10) to give [cis-EN1] SC-312 (67 mg, 39%) and [cis-EN2] SC-313 (63 mg, 37%).

[cis-EN1] SC-312—analytical chiral HPLC: chiralpak IC (250×4.6 mm 5μ), 1 ml/min, 35° C., heptane/EtOH 80/20, Ret. Time 16.332; ee >95%

[cis-EN2] SC-313—analytical chiral HPLC: chiralpak IC (250×4.6 mm 5μ), 1 ml/min, 35° C., heptane/EtOH 80/20, Ret. Time 21.846; ee >95%

5-[4-Methyl-4-[[3-(trifluoromethyl)phenyl]sulfonyl]-tetrahydro-pyran-2-yl]-2-(trifluoromethyl)-pyridine (Example 14)

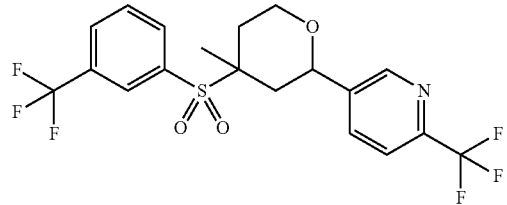 [SMILES: CC1(S(=O)(=O)c2cccc(C(F)(F)F)c2)CCOC(c2ccc(C(F)(F)F)nc2)C1]

Step 1: 2-(6-(Trifluoromethyl)pyridin-3-yl)tetrahydro-2H-pyran-4-yl Methanesulfonate Methanesulfonic acid (13.0 mL, 200 mmol) was dropwise added to a solution of 6-(trifluoromethyl)nicotinaldehyde (3.50 g, 20.0 mmol) and but-3-en-1-ol (1.72 mL, 20.0 mmol) in DCM (20 mL) while cooling with an icebath. The RM was stirred at RT for 4 h, diluted with DCM, washed with sat. aq. NaHCO$_3$ and separated with a phase separator. The organic layer was further diluted with DCM, washed with sat. aq. NaHCO$_3$ (2×), dried (Na$_2$SO$_4$) and concentrated. Crystallisation (EtOAc/heptane) of the residue gave the product (3.48 g, 54%) as white crystals. The mother liquor was concentrated and crystallisation (EtOAc/Heptane/i-Pr$_2$O) of the residue gave another crop of product (1.73 g, 27%) as white crystals. The crystals were combined to give the desired product (5.21 g, 80%).

Step 2: 2-(Trifluoromethyl)-5-(4-((3-(trifluoromethyl)phenyl)thio)tetrahydro-2H-pyran-2-yl)pyridine 2-(6-(Trifluoromethyl)pyridin-3-yl)tetrahydro-2H-pyran-4-yl methanesulfonate (4.19 g, 12.9 mmol) was dissolved in dry DMF (40 mL), the solution was degassed by N$_2$ bubbling for 1 h. K$_2$CO$_3$ (4.45 g, 32.2 mmol) was added, followed by 3-(trifluoromethyl)benzenethiol (3.43 mL, 25.8 mmol). The RM was stirred vigorously at 50° C. overnight and poured out into ice-water (400 mL), followed by addition of EtOAc (200 mL). The layers were separated, the aq. layer was extracted with EtOAc (50 mL). The combination of organic layers was washed with H$_2$O (50 mL), dried (brine and Na$_2$SO$_4$) and concentrated in vacuo. The residue was mixed with DCM (3 mL) and used for flash chromatography (silica, gradient heptane/EtOAc, 95:5 to 7:3) to result in the desired product (5.19 g, 99%) as a clear oil.

Step 3: 2-(Trifluoromethyl)-5-(4-((3-(trifluoromethyl)phenyl)sulfonyl)tetrahydro-2H-pyran-2-yl)pyridine 2-(Trifluoromethyl)-5-(4-((3-(trifluoromethyl)phenyl)thio)tetrahydro-2H-pyran-2-yl)pyridine (5.19 g, 12.7 mmol) was dissolved in MeOH (120 mL). A water bath was applied. Oxone (19.6 g, min. 55.1 mmol) was almost completely dissolved in H$_2$O (70 mL), the turbid solution was added portionwise. During the addition, a raise of temperature was observed, the temperature was kept below 25° C. The RM was stirred vigorously at RT for 4 h. The major part of the MeOH was removed in vacuo. The resulting suspension was mixed with H$_2$O (350 mL) and EtOAc (350 mL) to result in a clear two phase system. The layers were separated, the aq. layer was extracted with EtOAc (50 mL). The combination of organic layers was washed with sat. aq. NaHCO$_3$ (50 mL), dried (brine and Na$_2$SO$_4$) and concentrated in vacuo. Trituration with heptane (100 mL) and air-drying provided the desired product (4.99 g, 89%) as a white solid.

Step 4 was carried out in 2 batches as described below:

Step 4 (Batch 1): 5-[4-Methyl-4-[[3-(trifluoromethyl)phenyl]sulfonyl]-tetrahydro-pyran-2-yl]-2-(trifluoromethyl)-pyridine While cooling with an acetone/dry ice bath under Ar, KOt-Bu (230 mg, 2.05 mmol) was portionwise added to a solution of 2-(trifluoromethyl)-5-(4-((3-(trifluoromethyl)phenyl)sulfonyl)tetrahydro-2H-pyran-2-yl)pyridine (600 mg, 1.37 mmol) in dry THF (4 mL). After the RM was stirred for 5 min while still cooling with an acetone/dry ice bath, MeI (0.171 mL, 2.73 mmol) was added to the RM. The RM was stirred for 30 min while still cooling with an acetone/dry ice bath. The RM was allowed to warm to RT, diluted with DCM, washed with H$_2$O and brine and concentrated. The residue was subjected to flash chromatography (silica, gradient heptane/EtOAc, 95:5→1:1). Crystallisation (EtOAc/heptane) of the residue gave impure product. The crystals and the mother liquor were combined and concentrated. The residue was purified by flash chromatography (silica, gradient heptane/EtOAc, 94:6→34:66) and flash chromatography (silica, gradient heptane/EtOAc, 95:5 to 1:1) resulting in [cis-rac] 5-[4-methyl-4-[[3-(trifluoromethyl)phenyl]sulfonyl]-tetrahydro-pyran-2-yl]-2-(trifluoromethyl)-pyridine SC-306 (95 mg, 15%). Impure product, which was also obtained, was then further purified by flash chromatography (silica, gradient heptane/EtOAc, 95:5-1:1) and co-evaporated with MeOH and pentane to yield [trans-rac] 5-[4-methyl-4-[[3-(trifluoromethyl)phenyl]sulfonyl]-tetrahydro-pyran-2-yl]-2-(trifluoromethyl)-pyridine SC-307 (173 mg, 28%).

Step 4 (Batch 2): 5-[4-Methyl-4-[[3-(trifluoromethyl)phenyl]sulfonyl]-tetrahydro-pyran-2-yl]-2-(trifluoromethyl)-pyridine A solution of 2-(trifluoromethyl)-5-(4-((3-(trifluoromethyl)phenyl)sulfonyl)tetrahydro-2H-pyran-2-yl)pyridine (1.00 g, 2.28 mmol) in dry THF (15 mL) was prepared, the temperature was lowered to −78° C. A solution of 1 M KOt-Bu in THF (3.41 mL, 3.41 mmol) was added dropwise and the RM was stirred at −78° C. for 10 min. Dropwise addition of MeI (0.285 mL, 4.55 mmol) was followed by stirring the RM at −78° C. for 1 h. The flask was left in the cooling bath. Consequently, the temperature was kept at −78° C. for a few hours, followed by slow raise of temperature to RT and stirring overnight at RT. The RM was combined with aq. 1 M KHSO$_4$ (75 mL), some ice and EtOAc (100 mL) to result in a two phase system. The layers were separated, the aq. layer was extracted with EtOAc (25 mL). The combination of organic layers was washed with sat. aq. NaHCO$_3$ (50 mL), dried (brine and Na$_2$SO$_4$) and concentrated in vacuo. The residue was dissolved in DCM (5 mL) and used for flash chromatography (silica, gradient heptane/EtOAc, 95:5-6:4). The product was dissolved in EtOAc (200 mL), the solution was washed with aq. 1 M Na$_2$S$_2$O$_3$ (50 mL), dried (brine and Na$_2$SO$_4$) and concentrated in vacuo. The residue was dissolved in DCM (3 mL), followed by addition of heptane (15 mL) and concentration in vacuo. The residue was triturated in pentane (20 mL). Filtration and drying provided 566 mg (54%) of [cis-rac] 5-[4-methyl-4-[[3-(trifluoromethyl)phenyl]sulfonyl]-tetrahydro-pyran-2-yl]-2-(trifluoromethyl)-pyridine SC-306 as a white solid.

$^1$H-NMR (400 MHz, CDCl$_3$) of [cis-rac] 5-[4-methyl-4-[[3-(trifluoromethyl)phenyl]sulfonyl]-tetrahydro-pyran-2-yl]-2-(trifluoromethyl)-pyridine SC-306: δ=8.62 (d, J=1.6 Hz, 1H), 8.13 (s, 1H), 8.05 (d, J=7.9 Hz, 1H), 7.97 (d, J=7.8 Hz, 1H), 7.88 (dd, J=8.1, 1.7 Hz, 1H), 7.75 (t, J=7.8 Hz, 1H), 7.70 (d, J=8.1 Hz, 1H), 4.58 (dd, J=11.6, 1.8 Hz, 1H), 4.26-4.17 (m, 1H), 3.73 (td, J=12.4, 2.2 Hz, 1H), 2.39 (td, J=12.9, 5.4 Hz, 1H), 2.16 (t, J=12.3 Hz, 1H), 1.80 (dt, J=13.0, 2.2 Hz, 1H), 1.61-1.58 (m, 1H), 1.59 (s, 3H).

$^1$H-NMR (400 MHz, CDCl$_3$) of [trans-rac] 5-[4-methyl-4-[[3-(trifluoromethyl)phenyl]sulfonyl]-tetrahydro-pyran-2-yl]-2-(trifluoromethyl)-pyridine SC-307: δ=8.74 (s, 1H), 8.17 (s, 1H), 8.12 (d, J=7.9 Hz, 1H), 7.99 (d, J=7.8 Hz, 1H), 7.89 (d, J=6.8 Hz, 1H), 7.80 (t, J=7.8 Hz, 1H), 7.69 (d, J=8.1 Hz, 1H), 5.38 (d, J=9.9 Hz, 1H), 4.45 (td, J=12.5, 2.4 Hz, 1H), 4.10 (dd, J=11.9, 4.9 Hz, 1H), 2.54 (d, J=15.3 Hz, 1H), 2.27 (d, J=15.4 Hz, 1H), 1.86 (ddd, J=15.5, 12.8, 5.7 Hz, 1H), 1.65-1.52 (m, 1H), 1.25 (s, 3H).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis Racemic] 5-[4-methyl-4-[[3-(trifluoromethyl)phenyl]sulfonyl]-tetrahydro-pyran-2-yl]-2-(trifluoromethyl)-pyridine SC-306

[Cis-rac] 5-[4-methyl-4-[[3-(trifluoromethyl)phenyl]sulfonyl]-tetrahydro-pyran-2-yl]-2-(trifluoromethyl)-pyridine SC-306 (556 mg) was separated on a Jasco SFC (Chiralcel OJ-H, MeOH/EtOH 1:1; CO$_2$) to give 220 mg of [cis-EN1] SC-315 and 214 mg of [cis-EN2] SC-316.

[cis-EN1] SC-315—analytical chiral SFC: Jasco SFC, Chiralcel OJ, 5 um, 250×4.6 mm, 40° C., 2 ml/Min CO$_2$/10% MeOH:EtOH 1:1, Ret. Time 3.56; ee >95%

[cis-EN2] SC-316—analytical chiral SFC: Jasco SFC, Chiralcel OJ, 5 um, 250×4.6 mm, 40° C., 2 ml/Min CO$_2$/10% MeOH:EtOH 1:1, Ret. Time 4.34; ee >95%

3-[4-Ethyl-4-[[3-(trifluoromethyl)phenyl]sulfonyl]-tetrahydro-pyran-2-yl]-2,6-dimethyl-pyridine (Example 15)

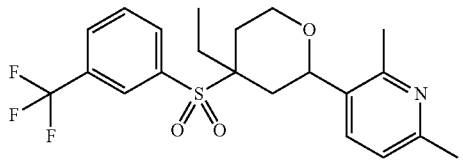 [SMILES: CCC1(S(=O)(=O)c2cccc(C(F)(F)F)c2)CCOC(c2ccc(C)nc2C)C1]

Step 1: 2-(2,6-Dimethylpyridin-3-yl)tetrahydro-2H-pyran-4-yl Methanesulfonate A solution of 2,6-dimethylnicotinaldehyde (4.87 g, 36.0 mmol) and but-3-en-1-ol (3.10 mL, 36.0 mmol) in DCM (35 mL) was cooled in a NaCl/ice bath to −16° C. MsOH (23.4 mL, 360 mmol) was added slowly via a syringe over 20 min, keeping the temperature below −10° C. The RM was poured out in a cooled solution of $Na_2CO_3$ (38.2 g, 360 mmol) in $H_2O$ (~300 mL) and the product was extracted with EtOAc (2×200 mL). The combined organic layers were washed with sat. aq. $NaHCO_3$ (2×50 mL) and brine (2×50 mL) before drying on $Na_2SO_4$ and concentration in vacuo. The product was purified using flash chromatography (silica, gradient heptane/acetone, 7:3 to 4:6) to give the desired product (5.86 g, 57%) as a brown oil.

Step 2: 2,6-Dimethyl-3-(4-((3-(trifluoromethyl)phenyl)thio)tetrahydro-2H-pyran-2-yl)pyridine A solution of 2-(2,6-dimethylpyridin-3-yl)tetrahydro-2H-pyran-4-yl methanesulfonate (3 g, 10.51 mmol) in dry DMF (60 mL) was degassed by applying vacuum for 1 min, then refill the flask with Ar. This sequence was repeated 5 times before $Cs_2CO_3$ (8.56 g, 26.3 mmol) and 3-(trifluoromethyl)benzenethiol (3.49 mL, 26.3 mmol) were added. The degassing sequence was performed two times and the mixture was subsequently stirred at 80° C. under argon for 2 h. The heating was stopped and the stirring was continued at RT for 16 h. The RM was poured out in sat. aq. $NaHCO_3$ (50 mL) and the product was extracted with EtOAc/i-$Pr_2O$ (1/1, v/v, 2×100 mL). The combined organic layers were washed with sat. aq. $NaHCO_3$ (2×50 mL) and brine (2×50 mL) before drying on $Na_2SO_4$ and concentration in vacuo. The product was purified using flash chromatography (silica, gradient heptane/EtOAc, 1:0 to 4:6) to give the desired product (2.89 g, 74%) as a light yellow oil.

Step 3: 2,6-Dimethyl-3-(4-((3-(trifluoromethyl)phenyl)sulfonyl)tetrahydro-2H-pyran-2-yl)pyridine To a solution of 2,6-dimethyl-3-(4-((3-(trifluoromethyl)phenyl)thio)tetrahydro-2H-pyran-2-yl)pyridine (2.89 g, 7.87 mmol) in MeOH (115 mL) was added a solution of oxone (4.84 g, min. 13.6 mmol) in $H_2O$ (80 mL) and the suspension was stirred at RT for 30 min. The MeOH was distilled off in vacuo. The residue was basified with sat. aq. $NaHCO_3$ and the product was extracted with i-$Pr_2O$/EtOAc (1/1, v/v, 250 mL). The organic layer was washed with sat. aq. $NaHCO_3$ (2×50 mL) and brine (2×50 mL) before drying on $Na_2SO_4$ and concentration in vacuo to give the desired product (2.95 g, 94%) as a white solid.

Step 4: 3-[4-Ethyl-4-[[3-(trifluoromethyl)phenyl]sulfonyl]-tetrahydro-pyran-2-yl]-2,6-dimethyl-pyridine To a solution of 2,6-dimethyl-3-(4-((3-(trifluoromethyl)phenyl)sulfonyl)tetrahydro-2H-pyran-2-yl)pyridine (2 g, 5.01 mmol) in dry THF (15 mL) under argon at −78° C. was added 1M KO-tBu in THF (15.02 mL, 15.02 mmol) dropwise over 10 min. The mixture was stirred for 30 min. Ethyl iodide (2.0 mL, 25.04 mmol) was added dropwise, and the stirring was continued at −78° C. for 4 h. More 1M KOt-Bu in THF (15.02 mL, 15.02 mmol) was added slowly via a syringe and the mixture was stirred at −78° C. for 30 min. Ethyl iodide (1.6 mL, 20.03 mmol) was added dropwise over 1 min and the stirring was continued, slowly warming up to RT for 72 h. The RM was diluted with sat. aq. $NaHCO_3$ (50 mL) and the product was extracted with EtOAc/i-$Pr_2O$ (1/1, v/v, 2×100 mL). The combined organic layers were washed with sat. aq. $NaHCO_3$ (2×50 mL), aq. 1M $Na_2S_2O_3$ (2×50 mL) and brine (2×50 mL) before drying on $Na_2SO_4$ and concentration in vacuo. The product was purified using flash chromatography (silica, gradient heptane/EtOAc, 9:1→3:7) to give impure [trans-rac] 3-[4-ethyl-4-[[3-(trifluoromethyl)-phenyl]sulfonyl]-tetrahydro-pyran-2-yl]-2,6-dimethyl-pyridine SC-319 and 905 mg (42%) of [cis-rac] 3-[4-ethyl-4-[[3-(trifluoromethyl)phenyl]sulfonyl]-tetrahydro-pyran-2-yl]-2,6-dimethyl-pyridine. Impure [trans-rac] 3-[4-ethyl-4-[[3-(trifluoromethyl)phenyl]sulfonyl]-tetrahydro-pyran-2-yl]-2,6-dimethyl-pyridine SC-319 was purified further using flash chromatography (silica, gradient heptane/EtOAc, 9:1→3:7) to give (383 mg, 17%) of pure [trans-rac] 3-[4-ethyl-4-[[3-(trifluoromethyl)phenyl]sulfonyl]-tetrahydro-pyran-2-yl]-2,6-dimethyl-pyridine SC-319 as a white solid.

$^1$H-NMR (400 MHz, $CDCl_3$) of [cis-rac] 3-[4-ethyl-4-[[3-(trifluoromethyl)phenyl]sulfonyl]-tetrahydro-pyran-2-yl]-2,6-dimethyl-pyridine: δ=8.12 (s, 1H), 8.03 (d, J=7.9 Hz, 1H), 7.95 (d, J=7.8 Hz, 1H), 7.74 (t, J=7.9 Hz, 1H), 7.59 (d, J=8.0 Hz, 1H), 7.03 (d, J=8.0 Hz, 1H), 4.58 (dd, J=9.6, 3.6 Hz, 1H), 4.14 (dd, J=11.8, 4.7 Hz, 1H), 3.71 (td, J=12.3, 1.8 Hz, 1H), 2.50 (d, J=13.6 Hz, 6H), 2.26 (td, J=12.9, 5.3 Hz, 1H), 2.17-1.91 (m, 4H), 1.71 (d, J=13.3 Hz, 1H), 1.18 (t, J=7.5 Hz, 3H).

$^1$H-NMR (400 MHz, $CDCl_3$) of [trans-rac] 3-[4-ethyl-4-[[3-(trifluoromethyl)phenyl]sulfonyl]-tetrahydro-pyran-2-yl]-2,6-dimethyl-pyridine SC-319: δ=8.18 (s, 1H), 8.10 (d, J=7.9 Hz, 1H), 7.96 (d, J=7.8 Hz, 1H), 7.76 (t, J=7.8 Hz, 1H), 7.64 (d, J=7.9 Hz, 1H), 7.02 (d, J=7.9 Hz, 1H), 5.47 (dd, J=11.6, 2.0 Hz, 1H), 4.48 (td, J=12.2, 2.7 Hz, 1H), 4.10 (dd, J=11.7, 5.1 Hz, 1H), 2.65 (s, 3H), 2.52 (s, 3H), 2.29 (d, J=15.4 Hz, 1H), 2.16-2.06 (m, 1H), 2.06-1.93 (m, 1H), 1.60 (dd, J=15.4, 11.6 Hz, 1H), 1.54-1.44 (m, 2H), 0.94 (t, J=7.4 Hz, 3H).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 3-[4-ethyl-4-[[3-(trifluoromethyl)phenyl]sulfonyl]-tetrahydro-pyran-2-yl]-2,6-dimethyl-pyridine

[Cis-rac] 3-[4-ethyl-4-[[3-(trifluoromethyl)phenyl]sulfonyl]-tetrahydro-pyran-2-yl]-2,6-dimethyl-pyridine (300 mg, 0.702 mmol) was subjected to preparative chiral-LC (IC-column, heptane/EtOH, 9:1) to give 131 mg (43%) of [cis-EN1] SC-317 and 126 mg (42%) of [cis-EN2] SC-318.

[cis-EN1] SC-317—analytical chiral HPLC: chiralpak IC (250×4.6 mm 5μ), 1 ml/min, 35° C., heptane/EtOH 80/20, Ret. Time 13.219; ee >95%

[cis-EN2] SC-318—analytical chiral HPLC: chiralpak IC (250×4.6 mm 5μ), 1 ml/min, 35° C., heptane/EtOH 80/20, Ret. Time 16.495; ee >95%

2-[4-Ethyl-4-[[3-(trifluoromethyl)phenyl]sulfonyl]-tetrahydro-pyran-2-yl]-6-methyl-pyridine (Example 16)

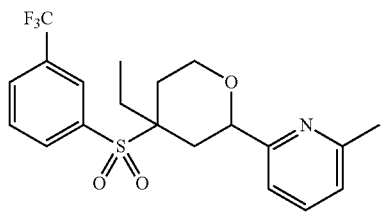 [SMILES: CCC1(S(=O)(=O)c2cccc(C(F)(F)F)c2)CCOC(c2cccc(C)n2)C1]

Chiral Resolution of [Cis rac] 2-methyl-6-(4-((3-(trifluoromethyl)phenyl)sulfonyl)tetrahydro-2H-pyran-2-yl)pyridine

[Cis rac] 2-methyl-6-(4-((3-(trifluoromethyl)phenyl)sulfonyl)tetrahydro-2H-pyran-2-yl)pyridine (350 mg, 0.847 mmol) was subjected to preparative chiral-LC (OD-column, heptane/EtOH, 95:5) and the products were lyophilised using MeCN/H₂O (3/1, v/v, 2 mL) to give 130 mg (37%) of [cis-EN1] SC-323 and 127 mg (36%) of [cis-EN2] SC-324.

[cis-EN1] SC-323—analytical chiral HPLC: chiralpak OD-H (250×4.6 mm 5μ), 1 ml/min, 35° C., heptane/EtOH 90/10, Ret. Time 6.670; ee >95%

[cis-EN2] SC-324—analytical chiral HPLC: chiralpak OD-H (250×4.6 mm 5μ), 1 ml/min, 35° C., heptane/EtOH 90/10, Ret. Time 9.340; ee >95%

3-Cyclopropyl-5-[4-methyl-4-[[3-(trifluoromethyl)phenyl]sulfonyl]-tetrahydro-pyran-2-yl]-pyridine (Example 17)

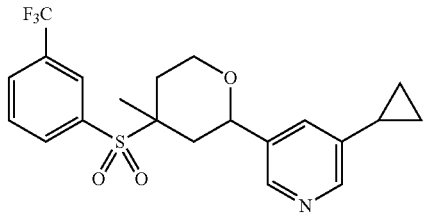 [SMILES: CC1(S(=O)(=O)c2cccc(C(F)(F)F)c2)CCOC(c2cncc(C3CC3)c2)C1]

Two enantiomers of cis racemic were separated by SFC using on a chiral pack OJ-H column to obtain two desired cis enantiomers (SC-325 and SC-326).

SC-325: 1ˢᵗ eluted enantiomer: [cis-EN1] SC-325
SC-326: 2ⁿᵈ eluted enantiomer: [cis-EN2] SC-326

2-Cyclopropyl-5-[4-methyl-4-[[3-(trifluoromethyl)phenyl]sulfonyl]-tetrahydro-pyran-2-yl]-pyrazine (Example 18)

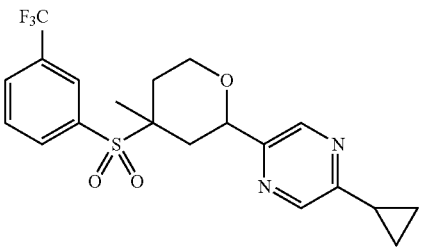 [SMILES: CC1(S(=O)(=O)c2cccc(C(F)(F)F)c2)CCOC(c2cnc(C3CC3)cn2)C1]

Step 1: 2-(5-Cyclopropylpyrazin-2-yl)tetrahydro-2H-pyran-4-yl Methanesulfonate

A solution of 5-cyclopropylpyrazine-2-carbaldehyde (4.80 g, 32.4 mmol) in DCM (30 mL) was prepared, followed by applying an ice/water bath and dropwise addition of MsOH (21.04 mL, 324 mmol). Subsequently, 3-buten-1-ol (3.35 mL, 38.9 mmol) was added dropwise. The RM was stirred at 0° C. for 1.5 h. Sat. aq. Na₂CO₃ (400 mL) was immersed in an ice/water bath. The RM was transferred into a separation funnel and added dropwise to the stirred and chilled Na₂CO₃ solution. The temperature was kept below 15° C. Subsequently, DCM (125 mL) and H₂O (100 mL) were added, followed by separation of the phases. The aq. layer was extracted with DCM (2×50 mL). The combination of organic layers was washed with sat. aq. NaHCO₃ (50 mL), dried (brine twice & Na₂SO₄) and concentrated to yield 9.59 g (99%) of the desired product as a brown oil.

Step 2: 2-Cyclopropyl-5-(4-((3-(trifluoromethyl)phenyl)thio)tetrahydro-2H-pyran-2-yl)pyrazine A solution of 2-(5-cyclopropylpyrazin-2-yl)tetrahydro-2H-pyran-4-yl methanesulfonate (9.59 g, 32.1 mmol) in dry MeCN (300 mL) was degassed by N₂ bubbling for 1 h. K₂CO₃ (7.55 g, 54.6 mmol) was added, followed by 3-(trifluoromethyl)benzenethiol (7.27 mL, 54.6 mmol). The RM was stirred at 50° C. overnight. Addition of EtOAc (100 mL) and silica (10 g) was followed by filtration over a cotton plug. The residue was washed with EtOAc (2×100 mL), the combination of filtrates was concentrated. The residue was mixed with DCM (100 mL). Silica (40 g) was added, the mixture was concentrated. The residue was placed on top of a silica column and used for flash chromatography (silica, gradient heptane/EtOAc, 100:0 to 7:3) to result in 7.62 g (62%) of the desired product as a colourless oil.

Step 3: 2-Cyclopropyl-5-(4-((3-(trifluoromethyl)phenyl)sulfonyl)tetrahydro-2H-pyran-2-yl)pyrazine 2-Cyclopropyl-5-(4-((3-(trifluoromethyl)phenyl)thio)tetrahydro-2H-pyran-2-yl)pyrazine (7.60 g, 19.98 mmol) was dissolved in MeOH (200 mL). An ice/water bath was applied. Oxone (30.7 g, min. 86.3 mmol) was almost completely dissolved in H₂O (100 mL) and the turbid solution was added portionwise. During the addition, a raise of temperature was observed. The temperature was kept below 15° C. The reaction mixture was stirred vigorously at RT for 2 h. The major part of the MeOH was removed from the RM by rotary evaporation. The resulting suspension was mixed with H$_2$O (500 mL) and EtOAc (500 mL) to result in a two phase system with a white solid. The layers were decanted and separated. The aq. layer was combined with the white solid and mixed with EtOAc (100 mL). The layers were decanted and separated. The combination of organic layers was washed with sat. aq. NaHCO$_3$ (100 mL), dried (brine and Na$_2$SO$_4$) and concentrated. The residue was dissolved in DCM (100 mL) and concentrated. The residue was dissolved in DCM (10 mL), followed by addition of MeOH (100 mL) and concentration. The residue was dissolved in MeOH (20 mL) by heating. Cooling to RT started crystallisation. Filtration, washing with MeOH (3×10 mL) and drying by suction provided 5.72 g (69%) of the desired product as a white powder.

Step 4: 2-Cyclopropyl-5-[4-methyl-4-[[3-(trifluoromethyl)phenyl]sulfonyl]-tetrahydro-pyran-2-yl]-pyrazine A solution of 2-cyclopropyl-5-(4-((3-(trifluoromethyl)phenyl)sulfonyl)tetrahydro-2H-pyran-2-yl)pyrazine (1.50 g, 3.64 mmol) in dry THF (20 mL) was prepared. The temperature was lowered to −78° C., 1 M KOt-Bu in THF (5.46 mL, 5.46 mmol) was added dropwise and the RM was stirred for 10 min. Dropwise addition of MeI (0.455 mL, 7.27 mmol) was followed by stirring the RM at −78° C. for a few hours, followed by slow raise of temperature to RT and stirring overnight at rt. The RM was combined with aq. 1 M KHSO$_4$ (100 mL) and EtOAc (120 mL) to result in a two phase system. The layers were separated, the aq. layer was extracted with EtOAc (25 mL). The combination of organic layers was washed with aq. 1 M Na$_2$S$_2$O$_3$ (30 mL), sat. aq. NaHCO$_3$ (50 mL) and dried (brine and Na$_2$SO$_4$), followed by concentration. The residue was dissolved in DCM (3 mL) and used for flash chromatography (silica, gradient heptane/EtOAc, 9:1 to 65:35). This resulted in two fractions, the first fraction was used for further purification in this experiment. The second fraction was collected to arrive at 0.90 g (58%) of [cis rac] 2-cyclopropyl-5-[4-methyl-4-[[3-(trifluoromethyl)phenyl]sulfonyl]-tetrahydro-pyran-2-yl]-pyrazine as a white solid. The first fraction mentioned above was dissolved in DCM (0.7 mL) and used for flash chromatography (silica, gradient heptane/EtOAc, 95:5 to 4:1). The product was dissolved in MeCN (10 mL), followed by concentration. The residue was dissolved in MeCN (2 mL), followed by addition of H$_2$O (2 mL) and freeze drying to result in 117 mg (7%) of [trans rac] 2-cyclopropyl-5-[4-methyl-4-[[3-(trifluoro-methyl)phenyl]sulfonyl]-tetrahydro-pyran-2-yl]-pyrazine SC-328.

$^1$H NMR (400 MHz, CDCl$_3$) of [cis racemic] 2-cyclopropyl-5-[4-methyl-4-[[3-(trifluoromethyl)phenyl]sulfonyl]-tetrahydro-pyran-2-yl]-pyrazine: δ 8.52-8.46 (m, 1H), 8.36 (d, J=1.3 Hz, 1H), 8.13 (s, 1H), 8.05 (d, J=7.9 Hz, 1H), 7.94 (d, J=7.8 Hz, 1H), 7.73 (t, J=7.8 Hz, 1H), 4.54 (dd, J=11.6, 2.2 Hz, 1H), 4.22 (dd, J=11.5, 4.7 Hz, 1H), 3.74 (td, J=12.3, 2.1 Hz, 1H), 2.37 (td, J=12.8, 5.4 Hz, 1H), 2.17 (t, J=12.3 Hz, 1H), 2.06 (p, J=6.5 Hz, 1H), 1.94 (dt, J=12.9, 2.2 Hz, 1H), 1.65-1.55 (m, 9.6H) [+H$_2$O], 1.07 (d, J=6.7 Hz, 4H).

$^1$H-NMR (400 MHz, CDCl$_3$) of [trans rac] 2-cyclopropyl-5-[4-methyl-4-[[3-(trifluoromethyl)phenyl]sulfonyl]-tetrahydro-pyran-2-yl]-pyrazine SC-328: δ 8.51 (s, 1H), 8.41 (d, J=1.3 Hz, 1H), 8.19 (s, 1H), 8.13 (d, J=7.7 Hz, 1H), 7.96 (d, J=7.7 Hz, 1H), 7.77 (t, J=7.8 Hz, 1H), 5.35 (dd, J=11.4, 2.5 Hz, 1H), 4.44 (td, J=12.2, 2.5 Hz, 1H), 4.13-4.03 (m, 1H), 2.52 (d, J=15.4 Hz, 1H), 2.36 (d, J=15.3 Hz, 1H), 2.14-2.03 (m, 1H), 1.98-1.82 (m, 2H), 1.24 (s, 3H), 1.06 (d, J=7.0 Hz, 4H).

The relative stereochemistry was assigned by comparing the central ring signals in the $^1$H-NMRs with the spectra of [cis rac] and [trans rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis Racemic] 2-cyclopropyl-5-[4-methyl-4-[[3-(trifluoromethyl)-phenyl]sulfonyl]-tetrahydro-pyran-2-yl]-pyrazine

[Cis rac] 2-cyclopropyl-5-[4-methyl-4-[[3-(trifluoromethyl)phenyl]sulfonyl]-tetrahydro-pyran-2-yl]-pyrazine (300 mg, 0.703 mmol) was subjected to preparative chiral-LC (IC-column, heptane/EtOH 9:1). The two products were dissolved in EtOAc (20 mL), followed by concentration. The residues were dissolved in DCM (5 mL), added to heptane (30 mL) followed by concentration. The residues were suspended in heptane (10 mL), filtration and drying by suction provided 114 mg (38%) of [cis-EN1] SC-327 and 101 mg (34%) of [cis-EN2] SC-329.

[cis-EN1] SC-327—analytical chiral HPLC: chiralpak IC (250×4.6 mm 5μ), 1 ml/min, 35° C., heptane/EtOH 80/20, Ret. Time 8.057; ee >95%

[cis-EN2] SC-329—analytical chiral HPLC: chiralpak IC (250×4.6 mm 5μ), 1 ml/min, 35° C., heptane/EtOH 80/20, Ret. Time 11.174; ee >95%

5-Cyclopropyl-3-[4-methyl-4-[[3-(trifluoromethyl)phenyl]sulfonyl]-tetrahydro-pyran-2-yl]-[1,2,4]oxadiazole (Example 19)

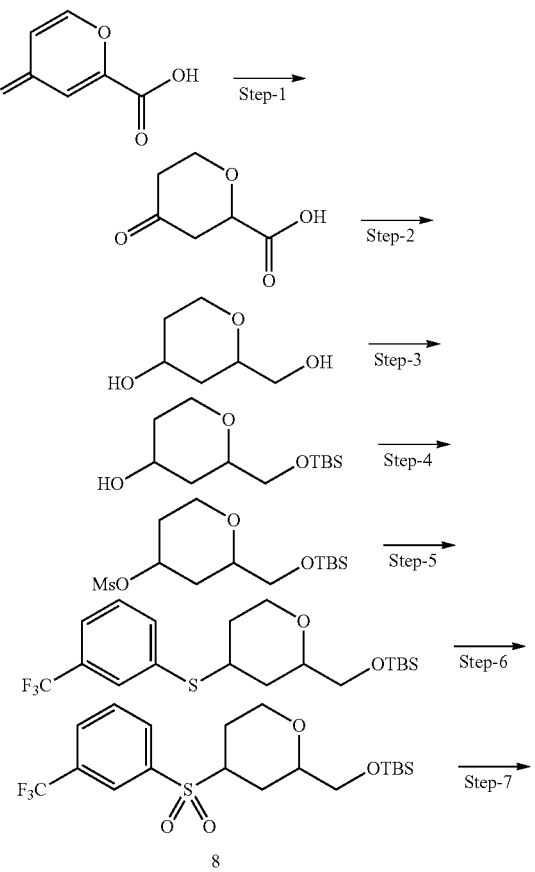

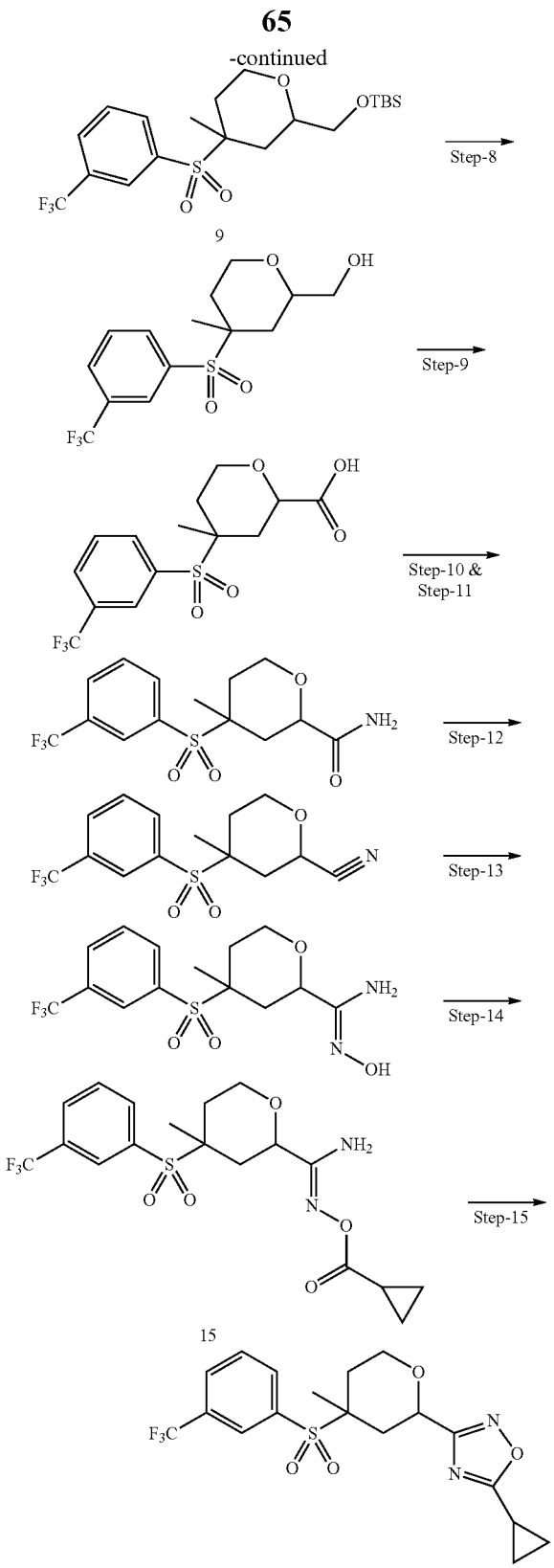

palladium/carbon (0.700 g, 10% by weight) and the mixture was again degassed thoroughly with Ar and stirred in a paar shaker for 16 h under H₂. Reaction was monitored by TLC. The RM was filtered through celite bed and organic portion was concentrated under reduced pressure to crude 4-oxotetrahydro-2H-pyran-2-carboxylic acid (3.8 g, 53%) as white solid which was used for next step without further purification.

Step 2: 2-(hydroxymethyl)tetrahydro-2H-pyran-4-ol

To a stirred solution of 4-oxotetrahydro-2H-pyran-2-carboxylic acid (3 g, 20.54 mmol, 1 eq) in THF (100 mL) borane dimethyl sulfoxide (18.24 g, 240 mmol, 12 eq) was slowly added at 0° C. and the mixture was stirred under reflux for 6 h. Reaction was monitored by TLC. The RM was slowly quenched with water at 0° C. and filtered through celite bed and organic layer was concentrated under reduced pressure to obtain crude product as a solid. Further this solid was washed with 30% i-PrOH/CHCl₃. The organic solvents were evaporated under reduced pressure to get crude 2-(hydroxymethyl)tetrahydro-2H-pyran-4-ol (2 g, 74%) as light brown liquid.

Step 3: 2-(((tert-butyldimethylsilyl)oxy)methyl)tetrahydro-2H-pyran-4-ol

To a solution of 2-(hydroxymethyl)tetrahydro-2H-pyran-4-ol (7.0 g, 53 mmol, 1 eq) in DCM (130 ml) was added TEA (8.8 mL, 63.6 mmol, 1.2 eq) and DMAP (0.258 g, 2.1 mmol, 0.04 eq) followed by tertiary butyl silyl chloride (6.3 g, 42.4 mmol, 0.8 eq) at 0° C. Then the RM was stirred at RT for 12 h. The RM was diluted with DCM (200 mL) and washed with water (3×100 mL), brine, dried over anhydr. Na₂SO₄, filtered and concentrated under reduced pressure to give the crude product. The crude product was purified by CC o afford pure 2-(((tert-butyldimethylsilyl)oxy)methyl)tetrahydro-2H-pyran-4-ol (3.5 g, 27%) as light yellow liquid.

Step 4: 2-(((tert-butyldimethylsilyl)oxy)methyl)tetrahydro-2H-pyran-4-yl Methanesulfonate To a solution of 2-(((tert-butyldimethylsilyl)oxy)methyl)tetrahydro-2H-pyran-4-ol (2.6 g, 10.5 mmol, 1 eq) in DCM (50 mL) was added TEA (4.3 mL, 30 mmol, 3 eq) followed by methane sulfonyl chloride (1.55 mL, 20 mmol, 1 eq) at 0° C. Then the RM was stirred at the same temperature for 1 h. The RM was diluted with DCM (100 mL) and washed with water (3×50 mL), brine, dried over anhydr. Na₂SO₄, filtered and concentrated under reduced pressure to give the crude 2-(((tert-butyldimethylsilyl)oxy)methyl)tetrahydro-2H-pyran-4-yl methanesulfonate (2.8 g, 82%) as a yellow liquid which was used for the next step without further purification.

Step 5: tert-butyldimethyl((4-((3-(trifluoromethyl)phenyl)thio)tetrahydro-2H-pyran-2-yl)methoxy)silane To a stirred solution of 2-(((tert-butyldimethylsilyl)oxy)methyl)tetrahydro-2H-pyran-4-yl methanesulfonate (3.5 g, 10.8 mmol, 1 eq) in DMF (100 mL) 3-(trifluoromethyl)benzenethiol (2.8 g, 15.7 mmol, 1.5 eq), K₂CO₃ (2.76 g, 20 mmol, 2 eq) was added and the mixture was heated to 70° C. for 12 h. The reaction was monitored by TLC. The RM was diluted with EtOAc (50 mL), washed with water (2×20

Step 1: 4-Oxo-tetrahydro-pyran-2-carboxylic Acid

To a degassed solution of 4-oxo-4H-pyran-2-carboxylic acid (7 g, 50.0 mmol, 1 eq) in EtOAc (130 mL) was added mL) and sat. brine, dried over anhydr. Na$_2$SO$_4$ and filtered. The organic solvent was evaporated under reduced pressure to get crude product which was purified by flash chromatography nt to afford pure tert-butyldimethyl((4-((3-(trifluoromethyl)phenyl)thio)tetrahydro-2H-pyran-2-yl)methoxy)silane (2 g, 47%) as a light yellow liquid.

Step 6: tert-butyldimethyl((4-((3-(trifluoromethyl)phenyl)sulfonyl)tetrahydro-2H-pyran-2-yl)methoxy)silane To a stirred solution of tert-butyldimethyl((4-((3-(trifluoromethyl)phenyl)thio)tetrahydro-2H-pyran-2-yl)methoxy)silane (2.2 g, 5.41 mmol, 1 eq) in (3:1) mixture of MeCN (72 mL) and water (24 mL), sodium periodate (3.47 g, 16.1 mmol, 2 eq) was added followed by addition of ruthenium (III)chloride hydrate (0.022 g, 0.106 mmol, 0.02 eq) at 0° C. The RM was stirred for 10 min at RT. The reaction was monitored by TLC and it was diluted with EtOAc (100 mL), washed with water (2×50 mL), and brine (50 ml). The organic layer was dried over Na$_2$SO$_4$, filtered and concentrated in reduced pressure to get crude product which was purified by CC to afford pure tert-butyldimethyl((4-((3-(trifluoro-methyl)phenyl)sulfonyl)tetrahydro-2H-pyran-2-yl)methoxy)silane (1.7 g, 74%) as off white solid.

Step 7: tert-butyldimethyl((4-methyl-4-((3-(trifluoromethyl)phenyl)sulfonyl)tetrahydro-2H-pyran-2-yl)methoxy)silane To a stirred solution of tert-butyldimethyl((4-((3-(trifluoromethyl)phenyl)sulfonyl)tetrahydro-2H-pyran-2-yl)methoxy)silane (2.5 g, 5.70 mmol, 1 eq) in THF (80 mL), NaHMDS (11.4 mL, 11.4 mmol, 2 eq) was added followed by addition of 15-crown-5 (2.5 g, 11.36 mmol, 2 eq) at −78° C. The reaction was continued for 20 min. MeI was added and the RM was maintained for 45 min at −78° C. and then allowed to warm up to RT and stirred for further 12 h. The reaction was monitored by TLC and it was diluted with EtOAc (100 mL), washed with water (2×50 mL), brine (50 mL), dried over anhydr. Na$_2$SO$_4$, filtered and evaporated under reduced pressure to give crude product which was further purified by CC to afford pure tert-butyldimethyl((4-methyl-4-((3-(trifluoromethyl)phenyl)sulfonyl)tetrahydro-2H-pyran-2-yl)methoxy)silane (1.3 g, 52%) as light yellow solid.

Step 8: (4-methyl-4-((3-(trifluoromethyl)phenyl)sulfonyl)tetrahydro-2H-pyran-2-yl)methanol To a cooled (0° C.) stirred solution of tert-butyldimethyl((4-methyl-4-((3-(trifluoromethyl)phenyl)sulfonyl)tetrahydro-2H-pyran-2-yl)methoxy)silane (0.83 g, 1.8 mmol, 1 eq) in THF (20 mL) TBAF solution (4.5 mL, 4.5 mmol, 2.5 eq) was added. The RM was stirred for 30 min at RT. Reaction was monitored by TLC, solvent was evaporated under reduced pressure to get crude product which was purified by CC to afford pure (4-methyl-4-((3-(trifluoromethyl)phenyl)sulfonyl)tetrahydro-2H-pyran-2-yl)-methanol (0.58 g, 94%) as a white solid.

Step 9: 4-methyl-4-((3-(trifluoromethyl)phenyl)sulfonyl)tetrahydro-2H-pyran-2-carboxylic Acid To a cooled (0° C.) solution of CrO$_3$ (7.39 g, 73.96 mmol, 5.0 eq) in H$_2$O (14.2 mL) was added H$_2$SO$_4$ (7.7 mL) dropwise under vigorous stirring. This freshly prepared solution (Jones reagent) was slowly added to (4-methyl-4-((3-(trifluoromethyl)phenyl)sulfonyl)tetrahydro-2H-pyran-2-yl)methanol in acetone at 0° C. and then the RM was stirred for 1 h at RT. The RM was poured into ice water, diluted with EtOAc (400 mL) washed with water (2×100 mL), brine (100 mL) and the organic part was dried over Na$_2$SO$_4$, concentrated to get pure 4-methyl-4-((3-(trifluoromethyl)phenyl)sulfonyl)tetrahydro-2H-pyran-2-carboxylic acid (4.0 g, 77%) as off white solid.

Step 10&11: 4-methyl-4-((3-(trifluoromethyl)phenyl)sulfonyl)tetrahydro-2H-pyran-2-carboxamide To a solution of 4-methyl-4-((3-(trifluoromethyl)phenyl)sulfonyl)tetrahydro-2H-pyran-2-carboxylic acid (4.0 g, 11.36 mmol) in dry THF (102 mL) and TEA (4.74 mL, 34.09 mmol, 3.0 eq) was added ethyl chloroformate (2.16 mL, 22.72 mmol, 2.0 eq.) in THF (51 mL) at −10° C. The RM was allowed to stir at 0° C. for 1 h and then at RT for another 1 h. Then ammonia gas was purged into RM for 30 min. RM was diluted with DCM (100 mL) and solid residue was filtered off. Organic layer was washed with water (50 mL), sat. NaHCO$_3$ solution (50 mL), brine (50 mL) dried over Na$_2$SO$_4$ and concentrated under reduced pressure to give the crude product. The crude product was triturated with hexane to give the sufficiently pure desired 4-methyl-4-((3-(trifluoromethyl)phenyl)-sulfonyl)tetrahydro-2H-pyran-2-carboxamide (3.0 g, 75%) as off white solid.

Step 12: 4-methyl-4-((3-(trifluoromethyl)phenyl)sulfonyl)tetrahydro-2H-pyran-2-carbonitrile To a solution of 4-methyl-4-((3-(trifluoromethyl)phenyl)sulfonyl)tetrahydro-2H-pyran-2-carboxamide (1.5 g, 4.27 mmol) in dry DMF (5.3 mL) was added cyanuric chloride (0.788 g, 4.27 mmol, 1.0 eq) at 0° C. and then the RM was stirred at RT for 2 h. The RM was diluted with water (100 mL) and extracted with EtOAc (2×150 mL). Organic layer was separated, washed with water (50 mL), brine (50 mL) dried over Na$_2$SO$_4$ and concentrated under reduced pressure and the residue was purified by CC to afford 4-methyl-4-((3-(trifluoromethyl)phenyl)sulfonyl)tetrahydro-2H-pyran-2-carbonitrile (0.6 g, 42%) as off white solid.

Step 13: (Z)—N'-hydroxy-4-methyl-4-((3-(trifluoromethyl)phenyl)sulfonyl)tetrahydro-2H-pyran-2-carboximidamide To a well-stirred solution of hydroxylamine hydrochloride (0.375 g, 5.4 mmol, 1.5 eq.) and TEA (1.0 ml, 7.2 mmol, 2 eq.) in 1,4-dioxane (10 ml) was added a solution of 4-methyl-4-((3-(trifluoromethyl)phenyl)sulfonyl)tetrahydro-2H-pyran-2-carbonitrile (1.2 g, 3.6 mmol) in dioxane (10 mL) at RT and then the RM was heated to reflux for 3 h. The RM was concentrated under reduced pressure and the residue was purified by CC to afford (Z)—N'-hydroxy-4-methyl-4-((3-(trifluoromethyl)phenyl)sulfonyl)tetrahydro-2H-pyran-2-carboximidamide (1.0 g, 76%) as off white solid.

Step 14: (Z)—N'-((cyclopropanecarbonyl)oxy)-4-methyl-4-((3-(trifluoromethyl)phenyl)sulfonyl)tetrahydro-2H-pyran-2-carboximidamide To a stirring solution of (Z)—N'-hydroxy-4-methyl-4-((3-(trifluoromethyl)phenyl)sulfonyl)tetrahydro-2H-pyran-2-carboximidamide (0.6 g, 1.63 mmol) in dichloromethane (10 mL) under N₂ at 0° C. was added TEA (0.68 mL, 4.91 mmol, 3.0 eq). Then cyclopropylcarbonylchloride (0.134 mL, 1.47 mmol, 0.9 eq [dissolved in 10 mL of DCM]) was added drop wise at 0° C. and the resulting RM was stirred for 2 h at 0° C. The RM was diluted with water (50 mL), extracted with DCM (2×50 mL) combined organic part was washed with brine (50 mL), dried over Na₂SO₄, concentrated under reduced pressure and the residue was purified by CC to afford (Z)—N'-((cyclopropanecarbonyl)oxy)-4-methyl-4-((3-(trifluoromethyl)phenyl)sulfonyl)-tetrahydro-2H-pyran-2-carboximidamide (0.6 g, 84%) as off white solid.

Step 15: 5-cyclopropyl-3-(4-methyl-4-((3-(trifluoromethyl)phenyl)sulfonyl)tetrahydro-2H-pyran-2-yl)-1,2,4-oxadiazole A solution of (Z)—N'-((cyclopropanecarbonyl)oxy)-4-methyl-4-((3-(trifluoromethyl)phenyl)sulfonyl)tetrahydro-2H-pyran-2-carboximidamide (1.0 g, 2.3 mmol) in dry toluene (50 mL) was heated to reflux for 48 h. The RM was concentrated under reduced pressure to give the crude product which was purified by CC to afford mixture of diastereomers (0.8 g, 83%, as off white solid). Diastereomers separation was done by reverse phase prep HPLC method. Major isomer was characterized as cis diastereomer.

cis-isomer (SC-110, SC-111): 1H NMR (400 MHz, DMSO-d₆, δ ppm): 1.07-1.10 (2H), 1.23-1.26 (2H), 1.45-1.47 (4H), 1.71-1.75 (1H), 2.04-2.10 (1H), 2.18-2.24 (1H), 2.30-2.34 (1H), 3.67-3.72 (1H), 3.67-3.72 (1H), 3.94-3.99 (1H), 4.74-4.78 (1H), 7.94-7.99 (1H), 8.03 (s, 1H), 8.16-8.19 (1H), 8.22-8.24 (1H).

Two enantiomers of this single diastereomer were separated by chiral prep HPLC using a CHIRALPAK IC column and EtOH/DEA (100/0.1) as mobile phase to obtain two cis enantiomers SC-110 and SC-111.

SC-110: (0.162 g, off white solid, 1$^{st}$ eluted enantiomer).
SC-111 (0.119 g, off white solid, 2$^{nd}$ eluted enantiomer).

2-Methyl-5-[[4-methyl-4-[[3-(trifluoromethyl)phenyl]sulfonyl]-tetrahydro-pyran-2-yl]-methoxy]-pyridine (Example 20)

Step 1: (4-methyl-4-((3-(trifluoromethyl)phenyl)sulfonyl)tetrahydro-2H-pyran-2-yl))methyl Methanesulfonate To a solution of (4-methyl-4-((3-(trifluoromethyl)phenyl)sulfonyl)tetrahydro-2H-pyran-2-yl)methanol (1.5 g g, 4.4 mmol, 1 eq) in DCM (35 mL) was added TEA (1.9 mL, 12.87 mmol, 3 eq) followed by methane sulfonyl chloride (0.64 mL, 8.2 mmol, 1.5 eq) at 0° C. Then the RM was stirred at the same temperature for 1 h. The reaction was monitored by TLC. The RM was diluted with DCM (50 mL) and washed with water (3×20 mL), brine (20 mL), dried over Na₂SO₄ and concentrated under reduced pressure to give crude (4-methyl-4-((3-(trifluoromethyl)phenyl)sulfonyl)tetrahydro-2H-pyran-2-yl)methyl methanesulfonate (1.28 g, 82%) as yellow liquid which was used for the next step without further purification.

Step 2: 2-Methyl-5-[[4-methyl-4-[[3-(trifluoromethyl)phenyl]sulfonyl]-tetrahydro-pyran-2-yl]-methoxy]-pyridine To a stirring solution of 6-methyl-pyridine-3-ol (0.518 g, 4.7 mmol, 1 eq) in DMF (10 mL), at 0° C. under N₂ was added NaH (60% in mineral oil) (0.259 g, 6.49 mmol, 1.5 eq) portion wise and stirred at RT for 30 min. The RM was again cooled to 0° C. and (4-methyl-4-((3-(trifluoromethyl)phenyl)sulfonyl)tetrahydro-2H-pyran-2-yl)methyl methanesulfonate (1.8 g, 4.3 mmol, 1.0 eq) (dissolved in 10 mL of DMF) was added. The RM was stirred at RT for 16 h. After completion of the reaction it was quenched with crushed ice and diluted with EtOAc (200 mL). The organic layer was separated, washed with chilled water (3×20 mL), brine (50 mL) dried over Na₂SO₄ and concentrated under reduced pressure. Crude product was purified by CC to afford pure 2-methyl-5-[[4-methyl-4-[[3-(trifluoromethyl)phenyl]sulfonyl]-tetrahydro-pyran-2-yl]-methoxy]-pyridine (0.45 g, 75%) as a white solid.

Separation of diastereoisomers was done using reverse phase prep HPLC method. Major isomer was characterized as cis diastereomer (SC-112, SC-113) and minor isomer as trans (SC-114, 0.023 g).

trans-isomer (SC-114): 1H NMR (400 MHz, DMSO-d₆, δ ppm): 1.15 (s, 3H), 1.57-1.63 (1H), 1.71-1.80 (1H), 2.07-2.09 (1H), 2.13-2.19 (1H), 2.23 (s, 3H), 3.83-3.87 (1H), 3.98-4.06 (3H), 4.34-4.37 (1H), 7.16-7.19 (1H), 7.28-7.31 (1H), 7.94-7.98 (1H), 8.07 (s, 1H), 8.15-8.16 (1H), 8.20-8.24 (2H).

cis-isomer (SC-112, SC-113): 1H NMR (400 MHz, DMSO-d₆, δ ppm): 1.38-1.42 (4H), 1.58-1.62 (1H), 1.84-1.91 (1H), 1.96-2.04 (1H), 2.37 (s, 3H), 3.52-3.58 (1H), 3.80-3.85 (1H), 3.86-3.93 (1H), 3.95-4.04 (2H), 7.13-7.16 (1H), 7.25-7.28 (1H), 7.94-7.99 (1H), 8.03 (s, 1H), 8.11-8.12 (1H), 8.16-8.18 (1H), 8.22-8.25 (1H).

Two enantiomers of cis diastereomer were separated by chiral prep HPLC using a CHIRALPAK IA column and EtOH/DEA (100/0.1) as mobile phase to obtain two cis enantiomers SC-112 and SC-113.

SC-112: (0.123 g, off white solid, 1$^{st}$ eluted enantiomer).
SC-113 (0.105 g, off white solid, 2$^{nd}$ eluted enantiomer).

3-[4-Methyl-4-[[3-(trifluoromethyl)phenyl]sulfonyl]-tetrahydro-pyran-2-yl]-5-(trifluoromethyl)-pyridine (Example 21)

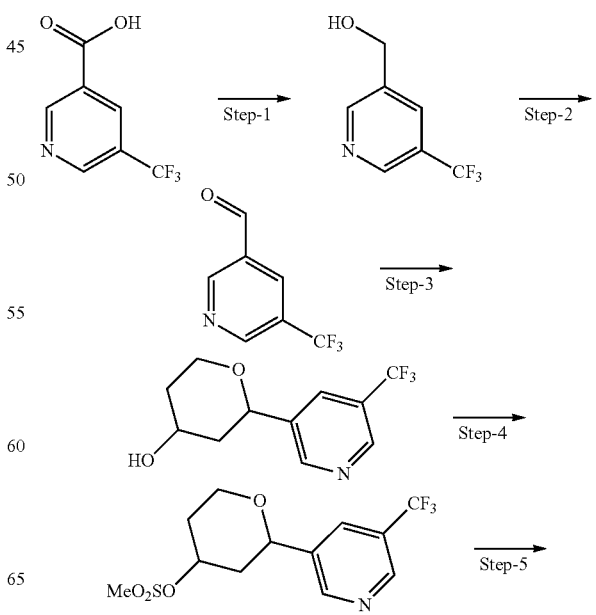

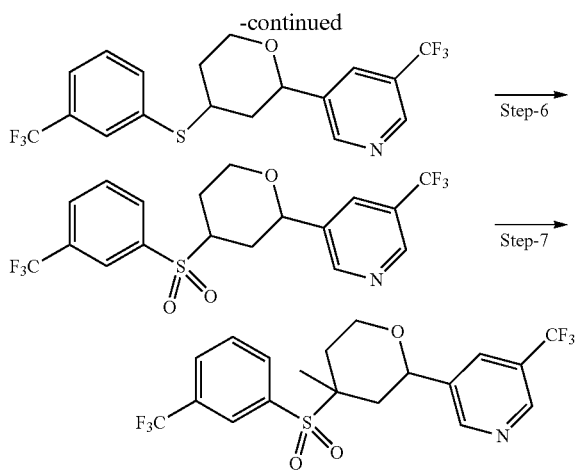

Step 1: (5-(trifluoromethyl)pyridin-3-yl)methanol

To a stirred solution of 5-(trifluoromethyl)nicotinic acid (0.5 g, 2.61 mmol, 1 eq) in benzene (20 mL) was added TEA (0.44 mL, 3.14 mmol, 1.2 eq) followed by ethylchloroformate (0.28 mL, 2.87 mmol, 1.1 eq) at RT and stirred for 1 h. The resulting precipitate was filtered and the filtrate was concentrated to afford mixed anhydride. This was used immediately in the next step.

To a stirred solution of LAH (0.109 g, 2.87 mmol, 1.1 eq) in THF (10 mL) was added above mixed anhydride in THF (10 mL) slowly at −78° C. and the mixture was stirred for 1 h at the same temperature. TLC showed completion of the reaction. Then the reaction mass was quenched with $H_2O$ and stirred for 30 min and the mixture was extracted with EtOAc (2×15 mL), washed with brine (10 mL), dried over $Na_2SO_4$ and concentrated. The crude product was purified by flash CC to afford (5-(trifluoromethyl)pyridin-3-yl)methanol (0.25 g, 54%) as yellow oil.

Step 2: 5-(trifluoromethyl)nicotinaldehyde

To a stirred solution of 5-(trifluoromethyl)pyridin-3-yl)methanol (0.2 g, 1.12 mmol, 1 eq) in DCM (6 mL) was added PCC (0.364 g, 1.68 mmol, 1.5 eq) and the mixture was stirred for 16 h at RT. TLC showed completion of the reaction. Then the reaction mass was filtered on celite bed and the filtrate volume was reduced to ~10% with $N_2$ (aldehyde was volatile) to afford 5-(trifluoromethyl)nicotinaldehyde (150 mg). This crude material was used in the next step without further purification.

Step 3: 2-(5-(trifluoromethyl)pyridin-3-yl)tetrahydro-2H-pyran-4-ol

Conc $H_2SO_4$ (0.7 mL) was added drop wise to an ice-cold mixture of 5-(trifluoromethyl)nicotinaldehyde (1.5 g, 8.5 mmol, 1 eq) and 3-butene-1-ol (1.6 mL, 17.1 mmol, 2 eq), the RM was stirred at RT for 16 h. TLC showed completion of the reaction. Then the RM was poured into ice, basified with sat $NaHCO_3$ solution and extracted with DCM (2×50 mL), washed with brine (20 mL), dried over anhydr. $Na_2SO_4$, concentrated under reduced pressure. The crude product was purified by CC to afford 2-(5-(trifluoromethyl)pyridin-3-yl)tetrahydro-2H-pyran-4-ol (0.5 g, 24%) as yellow liquid.

Step 4: 2-(5-(trifluoromethyl)pyridin-3-yl)tetrahydro-2H-pyran-4-yl Methanesulfonate Methanesulfonyl chloride (0.21 mL, 2.6 mmol, 1.3 eq) was added to an ice-cold solution of 2-(5-(trifluoromethyl)pyridin-3-yl)tetrahydro-2H-pyran-4-ol (0.5 g, 2 mmol, 1 eq) and TEA (0.42 mL, 3 mmol, 1.5 eq) in DCM (20 mL), and the RM was stirred at the same temperature for 2 h. Then the RM was quenched with $H_2O$ and extracted with DCM (2×20 mL), combined organic layer was dried over anhydr. $Na_2SO_4$ and concentrated to afford 2-(5-(trifluoromethyl)pyridin-3-yl)tetrahydro-2H-pyran-4-yl methanesulfonate (0.65 g) as a brown liquid. This crude product was used in the next step with out any purification.

Step 5: 3-(trifluoromethyl)-5-(4-((3-(trifluoromethyl)phenyl)thio)tetrahydro-2H-pyran-2-yl)pyridine $K_2CO_3$ (1.24 g, 9 mmol, 3 eq) was added to a solution of 2-(5-(trifluoromethyl)pyridin-3-yl)tetrahydro-2H-pyran-4-yl methanesulfonate (0.65 g 2 mmol, 1 eq) and 3-trifluoromethylthiol (0.41 mL, 3 mmol, 1.5 eq) in DMF (15 mL), and the reaction mass was heated to 80° C. and stirred for 2 h. Then the RM was cooled to RT and quenched with ice. The aq. layer was extracted with EtOAc (2×30 mL), combined organic layer was dried over anhydr. $Na_2SO_4$ and concentrated under reduced pressure to yield crude mass which was then purified by flash CC to afford 3-(trifluoromethyl)-5-(4-((3-(trifluoromethyl)phenyl)thio)tetrahydro-2H-pyran-2-yl)pyridine (0.55 g, 68%) as pale yellow oil.

Step 6: 3-(trifluoromethyl)-5-(4-((3-(trifluoromethyl)phenyl)sulfonyl)tetrahydro-2H-pyran-2-yl)pyridine To a stirred ice cold solution of 3-(trifluoromethyl)-5-(4-((3-(trifluoromethyl)phenyl)thio)tetrahydro-2H-pyran-2-yl)pyridine (0.55 g, 1.35 mmol, 1 eq) in THF:$H_2O$ (3:1) (20 mL) was added Oxone (3.31 g, 5.4 mmol, 4 eq) and the RM was stirred at RT for 1 h. Then the RM was diluted with $H_2O$, extracted with EtOAc (2×30 mL), combined organic layer was washed with $H_2O$ (30 mL), brine (30 mL), dried over anhydr. $Na_2SO_4$ and evaporated under reduced pressure to get crude product, which was further purified by flash CC to afford 3-(trifluoromethyl)-5-(4-((3-(trifluoromethyl)-phenyl)sulfonyl)tetrahydro-2H-pyran-2-yl)pyridine (0.55 g, 93%) as white solid.

Step 7: 3-(4-methyl-4-((3-(trifluoromethyl)phenyl)sulfonyl)tetrahydro-2H-pyran-2-yl)-5-(trifluoromethyl)pyridine To a stirred solution of 3-(trifluoromethyl)-5-(4-((3-(trifluoromethyl)phenyl)sulfonyl)tetrahydro-2H-pyran-2-yl)pyridine (0.6 g, 1.3 mmol, 1 eq) in THF (20 mL) was added t-BuOK (0.612 g, 5.4 mmol, 4 eq), 18-crown-6 (0.686 g, 2.6 mmol, 2 eq), followed by MeI (0.41 mmol, 6.5 mmol, 5 eq) at −78° C. The reaction mass was allowed to RT gradually and stirred at RT for 2 h. Then the reaction was diluted with $H_2O$, extracted with EtOAc (2×35 mL), combined organic layer was washed with $H_2O$ (20 mL), brine (20 mL), dried over anhydr. $Na_2SO_4$, evaporated under reduced pressure to get crude product which was further purified by flash CC to afford 3-(4-methyl-4-((3-(trifluoromethyl)phenyl)sulfonyl)tetrahydro-2H-pyran-2-yl)-5-(trifluoromethyl)pyridine (0.5 g) as a single diastereoisomer which was confirmed as cis diastereomer by NMR.

cis-isomer (SC-115, SC-116): 1H NMR (400 MHz, DMSO-$d_6$, δ ppm): 1.48-1.51 (4H), 1.87-1.98 (2H), 2.12-

2.17 (1H), 3.71-3.77 (1H), 4.08-4.12 (1H), 4.74-4.78 (1H), 7.92-7.96 (1H), 8.06 (s, 1H), 8.11 (s, 1H), 8.17-8.22 (2H).

Two enantiomers of cis diastereomer were separated by chiral prep HPLC using a CHIRALPAK IA column and Hexane/EtOAc/DEA (50/25/25) as mobile phase to obtain two cis enantiomers SC-115 and SC-116.

SC-115: (0.146 g, off white solid, 1$^{st}$ eluted enantiomer).
SC-116: (0.188 g, off white solid, 2$^{nd}$ eluted enantiomer).

2-Cyclopropyl-5-[[4-methyl-4-[[3-(trifluoromethyl) phenyl]sulfonyl]-tetrahydro-pyran-2-yl]-methoxy]-pyridine (Example 22)

To a solution of (4-methyl-4-((3-(trifluoromethyl)phenyl)sulfonyl)tetrahydro-2H-pyran-2-yl)methyl methanesulfonate (0.5 g, 1.2 mmol, 1 eq) in DMF (10 mL) was added 6-cyclopropyl-pyridin-3-ol (0.162 g, 1.2 mmol, 1 eq), $Cs_2CO_3$ (0.97 g, 3.0 mmol, 2.5 eq) and the mixture was heated up to 80° C. for 16 h. Then the reaction mass was cooled to RT and diluted with $H_2O$ (15 mL), extracted with EtOAc (2×20 mL), washed with $H_2O$ (15 mL), brine (15 mL), dried over $Na_2SO_4$ and concentrated. The crude product was purified by reverse phase prep. HPLC to give pure 2-cyclopropyl-5-((4-methyl-4-((3-(tri-fluoromethyl)phenyl)sulfonyl)tetrahydro-2H-pyran-2-yl)methoxy)pyridine (0.60 g) as a single diastereoisomer (cis).

cis-isomer (SC-117, SC-118): 1H NMR (400 MHz, DMSO-$d_6$, δ ppm): 0.79-0.80 (2H), 0.84-0.87 (2H), 1.38-1.42 (4H), 1.58-1.61 (1H), 1.84-1.90 (1H), 1.96-2.03 (2H), 3.51-3.58 (1H), 3.80-3.83 (1H), 3.88-3.93 (1H), 3.95-4.04 (2H), 7.17-7.19 (1H), 7.23-7.26 (1H), 7.94-7.99 (1H), 8.03 (s, 1H), 8.08-8.09 (1H), 8.15-8.18 (1H), 8.22-8.24 (1H).

Two enantiomers of cis racemic were separated by chiral HPLC, using CHIRALPAK IA column and EtOH/DEA: (100/0.1) as mobile phase to obtain two desired cis enantiomers (SC-117 and SC-117).

SC-117: (0.045 g, white solid, 1$^{st}$ eluted enantiomer).
SC-118: (0.035 g, white solid, 2$^{nd}$ eluted enantiomer).

3-Fluoro-5-methylsulfonyl-2-[4-methyl-4-[[3-(trifluoromethyl)phenyl]sulfonyl]-tetrahydro-pyran-2-yl]-pyridine (Example 23)

Step 1:
5-bromo-3-fluoro-N-methoxy-N-methylpicolinamide

To a solution of 5-bromo-3-fluoropicolinic acid (10.0 g, 45.45 mmol, 1 eq) in DMF (100 mL), EDC•HCl (12.68 g, 81.70 mmol, 1.8 eq), HOBT (9.82 g, 72.68 mmol, 1.6 eq) and TEA (16.88 mL, 117.02 mmol, 2.6 eq) was added at RT. After stirring the RM at RT for 10 min MeNH(OMe) (5.66 g, 58.95 mmol, 1.3 eq) was added and the mixture was stirred at RT for 16 h. After completion of reaction (monitored by TLC), RM was diluted with water (150 mL) and extracted with EtOAc (3×150 mL). The organic layer was washed with brine (100 mL), dried over $Na_2SO_4$, filtered and evaporated under reduced pressure to get the crude product which was purified by CC to afford 5-bromo-3-fluoro-N-methoxy-N-methylpicolinamide (6.0 g, 50%) as deep brown liquid.

Step 2: 5-bromo-3-fluoropicolinaldehyde

To a solution of 5-bromo-3-fluoro-N-methoxy-N-methylpicolinamide (8.0 g, 30.41 mmol eql) in THF (70 mL), the LAH solution (1M in THF) (15.2 mL, 15.2 mmol, 0.5 eq) was added at −70° C. for 15 min. Reaction was continued at the same temperature for another 2 h. After completion of reaction (monitored by TLC), RM was quenched with sat. $Na_2SO_4$ solution and extracted with EtOAc (3×250 mL). The organic layer was washed with water (300 mL), brine (200 mL), dried over $Na_2SO_4$, filtered and evaporated under reduced pressure to get the crude. The crude was purified by CC to afford 5-bromo-3-fluoropicolinaldehyde (5.5 g, 88.70%) as a brown gum.

Step 3: 2-(5-bromo-3-fluoropyridin-2-yl)tetrahydro-2H-pyran-4-ol

Conc $H_2SO_4$ (2.7 mL) was added drop wise to an ice-cold mixture of 3-buten-1-ol (4.75 mL, 52.84 mmol, 2 eq) and 5-bromo-3-fluoropicolinaldehyde (5.5 g, 26.96 mmol, 1 eq). The RM was allowed to warm to RT slowly and stirred for 16 h. Then the RM was poured into ice $H_2O$, basified with sat. $NaHCO_3$ solution and extracted with DCM (2×100 mL), combined organic layer was dried over anhydr. $Na_2SO_4$, concentrated under reduced pressure. The crude product was purified by CC to afford 2-(5-bromo-3-fluoropyridin-2-yl)tetrahydro-2H-pyran-4-ol (1.4 g, 20%) as deep brown liquid.

Step 4: 2-(5-bromo-3-fluoropyridin-2-yl)tetrahydro-2H-pyran-4-yl Methanesulfonate Methanesulfonyl chloride (0.62 mL, 7.6 mmol, 1.5 eq) was added to an ice-cold solution of 2-(5-bromo-3-fluoropyridin-2-yl)tetrahydro-2H-pyran-4-ol (1.4 g, 5.1 mmol, 1 eq) and TEA (2.2 mL, 15.32 mmol, 3 eq) in DCM (5 mL), the RM was stirred at the same temperature and for 2 h. The RM was quenched with $H_2O$. The aq. layer was extracted with DCM (2×100 mL), combined organic layer was washed with water and brine and dried over anhydr. $Na_2SO_4$, concentrated under reduced pressure to yield crude product which was purified by CC to afford 2-(5-bromo-3-fluoropyridin-2-yl)tetrahydro-2H-pyran-4-yl methanesulfonate (1.5 g, 83%) as colorless oil.

Step 5: 5-bromo-3-fluoro-2-(4-((3-(trifluoromethyl)phenyl)thio)tetrahydro-2H-pyran-2-yl)pyridine $K_2CO_3$ (1.75 g, 12.70 mmol, 3 eq) was added to the solution of 2-(5-bromo-3-fluoropyridin-2-yl)tetrahydro-2H-pyran-4-yl methanesulfonate (1.5 g 4.234 mmol, 1 eq), lithium iodide (0.56 g, 4.2 mmol) and 3-trifluoromethylthiol (0.9 mL, 6.352 mmol, 1.5 eq) in DMF (30 mL). The RM was stirred at 80° C. for 2 h. Then the RM was cooled to RT and then quenched with ice. The aq. layer was extracted with EtOAc (2×150 mL), combined organic layer was dried over anhydr. $Na_2SO_4$ and concentrated under reduced pressure to give crude product which was then purified by CC to afford 5-bromo-3-fluoro-2-(4-((3-(trifluoromethyl)phenyl)thio)tetrahydro-2H-pyran-2-yl)pyridine (1.3 g, 72%) as pale yellow oil.

Step 6: 5-bromo-3-fluoro-2-(4-((3-(trifluoromethyl)phenyl)sulfonyl)tetrahydro-2H-pyran-2-yl)pyridine To a stirred ice cold solution of 5-bromo-3-fluoro-2-(4-((3-(trifluoromethyl)phenyl)thio)tetrahydro-2H-pyran-2-yl)pyridine (1.4 g, 3.2 mmol, 1 eq) in THF:$H_2O$ (3:1) oxone (7.8 g, 12.83 mmol, 4 eq) was added and RM was stirred at RT for 2 h. After completion RM was evaporated and residue was diluted with water and extracted with EtOAc. The combined organic layer was washed with water, brine and dried over anhydr. $Na_2SO_4$. The solvent was evaporated under reduced pressure to get crude product which was further purified by CC to afford 5-bromo-3-fluoro-2-(4-((3-(trifluoromethyl)phenyl)thio)tetrahydro-2H-pyran-2-yl) pyridine (1.0 g, 88%) as white solid.

Step 6: 5-bromo-3-fluoro-2-(4-methyl-4-((3-(trifluoromethyl)phenyl)sulfonyl)tetrahydro-2H-pyran-2-yl)pyridine To a stirred solution of 5-bromo-3-fluoro-2-(4-((3-(trifluoromethyl)phenyl)thio)tetrahydro-2H-pyran-2-yl)pyridine (0.35 g, 0.74 mmol, 1 eq) in dry THF (20 mL), t-BuOK (0.33 g, 2.9 mmol, 4 eq) and 18-crown-6 (0.78 g, 2.9 mmol, 4 eq) was added at −78° C. under Ar and stirred for 5 min. Then methyl iodide (0.53 g, 3.7 mmol, 4 eq) was added at the same temperature and the mixture was stirred for 1 h. The RM was allowed to stir for 1 h at RT. The RM was quenched with water and extracted with EtOAc (3×50 mL). The combined organic layer was washed with sat. brine and dried over anhydr. $Na_2SO_4$ and evaporated under reduced pressure to get crude product which was further purified by CC to afford 5-bromo-3-fluoro-2-(4-methyl-4-((3-(trifluoromethyl)phenyl)sulfonyl)-tetrahydro-2H-pyran-2-yl)pyridine (0.68 g, 62%) as off white solid.

Step 7: 3-fluoro-2-(4-methyl-4-((3-(trifluoromethyl)phenyl)sulfonyl)tetrahydro-2H-pyran-2-yl)-5-(methylsulfonyl)pyridine To a stirred solution of 5-bromo-3-fluoro-2-(4-methyl-4-((3-(trifluoromethyl)phenyl)sulfonyl)tetrahydro-2H-pyran-2-yl)pyridine (0.68 g, 1.41 mmol, 1 eq) in DMSO (10 mL) was added sodium methanesulfinate (0.14 g, 1.41 mmol, 1.2 eq), and L-proline sodium salt (0.038 g, 0.281 mmol, 0.2 eq). The RM was degassed for 10 min, then CuI (0.028 g, 0.15 mmol, 0.1 eq) was added and the RM was heated to 100° C. for 16 h in a sealed tube. After completion of reaction (monitored by TLC), the reaction mass was diluted with $H_2O$ (40 mL), extracted with EtOAc (2×50 mL), organic layer was washed with $H_2O$ (60 mL), brine (60 mL), dried over anhydr. $Na_2SO_4$, filtered and evaporated under reduced pressure to get crude product which was further purified by flash CC to afford 3-fluoro-2-(4-methyl-4-((3-(trifluoromethyl)phenyl)sulfonyl)tetrahydro-2H-pyran-2-yl)-5-(methylsulfonyl)pyridine as single diastereomer and this was considered as cis (determined by NMR experiments).

cis-isomer (SC-119, SC-120): 1H NMR (400 MHz, $CDCl_3$, δ ppm): 1.22-1.26 (1H), 1.59-1.63 (4H), 1.79-1.82 (1H), 2.31-2.39 (1H), 2.47-2.53 (1H), 3.12 (s, 3H), 3.74-3.80 (1H), 4.17-4.22 (1H), 4.94-4.97 (1H), 7.72-7.74 (1H), 7.92-7.94 (2H), 8.06-8.08 (1H), 8.13 (s, 1H), 8.94 (s, 1H).

Enantiomers of cis diastereomer were directly separated in normal phase chiral prep HPLC using a CHIRALPAK IA column and EtOH/DEA: (100/0.1) to obtain two cis enantiomers (SC-119 and SC-120).

SC-119: (0.022 g, white solid, $1^{st}$ eluted enantiomer).
SC-120: (0.041 g, white solid, $2^{nd}$ eluted enantiomer).

2-[4-Methyl-4-[[3-(trifluoromethyl)phenyl]sulfonyl]-tetrahydro-pyran-2-yl]-5-(trifluoromethyl)-[1,3,4]oxadiazole (Example 24)

Step 1: Ethyl 4-methyl-4-((3-(trifluoromethyl)phenyl)sulfonyl)tetrahydro-2H-pyran-2-carboxylate To a stirred solution of 4-methyl-4-((3-(trifluoromethyl)phenyl)sulfonyl)tetrahydro-2H-pyran-2-carboxylic acid (5 g, 14.2 mmol) in EtOH (50 mL) was added $H_2SO_4$ (1 mL) and the mixture was heated to reflux for 16 h. Then the RM was concentrated and the crude product was basified with aq. $NaHCO_3$ solution, extracted with EtOAc (2×50 mL), washed with brine (30 mL), dried over $Na_2SO_4$ and concentrated to afford ethyl 4-methyl-4-((3-(trifluoromethyl)phenyl)sulfonyl)tetrahydro-2H-pyran-2-carboxylate (4.5 g) as an off white solid. This crude material was used for the next step with out any purification.

Step 2: 4-methyl-4-((3-(trifluoromethyl)phenyl)sulfonyl)tetrahydro-2H-pyran-2-carbohydrazide To a stirred solution of ethyl 4-methyl-4-((3-(trifluoromethyl)phenyl)sulfonyl)tetrahydro-2H-pyran-2-carboxylate (6 g, 15.8 mmol, 1 eq) in toluene (60 mL) was added hydrazine hydrate solution (1.18 mL, 23.7 mmol, 1.5 eq) and the mixture was heated to reflux for 16 h. Then EtOH was evaporated and the residue was diluted with EtOAc (100 mL), washed with $H_2O$ (2×30 mL), brine (30 mL), dried over $Na_2SO_4$ and concentrated to afford 4-methyl-4-((3-(trifluoromethyl)phenyl)sulfonyl)tetrahydro-2H-pyran-2-carbohydrazide (5.3 g, 91%) as white solid.

Step 3: 4-methyl-N'-(2,2,2-trifluoroacetyl)-4-((3-(trifluoromethyl)phenyl)sulfonyl)tetrahydro-2H-pyran-2-carbohydrazide To a stirred solution of 4-methyl-4-((3-(trifluoromethyl)phenyl)sulfonyl)tetrahydro-2H-pyran-2-carbohydrazide (1 g, 2.7 mmol, 1 eq) in DCM (30 mL) was added TEA (1.14 mL, 8.19 mmol, 3 eq), catalytic amount of DMAP, followed by trifluoroaceticanhydride (0.42 mL, 3.0 mmol, 3 eq) at 0° C. and the mixture was stirred for 2 h at RT. Then the reaction mass was quenched with $H_2O$ and extracted with DCM (2×25 mL), washed with brine (20 mL), dried over $Na_2SO_4$ and concentrated. The crude product was purified by CC to afford 4-methyl-4-((3-(trifluoromethyl)phenyl)sulfonyl)tetrahydro-2H-pyran-2-carbohydrazide (700 mg) as an off white solid.

Step 4: 2-(4-methyl-4-((3-(trifluoromethyl)phenyl)sulfonyl)tetrahydro-2H-pyran-2-yl)-5-(trifluoromethyl)-1,3,4-oxadiazole To a stirred solution of 4-methyl-4-((3-(trifluoromethyl)phenyl)sulfonyl)tetrahydro-2H-pyran-2-carbohydrazide (0.6 g, 1.3 mmol, 1 eq) in toluene (20 mL) was added $POCl_3$ (3 mL) and heated to reflux for 16 h. Then $POCl_3$ was evaporated and the crude product was basified with sat. $NaHCO_3$ solution and extracted with EtOAc (2×20 mL), washed with $H_2O$ (2×10 mL), brine (10 mL), dried over $Na_2SO_4$ and concentrated. The crude product was purified by CC to afford mixture of diastereomers (300 mg) as an off white solid. This diasteriomeric mixture was separated by reverse phase prep. HPLC to get cis diastereomer (SC-121, SC-122).

cis-isomer (SC-121, SC-122): 1H NMR (400 MHz, $CDCl_3$, δ ppm): 8.25 (d, J=7.84 Hz, 1H), 8.21 (d, J=7.92 Hz, 1H), 8.07 (s, 1H), 8.0 (t, J=15.7 Hz, 1H), 5.15 (dd, J=13.8 Hz, 1H), 4.06 (dd, J=16.48 Hz, 1H), 3.81 (t, J=22.88 Hz, 1H), 2.36 (t, J=24.8 Hz, 1H), 2.14 (m, 1H), 1.98 (d, J=12.8 Hz, 1H), 1.48 (s, 4H).

Two enantiomers of cis diastereoisomer was separated by chiral HPLC, using chiralcel OJ-H column and Hexane/EtOH/DEA: (90/10/0.1) as mobile phase to obtain two desired cis enantiomers (SC-121 and SC-122).

SC-121: (61 mg, white solid, $1^{st}$ eluted enantiomer).
SC-122: (43 mg, white solid, $2^{nd}$ eluted enantiomer).

2-(Difluoro-methyl)-5-[4-methyl-4-[[3-(trifluoromethyl)phenyl]sulfonyl]-tetrahydro-pyran-2-yl]-[1,3,4]oxadiazole (Example 25)

Step 1: N'-(2,2-difluoroacetyl)-4-methyl-4-((3-(trifluoromethyl)phenyl)sulfonyl)tetrahydro-2H-pyran-2-carbohydrazide To a stirred solution of 4-methyl-4-((3-(trifluoromethyl)phenyl)sulfonyl)tetrahydro-2H-pyran-2-carbohydrazide (1 g, 2.7 mmol, 1 eq) in DCM (30 mL) was added TEA (1.14 mL, 8.2 mmol, 3 eq), catalytic amount of DMAP, followed by difluoroaceticanhydride (0.37 mL, 3.0 mmol, 3 eq) at 0° C. and the mixture was stirred for 2 h at RT. Then the reaction mass was quenched with $H_2O$ and extracted with DCM (2×25 mL), washed with brine (20 mL), dried over $Na_2SO_4$ and concentrated. The crude product was purified by CC to afford N'-(2,2-difluoroacetyl)-4-methyl-4-((3-(trifluoromethyl)phenyl)sulfonyl)tetra-hydro-2H-pyran-2-carbohydrazide (650 mg) as an off white solid.

Step 2: 2-(difluoromethyl)-5-(4-methyl-4-((3-(trifluoromethyl)phenyl)sulfonyl)tetrahydro-2H-pyran-2-yl)-1,3,4-oxadiazole To a stirred solution of N'-(2,2-difluoroacetyl)-4-methyl-4-((3-(trifluoromethyl)phenyl)sulfonyl)tetrahydro-2H-pyran-2-carbohydrazide (0.65 g, 1.5 mmol, 1 eq) in toluene (22 mL) was added $POCl_3$ (3.5 mL) and the mixture was heated to reflux for 16 h. Then $POCl_3$ was evaporated and the residue was basified with sat. $NaHCO_3$ solution and extracted with EtOAc (2×25 mL), washed with $H_2O$ (2×10 mL), brine (15 mL), dried over $Na_2SO_4$ and concentrated. The crude product was purified by CC to afford mixture of diastereomers (270 mg) as an off white solid. This diasteriomers were separated by reverse phase prep. HPLC to afford one major diastereomer which was determined as cis isomer.

cis isomer (SC-123, SC-124): $^1$H NMR (400 MHz, DMSO-$d_6$): δ 8.25 (dd, J=25.64 Hz, 2H), 8.07 (s, 1H), 8.0 (t, J=15.72 Hz, 1H), 7.5 (m, 1H), 5.10 (d, J=10.28 Hz, 1H), 4.04 (dd, J=15.6 Hz, 1H), 3.81 (t, J=23.3 Hz, 1H), 2.35 (t, J=24.64 Hz, 1H), 2.14 (m, 1H), 1.98 (d, J=13.04 Hz, 1H), 1.48 (s, 4H).

Two enantiomers of cis diastereoisomer were separated by chiral HPLC, using chiralpak ID column and Hexane/EtOH/DEA: (90/10/0.1) as mobile phase to obtain two desired cis enantiomers (SC-123 and SC-124).

SC-123: (31.8 mg, white solid, $1^{st}$ eluted enantiomer).
SC-124: (34.2 mg, white solid, $2^{nd}$ eluted enantiomer).

2-Isopropyl-5-[4-methyl-4-[[3-(trifluoromethyl)phenyl]sulfonyl]-tetrahydro-pyran-2-yl]-[1,3,4]oxadiazole (Example 26)

Step 1: N'-isobutyryl-4-methyl-4-((3-(trifluoromethyl)phenyl)sulfonyl)tetrahydro-2H-pyran-2-carbohydrazide To a stirred solution of 4-methyl-4-((3-(trifluoromethyl)phenyl)sulfonyl)tetrahydro-2H-pyran-2-carbohydrazide (1 g, 2.7 mmol, 1 eq) in DCM (30 mL) was added TEA (1.14 mL, 8.2 mmol, 3 eq), followed by isobutyrylchloride (0.32 mL, 3.0 mmol, 3 eq) at 0° C. and the mixture was stirred for 2 h at RT. Then the reaction mass was quenched with $H_2O$ and extracted with DCM (2×25 mL), washed with brine (20 mL), dried over $Na_2SO_4$ and concentrated. The crude product was purified by CC to afford N'-isobutyryl-4-methyl-4-((3-(trifluoromethyl)phenyl)sulfonyl)tetrahydro-2H-pyran-2-carbohydrazide (670 mg) as an off white solid.

Step 2: 2-isopropyl-5-(4-methyl-4-((3-(trifluoromethyl)phenyl)sulfonyl)tetrahydro-2H-pyran-2-yl)-1,3,4-oxadiazole To a stirred solution of N'-isobutyryl-4-methyl-4-((3-(trifluoromethyl)phenyl)sulfonyl)tetrahydro-2H-pyran-2-carbohydrazide (0.6 g, 1.4 mmol, 1 eq) in toluene (20 mL) was added $POCl_3$ (3 mL) and heated to reflux for 16 h. Then $POCl_3$ was evaporated and the crude was basified with sat. $NaHCO_3$ solution and extracted with EtOAc (2×25 mL), washed with $H_2O$ (2×10 mL), brine (15 mL), dried over $Na_2SO_4$ and concentrated. The crude product was purified by CC to afford mixture of diastereomers (260 mg) as an off white solid. This diasteriomers were separated by reverse phase prep. HPLC to afford one major diastereomer which was determined as cis isomer by NMR.

cis-isomer (SC-125, SC-126): $^1$H NMR (400 MHz, DMSO-$d_6$): δ 8.25 (d, J=7.8 Hz, 1H), 8.2 (d, J=7.88, 1H) 8.06 (s, 1H), 7.99 (t, J=15.76 Hz, 1H), 4.94 (dd, J=13.8 Hz, 1H), 4.01 (dd, J=17.04 Hz, 1H), 3.77 (t, J=22.88 Hz, 1H), 3.32 (m, 1H), 2.32 (m, 1H), 2.11 (m, 1H), 1.90 (d, J=12.92 Hz, 1H), 1.48 (s, 4H), 1.29 (d, J=7.6 Hz, 6H).

Two enantiomers of cis diastereoisomer were separated by chiral HPLC, using chiralpak IC column and Hexane/EtOH/DEA: (80/20/0.1) as mobile phase to obtain two desired cis enantiomers (SC-125 and SC-126)

SC-125: (36 mg, white solid, $1^{st}$ eluted enantiomer).
SC-126: (36 mg, white solid, $2^{nd}$ eluted enantiomer).

2-Cyclopropyl-5-[4-methyl-4-[[3-(trifluoromethyl)phenyl]sulfonyl]-tetrahydro-pyran-2-yl]-[1,3,4]oxadiazole (Example 27)

Step 1: N'-(cyclopropanecarbonyl)-4-methyl-4-((3-(trifluoromethyl)phenyl)sulfonyl)tetrahydro-2H-pyran-2-carbohydrazide To a stirred solution of 4-methyl-4-((3-(trifluoromethyl)phenyl)sulfonyl)tetrahydro-2H-pyran-2-carbohydrazide (2 g, 5.5 mmol, 1 eq) in DMF (30 mL), was added HATU (2.7 g, 7.1 mmol, 1.3 eq), DIPEA (2.38 mL, 13.7 mmol, 2.5 eq) followed by cyclopropylcarboxylic acid (0.56 g, 6.6 mmol, 1.2 eq) and the mixture was stirred for 3 h. Then the RM was quenched with ice and extracted with EtOAc (2×50 mL), washed with $H_2O$ (2×20 mL), brine (20 mL), dried over $Na_2SO_4$ and concentrated. The crude product was purified by CC to afford N'-(cyclopropanecarbonyl)-4-methyl-4-((3-(trifluoromethyl)-phenyl)sulfonyl)tetrahydro-2H-pyran-2-carbohydrazide (1.4 g, 60%) as an off white solid.

Step 2: 2-cyclopropyl-5-(4-methyl-4-((3-(trifluoromethyl)phenyl)sulfonyl)tetrahydro-2H-pyran-2-yl)-1,3,4-oxadiazole To a stirred solution of N'-(cyclopropanecarbonyl)-4-methyl-4-((3-(trifluoromethyl)phenyl)sulfonyl)tetrahydro-2H-pyran-2-carbohydrazide (3.5 g, 8.1 mmol, 1 eq) in toluene (60 mL) was added $POCl_3$ (14 mL) and the mixture was heated to reflux for 16 h. Then $POCl_3$ was evaporated and the residue was basified with sat. $NaHCO_3$ solution and extracted with EtOAc (2×60 mL), washed with $H_2O$ (2×20 mL), brine (20 mL), dried over $Na_2SO_4$ and concentrated. The crude product was purified by CC to afford mixture of diastereomers (2 g) as an off white solid. This diasteriomers were separated by reverse phase prep. HPLC to afford one cis diastereomer and one trans diastereomer (233 mg). The relative stereochemistry of both isomers was confirmed by NOE experiments.

trans-isomer (SC-127): $^1$H NMR (400 MHz, DMSO-$d_6$): δ 8.26 (m, 2H), 8.11 (s, 1H), 7.98 (t, J=15.56 Hz, 1H), 5.3 (dd, J=10.04 Hz, 1H), 4.14 (t, J=20.48 Hz, 1H), 3.92 (m, 1H), 2.46 (m, 1H), 2.25 (m, 1H), 2.11 (m, 2H) 1.83 (m, 1H), 1.17 (m, 5H), 1.07 (m, 2H).

cis-isomer (SC-128, SC-129): $^1$H NMR (400 MHz, DMSO-d$_6$): δ 8.24 (d, J=7.76 Hz, 1H), 8.20 (d, J=7.84 Hz, 1H), 8.06 (s, 1H), 7.99 (t, J=15.6 Hz, 1H), 4.89 (d, J=10.6 Hz, 1H), 4.0 (dd, J=16.52 Hz, 1H), 3.75 (t, J=23.24 Hz, 1H), 2.23 (m, 2H), 2.08 (m, 1H), 1.87 (d, J=12.7 Hz, 1H), 1.45 (s, 4H), 1.14 (m, 2H), 0.98 (m, 2H).

Two enantiomers of cis isomer were separated by chiral HPLC, using chiral pack 1A column and Hexane/EtOH/DEA: (80/20/0.1) as mobile phase to obtain two desired cis enantiomers (SC-128 and SC-129).

SC-128: (552 mg, white solid, 1$^{st}$ eluted enantiomer).
SC-129: (550 mg, white solid, 2$^{nd}$ eluted enantiomer).

3-Chloro-5-methylsulfonyl-2-[4-methyl-4-[[3-(trifluoromethyl)phenyl]sulfonyl]-tetrahydro-pyran-2-yl]-pyridine (Example 28)

Step 1: 5-bromo-3-chloro-N-methoxy-N-methylpicolinamide

To a solution of 5-bromo-3-chloropicolinic acid (15.0 g, 63.424 mmol, 1 eq) in DMF (150 mL), EDCl (17.72 g, 114.16 mmol, 1.8 eq), HOBT (13.71 g, 101.47 mmol, 1.6 eq) and DIPEA (23.0 mL, 164.9 mmol, 2.6 eq) was added at RT. After stirring the RM at RT for 10 min MeNH(OMe) (7.95 g, 82.45 mmol, 1.3 eq) was added and the mixture was stirred at RT for 16 h. After completion of reaction (monitored by TLC), RM was diluted with water (250 mL) and extracted with EtOAc (3×250 mL). The organic layer was washed with brine (500 mL), dried over Na$_2$SO$_4$, filtered and evaporated under reduced pressure to get the crude product which was purified by flash CC to afford 5-bromo-3-chloro-N-methoxy-N-methylpicolinamide (9.0 g, 51%) as white solid.

Step 2: 5-bromo-3-chloropicolinaldehyde

To a solution of 5-bromo-3-chloro-N-methoxy-N-methylpicolinamide (9.0 g, 32.3 mmol, 1 eq) in THF (100 mL), the LAH solution (1M in THF) (16.12 mL, 16.1 mmol, 0.5 eq) was added at −70° C. for 15 min. Reaction was continued at the same temperature for another 2 h. After completion of reaction (monitored by TLC), RM was quenched with sat. Na$_2$SO$_4$ solution and extracted with EtOAc (3×250 mL). The organic layer was washed with water (500 mL), brine (500 mL), dried over Na$_2$SO$_4$, filtered and the solvent was evaporated under reduced pressure to get the crude product which was purified by flash CC to afford 5-bromo-3-chloropicolinaldehyde (5.0 g, 71%) as brown gum.

Step 3: 2-(5-bromo-3-chloropyridin-2-yl)tetrahydro-2H-pyran-4-ol

Conc. sulfuric acid (5.0 mL) was added to an ice-cold (0° C.) mixture of 5-bromo-3-chloropicolinaldehyde (5 g, 22.7 mmol, 1 eq) and 3-butene-1-ol (4.1 mL, 45.5 mmol, 2 eq) and the mixture was stirred for 16 h at RT. The reaction mass was poured into crushed ice, neutralized by addition of solid NaHCO$_3$, extracted with EtOAc (2×100 mL) and the organic layer was washed with brine (150 ml). Combined organic layer was dried over anhydr. Na$_2$SO$_4$, filtered and the solvent was evaporated under reduced pressure to get crude mass which was then purified by combiflash CC to afford 2-(5-bromo-3-chloropyridin-2-yl)tetrahydro-2H-pyran-4-ol (1.1 g, 17%) as colorless oil.

Step 4: 2-(5-bromo-3-chloropyridin-2-yl)tetrahydro-2H-pyran-4-yl Methanesulfonate Methanesulfonyl chloride (0.55 mL, 7.2 mmol, 1.5 eq) was added to an ice-cold solution of 2-(5-bromo-3-chloropyridin-2-yl)tetrahydro-2H-pyran-4-ol (1.4 g, 4.8 mmol, 1 eq) and TEA (2.0 mL, 14.4 mmol, 3 eq) in DCM (15 mL). The RM was stirred at the same temperature for 3 h. The RM was quenched with H$_2$O (50 mL). The aq. layer was extracted with DCM (2×100 mL), combined organic layer was dried over anhydr. Na$_2$SO$_4$, filtered and the solvent was evaporated under reduced pressure to give crude product which was purified by combiflash CC to afford 2-(5-bromo-3-chloropyridin-2-yl)tetrahydro-2H-pyran-4-yl methanesulfonate (1.6 g, 90%) as colorless oil.

Step 5: 5-bromo-3-chloro-2-(4-((3-(trifluoromethyl)phenyl)thio)tetrahydro-2H-pyran-2-yl)pyridine K$_2$CO$_3$ (1.79 g, 13.0 mmol, 3 eq) was added to the solution of 2-(5-bromo-3-chloropyridin-2-yl)tetrahydro-2H-pyran-4-yl methanesulfonate (1.6 g, 4.3 mmol, 1 eq) and triflouromethylbenzenethiol (1.15 g, 6.5 mmol, 1.5 eq) in DMF (20 mL). The RM was stirred at 60° C. for 2 h. Then the RM was cooled to RT and then quenched with ice. The RM was extracted with EtOAc (2×50 mL) and combined organic layers were washed repeatedly with cold water (75 mL) and brine (75 mL). Combined organic layer was dried over anhydr. Na$_2$SO$_4$, filtered and the solvent was evaporated under reduced pressure to give crude mass which was then purified by combiflash CC to afford 5-bromo-3-chloro-2-(4-((3-(trifluoromethyl)phenyl)thio)tetrahydro-2H-pyran-2-yl)pyridine (1.2 g, 61.5%) as white solid.

Step 6: 5-bromo-3-chloro-2-(4-((3-(trifluoromethyl)phenyl)sulfonyl)tetrahydro-2H-pyran-2-yl)pyridine To a stirred ice cold solution of 5-bromo-3-chloro-2-(4-((3-(trifluoromethyl)phenyl)thio)tetrahydro-2H-pyran-2-yl)pyridine (1.1 g, 2.4 mmol, 1 eq) in THF:H$_2$O (3:1) (50 mL) oxone (5.97 g, 9.7 mmol, 4 eq) was added and RM was stirred at RT for 2 h. After completion of the reaction it was diluted with water (50 mL) and extracted with EtOAc (3×75 mL). The combined organic layer was washed with water (100 mL), sat. brine (100 mL), dried over Na$_2$SO$_4$, filtered and the solvent was evaporated under reduced pressure to get crude product, which was further purified by combiflash CC to afford 5-bromo-3-chloro-2-(4-((3-(trifluoro-methyl)phenyl)sulfonyl)tetrahydro-2H-pyran-2-yl)pyridine (1.1 g, 85%) as white solid.

Step 7: 5-bromo-3-chloro-2-(4-methyl-4-((3-(trifluoromethyl)phenyl)sulfonyl)tetrahydro-2H-pyran-2-yl)pyridine To a stirred solution of 5-bromo-3-chloro-2-(4-((3-(trifluoromethyl)phenyl)sulfonyl)tetrahydro-2H-pyran-2-yl)pyridine (1.0 g, 2.1 mmol, 1 eq) in THF (40 mL) was added t-BuOK (0.93 g, 8.3 mmol, 4 eq), 18-crown-6 (2.2 g, 8.3 mmol, 4 eq), followed by MeI (0.646 ml, 10.33 mmol, 5 eq) at −78° C. and stirred for 1 h at the same temperature. Then reaction mass was allowed to RT gradually and stirred at RT for further 1 h. After completion of reaction (monitored by TLC), the reaction was diluted with H$_2$O (50 mL), extracted with EtOAc (2×75 mL). Combined organic layer was washed with H$_2$O (100 mL), brine (100 mL), dried over anhydr. Na$_2$SO$_4$, filtered and the solvent was evaporated under reduced pressure to get crude product which was further purified by combiflash CC to afford 5-bromo-3-chloro-2-(4-methyl-4-((3-(trifluoromethyl)-phenyl)sulfonyl)tetrahydro-2H-pyran-2-yl)pyridine (0.75 g, 74%) as off white solid.

Step 8: 3-chloro-2-(4-methyl-4-((3-(trifluoromethyl)phenyl)sulfonyl)tetrahydro-2H-pyran-2-yl)-5-(methylsulfonyl)pyridine To a stirred solution of 5-bromo-3-chloro-2-(4-methyl-4-((3-(trifluoromethyl)phenyl)sulfonyl)tetrahydro-2H-pyran-2-yl)pyridine (0.75 g, 1.51 mmol, 1 eq) in DMSO (7 mL) was added sodium methanesulfinate (0.184 g, 1.81 mmol, 1.2 eq), and L-proline sodium salt (0.041 g, 0.30 mmol, 0.2 eq). The RM was degassed for 10 min and then CuI (28.6 mg, 0.15 mmol, 0.1 eq) was added and the RM was heated to 100° C. for 16 h in a sealed tube. After completion of reaction (monitored by TLC), the reaction mass was diluted with $H_2O$ (40 mL), extracted with EtOAc (2×50 mL), organic layer was washed with $H_2O$ (60 mL), brine (60 mL), dried over anhydr. $Na_2SO_4$, filtered and evaporated under reduced pressure to get crude product which was further purified by combiflash CC to afford 3-chloro-2-(4-methyl-4-((3-(trifluoromethyl)phenyl)-sulfonyl)tetrahydro-2H-pyran-2-yl)-5-(methylsulfonyl)pyridine as mixture of diastereomers (95:5 diastereomeric ratio, 460 mg). The major diastereomer was isolated by reverse phase prep HPLC and this was considered as cis (determined by NMR experiments). cis-isomer (SC-130, SC-131): 1H NMR (400 MHz, $CDCl_3$, δ ppm): 1.45-1.50 (4H), 1.71-1.75 (1H), 2.10-2.17 (1H), 2.58-2.67 (1H), 3.95 (s, 3H), 3.73-3.79 (1H), 4.00-4.04 (1H), 5.02-5.04 (1H), 7.94-7.97 (1H), 8.07 (s, 1H), 8.18-8.20 (1H), 8.22-8.24 (1H), 8.46-8.47 (1H), 9.00-9.01 (1H).

Enantiomers of cis diastereomer were directly separated in normal phase chiral prep HPLC using a CHIRALCEL OJ-H column and MeOH/DEA: (100/0.1) to obtain two cis enantiomers (SC-130 and SC-131).

SC-130: (0.105 g, white solid, $1^{st}$ eluted enantiomer)/specific rotation $[\alpha]_D^{24.0}$ −26.6° (c 0.70; DCM).

SC-131: (0.110 g, white solid, $2^{nd}$ eluted enantiomer)/specific rotation $[\alpha]_D^{24.3}$ +34.9° (c 0.58; DCM).

2-Cyclopropyl-5-[[4-methyl-4-[[3-(trifluoromethyl)phenyl]sulfonyl]-tetrahydro-pyran-2-yl]-methoxy]-pyrazine (Example 29)

Step 1: 2-chloro-5-((4-methyl-4-((3-(trifluoromethyl)phenyl)sulfonyl)tetrahydro-2H-pyran-2-yl)methoxy)pyrazine To a stirred solution of (4-methyl-4-((3-(trifluoromethyl)phenyl)sulfonyl)tetrahydro-2H-pyran-2-yl)methanol (1 g, 2.9 mmol, 1 eq) in toluene (20 mL) was added 2,5-dichloropyrazine (0.3 mL, 2.9 mmol, 1 eq), $Cs_2CO_3$ (1.8 g, 5.9 mmol, 2 eq) and the mixture was heated to reflux for 48 h. Then the reaction mass was cooled to RT, diluted with $H_2O$ (15 mL), extracted with EtOAc (2×30 mL), washed with brine (20 mL), dried over $Na_2SO_4$ and concentrated. The crude product was purified by CC to afford 2-chloro-5-((4-methyl-4-((3-(trifluoromethyl)phenyl)sulfonyl)tetrahydro-2H-pyran-2-yl)methoxy)pyrazine (0.7 g, 53%) as yellow gum.

Step 2: 2-cyclopropyl-5-((4-methyl-4-((3-(trifluoromethyl)phenyl)sulfonyl)tetrahydro-2H-pyran-2-yl)methoxy)pyrazine To a stirred solution of 2-chloro-5-((4-methyl-4-((3-(trifluoromethyl)phenyl)sulfonyl)tetrahydro-2H-pyran-2-yl)methoxy)pyrazine (1.6 g, 3 mmol, 1 eq.) in toluene/$H_2O$ (20 mL) was added $Cs_2CO_3$ (2.9 g, 8.9 mmol, 3 eq), potassium cyclopropyl trifluoroborate (0.526 g, 3 mmol, 1 eq), and the solution was degassed with Ar for 10 min. Then di-(1-adamantyl)-n-butylphosphine (0.032 g, 0.089 mmol, 0.03 eq.) and Pd(OAc)$_2$ (0.015 g, 0.08 mmol, 0.0.2 eq) were added. Then the RM was heated to 120° C. for 16 h in a sealed tube. After completion of the reaction (monitored by TLC), the RM was filtered on celite bed, washed with EtOAc (2×35 mL), the filtrate was washed with $H_2O$ (25 mL), brine (25 mL), dried over $Na_2SO_4$ and concentrated. The crude product was purified by reverse phase prep. HPLC to give pure cis-diastereomer (0.30 g).

cis-isomer (SC-132, SC-133): $^1$H NMR (400 MHz, $CDCl_3$): 0.90-0.97 (4H), 1.49-1.54 (4H), 1.62-1.66 (1H), 1.94-2.06 (2H), 2.18-2.26 (1H), 3.55-3.61 (1H), 3.80-3.84 (1H), 4.03-4.07 (1H), 4.25-4.33 (2H), 7.71-7.75 (1H), 7.92-7.95 (1H), 8.03-8.06 (1H), 8.08 (s, 1H), 8.12 (bs, 1H).

Two enantiomers of cis isomer were separated by chiral HPLC, using chiral pack-IC column and EtOH/DEA: (100/0.1) as mobile phase to obtain two desired cis enantiomers (SC-132 and SC-133).

SC-132: (0.075 g, white solid, $1^{st}$ eluted enantiomer).

SC-133: (0.055 g, white solid, $2^{nd}$ eluted enantiomer).

3-Cyclopropyl-5-[4-methyl-4-[[3-(trifluoromethyl)phenyl]sulfonyl]-tetrahydro-pyran-2-yl]-pyridine (Example 17)

Step 1: 2-(5-bromopyridin-3-yl)tetrahydro-2H-pyran-4-ol

Conc. sulfuric acid (3.8 mL) was added to an ice-cold (0° C.) mixture of 5-bromonicotinaldehyde (5 g, 26.9 mmol, 1 eq) and 3-butene-1-ol (4.6 mL, 53.8 mmol, 2 eq) and the mixture was stirred for 14 h at RT. The reaction mass was poured into crushed ice, neutralized by addition of solid $NaHCO_3$, extracted with DCM (2×150 mL) and the organic layer was washed with brine. Combined organic layer was dried over anhydr. $Na_2SO_4$, concentrated under reduced pressure to give crude mass which was then purified by CC to afford 2-(5-bromopyridin-3-yl)tetrahydro-2H-pyran-4-ol (4.6 g, 67%) as a colorless oil.

Step 2: 2-(5-bromopyridin-3-yl)tetrahydro-2H-pyran-4-yl Methanesulfonate

Methanesulfonyl chloride (2.7 mL, 26.8 mmol, 1.5 eq) was added to an ice-cold solution of 2-(5-bromopyridin-3-yl)tetrahydro-2H-pyran-4-ol (4.6 g, 17.9 mmol, 1 eq) and TEA (7.5 mL, 53.7 mmol, 3 eq) in DCM (5 mL), the RM was stirred at the same temperature and for 2 h. The RM was quenched with $H_2O$. The aq. layer was extracted with DCM (2×100 mL), combined organic layer was dried over anhydr. $Na_2SO_4$, concentrated under reduced pressure to give crude product which was purified by CC to afford 2-(5-bromopyridin-3-yl)tetrahydro-2H-pyran-4-yl methanesulfonate (0.6 g, 92%) as a colorless oil.

Step 3: 3-bromo-5-(4-((3-(trifluoromethyl)phenyl) thio)tetrahydro-2H-pyran-2-yl)pyridine $K_2CO_3$ (3.8 g, 28.0 mmol, 2 eq) was added to the solution of 2-(5-bromopyridin-3-yl)tetrahydro-2H-pyran-4-yl methanesulfonate (4.7 g, 14.0 mmol, 1 eq) and trifloromethylbenzenethiol (2.5 g, 14.0 mmol, 1.2 eq) in DMF (10 mL). The RM was stirred at 100° C. for 16 h. Then the RM was cooled to RT and then quenched with ice. The aq. layer was extracted with EtOAc (2×100 mL) and washed repeatedly with cold water and brine. Combined organic layer was dried over anhydr. $Na_2SO_4$, concentrated under reduced pressure to give crude mass which was then purified by CC to afford 3-bromo-5-(4-((3-(trifluoromethyl)phenyl)thio)tetrahydro-2H-pyran-2-yl)pyridine (3.3 g, 57%) as a white solid.

Step 4: 3-bromo-5-(4-((3-(trifluoromethyl)phenyl) sulfonyl)tetrahydro-2H-pyran-2-yl)pyridine To a stirred ice cold solution of 3-bromo-5-(4-((3-(trifluoromethyl)phenyl)thio)tetrahydro-2H-pyran-2-yl)pyridine (3.3 g, 7.9 mmol, 1 eq) in $THF:H_2O$ (3:1) oxone (19.4 g, 31.6 mmol, 4 eq) was added and RM was stirred at RT for 2 h. The RM was diluted with water and extracted with EtOAc. The combined organic layer was washed with water, sat. brine and dried over anhydr. $Na_2SO_4$ and evaporated under reduced pressure to get crude product which was further purified by CC to afford 3-bromo-5-(4-((3-(trifluoromethyl)phenyl)sulfonyl)tetrahydro-2H-pyran-2-yl)pyridine (2.7 g, 66%) as a white solid.

Step 5: 3-bromo-5-(4-methyl-4-((3-(trifluoromethyl) phenyl)sulfonyl)tetrahydro-2H-pyran-2-yl)pyridine To a stirred solution of 3-bromo-5-(4-((3-(trifluoromethyl)phenyl)sulfonyl)tetrahydro-2H-pyran-2-yl)pyridine (1.35 g, 3.0 mmol, 1 eq) in THF (20 mL) was added t-BuOK (0.68 g, 6.0 mmol, 2 eq), 18-crown-6 (1.6 g, 6.0 mmol, 2 eq), followed by MeI (1.5 g, 11.1 mmol, 5 eq) at −78° C. and stirred for 1 h at the same temperature. Then reaction mass was allowed to RT gradually and stirred for further 1 h. Then the RM was diluted with $H_2O$, extracted with EtOAc (2×35 mL), combined organic layer was washed with $H_2O$ (20 mL), brine (20 mL), dried over anhydr. $Na_2SO_4$, evaporated under reduced pressure to get crude product which was further purified by CC to afford 3-bromo-5-(4-methyl-4-((3-(trifluoromethyl)phenyl)sulfonyl)tetrahydro-2H-pyran-2-yl) pyridine (0.65 g, 65%) as an off white solid.

Step 6: 3-cyclopropyl-5-(4-methyl-4-((3-(trifluoromethyl)phenyl)sulfonyl)tetrahydro-2H-pyran-2-yl) pyridine To a stirred solution of 3-bromo-5-(4-methyl-4-((3-(trifluoromethyl)phenyl)sulfonyl)tetrahydro-2H-pyran-2-yl) pyridine (1.5 g, 3.24 mmol, 1 eq) in toluene (45 ml) in a sealed tube was added NaBr (0.33 g, 3.24 mmol, 1 eq), KF (0.75 g, 12.96 mmol, 4 eq) followed by cyclopropyl borinic acid (0.42 g, 4.86 mmol, 1.5 eq). The mixture was then degassed for 15 min and $Pd(PPh_3)_4$ (0.375 g, 0.324 mmol, 0.1 eq) and X-Phos (0.156 g, 0.324 mmol, 0.1 eq) was added. The RM was degassed again for 10 min before closing the seal tube tightly. The mixture was heated to 90° C. for 16 h. Then the reaction mass was diluted with $H_2O$, extracted with EtOAc (2×50 mL), organic layer was washed with $H_2O$ (50 mL), brine (50 mL), dried over anhydr. $Na_2SO_4$ and evaporated under reduced pressure to get crude product which was further purified by CC to afford 3-cyclopropyl-5-(4-methyl-4-((3-(trifluoromethyl)-phenyl)sulfonyl)tetrahydro-2H-pyran-2-yl)pyridine as a mixture diastereomers (0.45 g). Diastereomers were separated by reverse phase prep. HPLC to obtain pure cis isomer (0.310 g).

cis-isomer (SC-325, SC-326): $^1H$ NMR (400 MHz, $CDCl_3$): 0.70-0.73 (2H), 0.96-1.02 (2H), 1.46-1.49 (4H), 1.71-1.75 (1H), 1.87-1.97 (2H), 2.07-2.11 (1H), 3.69-3.72 (1H), 4.03-4.07 (1H), 4.55-4.58 (1H), 7.92-9.96 (1H), 8.05 (s, 1H), 8.16-8.22 (2H), 8.28-8.31 (2H).

The enantiomers of cis isomer were separated by SFC using a CHIRALPAK IA column to give SC-325 and SC-326.

SC-325: (0.115 g, white solid, $1^{st}$ eluted enantiomer).
SC-326: (0.124 g, white solid, $2^{nd}$ eluted enantiomer).

3-Chloro-2-(4-methyl-4-((3-(trifluoromethyl)phenyl) sulfonyl)tetrahydrofuran-2-yl)-5-(methylsulfonyl) pyridine (Example 30)

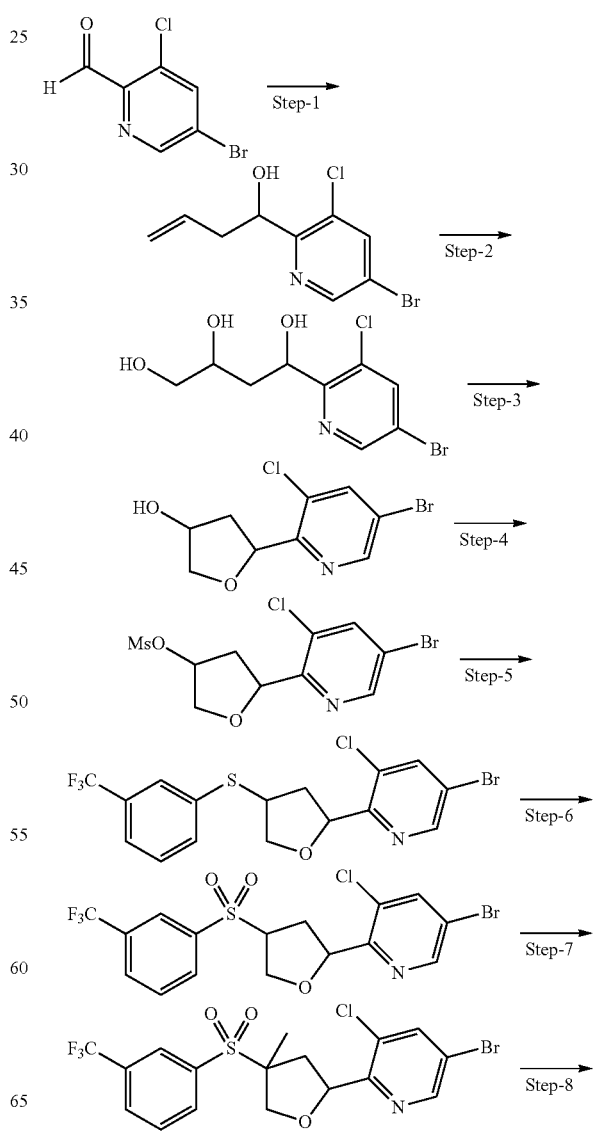

-continued

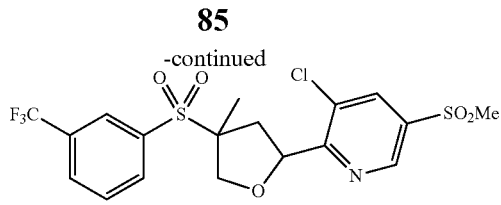

Step 1: 1-(5-bromo-3-chloropyridin-2-yl)but-3-en-1-ol

To a stirred solution of 5-bromo-3-chloropicolinaldehyde (8.5 g, 38.6 mmol, 1 eq) in THF (135 mL) was added allylbromide (5.0 mL, 90.6 mmol, 1.5 eq) and sat. NH$_4$Cl solution followed by zinc dust (5.0 g, 77.3 mmol, 2 eq). After complete addition the RM was stirred for 2 h at RT. Then the RM was diluted with water (100 mL) and extracted with EtOAc (3×100 mL), dried over anhydr. Na$_2$SO$_4$ and evaporated under reduced pressure to give crude product which was purified by CC to afford 1-(5-bromo-3-chloropyridin-2-yl)but-3-en-1-ol (4.5 g, 44%) as an off white solid.

Step 2: 4-(5-bromo-3-chloropyridin-2-yl)butane-1,2,4-triol

To a stirred solution of 1-(5-bromo-3-chloropyridin-2-yl)but-3-en-1-ol (1.8 g, 6.8 mmol, 1 eq) in a mixture of acetone (38 mL) and water (16 mL) was added NMO at 0° C. (1.08 g, 8.91 mmol, 1.3 eq) followed by OsO$_4$ (0.017 g, 0.067 mmol, 0.012 eq) and the mixture was stirred for 16 h at RT. After completion of the reaction the RM was concentrated, diluted with EtOAc (100 mL), washed with water (2×50 mL), dried over anhydr. Na$_2$SO$_4$, and the solvent was evaporated under reduced pressure to give crude product as a black oil which was purified by CC to afford 4-(5-bromo-3-chloropyridin-2-yl)butane-1,2,4-triol (1.4 g, 70%) as an off white solid.

Step 3: 5-(5-bromo-3-chloropyridin-2-yl)tetrahydrofuran-3-ol

To a stirred solution of 1-(5-bromo-3-chloropyridin-2-yl)butane-1,2,4-triol (7.5 g, 25.3 mmol, 1 eq) in DCE (250 mL) was added triflic acid (6 mL) and the mixture was heated to reflux for 16 h. After completion of the reaction (monitored by TLC), the RM was neutralized with sat. NaHCO$_3$ solution, extracted with DCM (2×75 mL), washed with brine (50 mL), dried over Na$_2$SO$_4$ and concentrated to give light yellow oil which was purified by CC to afford 5-(5-bromo-3-chloropyridin-2-yl)tetrahydrofuran-3-ol (2.5 g, 36%) as an off white solid.

Step 4: 5-(5-bromo-3-chloropyridin-2-yl)tetrahydrofuran-3-yl Methanesulfonate Methanesulfonyl chloride (1.2 mL, 13.5 mmol, 1.5 eq) was added to an ice-cold solution of 5-(5-bromo-3-chloropyridin-2-yl)tetrahydrofuran-3-ol (2.5 g, 8.99 mmol, 1 eq) and TEA (4 mL, 26.96 mmol, 3 eq) in DCM (40 mL). The RM was stirred at the same temperature and for 2 h. The RM was quenched with H$_2$O (100 mL). The aq. layer was extracted with DCM (2×200 mL), combined organic layer was dried over anhydr. Na$_2$SO$_4$, filtered and evaporated under reduced pressure to give crude product which was purified by CC to afford 5-(5-bromo-3-chloropyridin-2-yl)tetrahydrofuran-3-yl methanesulfonate (2.5 g, 42%) as colorless oil.

Step 5: 5-bromo-3-chloro-2-(4-((3-(trifluoromethyl)phenyl)thio)tetrahydrofuran-2-yl)pyridine K$_2$CO$_3$ (5.6 g, 40.6 mmol, 3 eq) was added to a solution of 5-(5-bromo-3-chloropyridin-2-yl)tetrahydrofuran-3-yl methanesulfonate (4.8 g, 13.48 mmol, 1 eq) and trifloromethylbenzenethiol (3.6 g, 20.2 mmol, 1.5 eq) in DMF (60 mL). The RM was stirred at 90° C. for 16 h. Then the RM was cooled to RT and then quenched with ice. The aq. layer was extracted with EtOAc (2×150 mL), washed repeatedly with cold water (150 ml) and brine (150 mL). Combined organic layer was dried over anhydr. Na$_2$SO$_4$, filtered and evaporated under reduced pressure to give crude mass which was then purified by using CC to afford 5-bromo-3-chloro-2-(4-((3-(trifluoromethyl)phenyl)thio)-tetrahydrofuran-2-yl)pyridine (5.2 g, 88%) as a colorless oil.

Step 6: 5-bromo-3-chloro-2-(4-((3-(trifluoromethyl)phenyl)sulfonyl)tetrahydrofuran-2-yl)pyridine To a stirred solution of 5-bromo-3-chloro-2-(4-((3-(trifluoromethyl)phenyl)thio)tetrahydrofuran-2-yl)pyridine (6.0 g, 13.69 mmol, 1 eq) in THF:H$_2$O (3:1) (100 mL), oxone (33.6 g, 54.7 mmol, 4 eq) was added and the RM was stirred at RT for 1 h. The RM was diluted with water (100 mL) and extracted with EtOAc (3×150 mL). The combined organic layer was washed with water (100 mL), brine (100 mL), dried over Na$_2$SO$_4$, filtered and evaporated under reduced pressure to get crude product, which was further purified by CC to afford 5-bromo-3-chloro-2-(4-((3-(trifluoromethyl)phenyl)sulfonyl)tetrahydrofuran-2-yl)pyridine (2.5 g, 39%) as white solid.

Step 7: 5-bromo-3-chloro-2-(4-methyl-4-((3-(trifluoromethyl)phenyl)sulfonyl)tetrahydrofuran-2-yl)pyridine To a stirred solution of 5-bromo-3-chloro-2-(4-((3-(trifluoromethyl)phenyl)sulfonyl)tetrahydrofuran-2-yl)pyridine (1.6 g, 3.40 mmol, 1 eq) in THF (100 mL) was added t-BuOK (1M in THF; 5.1 mL; 5.10 mmol, 1.5 eq), 18-crown-6 (1.37 g, 5.10 mmol, 1.5 eq), followed by MeI (0.42 mL, 6.80 mmol, 2 eq) at −100° C. and the mixture was stirred for 5 min at the same temperature. After completion of reaction (monitored by TLC), the RM was diluted with H$_2$O (50 mL), extracted with EtOAc (2×75 ml). Combined organic layer was washed with H$_2$O (100 mL), brine (100 mL), dried over anhydr. Na$_2$SO$_4$, filtered and the solvent was evaporated under reduced pressure to get crude product which was further purified by CC to afford 5-bromo-3-chloro-2-(4-methyl-4-((3-(trifluoromethyl)phenyl)sulfonyl)tetrahydrofuran-2-yl)pyridine (1.2 g, 73%) as an off white solid.

Step 8: 3-chloro-2-(4-methyl-4-((3-(trifluoromethyl)phenyl)sulfonyl)tetrahydrofuran-2-yl)-5-(methylsulfonyl)pyridine To a stirred solution of 5-bromo-3-chloro-2-(4-methyl-4-((3-(trifluoromethyl)phenyl)sulfonyl)tetrahydrofuran-2-yl)pyridine (1.6 g, 3.30 mmol, 1 eq) in DMSO (30 mL) was added sodium methanesulfinate (404 mg, 3.96 mmol, 1.2 eq), and L-proline sodium salt (90 mg, 0.661 mmol, 0.2 eq)

and the mixture was degassed with $N_2$ for 10 min. CuI (62 mg, 0.330 mmol, 0.1 eq) was added and the RM was heated to 100° C. for 16 h in a sealed tube. After completion of reaction (monitored by TLC), the reaction mass was diluted with $H_2O$ (75 mL), extracted with EtOAc (2×75 mL), organic layer was washed with $H_2O$ (60 mL), brine (60 mL), dried over anhydr. $Na_2SO_4$, filtered and the solvent was evaporated under reduced pressure to get crude product which was further purified by CC to afford 3-chloro-2-(4-methyl-4-((3-(tri-fluoromethyl)phenyl)sulfonyl)tetrahydrofuran-2-yl)-5-(methylsulfonyl)pyridine as a mixture of diastereoisomers. Diastereomers were separated by reverse phase prep HPLC to give trans isomer (600 mg) and cis isomer (100 mg) and the relative configuration of both isomers was confirmed by NOE experiment.

cis-isomer (SC-150, SC-151): $^1$H NMR (400 MHz, DMSO-$d_6$): δ 8.89 (s, 1H), 8.44 (s, 1H), 8.25 (d, J=7.56 Hz, 1H), 8.19 (d, J=7.68 Hz, 1H), 8.11 (s, 1H), 7.94 (t, J=15.6 Hz, 1H), 5.52 (t, J=15.16 Hz, 1H), 4.54 (d, J=9.64 Hz, 1H), 3.78 (d, J=9.68 Hz, 1H), 3.38 (s, 3H), 3.11 (m, 1H), 2.31 (m, 1H), 1.56 (s, 3H).

Two enantiomers of cis isomer was separated by chiral HPLC, using chiral pack 1A column and EtOH/DEA: (100/0.1) as mobile phase to obtain two desired cis enantiomers (SC-150 and SC-151).

SC-150: (27 mg, white solid, $1^{st}$ eluted enantiomer).
SC-151: (24 mg, white solid, $2^{nd}$ eluted enantiomer).
trans-isomer (SC-152, SC-153): $^1$H NMR (400 MHz, DMSO-$d_6$): δ 8.98 (s, 1H), 8.45 (s, 1H), 8.35 (d, J=7.8 Hz, 1H), 8.25 (d, J=8.88 Hz, 2H), 7.99 (t, J=14.44 Hz, 1H), 5.33 (t, J=14.28 Hz, 1H), 4.47 (d, J=10.28 Hz, 1H), 3.91 (d, J=10.28 Hz, 1H), 3.37 (s, 3H), 3.08 (m, 1H), 2.43 (m, 1H), 1.51 (s, 3H).

Two enantiomers of trans isomer was separated by chiral HPLC, using chiral pack 1C column and Hexane/EtOH/DEA: (80/20/0.1) as mobile phase to obtain two desired cis enantiomers (SC-152 and SC-153).

SC-152: (220 mg, white solid, $1^{st}$ eluted enantiomer).
SC-153: (210 mg, white solid, $2^{nd}$ eluted enantiomer).

3-Methyl-2-(4-methyl-4-((3-(trifluoromethyl)phenyl)sulfonyl)tetrahydrofuran-2-yl)-5-(methylsulfonyl)pyridine (Example 31)

Starting from 5-bromo-3-methylpicolinaldehyde, 3-methyl-2-(4-methyl-4-((3-(trifluoromethyl)phenyl)sulfonyl)tetrahydrofuran-2-yl)-5-(methylsulfonyl)pyridine was synthesized in analogy to the protocol described for 3-chloro-2-(4-methyl-4-((3-(trifluoromethyl)phenyl)sulfonyl)tetrahydrofuran-2-yl)-5-(methylsulfonyl)pyridine (Example XX). Diasteromeric mixture of 3-methyl-2-(4-methyl-4-((3-(trifluoromethyl)-phenyl)sulfonyl)tetrahydrofuran-2-yl)-5-(methylsulfonyl)pyridine was separated by reverse phase prep HPLC purification to give cis (120 mg) and trans diasteromers (560 mg).

cis-isomer (SC-154, SC-155): $^1$H NMR (400 MHz, DMSO-$d_6$): δ 8.76 (s, 1H), 8.24 (d, J=7.8 Hz, 1H), 8.11-8.17 (m, 3H), 7.90 (t, J=7.76 Hz, 1H), 5.32-5.36 (m, 1H), 4.51 (d, J=9.8 Hz, 1H), 3.73 (d, J=9.84 Hz, 1H), 3.29 (s, 3H), 3.19 (t, J=3.08 Hz, 1H), 2.40 (s, 3H), 2.17-2.21 (m, 1H), 1.56 (s, 3H).

Two enantiomers of cis isomer was separated by chiral HPLC, using chiral pack 1A column and EtOH/DEA: (100/0.1) as mobile phase to obtain two desired cis enantiomers (SC-154 and SC-155).

SC-154: (32 mg, off white solid, $1^{st}$ eluted enantiomer).
SC-155: (25 mg, off white solid, $2^{nd}$ eluted enantiomer).

trans-isomer (SC-156, SC-157): $^1$H NMR (400 MHz, DMSO-$d_6$): δ 8.84 (s, 1H), 8.33 (d, J=7.8 Hz, 1H), 8.22-8.25 (m, 2H), 8.15 (s, 1H), 7.97 (t, J=7.8 Hz, 1H), 5.20 (t, J=7.32 Hz, 1H), 4.42 (d, J=10.28 Hz, 1H), 3.81 (d, J=10.24 Hz 1H), 3.29 (s, 3H), 2.95-3.01 (m, 1H), 2.54-2.59 (m, 1H), 2.39 (s, 3H), 1.50 (s, 3H).

Two enantiomers of trans isomer was separated by chiral HPLC, using chiral pack 1C column and Hexane/EtOH/DEA: (80/20/0.1) as mobile phase to obtain two desired cis enantiomers (SC-156 and SC-157).

SC-156: (213 mg, off white solid, $1^{st}$ eluted enantiomer).
SC-157: (146 mg, off white solid, $2^{nd}$ eluted enantiomer).

4-Cyclopropyl-2-[4-methyl-4-[[3-(trifluoromethyl)phenyl]sulfonyl]-tetrahydro-pyran-2-yl]-oxazole (Example 32)

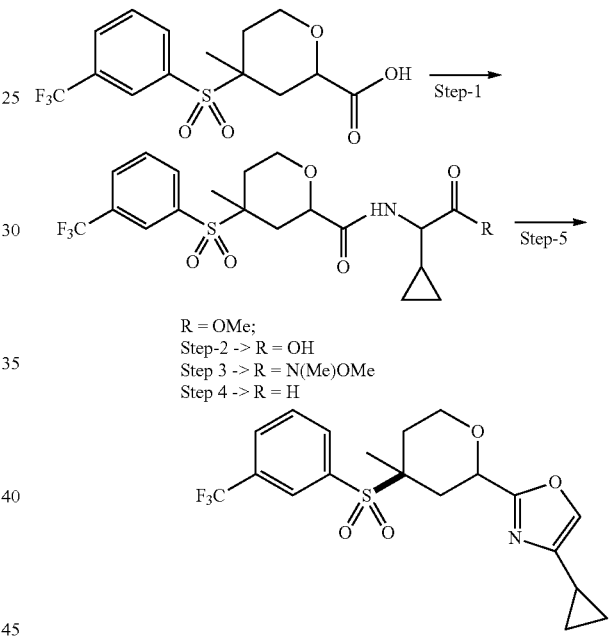

Step 1: Methyl 2-cyclopropyl-2-(4-methyl-4-((3-(trifluoromethyl)phenyl)sulfonyl)tetrahydro-2H-pyran-2-carboxamido)acetate To a cold stirring solution of methyl 2-amino-2-cyclopropylacetate (0.072 g, 0.558 mmol, 1 eq) in DMF (4 mL) was added diisopropylethylamine (0.29 mL, 1.68 mmol, 3 eq). The RM then stirred for 10 min at RT. HATU (0.319 g, 0.839 mmol, 1.5 eq) and 4-methyl-4-((3-(trifluoromethyl)phenyl)sulfonyl)tetrahydro-2H-pyran-2-carboxylic acid (0.2 g, 0.56 mmol, 1 eq) was then added to the RM at 0° C. and finally the RM stirred for 12 h at RT. The RM was diluted with EtOAc (40 mL) and washed with water (5×10 mL) and brine (20 mL). The organic layer was dried over $Na_2SO_4$ and concentrated under reduced pressure to get crude product which was purified by CC to afford pure methyl 2-cyclopropyl-2-(4-methyl-4-((3-(trifluoromethyl) phenyl)sulfonyl) tetrahydro-2H-pyran-2-carboxamido)acetate (0.15 g, 57%) as yellow liquid.

Step 2: 2-cyclopropyl-2-(4-methyl-4-((3-(trifluoromethyl)phenyl)sulfonyl)tetrahydro-2H-pyran-2-carboxamido)acetic Acid To a stirred solution of methyl 2-cyclopropyl-2-(4-methyl-4-((3-(trifluoromethyl)phenyl)sulfonyl)tetrahydro-2H-pyran-2-carboxamido)acetate (0.11 g, 0.237 mmol, 1 eq) in (2:1:1) ratio of THF (4 mL), MeOH (2 mL) and water (2 mL), LiOH (0.024 g, 0.575 mmol, 2.5 eq) was added. The RM was stirred for 2 h at RT. The reaction was monitored by TLC. The RM was concentrated under reduced pressure, diluted with water (20 mL) and washed with diethylether (2×10 mL). The aq. layer was acidified with 2N HCl solution, and the desired product was extracted with DCM (3×15 mL), dried over anhydr. $Na_2SO_4$ and concentrated under reduced pressure to afford methyl 2-cyclopropyl-2-(4-methyl-4-((3-(trifluoromethyl)phenyl)sulfonyl)tetrahydro-2H-pyran-2-carboxamido)acetate (0.08 g, 75%) as white solid.

Step 3: N-(1-cyclopropyl-2-(methoxy(methyl)amino)-2-oxoethyl)-4-methyl-4-((3-(trifluoromethyl)phenyl)sulfonyl)tetrahydro-2H-pyran-2-carboxamide To a cold stirring solution of N, O-dimethylhydroxylamine hydrochloride (0.126 g, 1.3 mmol, 1.8 eq) in DMF (5 mL) was added DIPEA (0.19 mL, 1.09 mmol, 1.5 eq). The RM was then stirred for 10 min at RT. HATU (0.305 g, 0.802 mmol, 1.1 eq) and compound 5 2-cyclopropyl-2-(4-methyl-4-((3-(trifluoromethyl)phenyl)sulfonyl)tetrahydro-2H-pyran-2-carboxamido)acetic acid (0.33 g, 0.73 mmol, 1 eq) was then added to the RM at 0° C. and finally the RM was stirred for 12 h at RT. The RM was diluted with EtOAc (40 mL) and washed with water (5×10 mL) and brine (20 mL). The organic layer was dried over $Na_2SO_4$ concentrated under reduced pressure to give crude product which was purified by CC to afford pure N-(1-cyclopropyl-2-(methoxy(methyl)amino)-2-oxoethyl)-4-methyl-4-((3-(trifluoromethyl)phenyl)sulfonyl)tetrahydro-2H-pyran-2-carboxamide (0.230 g, 64%) as yellow liquid.

Step 4: N-(1-cyclopropyl-2-oxoethyl)-4-methyl-4-((3-(trifluoromethyl)phenyl)sulfonyl)tetrahydro-2H-pyran-2-carboxamide To a stirred solution of LAH (0.55 ml, 0.55 mmol, 1 eq) in THF (4 mL), was added N-(1-cyclopropyl-2-(methoxy(methyl)amino)-2-oxoethyl)-4-methyl-4-((3-(trifluoromethyl)phenyl)sulfonyl)tetrahydro-2H-pyran-2-carboxamide (0.275 g, 0.55 mmol, 1 eq) at −78° C. The RM was stirred for 20 min at 0° C. The reaction was monitored by TLC. After completion the RM was cooled to −78° C., and it was quenched with aq. $KHSO_4$ solution. The RM was diluted with EtOAc (40 mL), washed with water (2×10 mL) and brine (10 mL), dried over anhydr. $Na_2SO_4$ and the solvent was evaporated under reduced pressure to give crude N-(1-cyclopropyl-2-oxoethyl)-4-methyl-4-((3-(trifluoromethyl)phenyl)sulfonyl)tetrahydro-2H-pyran-2-carboxamide (0.16 g, 70%) as light yellow liquid.

Step 5: 4-cyclopropyl-2-[4-methyl-4-[[3-(trifluoromethyl)phenyl]sulfonyl]-tetrahydro-pyran-2-yl]-oxazole To a stirred solution of N-(1-cyclopropyl-2-oxoethyl)-4-methyl-4-((3-(trifluoromethyl)phenyl)sulfonyl)tetrahydro-2H-pyran-2-carboxamide (0.65 g, 1.5 mmol, 1 eq) in toluene (20 mL), $POCl_3$ (4.5 mL, 4.5 mmol, 2.5 eq) was added. The RM was stirred for 12 h at 65° C. Reaction was monitored by TLC, the solvent was evaporated and the RM was diluted with EtOAc (70 mL), washed with water (2×20 mL) and brine (20 mL), dried over anhydr. $Na_2SO_4$ and the solvent was evaporated under reduced pressure to give crude product which was purified by CC to afford pure 4-cyclopropyl-2-[4-methyl-4-[[3-(trifluoromethyl)phenyl]sulfonyl]-tetrahydro-pyran-2-yl]-oxazole (0.055 g, 9%) as yellow liquid.

SC-158: 1H NMR (400 MHz, DMSO-$d_6$, δ ppm): 0.73-0.76 (2H), 0.82-0.87 (2H), 1.52 (s, 3H), 1.70-1.76 (1H), 1.87-1.90 (1H), 2.25-2.32 (1H), 2.39-2.45 (1H), 3.64-3.71 (1H), 4.11-4.15 (1H), 4.55-4.58 (1H), 7.35 (s, 1H), 7.72-7.75 (1H), 7.93-7.95 (1H), 8.06-8.08 (1H), 8.13 (s, 1H).

5-Cyclopropyl-3-[4-ethyl-4-[[3-(trifluoromethyl)phenyl]sulfonyl]-tetrahydro-pyran-2-yl]-[1,2,4]oxadiazole (Example 46)

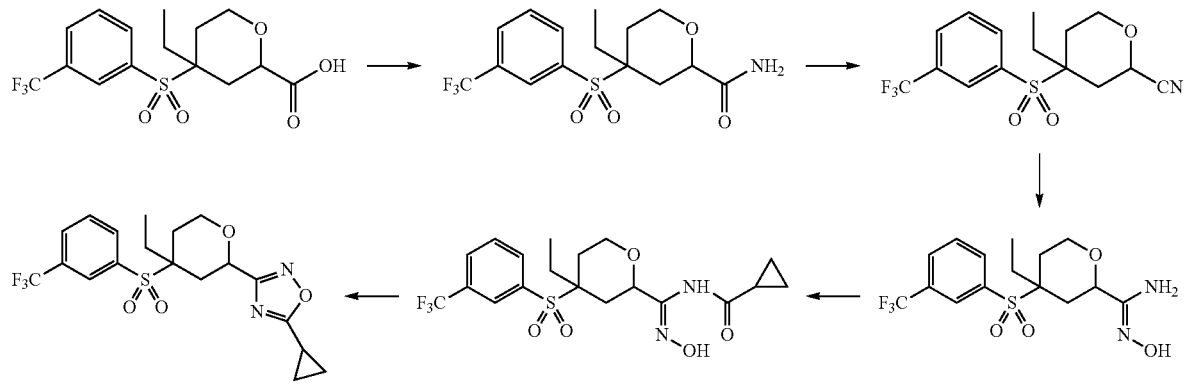

Step 1: 4-ethyl-4-(3-(trifluoromethyl)phenylsulfonyl)tetrahydro-2H-pyran-2-carboxamide EDC.HCl (2.093 g, 13.66 mmol) and HOBT (1.84 g, 13.66 mmol) were added to a stirred solution of 4-ethyl-4-[[3-(trifluoromethyl)phenyl]sulfonyl]-tetrahydro-pyran-2-carboxylic acid (2.5 g, 6.83 mmoL) in THF (50 mL) at 0° C., stirred for 15 min and added TEA (4.77 mL, 34.15 mmol) followed by $NH_4Cl$ (1.10 g, 20.49 mmol). The resulting mixture was allowed to warm to RT and stirred for 16 h. Reaction mass was diluted with chilled water (40 mL) and extracted with EtOAc (2×100 mL). Combined organic extract was washed with brine solution (50 mL), dried (Na$_2$SO$_4$) and concentrated under reduced pressure to get crude compound. The crude compound was triturated with diethylether to afford 1.7 g (68%) of 4-ethyl-4-(3-(trifluoromethyl)phenylsulfonyl)tetrahydro-2H-pyran-2-carboxamide as off white solid. The crude was used as such in the next step without purification.

Step 2: 4-ethyl-4-(3-(trifluoromethyl)phenylsulfonyl)tetrahydro-2H-pyran-2-carbonitrile POCl$_3$ (0.65 mL, 6.98 mmol) was added to a stirred solution of 4-ethyl-4-(3-(trifluoromethyl)phenylsulfonyl) tetrahydro-2H-pyran-2-carboxamide (1.7, 4.65 mmol) in dry pyridine (3.4 mL) at 70° C. over 10 min. The resulting mixture was cooled to RT and stirred for 16 h. It was then diluted with chilled water (30 mL) and extracted with diethylether (3×50 mL). Combined organic extract was washed with brine (50 mL), dried (Na$_2$SO$_4$) and concentrated under reduced pressure to get crude compound. The crude was triturated with Et$_2$O to afford 1.1 g (68%) of 4-ethyl-4-(3-(trifluoromethyl)-phenyl-sulfonyl)tetrahydro-2H-pyran-2-carbonitrile as a solid.

Step 3: 4-ethyl-N-hydroxy-4-(3-(trifluoromethyl) phenylsulfonyl)tetrahydro-2H-pyran-2-carboximidamide TEA (0.88 mL, 6.34 mmol) and NH$_2$OH.HCl (0.33 g, 4.75 mmol) were added to a stirred solution of 4-ethyl-4-(3-(trifluoromethyl)phenylsulfonyl)tetrahydro-2H-pyran-2-carbonitrile (1.7, 4.65 mmol) in EtOH (22 mL) at 0° C. The resulting mixture was stirred at RT for 16 h. The RM was concentrated under reduced pressure. The residue was quenched with chilled water (30 mL) and extracted with DCM (3×50 mL). Combined organic extract was washed with brine (50 mL), dried (Na$_2$SO$_4$) and concentrated under reduced pressure to get crude compound. The crude was triturated with Et$_2$O to give 4-ethyl-N-hydroxy-4-(3-(trifluoromethyl)phenylsulfonyl)tetrahydro-2H-pyran-2-carboximidamide (1.0 g, 83%).

Step 4: 4-ethyl-N-hydroxy-4-(3-(trifluoromethyl) phenylsulfonyl)tetrahydro-2H-pyran-2-yl)(hydroxyamino) methyl)cyclopropanecarboxamide Cyclopropane carbonyl chloride (0.27 g, 2.63 mmol) was added dropwise to a stirred solution of 4-ethyl-N-hydroxy-4-(3-(trifluoromethyl)phenylsulfonyl)tetrahydro-2H-pyran-2-carboximidamide (1.0 g, 2.63 mmoL) and TEA (0.73 mL, 5.26 mmoL) in DCM (20 mL) at 0° C. over a period of 10 min. The resulting mixture was stirred at 0° C. for 2 h, diluted with DCM (50 mL). Combined organic layer was washed with water (50 mL), brinesolution (50 mL), dried (Na$_2$SO$_4$) and concentrated under reduced pressure to get crude compound. The crude was triturated with n-pentane to get 1.0 g of 4-ethyl-N-hydroxy-4-(3-(trifluoromethyl)phenyl-sulfonyl)tetrahydro-2H-pyran-2-yl)(hydroxyamino)-methyl)-cyclopropanecarboxamide as. The crude was used as such in next step with out purification.

Step 5: 5-Cyclopropyl-3-[4-ethyl-4-[[3-(trifluoromethyl)phenyl]sulfonyl]-tetrahydro-pyran-2-yl]-[1,2,4] oxadiazole CH$_3$COONa (0.36 g, 4.46 mmol) was added to a solution of 4-ethyl-N-hydroxy-4-(3-(trifluoro-methyl)phenylsulfonyl)tetrahydro-2H-pyran-2-yl)(hydroxyamino)methyl)cyclopropanecarboxamide (1.0 g, 2.33 mmol) in EtOH (10 mL), water (8 mL) and stirred at 80° C. for 48 h. The reaction mass was concentrated under reduced pressure, quenched with ice water (20 mL) and extracted with DCM (3×20 mL). Combined organic extract was washed with water (30 mL), brine (50 mL), dried (Na$_2$SO$_4$) and concentrated under reduced pressure to get crude. The crude was purified by CC (0-2% MeOH in CHCl$_3$) to give 600 mg (63%) of 5-Cyclopropyl-3-[4-ethyl-4-[[3-(trifluoromethyl) phenyl]sulfonyl]-tetrahydro-pyran-2-yl]-[1,2,4]oxadiazole as a viscous oil. $^1$H-NMR (600 MHz, [d$_6$]-DMSO): δ=8.23-8.24 (1H), 8.17-8.18 (1H), 8.03 (1H), 7.97-7.99 (1H), 4.73-4.75 (1H), 3.93-3.96 (1H), 3.67-3.71 (1H), 2.31-2.35 (1H), 2.09-2.14 (1H), 1.91-2.01 (4H), 1.65-1.67 (1H), 1.23-1.25 (2H), 1.08-1.09 (2H), 0.97-1.00 (3H).

NOE: C-2 proton & ethyl=cis

Chiral Resolution of [Cis-rac] 5-Cyclopropyl-3-[4-ethyl-4-[[3-(trifluoromethyl)phenyl]sulfonyl]-tetrahydro-pyran-2-yl]-[1,2,4]oxadiazole

[Cis-rac] 5-Cyclopropyl-3-[4-ethyl-4-[[3-(trifluoromethyl)phenyl]sulfonyl]-tetrahydro-pyran-2-yl]-[1,2,4]oxadiazole was subjected to preparative chiral-SFC (IC-column, MeOH, 90%). The products were dried to give [cis-EN1] SC-238 and [cis-EN2] SC-239.

[cis-EN1] SC-238—analytical chiral SFC: chiralpak IC (250×4.6 mm 5μ), 3 g/min, RT, 0.5% DEA in MeOH, 20%, Ret. Time 2.02; ee >95%

[cis-EN2] SC-239—analytical chiral SFC: chiralpak IC (250×4.6 mm 5μ), 3 g/min, RT, 0.5% DEA in MeOH, 20%, Ret. Time 2.42; ee >95%

5-[[4-Methyl-4-[[3-(trifluoromethyl)phenyl]sulfonyl]-tetrahydro-pyran-2-yl]-methoxy]-2-(trifluoromethyl)-pyridine (Example 33)

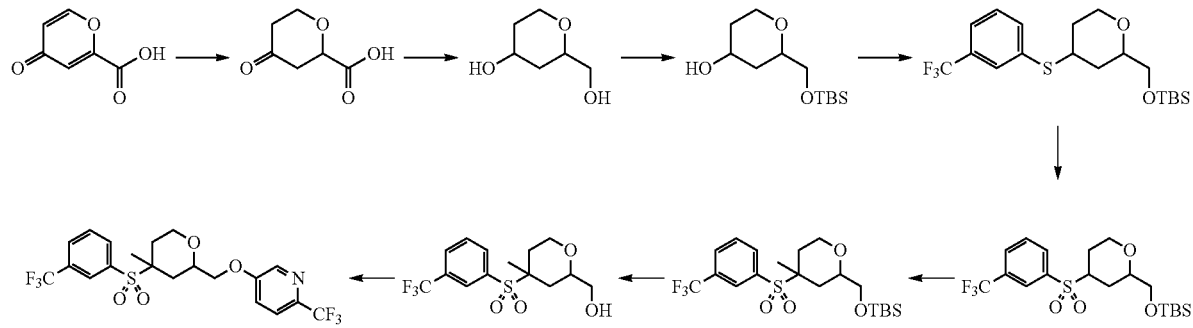

Step 1: 4-Oxo-tetrahydro-pyran-2-carboxylic Acid

To a degassed solution of 4-oxo-4H-pyran-2-carboxylic acid (7 g, 50.0 mmol) in EtOAc (130 ml) was added palladium carbon (0.700 g, 10% by weight) and the mixture was again degassed thoroughly with Ar and stirred in a paar shaker for 16 hours under hydrogen atmosphere. Reaction was monitored by TLC. The RM was filtered through celite bed and organic portion was concentrated under reduced pressure to obtain, crude 4-Oxo-tetrahydro-pyran-2-carboxylic acid (3.8 g, 52%) as white solid. which was used for next step without further purification.

Step 2: 2-Hydroxymethyl-tetrahydro-pyran-4-ol

To a stirred solution of 4-Oxo-tetrahydro-pyran-2-carboxylic acid (3 g, 20.54 mmol) in THF (100 ml), Borane dimethyl sulfoxide solution (18.24 g, 240 mmol) was slowly added at 0° C. and refluxed for 6 hours at 80° C. Reaction was monitored by TLC, The RM was quenched with water slowly at 0° C. and filtered through celite bed and organic layer was concentrated under reduced pressure to obtain solid. Further this solid was washed with 30% IPA-CHCl$_3$ The organic portion was evaporated under reduced pressure to get crude 2-Hydroxymethyl-tetrahydro-pyran-4-ol (2 g, 74%) as light brown liquid.

Step 3: 2-(tert-Butyl-dimethyl-silanyloxymethyl)-tetrahydro-pyran-4-ol

To a solution of 2-Hydroxymethyl-tetrahydro-pyran-4-ol (7.0 g, 53.03 mmol) in DCM (130 ml) was added TEA (8.8 ml, 63.6 mmol) and DMAP (0.258 g, 2.1 mmol) followed by tert-butyl silyl chloride (6.3 g, 42.4 mmol) at 0° C. Then the RM was stirred at the RT for 12 h. The RM was diluted with DCM (200 ml) and washed with water (3×100 ml), brine, dried over anhydr. Na$_2$SO$_4$ and concentrated under reduced pressure to give the crude product. The crude was purified by CC by using 25% EA-Hexane as eluent to afford pure 2-(tert-Butyl-dimethyl-silanyloxymethyl)-tetrahydro-pyran-4-ol (3.5 g, 26%) as light yellow liquid.

Step 4: Methanesulfonic Acid 2-(tert-butyl-dimethyl-silanyloxymethyl)-tetrahydro-pyran-4-yl Ester To a solution of 2-(tert-Butyl-dimethyl-silanyloxymethyl)-tetrahydro-pyran-4-ol (2.6 g g, 10.5 mmol) in DCM (50 ml) was added TEA (4.3 ml, 30 mmol) followed by methane sulphonyl chloride (1.55 ml, 20 mmol) at 0° C. Then the RM was stirred at the same temperature for 1 h. The RM was diluted with DCM (100 ml) and washed with water (3×50 ml), brine, dried over anhydr. Na$_2$SO$_4$ and concentrated under reduced pressure to give the crude Methanesulfonic acid 2-(tert-butyl-dimethyl-silanyloxymethyl)-tetrahydro-pyran-4-yl ester (2.8 g, 82%) as yellow liquid, which was used for the next step without further purification.

Step 5: tert-Butyl-dimethyl-[4-(3-trifluoromethyl-phenylsulfanyl)-tetrahydro-pyran-2-ylmethoxy]-silane To a stirred solution of Methanesulfonic acid 2-(tert-butyl-dimethyl-silanyloxymethyl)-tetrahydro-pyran-4-yl ester (3.5 g, 10.8 mmol) in DMF (100 ml), Compound 6 (2.8 g, 15.7 mmol), K$_2$CO$_3$ (2.76 g, 20 mmol) was added and heated to 70° C. for 12 h. Reaction was monitored by TLC. The RM was diluted with EtOAc (50 ml), washed with water (20 ml×2), sat. brine, dried over anhydr. Na$_2$SO$_4$, The organic portion was evaporated under reduced pressure to get crude which was purified by (230-400 mesh silica gel), using 2% EtOAc-hexane as eluent to afford pure tert-Butyl-dimethyl-[4-(3-trifluoro-methyl-phenylsulfanyl)-tetrahydro-pyran-2-ylmethoxy]-silane (2 g, 46%) as light yellow liquid.

Step 6: tert-Butyl-dimethyl-[4-(3-trifluoromethyl-benzenesulfonyl)-tetrahydro-pyran-2-ylmethoxy]-silane To a stirred solution of tert-Butyl-dimethyl-[4-(3-trifluoromethyl-phenylsulfanyl)-tetrahydro-pyran-2-ylmethoxy]-silane (2.2 g, 5.41 mmol) in (3:1) ratio of MeCN (72 ml), water (24 ml), sodium periodate (3.47 g, 16.1 mmol) was added followed by addition of Ruthenium(III)chloride hydrate (0.022 g, 0.106 mmol) at 0° C. The reaction was continued for 10 min at RT. The reaction was monitored by TLC and it was diluted with EtOAc (100 ml), washed with water (50 ml×2), and brine (50 ml). The organic layer dried over Na2SO4 concentrated in reduced pressure to get the crude material. Crude was purified by CC (100-200 mesh silicagel), using 10% EtOAc/Hexan as eluent to afford pure tert-Butyl-di methyl-[4-(3-trifluoromethyl-benzenesulfonyl)-tetrahydro-pyran-2-ylmethoxy]-silane (1.7 g, 73.91%) as off white solid.

Step 7: tert-Butyl-dimethyl-[4-methyl-4-(3-trifluoromethyl-benzenesulfonyl)-tetrahydro-pyran-2-yl-methoxy]-silane To a stirred solution of tert-Butyl-dimethyl-[4-(3-trifluoromethyl-benzenesulfonyl)-tetrahydro-pyran-2-ylmethoxy]-silane (2.5 g, 5.70 mmol) in THF (80 ml), NaHMDS (11.4 ml, 11.4 mmol) was added followed by addition 15-Crown-5 (2.5 g, 11.36 mmol) at −78° C. The reaction was continued for 20 min. MeI was added and maintained for 45 min at −78° C. and finally the RM stirred for 12 hr at RT. The reaction was monitored by TLC and it was diluted with EtOAc (100 ml), washed with water (50 ml×2), brine (50 ml) dried over anhydr. Na$_2$SO$_4$ and evaporated under reduced pressure to give crude which was further purified by CC (silica gel 230-400) using 8% EtOAc/hexane as eluent to afford tert-Butyl-dimethyl-[4-methyl-4-(3-trifluoromethyl-benzenesulfonyl)-tetrahydro-pyran-2-ylmethoxy]-silane (1.3 g, 52.0%) as light yellow solid.

Step 8: [4-Methyl-4-(3-trifluoromethyl-benzenesulfonyl)-tetrahydro-pyran-2-yl]-methanol To a cold stirred solution of tert-Butyl-dimethyl-[4-methyl-4-(3-trifluoromethyl-benzenesulfonyl)-tetrahydro-pyran-2-ylmethoxy]-silane (0.830 g, 1.8 mmol) in THF (20 ml) TBAF solution (4.5 ml, 4.5 mmol) was added. The RM was stirred for 30 min at RT. Reaction was monitored by TLC, solvent was evaporated under reduced pressure to get crude compound. Crude was purified by CC (silica gel 230-400) using 30% EtOAc/hexane as eluent to afford pure [4-Methyl-4-(3-trifluoromethyl-benzenesulfonyl)-tetrahydro-pyran-2-yl]-methanol (0.580 g, 93.5%) as a white solid.

Step 9: 5-[4-Methyl-4-(3-trifluoromethyl-benzenesulfonyl)-tetrahydro-pyran-2-ylmethoxy]-2-trifluoromethyl-pyridine)

To a stirred solution of [4-Methyl-4-(3-trifluoromethyl-benzenesulfonyl)-tetrahydro-pyran-2-yl]methanol (0.3 g, 0.88 mmol) in 10 ml THF was added 6-trifluoromethyl-pyridin-3-ol (0.143 g, 0.88 mmol), PPh$_3$ (0.345 g, 1.32 mmol) and heated to reflux. Then added DEAD (0.208 ml, 1.32 mmol) and heating continued for 16 h. Then the reaction mass cooled to RT diluted with H$_2$O and extracted with EtOAc (2×20 ml), washed with brine (15 ml), dried over Na$_2$SO$_4$ and concentrated. The crude was purified by reverse phase prep. HPLC to get pure cis-diastereomer (0.20).

$^1$H-NMR (600 MHz, [d$_6$]-DMSO): δ=8.43 (1H), 8.23-8.24 (1H), 8.18-8.19 (1H), 8.05 (1H), 7.97-7.99 (1H), 7.83-7.84 (1H), 7.60-7.62 (1H), 4.15-4.22 (2H), 3.87-3.92 (2H), 3.55-3.60 (1H), 2.00-2.05 (1H), 1.90-1.94 (1H), 1.62-1.65 (1H), 1.41-1.44 (4H).

Chiral Resolution of [Cis Racemic]: 5-[4-Methyl-4-(3-trifluoromethyl-benzenesulfonyl)-tetrahydro-pyran-2-ylmethoxy]-2-trifluoromethyl-pyridine)

[Cis-rac]: 5-[4-Methyl-4-(3-trifluoromethyl-benzenesulfonyl)-tetrahydro-pyran-2-ylmethoxy]-2-trifluoromethyl-pyridine) was subjected to preparative chiral-HPLC (Chiralpal IA, 0.1% DEA in MeOH, 100 bar, to give [cis-EN1] SC-208 and [cis-EN2] SC-209.

[cis-EN1] SC-208—analytical chiral HPLC: Chiralpak IA (250×4.6 mm 5μ), 0.5 mL/min, RT, 0.1% DEA in EtOH 100%, Ret. Time 9.99; ee >95%

[cis-EN2] SC-209—analytical chiral HPLC: Chiralpak IA (250×4.6 mm 5μ), 0.5 mL/min, RT, 0.1% DEA in EtOH 100%, Ret. Time 11.85; ee >95%

2-[4-Ethyl-4-[[3-(trifluoromethyl)phenyl]sulfonyl]-tetrahydro-pyran-2-yl]-5-(trifluoromethyl)-[1,3,4]oxadiazole (Example 47)

afford 800 mg of methyl 4-ethyl-(3-(trifluoromethyl)phenyl-sulfonyl)tetrahydro-2H-pyran-2-carboxylate as a solid.

Step 2: 4-ethyl-4-((3-(trifluoromethyl)phenyl)sulfonyl)tetrahydro-2H-pyran-2carbohydrazide Hydrazine hydrate (0.286 g, 8.94 mmol, 99% pure) was added to a solution of the product of step 1 (1.7 g, 4.47 mmoL) in EtOH (34 mL, 20 vol) and stirred at 80° C. for 4 h. The reaction mass was concentrated under reduced pressure and the residue was triturated with Et$_2$O (20 mL) to give 1.2 g (70%) of 4-ethyl-4-((3-(trifluoromethyl)-phenyl)sulfonyl)tetrahydro-2H-pyran-2-carbohydrazide as an off white solid.

Step 3: 4-ethyl-N-(2,2,2-trifluoroacetyl)-4-ethyl-4-((3-(trifluoromethyl)phenyl)sulfonyl)tetrahydro-2H-pyran-2-carbohydrazide Trifluoro acetic anhydride (0.53 mL, 3.78 mmol) was added to a stirred solution of of 4-ethyl-4-((3-(trifluoromethyl)phenyl)sulfonyl)tetrahydro-2H-pyran-2-carbohydrazide (1.2 g, 3.15 mmol), TEA (0.44 mL, 3.15 mmol) in THF (24 mL) and stirred at RT for 16 h. The RM was quenched into ice cold water (20 mL) and extracted with EtOAc (3×20 mL). The combined organic layer was washed with brine (20 mL), dried (Na$_2$SO$_4$) and concentrated under reduced pressure to get crude. The crude was triturated with Et$_2$O (20 mL) to give 1.1 g (73%) of 4-ethyl-N-(2,2,2-trifluoroacetyl)-4-ethyl-4-((3-(trifluoro-methyl)phenyl)sulfonyl)tetrahydro-2H-pyran-2carbohydrazide as an off white solid.

Step 4: 2-[4-Ethyl-4-[[3-(trifluoromethyl)phenyl]sulfonyl]-tetrahydro-pyran-2-yl]-5-(trifluoromethyl)-[1,3,4]oxadiazole POCl$_3$ (0.3 mL, 3.19 mmol) was added to a solution of 4-ethyl-N-(2,2,2-trifluoroacetyl)-4-ethyl-4-((3-(trifluorom-

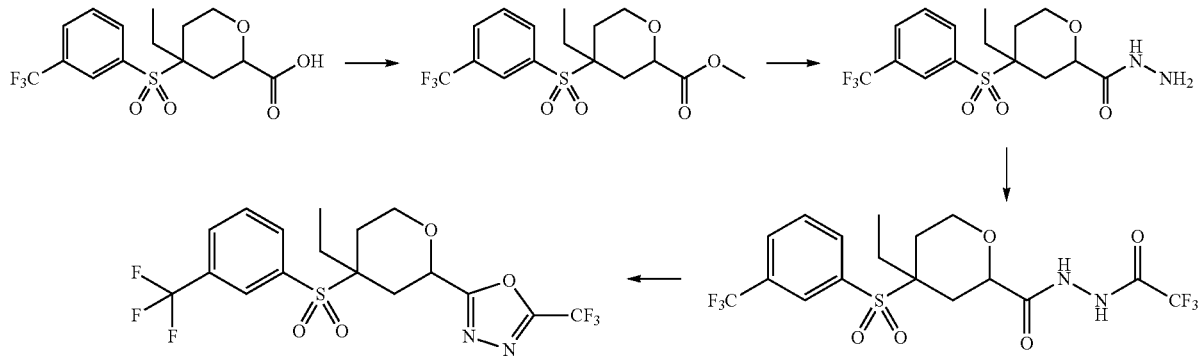

Step 1: Methyl4-ethyl-(3-(trifluoromethyl)phenyl-sulfonyl)tetrahydro-2H-pyran-2-carboxylate Conc. sulfuric acid (0.1 mL) was added to a stirred solution of 4-Ethyl-4-[[3-(trifluoromethyl)phenyl]sulfonyl]-tetrahydro-pyran-2-carboxylic acid (1 g, 2.73 mmol) in MeOH (20 mL) at 0° C. and stirred at reflux for 4 h. The RM was concentrated under reduced pressure and the residue was quenched into chilled water (20 ml) and extracted with DCM (3×30 mL). Combined organic extract was washed with aq. NaHCO$_3$ solution (50 mL) and brine (50 mL), dried (Na$_2$SO$_4$) and concentrated under reduced pressure to get crude. The crude was triturated with n-pentane (10 mL) to ethyl)phenyl)sulfonyl)tetrahydro-2H-pyran-2carbohydrazide (1.2 g, 3.19 mmoL) in MeCN (24 mL) and stirred at 80° C. for 48 h. The reaction mass was concentrated under reduced pressure and the residue was quenched into ice water (50 mL) and extracted with DCM (3×30 mL). The combined organic extract was washed with aq.NaHCO$_3$ solution (20 mL), water (30 mL), brine solution (50 mL), and dried (Na$_2$SO$_4$), concentrated under reduced pressure to get the crude product. The crude was purified by CC (silica gel, 100-200 mesh), 0-0.6% MeOH in CHCl$_3$ to give 0.9 g. Further purification by prep. TLC (GF254 silica, 3% MeOH in CHCl$_3$ as eluent) afforded 600 mg of 2-[4-ethyl-4-[[3-

(trifluoromethyl)phenyl]sulfonyl]-tetrahydro-pyran-2-yl]-5-(trifluoromethyl)-[1,3,4]oxadiazole (SC-242) as a white solid.

$^1$H-NMR (600 MHz, [d$_6$]-DMSO): δ=8.24-8.26 (1H), 8.19-8.21 (1H), 8.06 (1H), 7.99-8.01 (1H), 5.08-5.10 (1H), 4.00-4.04 (1H), 3.76-3.80 (1H), 2.23-2.28 (1H), 2.16-2.19 (1H), 1.96-2.07 (4H), 1.69-1.72 (1H), 0.99-1.01 (3H).

NOE: C-2 proton & ethyl=cis

Chiral Resolution of 2-[4-Ethyl-4-[[3-(trifluoromethyl)phenyl]sulfonyl]-tetrahydro-pyran-2-yl]-5-(trifluoromethyl)-[1,3,4]oxadiazole (SC-242)

Cis-rac 2-[4-ethyl-4-[[3-(trifluoromethyl)phenyl]sulfonyl]-tetrahydro-pyran-2-yl]-5-(trifluoromethyl)-[1,3,4]-oxadiazole was subjected to preparative chiral-HPLC (Chiralcel OJ-H column, hexane: EtOH, 75:25) to give cis-EN1 SC-240 and cis-EN2 SC-241.

[cis-EN1] SC-240—analytical chiral HPLC: Chiralpak OJ-H (250×4.6 mm 5μ), 0.2% DEA in hexane: MeOH, 75:25, 1 mL/min, Ret. Time 7.55; ee >95%

[cis-EN2] SC-241—analytical chiral HPLC: Chiralpak OJ-H (250×4.6 mm 5μ), 0.2% DEA in hexane: MeOH, 75:25, 1 mL/min, Ret. Time 9.88; ee >95%

5-Chloro-2-[4-methyl-4-[[3-(trifluoromethyl)phenyl]sulfonyl]-tetrahydro-pyran-2-yl]-pyridine (Example 48)

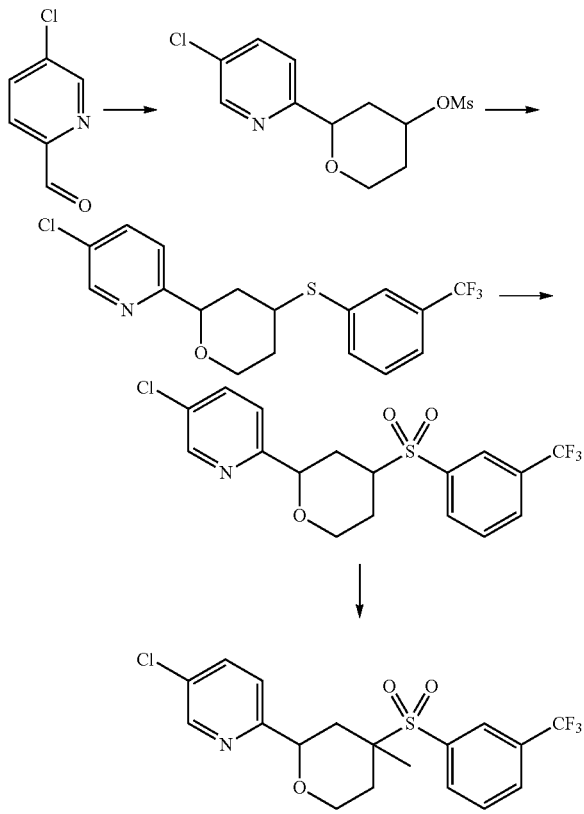

Step 1:
2-(5-chloropyridin-2-yl)tetrahydro-2H-pyran-4-yl Methanesulfonate

Methanesulfonic acid (20.3 g, 212.0 mmol) was added to a solution of 5-chloropicolinaldehyde (3 g, 21.20 mmol) and 3-buten-1-ol (2.2 g, 31.80 mmol) in DCM (30 mL) at 0° C., stirred for 3 h at 0° C.-15° C. The RM was quenched into ice water, diluted with DCM (15 mL) and washed sequentially with sat. aq. NaHCO$_3$ solution (2×50 mL), water (100 mL), brine (100 mL), dried (anhydr. Na$_2$SO$_4$) and concentrated under reduced pressure to get crude 2-(5-chloropyridin-2-yl)tetrahydro-2H-pyran-4-yl methanesulfonate (6.2 g crude) as a brown oil. This was taken to the next step without further purification.

Step 2: 5-chloro-2-(4-((3-(trifluoromethyl)phenyl)thio)tetrahydro-2H-pyran-2-yl)pyridine 3-(Trifluoromethyl)benzene thiol (7.6 g, 42.61 mmol) was added to a suspension of K$_2$CO$_3$ (6 g, 42.61 mmol), 2-(5-chloropyridin-2-yl)tetrahydro-2H-pyran-4-yl methanesulfonate (6.2 g, 21.30 mmol) in DMF (50 mL) and the RM was heated at 60° C. for 5 h and stirred for 14 h at RT. After completion of reaction, the mixture was diluted with water (100 mL) and extracted with EtOAc (50 mL×3). The organic extract was washed with water (100 mL), brine (100 mL), dried (anhydr. Na$_2$SO$_4$) and concentrated under reduced pressure to get crude compound. The crude compound was purified by CC (silica gel 60-120 mesh, 0-10% EtOAc in PE) to obtain 5.5 g (70%) of 5-chloro-2-(4-((3-(trifluoromethyl)phenyl)thio)tetrahydro-2H-pyran-2-yl)pyridine as thick oily liquid.

Step 3: 5-chloro-2-(4-((3-(trifluoromethyl)phenyl)sulfonyl)tetrahydro-2H-pyran-2-yl)pyridine 5-chloro-2-(4-((3-(trifluoromethyl)phenyl)thio)tetrahydro-2H-pyran-2-yl)pyridine (5.5 g, 14.74 mol) was dissolved in EtOH (110 mL) and a solution of oxone (27 g, 44.23 mmol) in water (55 mL) was added. The total reaction mass was stirred at RT for 16 h. The RM was diluted with water (100 mL) and extracted with DCM (3×50 mL). The combined organic extract was washed with brine (100 mL), dried (anhydr. Na$_2$SO$_4$) and concentrated to get crude. The crude compound was purified by CC (silica gel 60-120 mesh, 0-30% EtOAc in PE) to obtain 5-chloro-2-(4-((3-(trifluoromethyl)phenyl)sulfonyl)tetrahydro-2H-pyran-2-yl)pyridine (2 g, 51%) as a solid.

Step 4: 5-Chloro-2-[4-methyl-4-[[3-(trifluoromethyl)phenyl]sulfonyl]-tetrahydro-pyran-2-yl]-pyridine A solution of 5-chloro-2-(4-((3-(trifluoromethyl)phenyl)sulfonyl)tetrahydro-2H-pyran-2-yl)pyridine (2 g, 4.93 mmol) in THF (20 mL) was cooled to −78° C. and t-BuOK (1M solution in THF; 10 mL, 9.87 mmol) was added drop-wise, stirred for 30 min at same temperature. MeI (0.65 mL, 9.87 mmol) was added and the resulting mixture was warmed to RT and stirred for 16 h. The reaction mass was diluted with water (50 mL), EtOAc (50 mL). The combined organic layer was washed with water (100 mL) and brine (100 mL), dried (anhydr. Na$_2$SO$_4$) and concentrated under reduced pressure to get crude compound. The crude compound was purified by CC (silica gel 60-120 mesh, 0-35% EtOAc in PE) to obtain 1.1 g of 5-chloro-2-[4-methyl-4-[[3-(trifluoromethyl)phenyl]sulfonyl]-tetrahydro-pyran-2-yl]-pyridine as an off white solid. The compound was further purified by preparative HPLC (Kromosil C17, 250×25 mm, 5 m, 70% MeOH).

$^1$H-NMR (600 MHz, [d$_6$]-DMSO): δ=8.55 (1H), 8.20-8.22 (1H), 8.15-8.17 (1H), 8.04 (1H), 7.93-7.97 (2H), 7.46-

7.48 (1H), 4.61-4.64 (1H), 4.07-4.10 (1H), 3.72-3.77 (1H), 2.11-2.16 (1H), 1.93-1.97 (1H), 1.85-1.88 (1H), 1.47-1.50 (4H).

NOE: C-2 proton & methyl=cis

Chiral Resolution of 5-Chloro-2-[4-methyl-4-[[3-(trifluoromethyl)phenyl]sulfonyl]-tetrahydro-pyran-2-yl]-pyridine Cis-rac 5-Chloro-2-[4-methyl-4-[[3-(trifluoromethyl)phenyl]sulfonyl]-tetrahydro-pyran-2-yl]-pyridine was subjected to preparative chiral-SFC (Chiralpak AD-H, 20% MeOH) to give cis-EN1 SC-243 and cis-EN2 SC-244.

[cis-EN1] SC-243—analytical chiral SFC: Chiralpak AD-H (250×4.6 mm 5μ), 0.5% DEA in MeOH 30%, 3 g/min, Ret. Time 2.62; ee >95%.

[cis-EN2] SC-244—analytical chiral SFC: Chiralpak AD-H (250×4.6 mm 5μ), 0.5% DEA in MeOH 30%, 3 g/min, Ret. Time 3.07; ee >95%.

Synthesis of Heteroaryl-Aldehydes 4,6-dimethoxynicotinaldehyde

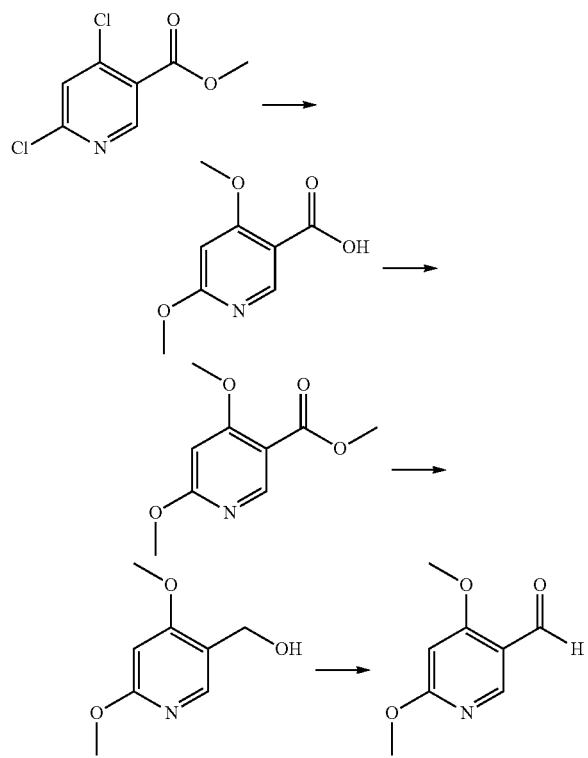

Step 1: 4,6-dimethoxynicotinic Acid

Sodium (8.23 g, 358.20 mmol) was added to dry MeOH (180 mL) at RT, then methyl 4,6-dichloronicotinate (9.0 g, 44.77 mmol) was added at RT. The reaction was heated at reflux for 18 h and subsequently concentrated in vacuo. The residue was diluted with water (50 mL) and acidified with aq HCl solution up to pH-2.0. A solid precipitated. The solid was filtered and washed with water and dried in vacuo for 2 h to get 4,6-dimethoxynicotinic acid (6.5 g, 80%) as a white solid.

Step 2: Methyl 4,6-dimethoxynicotinate

Dimethylsulfate (5.0 mL, 53.27 mmol) was added to a suspension of 4,6-dimethoxynicotinic acid (6.5 g, 35.51 mmol) and $K_2CO_3$ (7.35 mmol, 35.51) in DMF (100 mL) at RT and then stirred for 5 h. After completion of the reaction, the mixture was diluted with water (250 mL) and extracted with EtOAc (250 mL×3). The organic extract was washed with water (300 mL), brine (200 mL), dried ($Na_2SO_4$) and concentrated under reduced pressure to get methyl 4,6-dimethoxynicotinate (6.0 g, 86%) as a white solid.

Step 3: (4,6-dimethoxypyridin-3-yl) Methanol

A solution of methyl 4,6-dimethoxynicotinate (6.0 g, 30.45 mmol) in THF (30 mL) was added to a suspension of $LiAlH_4$ (1.73 g, 45.68 mmol) in THF (60 mL) at 0° C. The total reaction mass was stirred at 0° C. for 2 h. After completion of reaction, the RM was quenched with sat. $Na_2SO_4$ at 0° C., then diluted with EtOAc (150 mL) and filtered through celite pad, then reaction mass was extracted with EtOAc (150 mL×2). The organic extract was washed with water (300 mL), brine (200 mL), dried $Na_2SO_4$ and concentrated under reduced pressure to get (4,6-dimethoxypyridin-3-yl) methanol (4.8 g, 94%) as a white solid.

Step 4: 4,6-dimethoxynicotinaldehyde

DMP (18.1 g, 42.85 mmol) was added to a clear solution of (4,6-dimethoxypyridin-3-yl) methanol (4.8 g, 28.57 mmol) in DCM (100 mL) at 0° C. The total RM was slowly warmed to RT and stirred for 12 h. The RM was filtered through celite and washed with DCM. The total organic layer was washed with water (100 mL) followed by sat. $NaHCO_3$ solution (100 mL) and brine, dried over $Na_2SO_4$. Concentrated under reduced pressure to get 4,6-dimethoxynicotinaldehyde (4.0 g, 85%) as a white solid.

6-methoxy-4-methylnicotinaldehyde

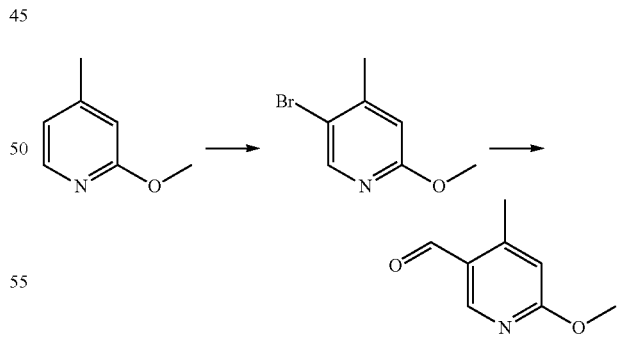

Step 1: 5-bromo-2-methoxy-4-methylpyridine

Sodium acetate (3.54 g, 43.23 mmol) was added to a solution of 2-methoxy-4-methylpyridine 54-5-1 (5.0 g, 39 mmol) in EtOAc (25 mL). $Br_2$ (1.52 mL, 58 mmol) was added drop wise over 20 min at 0° C. The RM was stirred at 50° C. for 18 h. The total reaction mass was cooled and after diluting with water, the pH was adjusted to 8 with aq.

NaOH. The organic layer was separated and aq. layer extracted with EtOAc (250 mL×3). The combined extract was washed with water (300 mL), brine (200 mL), dried (Na₂SO₄) and concentrated under reduced pressure to get crude compound. The crude compound was purified by CC (silica gel 100-200 mesh, 0-5% EtOAc in PE) to obtain 5-bromo-2-methoxy-4-methylpyridine (2.82 g, 40%) as liquid.

Step 2: 6-methoxy-4-methylnicotinaldehyde

A solution of BuLi (1.6 M in Hexane; 15.6 mL, 25 mmol) was added to 5-bromo-2-methoxy-4-methylpyridine (4.6 g, 22.77 mmol) in dry THF (60 mL) under Ar at −75° C. for 20 min. The RM was stirred at −75° C. for 1 h and then anhydr. DMF (2.5 mL, 34 mmol) was added slowly. The RM was warmed to RT and stirred for 12 h. The RM was quenched with sat. NH₄Cl and was extracted with DCM. The organic layer was dried over Na₂SO₄ and concentrated under reduced pressure to get 6-methoxy-4-methylnicotinaldehyde (4.0 g, 85%) as a white solid.

5-fluoro-6-methoxynicotinaldehyde

Step 3: (5-fluoro-6-methoxypyridin-3-yl) Methanol

LiAlH4 (1.64 g, 43.24 mmol) was added portion wise to a stirred solution of methyl 5-fluoro-6-methoxynicotinate (8 g, 43.24 mmol) in dry THF (160 mL) at −20° C. and stirred for 2 h at −20° C. to −15° C. The RM was slowly quenched with sat. Na₂SO₄ solution (100 mL). The precipitated salts were filtered through celite bed and the cake was washed with EtOAc (3×50 mL). The filtrate was concentrated under reduced pressure to give crude (5-fluoro-6-methoxypyridin-3-yl) methanol (6.8 g, crude) as a liquid.

Step 4: 5-fluoro-6-methoxynicotinaldehyde

DMP (27.37 g, 64.41 mmol) was added portion wise to a stirred solution of (5-fluoro-6-methoxypyridin-3-yl)methanol (6.8 g, 43.83 mmol) in DCM (150 mL) at 0° C. and stirred for 16 h at RT. The RM was filtered through celite and washed with DCM (3×50 mL). The filtrate was washed with aq. NaHCO₃ (200 mL), water (100 mL), brine (150 mL), dried (Na₂SO₄), filtered, concentrated under reduced pressure to give crude. The crude was purified by CC (silica-gel 60-120 mesh, 0-15% EtOAc in PE) to give 5-fluoro-6-methoxynicotinaldehyde (6.0 g, 89%) as a white solid.

4-fluoro-6-methoxynicotinaldehyde

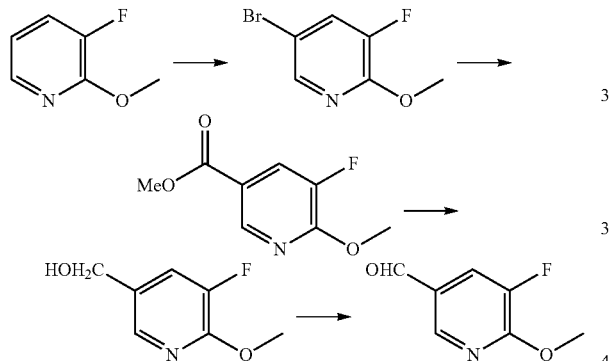

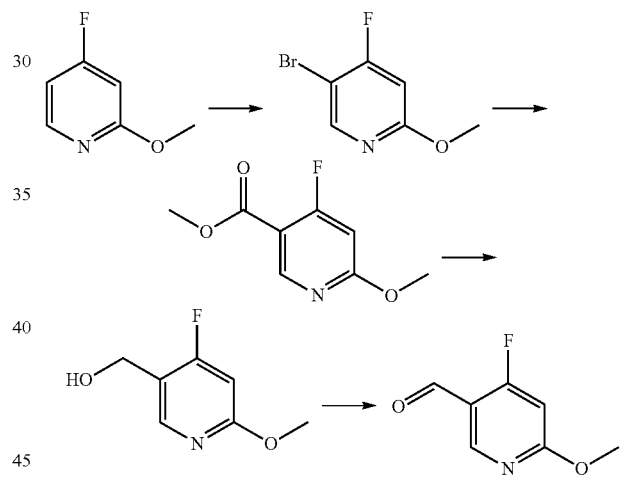

Step 1: 5-Bromo-3-fluoro-2-methoxypyridine

To a solution of 3-fluoro-2-methoxypyridine (20 g, 157.48 mmol), sodium acetate (25.74 g, 314.0 mmol) in AcOH (60 mL) was added dropwise a solution of Br₂ (20.32 mL, 393.70 mmol) in AcOH (40 mL) at 10° C. and the RM stirred at RT for 16 h. The RM was quenched into ice water (200 mL) and then basified with 6N NaOH solution to pH 9 and filtered the solid. The solid was dissolved in Et₂O (300 mL), washed with brine, dried (Na₂SO₄), filtered, concentrated under reduced pressure to give 5-bromo-3-fluoro-2-methoxypyridine (20 g, 61%) as white solid Step 2: Methyl 5-fluoro-6-methoxynicotinate TEA (10.21 mL, 72.81 mmol) was added to a mixture of 54-9-2 (5 g, 24.27 mmol), BINAP (1.51 g, 2.42 mmol) and Pd (dppf) Cl₂ DCM complex (1.98 g, 2.42 mmol) in MeOH (100 mL) in a steel bomb. The steel bomb was filled with CO gas (120 psi) and stirred at 120° C. for 20 h. The reaction mass was cooled to RT, excess gas evacuated in vacuo and filtered through a celite bed, and washed with EtOAc. The filtrate was concentrated under reduced pressure. The residue was purified by CC (0-5% EtOAc in PE) to give methyl 5-fluoro-6-methoxynicotinate (2 g, 44.5%) as a white solid.

Step 1: 5-bromo-4-fluoro-2-methoxypyridine

Sodium acetate (3.54 g, 43.23 mmol), EtOAc (25 mL) and 2-methoxy-4-fluoropyridine (5.0 g) were mixed in a round bottom flask. Br₂ (1.52 mL, 0.058 mol) was added drop wise to this solution over 20 min at 0° C. The RM was stirred at 50° C. for 18 h. The total RM was cooled and water was added to RM. Aq. NaOH was added drop wise to pH-8. The organic layer was separated and the aq. layer extracted with EtOAc (250 mL×3). The organic extract was washed with water (300 mL), brine (200 mL), dried (Na₂SO₄) and concentrated under reduced pressure to get the crude compound. The crude compound was purified by CC (0-5% EtOAc in PE) to obtain the desired product (2.82 g, 35%) as a liquid.

Step 2: Methyl 4-fluoro-6-methoxynicotinate

TEA (17.9 mL, 0.1323 mol) was added to a mixture of 5-bromo-4-fluoro-2-methoxypyridine (8 g, 0.044 mol), BINAP (2.74 g, 4.41 mmol) and Dichloro(1,1'-bis(dppf) palladium(II) DCM complex (3.60 g, 4.41 mmol) in MeOH (100 mL) in a steel bomb, charged with CO gas (120 psi) and heated at 120° C. for 20 h. The reaction mass was cooled to RT, excess gas evacuated in vacuo and filtered over celite. The filtrate was concentrated under reduced pressure. The residue upon purification by CC (0-5% EtOAc in PE) gave methyl 4-fluoro-6-methoxynicotinate (4.08 g, 56%) as a white solid.

Step 3: (4-fluoro-6-methoxypyridin-3-yl)methanol

LiAlH$_4$ (0.985 g, 25.9 mmol) was added portion wise to a stirred solution of methyl 4-fluoro-6-methoxynicotinate (4 g, 43.24 mmol) in dry THF (60 mL) at −20° C. and stirred for 2 h at −20° C. to −15° C. The RM was slowly quenched with sat. Na$_2$SO$_4$ solution (50 mL). The precipitated salts were filtered through celite and cake was washed with EtOAc (3×250 mL). The filtrate was concentrated under reduced pressure to give crude (4-fluoro-6-methoxypyridin-3-yl)methanol (3.0 g, crude, 88%) as a liquid.

Step 4: 4-fluoro-6-methoxynicotinaldehyde

DMP (12.1 g, 28.32 mmol) was added portion wise to a stirred solution of (4-fluoro-6-methoxypyridin-3-yl)methanol (3 g, 19.10 mmol) in DCM (50 mL) at 0° C. and stirred for 16 h at RT. The RM was filtered through celite and washed with DCM (3×50 mL). The filtrate was washed with aq. NaHCO$_3$ (200 mL), water (100 mL), brine (150 mL), dried (Na$_2$SO$_4$), filtered, concentrated under reduced pressure to give the crude reaction product. The crude product was purified by CC (0-15% EtOAc in PE) to give 4-fluoro-6-methoxynicotinaldehyde (1.6 g, 55%) as a white solid.

4-fluoro-6-methoxynicotinaldehyde

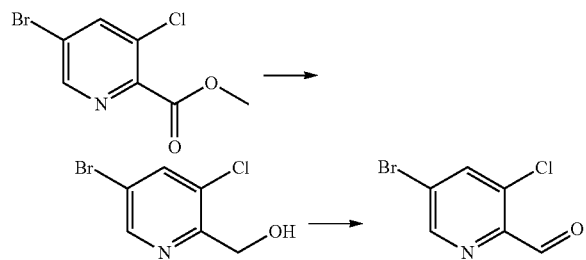

Step 1: (5-bromo-3-chloropyridin-2-yl)methanol

NaBH$_4$ (18.24 g, 480.0 mmol) was added portion wise to a stirred solution of methyl 5-bromo-3-chloropicolinate (20 g, 80.0 mmol) in dry THF (200 mL) and MeOH (200 ml) at 0° C. and stirred for 6 h at RT. The RM was slowly quenched with water (500 mL) and extracted with EtOAc (3×200 mL). The organic layer was washed with brine (300 mL), then dried (Na$_2$SO$_4$), filtered and evaporated the solvent in vacuo to give (5-bromo-3-chloropyridin-2-yl)methanol (16 g, crude), as a thick liquid. The crude was taken into next step.

Step 2: 5-bromo-3-chloropicolinaldehyde

DMP (45.83 g, 102.10 mmol) was added portion wise to a stirred solution of (5-bromo-3-chloropyridin-2-yl)metha- nol (16 g, 72.07 mmol) in DCM (320 mL) at 0° C. and stirred for 16 h at RT. The RM was filtered through celite and washed with DCM (3×100 mL). The filtrate was washed with Aq. NaHCO$_3$ (200 mL), water (200 mL), brine (250 mL), dried (Na$_2$SO$_4$), filtered, concentrated under reduced pressure to give crude. The crude was purified by CC (0-5% EtOAc in PE) to give 5-bromo-3-chloropicolinaldehyde (10 g, 66%) as light yellow solid.

3-chloro-5-(trifluoromethyl)picolinaldehyde

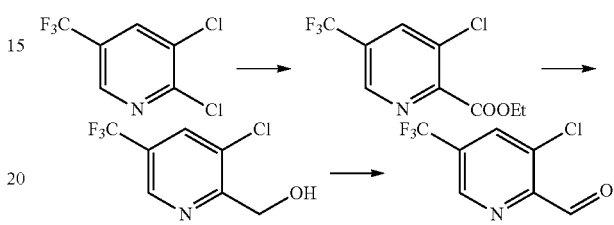

Step 1: Ethyl 3-chloro-5-(trifluoromethyl)picolinate

Sodium acetate (15.3 g, 186.9 mmol) was added to a mixture of 2,3-dichloro-5-(trifluoromethyl)pyridine (40 g, 186.9 mmol), Pd(OAc)$_2$ (5.4 g, 24.2 mmol) and Pd(dppf)Cl$_2$ DCM complex (13.4 g, 24.2 mmol) in EtOH (400 mL) in an autoclave. The autoclave was filled with CO gas (220 psi) and stirred at 90° C. for 6 h. The reaction mass was cooled to RT, excess gas evacuated in vacuo and the reaction mass was filtered through a celite bed. It was washed with EtOAc and the clear filtrate was concentrated under reduced pressure. The residue was purified by CC (0-5% EtOAc in PE) and the pure fractions were concentrated at below 40° C. to get ethyl 3-chloro-5-(trifluoromethyl)picolinate (40 g, 85%) as a white solid.

Step 2: (3-chloro-5-(trifluoromethyl)pyridin-2-yl)methanol

NaBH$_4$ (12 g, 31.6 mmol) was added portion wise to a stirred solution of ethyl 3-chloro-5-(trifluoromethyl)picoli- nate (40 g, 15.8 mmol) in MeOH (200 ml) at 0° C. and stirred for 4 h at RT. The RM was slowly quenched with water (500 mL) and the organic product was extracted with EtOAc (3×200 mL). The organic layer was washed with brine (300 mL), then dried over anhydr. Na$_2$SO$_4$, filtered and evaporated the solvent under vacuo to give crude product. The crude was purified by CC (0-15% EtOAc in PE) and the pure fractions were concentrated at below 40° C. to give (3-chloro-5-(trifluoromethyl)pyridin-2-yl)methanol (20 g, 60%), as a thick liquid.

Step 3: (3-chloro-5-(trifluoromethyl)pyridin-2-yl)methanol

DMP (60.2 g, 142.10 mmol) was added portion wise to a stirred solution of (3-chloro-5-(trifluoromethyl)pyridin-2-yl)methanol (15 g, 71.0 mmol) in DCM (100 mL) at 0° C. and stirred for 3 h at RT. The RM was filtered through a celite bed and washed with DCM (3×100 mL). The clear filtrate was washed with aq. NaHCO$_3$ (200 mL), water (200 mL), brine (250 mL), dried over anhydr. Na$_2$SO$_4$, filtered, concentrated under reduced pressure to get the crude product. The crude was purified by CC (0-5% EtOAc in PE) to give (3-chloro-5-(trifluoromethyl)pyridin-2-yl)methanol (8 g, 57%) as liquid.

5-bromo-3-(trifluoromethyl) Picolinaldehyde

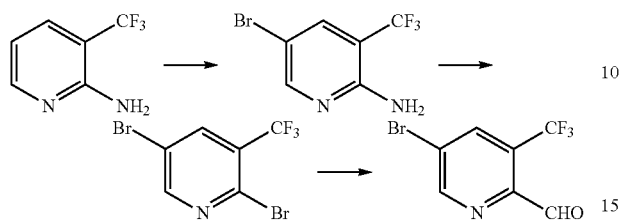

Step 1: 5-bromo-3-(trifluoromethyl)pyridin-2-amine

N-bromosuccinimide (20.83 g, 117.28 mmol) was portion wise added to a stirred solution of 3-(trifluoromethyl)pyridin-2-amine (19 g, 117.28 mmol) in MeCN (380 mL) at 0° C. The RM was stirred for 4 h at RT. The RM was quenched with aq. NaHCO₃ solution (pH~8) and then filtered. The solid was washed with water (200 mL), and the product was dissolved with EtOAc (300 mL). The organic layer was dried over anhydr. Na₂SO₄, filtered and solvent was concentrated under reduced pressure to give 5-bromo-3-(trifluoromethyl)pyridin-2-amine (25 g, 88%) as a solid.

Step 2: 2,5-dibromo-3-(trifluoromethyl)pyridine

Br₂ (8.60 mL, 166.6 mmol) was added drop wise to a stirred solution of 5-bromo-3-(trifluoromethyl)pyridin-2-amine (25 g, 104.1 mmol) and 47% HBr in water (100 mL) at −15° C. To the RM was added aq. sodium nitrite solution (19.4 g, 281.24 mmol in 50 mL of water) drop wise at the same temperature for 3 h. The RM was stirred for 4 h at RT. The RM was cooled to −15° C. and basified with 3N KOH solution (pH~9) and then filtered. The solid was washed with water (300 mL) and solid was dissolved into DCM (300 mL). The organic layer was dried over anhydr. Na₂SO₄, filtered and solvent was concentrated under reduced pressure to give 2,5-dibromo-3-(trifluoromethyl)pyridine (20 g, 63%) as a solid.

Step 3: 5-bromo-3-(trifluoromethyl) Picolinaldehyde 1.6M nBuLi in hexane (4.1 mL, 6.57 mmol) was added drop wise to a stirred solution of 2,5-dibromo-3-(trifluoromethyl)pyridine (18 g, 29.60 mmol) in DCM (180 mL) at −78° C. The RM was stirred at same temperature for 20 min. To the RM was added N-formylmorpholine (5.38 mL, 53.28 mmol) drop wise at −78° C. The RM was stirred for 1 h at −78° C. The RM was quenched with aq. NH₄Cl solution at −78° C. and the organic compound was extracted with DCM (3×100 mL); the organic layer was washed with brine and dried over anhydr. Na₂O₄, filtered and solvent was concentrated under reduced pressure to give 5-bromo-3-(trifluoromethyl) picolinaldehyde (7.5 g, 50%) as a solid.

5-bromo-3-(trifluoromethyl) Picolinaldehyde

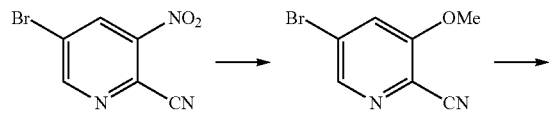

Step 1: 5-bromo-3-methoxypicolinonitrile

To a stirred solution of 5-bromo-2-cyano-3-nitropyridine (5 g, 0.021 mol) in MeOH (50 mL) at 0° C. was added 0.5M sodium methoxide (40 mL) and the RM was heated to reflux and stirred for 8 hr. After reaction completion the mixture was concentrated under reduced pressure to give crude 5-bromo-3-methoxypicolinonitrile. The crude was purified by CC (0-15% EtOAc in PE) and concentrated at below 45° C. to give 5-bromo-3-methoxypicolinonitrile (3.4 g, 70%), as a solid.

Step 2: 5-bromo-3-methoxypicolinic Acid Hydrochloride

5-Bromo-3-methoxypicolinonitrile (7 g, 0.033 mol) was dissolved in 12N HCl (10 mL) at 0° C. The RM was heated to reflux and stirred for 8 hr. After reaction completion the RM was concentrated under reduced pressure to give crude 5-bromo-3-methoxypicolinic acid hydrochloride which is directly used for the next step. (7.8 g, 97%), as a solid.

Step 3: methyl 5-bromo-3-methoxypicolinate

5-Bromo-3-methoxypicolinic acid hydrochloride (8 g, 0.034 mol) was dissolved in MeOH (80 mL) cooled to 0° C. then charged thionyl chloride (24 mL 0.347 mol). The RM heated to reflux and stirred for 8 h. After reaction completion the RM was concentrated under reduced pressure. The RM was poured on ice-water and neutralized with sodium bicarbonate and extracted with EtOAc (3×200 mL). The organic layer was washed with brine (300 mL), then dried (Na₂SO₄), filtered and evaporated the solvent under vacuo to give crude methyl 5-bromo-3-methoxypicolinate. The residue was purified by CC (0-15% EtOAc in PE) and concentrated at below 45° C. to give methyl 5-bromo-3-methoxypicolinate (6 g, 81%), as a thick liquid.

Step 4: (5-bromo-3-methoxypyridin-2-yl)methanol

NaBH₄ (3.26 g, 0.085 mol) was added portion wise to a stirred solution of methyl 5-bromo-3-methoxypicolinate 61-19-4 (7 g, 0.028 mol) in EtOH (100 mL) at 0° C. and stirred for 4 h at RT. The RM was slowly quenched with water (500 mL) and extracted with EtOAc (3×200 mL). The organic layer was washed with brine (300 mL), then dried (Na₂SO₄), filtered and evaporated the solvent under vacuo to give crude (5-bromo-3-methoxypyridin-2-yl)methanol. The residue was purified by CC (0-15% EtOAc in PE) and concentrated at below 40° C. to give (5-bromo-3-methoxypyridin-2-yl)methanol (5.8 g, 92%), as a thick liquid.

Step 5: 5-bromo-3-methoxypicolinaldehyde

DMP (14.5 g, 0.034 mol) was added portion wise to a stirred solution of 61-19-5 (5 g, 0.022 mol) in DCM (50 mL) at 0° C. and stirred for 3 h at RT. The RM was filtered through celite and washed with DCM (3×100 mL). The filtrate was washed with aq. NaHCO$_3$ (100 mL), water (100 mL), brine (150 mL), dried (Na$_2$SO$_4$), filtered, concentrated under reduced pressure to give crude. The crude was purified by CC (0-5% EtOAc in PE) to give 2,5-dibromo-3-(trifluoromethyl)pyridine (2.6 g, 53%) as solid.

3-bromo-5-chloropicolinaldehyde

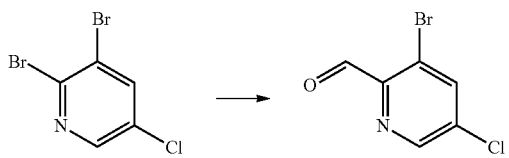 [SMILES: Clc1cnc(Br)c(Br)c1 ; O=Cc1ncc(Cl)cc1Br]

Step 1: 3-bromo-5-chloropicolinaldehyde n-BuLi (46.0 ml, 73.71 mmol) was added drop wise to a stirred solution of 2,3-dibromo-5-chloropyridine (20 g, 73.71 mmol) in DCM (200 ml) at −78° C. and stirred for 30 min. To the RM was added DMF (6.9 ml, 88.45 mmol) at −78° C. and stirred for 30 min. The RM was slowly quenched with sat. aq. NH$_4$Cl solution (100 mL) and the organic product was extracted with EtOAc (3×100 mL). The organic layer was washed with brine (200 mL), then dried over anhydr. Na$_2$SO$_4$, filtered and evaporated the solvent in vacuo to get crude product. The crude product was purified by CC (0-5% EtOAc in PE) to get 3-bromo-5-chloropicolinaldehyde (3.4 g, 26%) as a thick liquid.

3-chloro-5-(difluoromethoxy)picolinaldehyde

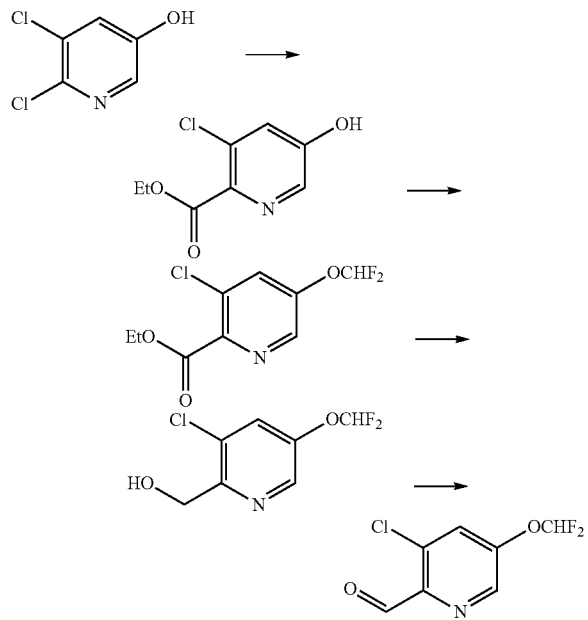

Step 1: Ethyl 3-chloro-5-hydroxypicolinate

Sodium acetate (4.0 g, 49.38 mmol) was added to a mixture of 5,6-dichloropyridin-3-ol (8 g, 49.38 mmol), Pd(OAc)$_2$ (1.43 g, 6.41 mmol) and Pd(dppf)Cl$_2$ DCM complex (5.23 g, 6.41 mmol) in EtOH (100 mL) in an autoclave. The autoclave was filled with CO gas (220 psi) and stirred at 90° C. for 6 h. The reaction mass was cooled to RT, excess gas evacuated in vacuo and the reaction mass was filtered through a celite bed. It was washed with EtOAc and the clear filtrate was concentrated under reduced pressure. The residue was purified by CC (0-40% EtOAc in PE) and the pure fractions were concentrated to get ethyl 3-chloro-5-hydroxypicolinate (9.2 g, 93%) as a white solid.

Step 2: Ethyl 3-chloro-5-(difluoromethoxy)picolinate

To stirred solution of ethyl 3-chloro-5-hydroxypicolinate (9.2 g, 45.77 mmol) in dry DMF (100 mL) was added K$_2$CO$_3$ (18.9 g, 137.31 mmol) at RT. The RM was heated to 90° C. and purged with Freon gas for 2 h. The RM was diluted with water (250 mL) and the organic product was extracted with EtOAc (250 mL×2). The organic extract was washed with water (2×150 mL), brine (100 mL), dried (anhydr. Na$_2$SO$_4$) and concentrated under reduced pressure to get compound ethyl 3-chloro-5-(difluoro-methoxy)picolinate (9.0 g, crude) as a yellow liquid. The crude was taken as such for the next step.

Step 3: (3-chloro-5-(difluoromethoxy)pyridin-2-yl)methanol

NaBH$_4$ (5.42 g, 143.43 mmol) was added portion wise to a stirred solution of ethyl 3-chloro-5-(difluoromethoxy)picolinate (9.0 g, 35.85 mmol) in MeOH (100 ml) at 0° C. and stirred for 4 h at RT. The RM was slowly quenched with water (200 mL) and the organic product was extracted with EtOAc (3×200 mL). The organic layer was washed with brine (300 mL), then dried over anhydr. Na$_2$SO$_4$, filtered and evaporated the solvent under vacuo to give crude product. The crude was purified by CC (0-15% EtOAc in PE) and the pure fractions were concentrated at below 40° C. to give (3-chloro-5-(difluoro-methoxy)pyridin-2-yl)methanol (7.0 g, 92% (for two steps), as a thick liquid.

Step 4: 3-chloro-5-(difluoromethoxy)picolinaldehyde

DMP (21.6 g, 50.97 mmol) was added portion wise to a stirred solution of (3-chloro-5-(difluoromethoxy)pyridin-2-yl)methanol (7.0 g, 33.98 mmol) in DCM (100 mL) at 0° C. and stirred for 16 h at RT. The RM was filtered through a celite bed and washed with DCM (3×100 mL). The clear filtrate was washed with aq. NaHCO$_3$ (200 mL), water (200 mL), brine (250 mL), dried over anhydr. Na$_2$SO$_4$, filtered, concentrated under reduced pressure to get the crude product. The crude was purified by CC (0-5% EtOAc in PE) to give 3-chloro-5-(difluoromethoxy)picolinaldehyde (5.8 g, 85%) as liquid.

3-chloro-5-(difluoromethyl)picolinaldehyde

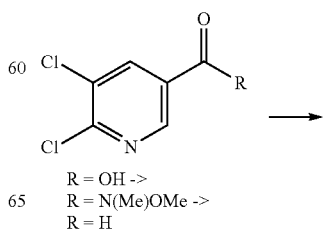

R = OH -><br>
R = N(Me)OMe -><br>
R = H

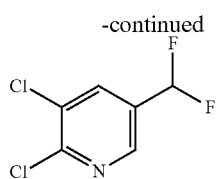

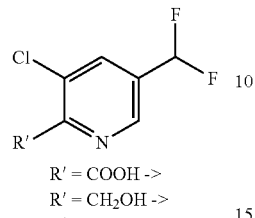

R' = COOH ->
R' = CH₂OH ->
R' = CHO

Step 1:
5,6-dichloro-N-methoxy-N-methylnicotinamide

EDC•HCl (24.92 g, 130.2 mmol), HOBt (17.95 g, 130.2 mmol) were added sequentially to a stirred solution of 5,6-dichloro nicotinic acid (12.5 g, 130.2 mmol), TEA (27 mL, 130.2 mmol) in DCM (250 mL) at 0° C. and stirred for 30 min at same temperature. To the RM was added N,O-dimethylhydroxylamine•HCl (12.7 g, 130.2 mmol) and slowly warmed to RT. The RM was stirred for 17 h at RT and quenched with water (100 mL), the organic product was extracted with DCM (2×50 mL). The organic layer was washed with brine (2×50 mL), then dried (anhydr. Na₂SO₄), filtered and evaporated the solvent under vacuo to give 5,6-dichloro-N-methoxy-N-methylnicotinamide (9.3 g, 60%) as a thick liquid Step 2: 5,6-dichloronicotinaldehyde A 2M solution of LiAlH₄ in THF (19.2 mL, 38.29 mmol) was added to a solution of 5,6-dichloro-N-methoxy-N-methylnicotinamide (22 g, 76.59 mol) in THF (360 mL) at −78° C. and stirred for 30 min at same temperature. The RM was quenched with sat. Na2SO4 solution and filtered the salts through celite bed, washed with EtOAc. The filtrate was dried (anhydr. Na₂SO₄), filtered and evaporated the solvent under vacuo to give crude as a thick liquid. The crude was purified by CC (0-5% EtOAc in PE) to give 12 g (75%) of 5,6-dichloronicotinaldehyde as liquid.

Step 3: 2,3-dichloro-5-(difluoromethyl)pyridine

DAST (32.8 mL, 38.29 mmol) was added to a solution of 5,6-dichloronicotinaldehyde (11 g, 62.59 mol) in DCM (110 mL) at −78° C. and stirred for 30 min and slowly warmed to RT and stirred for 17 h. The RM was quenched carefully with sat. NaHCO₃ solution and the organic product was extracted with EtOAc. The organic layer was washed with brine (2×100 mL), then dried (anhydr. Na₂SO₄), filtered and evaporated the solvent under vacuo to give crude, which was purified by CC (0-10% EtOAc in PE) to give 10 g (81%) of 2,3-dichloro-5-(difluoromethyl)pyridine.

Step 4: Ethyl 3-chloro-5-(difluoromethyl) Picolinate

CH₃COONa (4.2 g, 51.10 mmol) was added to a mixture of 2,3-dichloro-5-(difluoromethyl)pyridine (10 g, 51.10 mmol), Pd(OAc)₂ (1.5 g, 6.6 mmol) and PdCl₂(dppf) DCM complex (3.6 g, 6.6 mmol) in EtOH (100 mL) in a steel bomb, charged with CO gas (220 psi) and heated at 90° C. for 6-8 h. The reaction mass was cooled to RT, excess gas was evacuated in vacuo and RM was concentrated under reduced pressure. The residue was purified by CC (0-10% EtOAc in PE) to get 10 g (80%) of ethyl 3-chloro-5-(difluoromethyl) picolinate as a thick liquid.

Step 5: (3-chloro-5-(difluoromethyl)pyridin-2-yl)methanol

NaBH₄ (2.41 g, 63.90 mmol) was slowly added to a solution of ethyl 3-chloro-5-(difluoromethyl)-picolinate (10 g, 42.6 mmol) at 0° C. and slowly warmed to RT and stirred for 4 h. The RM was evaporated and the residue was quenched with water (200 mL) and the organic product was extracted with EtOAc (2×100 mL). The organic layer was washed with brine (2×100 mL), then dried (anhydr. Na₂SO₄), filtered and evaporated the solvent under vacuo to give 7 g (86%) of (3-chloro-5-(difluoromethyl)pyridin-2-yl)methanol as a thick liquid.

Step 6: 3-chloro-5-(difluoromethyl)picolinaldehyde

DMP (7 g, 72.60 mmol) was slowly added to a solution of (3-chloro-5-(difluoromethyl)pyridin-2-yl)methanol (7 g, 36.30 mmol) at 0° C. and slowly warmed to RT and stirred for 17 h. The RM was filtered through celite bed and washed with DCM. The filtrate was sat. NaHCO₃ (2×100 mL), brine (2×100 mL), then dried (anhydr. Na₂SO₄), filtered and evaporated the solvent under vacuo to give crude. The crude was purified by CC (60-10% EtOAc in PE) to get 7 g (86%) of 3-chloro-5-(difluoromethyl)picolinaldehyde as oil.

The following compounds (examples 49-55) were prepared from the aldehydes described above or from commercially available aldehydes or from intermediates described within this application in analogy to 5-chloro-2-[4-methyl-4-[[3-(trifluoromethyl)phenyl]sulfonyl]-tetrahydro-pyran-2-yl]-pyridine (example 48)

2,4-Dimethoxy-5-[4-methyl-4-[[3-(trifluoromethyl)phenyl]sulfonyl]-tetrahydro-pyran-2-yl]-pyridine (Example 49)

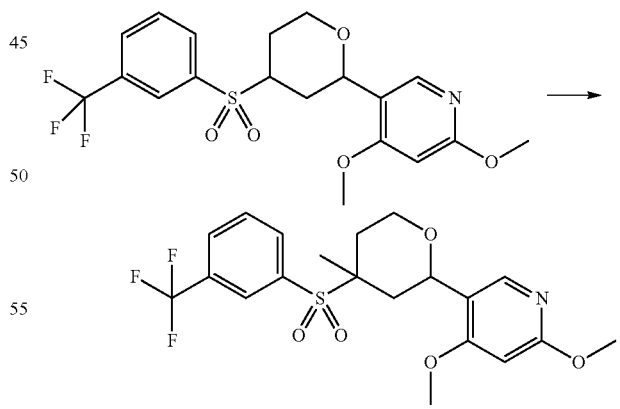

A solution of 2,4-dimethoxy-5-(4-(3-(trifluoromethyl)phenylsulfonyl)tetrahydro-2H-pyran-2-yl)pyridine (1.8 g, 4.176 mmol) in THF (40 mL) was cooled to −78° C. and t-BuOK (1M solution in THF (8.5 mL, 8.35 mmol) was added drop-wise. The total reaction mass was stirred at −78° C. for 30 min, then MeI (0.7 mL, 10.44 mmol) was added and the resulting mixture was warmed to RT and stirred for 16 h. The reaction mass was diluted with EtOAc (150 mL)

and washed with water (50 mL) and brine (100 mL), dried (Na$_2$SO$_4$) and concentrated under reduced pressure to get crude compound. The crude compound was purified by column (0-20% EtOAc in PE to obtain 2,4-Dimethoxy-5-[4-methyl-4-[[3-(trifluoromethyl)phenyl]sulfonyl]-tetrahydro-pyran-2-yl]-pyridine (1.1 g, 61% LCMS 90%&8%). The isomers were separated by prep HPLC (reverse phase) to get cis (0.7 g, 39%) and Trans (30 mg) as a white solids trans-rac 2,4-Dimethoxy-5-[4-methyl-4-[[3-(trifluoromethyl)phenyl]sulfonyl]-tetrahydro-pyran-2-yl]-pyridine SC-247

$^1$H-NMR (600 MHz, [d$_6$]-DMSO): δ=8.22-8.23 (2H), 8.08 (1H), 8.00-8.02 (1H), 7.97 (1H), 6.4 (1H), 5.25-5.27 (1H), 4.11-4.15 (1H), 3.97-4.00 (1H), 3.92 (3H), 3.82 (3H), 2.29-2.31 (1H), 2.16-2.19 (1H), 1.85-1.90 (1H), 1.55-1.59 (1H), 1.14 (3H).

Cis-rac 2,4-Dimethoxy-5-[4-methyl-4-[[3-(trifluoromethyl)phenyl]sulfonyl]-tetrahydro-pyran-2-yl]-pyridine $^1$H-NMR (600 MHz, [d$_6$]-DMSO): δ=8.20-8.22 (1H), 8.17-8.18 (1H), 8.05 (1H), 7.94-7.97 (1H), 7.91 (1H), 6.37 (1H), 4.63-4.66 (1H), 4.01-4.04 (1H), 3.82 (3H), 3.77 (3H), 3.65-3.70 (1H), 2.07-2.13 (1H), 1.89-1.93 (1H), 1.70-1.73 (1H), 1.44-1.47 (4H).

NOE: C-2 proton & methyl=cis

Chiral Resolution of 2,4-Dimethoxy-5-[4-methyl-4-[[3-(trifluoromethyl)phenyl]sulfonyl]-tetrahydro-pyran-2-yl]-pyridine Cis-rac 2,4-Dimethoxy-5-[4-methyl-4-[[3-(trifluoromethyl)phenyl]sulfonyl]-tetrahydro-pyran-2-yl]-pyridine was subjected to preparative chiral-SFC (Chiralcel OD-H column, MeOH, 30%) to give cis-EN1 SC-245 and cis-EN2 SC-246.

[cis-EN1] SC-245—analytical chiral SFC: Chiralcel OD-H (250×4.6 mm 5μ), 0.5% DEA in MeOH 30%, 3 g/min, Ret. Time 2.09; ee >95%

[cis-EN2] SC-246—analytical chiral SFC: Chiralcel OD-H (250×4.6 mm 5μ), 0.5% DEA in MeOH 30%, 3 g/min, Ret. Time 2.77; ee >95%

2-Methoxy-4-methyl-5-[4-methyl-4-[[3-(trifluoromethyl)phenyl]sulfonyl]-tetrahydro-pyran-2-yl]-pyridine (Example 50)

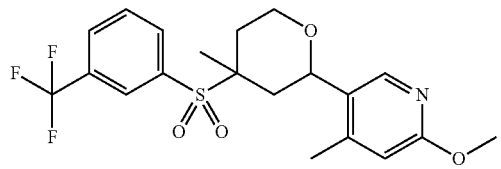 [SMILES: COc1cc(C)c(C2CC(C)(S(=O)(=O)c3cccc(C(F)(F)F)c3)CCO2)cn1]

$^1$H-NMR (600 MHz, [d$_6$]-DMSO): δ=8.20-8.22 (2H), 8.08 (1H), 8.03 (1H), 7.94-7.97 (1H), 6.62 (1H), 4.64-4.66 (1H), 4.02-4.05 (1H), 3.82 (3H), 3.70-3.74 (1H), 2.23 (3H), 2.10-2.15 (1H), 2.01-2.07 (1H), 1.65-1.68 (1H), 1.48-1.52 (4H).

NOE: C-2 proton & methyl=cis

Chiral Resolution of 2-Methoxy-4-methyl-5-[4-methyl-4-[[3-(trifluoromethyl)phenyl]sulfonyl]-tetrahydro-pyran-2-yl]-pyridine Cis-rac 2-Methoxy-4-methyl-5-[4-methyl-4-[[3-(trifluoromethyl)phenyl]sulfonyl]-tetrahydro-pyran-2-yl]-pyridine was subjected to preparative chiral-SFC (Chiralpak AD-H column, MeOH, 15%) to give cis-EN1 SC-248 and cis-EN2 SC-249.

[cis-EN1] SC-248—analytical chiral SFC: Chiralpak AS-H (250×4.6 mm 5μ), 0.5% DEA in MeOH 10%, 3 g/min, Ret. Time 2.66; ee >95%

[cis-EN2] SC-249—analytical chiral SFC: Chiralpak AS-H (250×4.6 mm 5μ), 0.5% DEA in MeOH 10%, 3 g/min, Ret. Time 3.42; ee >95%

[trans]-rac 2-Methoxy-4-methyl-5-[4-methyl-4-[[3-(trifluoromethyl)phenyl]sulfonyl]-tetrahydro-pyran-2-yl]-pyridine SC-252

$^1$H-NMR (600 MHz, [d$_6$]-DMSO): δ=8.22-8.24 (2H), 8.10 (2H), 7.97-8.00 (1H), 6.64 (1H), 5.18-5.20 (1H), 4.17-4.22 (1H), 3.97-4.01 (1H), 3.81 (3H), 2.28-2.35 (4H), 2.14-2.18 (1H), 1.84-1.90 (1H), 1.75-1.79 (1H), 1.16 (3H).

2-Methoxy-5-[4-methyl-4-[[3-(trifluoromethyl)phenyl]sulfonyl]-tetrahydro-pyran-2-yl]-pyridin-4-ol (Example 51)

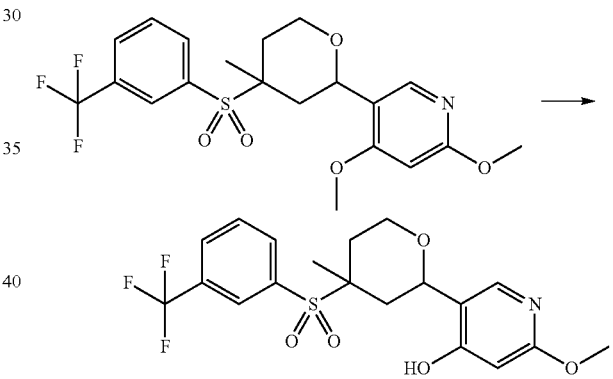

Sodium thiomethoxide (0.4 g, 5.39 mmol) was added to a solution of 2,4-Dimethoxy-5-[4-methyl-4-[[3-(trifluoromethyl)phenyl]sulfonyl]-tetrahydro-pyran-2-yl]-pyridine (1.2 g, 2.69 mmol) in dry DMF (15 mL) at RT and the reaction was subjected to microwave irradiation at 110° C. for 90 min. The RM was poured into cold water and acidified with dilute HCl solution up to pH-7.0. A Solid precipitated. The solid was filtered, washed with water and dried in vacuo to get 2-Methoxy-5-[4-methyl-4-[[3-(trifluoromethyl)-phenyl]sulfonyl]-tetrahydro-pyran-2-yl]-pyridin-4-ol (0.75 g, 68%) as a white solid. $^1$H-NMR (600 MHz, [d$_6$]-DMSO): δ=8.21-8.22 (1H), 8.16-8.18 (1H), 8.05 (1H), 7.94-7.97 (1H), 7.87 (1H), 6.13 (1H), 4.62-4.64 (1H), 4.02-4.06 (1H), 3.77 (3H), 3.66-3.70 (1H), 2.10-2.15 (1H), 1.87-1.92 (1H), 1.73-1.75 (1H), 1.44-1.47 (4H).

NOE: C-2 proton & methyl=cis

Chiral Resolution of 2-Methoxy-5-[4-methyl-4-[[3-(trifluoromethyl)phenyl]sulfonyl]-tetrahydro-pyran-2-yl]-pyridin-4-ol Cis-rac 2-Methoxy-5-[4-methyl-4-[[3-(trifluoromethyl)phenyl]sulfonyl]-tetrahydro-pyran-2-yl]-pyridin-4-ol was subjected to preparative chiral-SFC (Chiralcel OX-H column, MeOH, 35%) to give cis-EN1 SC-250 and cis-EN2 SC-251.

[cis-EN1] SC-250—analytical chiral SFC: Chiralcel OX-H (250×4.6 mm 5μ), 0.5% DEA in MeOH 30%, 3 g/min, Ret. Time 1.19; ee >95%

[cis-EN2] SC-251—analytical chiral SFC: Chiralcel OX-H (250×4.6 mm 5μ), 0.5% DEA in MeOH 30%, 3 g/min, Ret. Time 1.46; ee >95%

[cis-EN1]-4-(Difluoro-methoxy)-2-methoxy-5-[4-methyl-4-[[3-(trifluoromethyl)phenyl]sulfonyl]-tetrahydro-pyran-2-yl]-pyridine (Example 52)

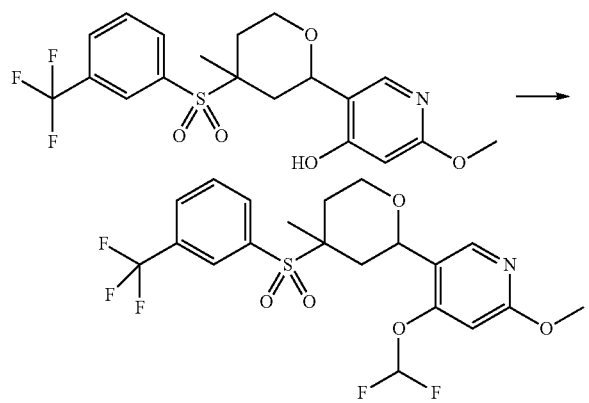

K$_2$CO$_3$ (0.32 g, 2.32 mmol) was added to clear solution of [cis-EN1] SC-250 (0.5 g, 1.16 mmol) in dry DMF (10 mL) at RT. The total reaction mass was heated to 90° C., and purged with Freon gas (CHF$_2$Cl) for 30 min. The RM was diluted with water (50 mL) and extracted with EtOAc (50 mL×2). The organic extract was washed with water (2×50 mL), brine (100 mL), dried (Na$_2$SO$_4$) and concentrated under reduced pressure to get crude compound. The crude compound was purified by CC (0-20% EtOAc in PE) to obtain [cis-EN1]-2-Methoxy-5-[4-methyl-4-[[3-(trifluoromethyl)phenyl]sulfonyl]-tetrahydro-pyran-2-yl]-pyridin-4-ol (0.14 g, 26%) as a white solid.

$^1$H-NMR (600 MHz, [d$_6$]-DMSO): δ=8.18-8.22 (2H), 8.14 (1H), 8.06 (1H), 7.94-7.96 (1H), 7.26-7.51 (1H), 6.58 (1H), 4.66-4.69 (1H), 4.05-4.08 (1H), 3.87 (3H), 3.70-3.75 (1H), 2.10-2.16 (1H), 1.95-1.99 (1H), 1.70-1.73 (1H), 1.48-1.51 (4H).

NOE: C-2 proton & methyl=cis

[cis-EN1] SC-253—analytical chiral SFC: Amylose C-S-5μ (250×4.6 mm 5μ), 0.5% DEA in MeOH 35%, 3 g/min, Ret. Time 2.18; ee >95%

[cis-EN2]-4-(Difluoro-methoxy)-2-methoxy-5-[4-methyl-4-[[3-(trifluoromethyl)phenyl]sulfonyl]-tetrahydro-pyran-2-yl]-pyridine (Example 52)

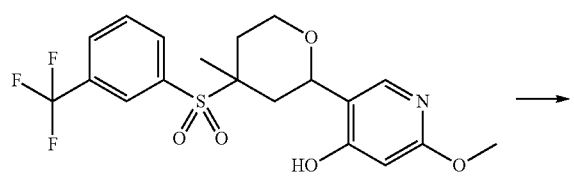

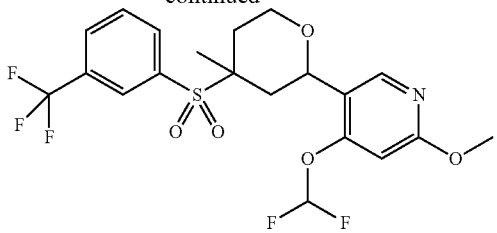

K$_2$CO$_3$ (0.32 g, 2.32 mmol) was added to clear solution of [cis-EN2] SC-251 (0.5 g, 1.16 mmol) in dry DMF (10 mL) at RT. The total reaction mass was heated to 90° C., then purged with Freon gas for 30 min. The RM was diluted with water (50 mL) and extracted with EtOAc (50 mL×2). The organic extract was washed with water (2×50 mL), brine (100 mL), dried (Na2SO4) and concentrated under reduced pressure to get crude compound. The crude compound was purified by CC (0-20% EtOAc in PE) to obtain [cis-EN2]-2-Methoxy-5-[4-methyl-4-[[3-(trifluoromethyl)phenyl]sulfonyl]-tetrahydro-pyran-2-yl]-pyridin-4-ol (0.16 g, 29%) as a white solid.

$^1$H-NMR (600 MHz, [d$_6$]-DMSO): δ=8.18-8.22 (2H), 8.14 (1H), 8.05 (1H), 7.93-7.96 (1H), 7.26-7.51 (1H), 6.59 (1H), 4.66-4.69 (1H), 4.05-4.08 (1H), 3.86 (3H), 3.70-3.75 (1H), 2.10-2.15 (1H), 1.95-1.99 (1H), 1.70-1.73 (1H), 1.47-1.51 (4H).

[cis-EN2] SC-254—analytical chiral SFC: Amylose C-S-5μ (250×4.6 mm 5μ), 0.5% DEA in MeOH 35%, 3 g/min, Ret. Time 3.1; ee >95%

3-Fluoro-2-methoxy-5-[4-methyl-4-[[3-(trifluoromethyl)phenyl]sulfonyl]-tetrahydro-pyran-2-yl]-pyridine (Example 53)

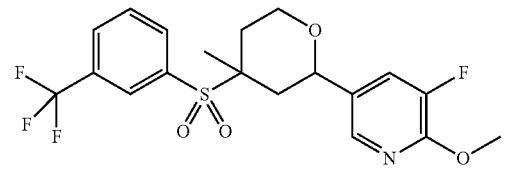 [SMILES: COc1ncc(C2CC(C)(S(=O)(=O)c3cccc(C(F)(F)F)c3)CCO2)cc1F]

$^1$H-NMR (600 MHz, [d$_6$]-DMSO): δ=8.17-8.21 (2H), 8.06 (1H), 7.94-7.96 (2H), 7.60-7.63 (1H), 4.58-4.60 (1H), 4.03-4.06 (1H), 3.93 (3H), 3.68-3.72 (1H), 2.11-2.16 (1H), 1.92-1.96 (1H), 1.71-1.74 (1H), 1.47-1.50 (4H).

NOE: C-2 proton & methyl=cis

Chiral Resolution of 3-Fluoro-2-methoxy-5-[4-methyl-4-[[3-(trifluoromethyl)phenyl]sulfonyl]-tetrahydro-pyran-2-yl]-pyridine Cis-rac 3-fluoro-2-methoxy-5-[4-methyl-4-[[3-(trifluoromethyl)phenyl]sulfonyl]-tetrahydro-pyran-2-yl]-pyridine was subjected to preparative chiral-SFC (LUX Amylose-2 column, MeOH, 30%) to give cis-EN1 SC-255 and cis-EN2 SC-256.

[cis-EN1] SC-255—analytical chiral SFC: Lux Amylose-2 (250×4.6 mm 5μ), iPrOH 20%, 3 g/min, Ret. Time 3.52; ee >95%

[cis-EN2] SC-256—analytical chiral SFC: Lux Amylose-2 (250×4.6 mm 5μ), iPrOH 20%, 3 g/min, Ret. Time 4.42; ee >95%

4-Fluoro-2-methoxy-5-[4-methyl-4-[[3-(trifluoromethyl)phenyl]sulfonyl]-tetrahydro-pyran-2-yl]-pyridine (Example 54)

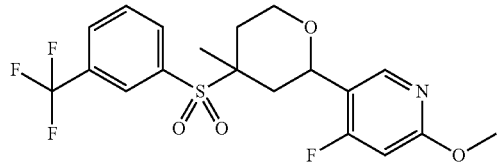 [SMILES: COc1cc(F)c(C2CC(C)(S(=O)(=O)c3cccc(C(F)(F)F)c3)CCO2)cn1]

$^1$H-NMR (600 MHz, [d$_6$]-DMSO): δ=8.17-8.23 (3H), 8.07 (1H), 7.94-7.97 (1H), 6.73-6.75 (1H), 4.70-4.73 (1H), 4.02-4.05 (1H), 3.87 (3H), 3.69-3.74 (1H), 2.10-2.16 (2H), 1.65-1.68 (1H), 1.48-1.51 (4H).

NOE: C-2 proton & methyl=cis

Chiral Resolution of 4-Fluoro-2-methoxy-5-[4-methyl-4-[[3-(trifluoromethyl)phenyl]sulfonyl]-tetrahydro-pyran-2-yl]-pyridine Cis-rac 4-fluoro-2-methoxy-5-[4-methyl-4-[[3-(trifluoromethyl)phenyl]sulfonyl]-tetrahydro-pyran-2-yl]-pyridine was subjected to preparative chiral-SFC (Chiralpak AD-H column, 0.5% DEA in MeOH, 25%) to give cis-EN1 SC-257 and cis-EN2 SC-258.

[cis-EN1] SC-257—analytical chiral SFC: Chiralpak AD-H (250×4.6 mm 5μ), 0.5% DEA in MeOH, 25%, 3 g/min, Ret. Time 2.56; ee >95%

[cis-EN2] SC-258—analytical chiral SFC: Chiralpak AD-H (250×4.6 mm 5μ), 0.5% DEA in MeOH, 25%, 3 g/min, Ret. time 3.2; ee >95%

[trans]-rac 4-fluoro-2-methoxy-5-[4-methyl-4-[[3-(trifluoromethyl)phenyl]sulfonyl]-tetrahydro-pyran-2-yl]-pyridine SC-259

$^1$H-NMR (600 MHz, [d$_6$]-DMSO): δ=8.22-8.25 (3H), 8.10 (1H), 7.97-8.00 (1H), 6.75-6.77 (1H), 5.27-5.29 (1H), 4.18-4.22 (1H), 4.00-4.03 (1H), 3.87 (3H), 2.18-2.26 (1H), 1.79-1.92 (2H), 1.18 (3H).

2-Methoxy-5-[4-methyl-4-[[3-(trifluoromethyl)phenyl]sulfonyl]-tetrahydro-pyran-2-yl]-isonicotinonitrile (Example 55)

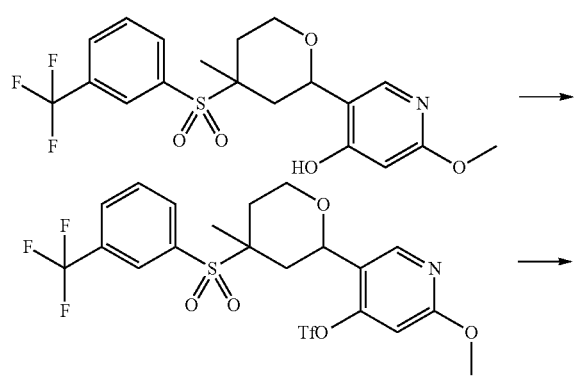

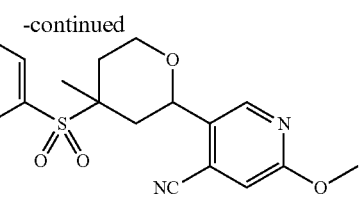

Step 1: 2-methoxy-5-(4-methyl-4-(3-(trifluoromethyl)phenylsulfonyl)tetrahydro-2H-pyran-2-yl)pyridin-4-yl Trifluoromethanesulfonate TEA (1.46 mL, 10.44 mmol) was added to a solution of 2-methoxy-5-[4-methyl-4-[[3-(trifluoromethyl)phenyl]sulfonyl]-tetrahydro-pyran-2-yl]-pyridin-4-ol (1.5 g, 3.48 mmol) in dichloromethane at 0° C., then trifluoromethanesulfonic anhydride (1.2 mL, 6.96 mmol) was added slowly drop by drop at same temperature. After completion of addition the reaction was warmed to RT and stirred at this temperature for 5 h. The mixture was diluted with water (250 mL) and extracted with DCM (150 mL×3). The organic extract was washed with NaHCO3 (100 mL), water (100 mL), brine (200 mL), dried (Na$_2$SO$_4$) and concentrated under reduced pressure to get 2-methoxy-5-(4-methyl-4-(3-(trifluoro-methyl)phenylsulfonyl)tetrahydro-2H-pyran-2-yl) pyridin-4-yl trifluoromethanesulfonate (1.9 g, 98%) as a dark brown solid.

Step 2: 2-Methoxy-5-[4-methyl-4-[[3-(trifluoromethyl)phenyl]sulfonyl]-tetrahydro-pyran-2-yl]-isonicotinonitrile Zinc cyanide (625 mg, 5.32 mmol) was added to an Ar purged solution of 2-methoxy-5-(4-methyl-4-(3-(trifluoromethyl)phenylsulfonyl)tetrahydro-2H-pyran-2-yl)pyridin-4-yl trifluoromethanesulfonate (2.0 g, 3.55 mmol) in dry DMF (20 mL), Then dppf (157 mg, 0.28 mmol), Zinc powder (69 mg, 1.06 mmol) and Pd$_2$(dba)$_3$ (97.5 mg, 0.16 m·mol) were added and the reaction was heated to 120° C. for 12 h. The mixture was filtered through celite and washed with EtOAc. The filtrate was diluted with water (50 mL) and extracted with EtOAc (50 mL×3). The combined organic extracts were washed with water (100 mL), brine (100 mL), dried (Na$_2$SO$_4$) and concentrated under reduced pressure to get the crude product. The crude compound was purified by CC (0-30% EtOAc in PE) to obtain 2-methoxy-5-[4-methyl-4-[[3-(trifluoromethyl)phenyl]sulfonyl]-tetrahydro-pyran-2-yl]-isonicotinonitrile (0.8 g, 51%) as a white solid.

$^1$H-NMR (600 MHz, [d$_6$]-DMSO): δ=8.36-8.37 (1H), 8.21-8.22 (1H), 8.09 (1H), 7.94-7.97 (1H), 7.39 (1H), 4.74-4.76 (1H), 4.07-4.10 (1H), 3.91 (3H), 3.73-3.78 (1H), 2.11-2.17 (2H), 1.78-1.81 (1H), 1.52-1.55 (4H).

NOE: C-2 proton & methyl=cis

Chiral Resolution of 2-Methoxy-5-[4-methyl-4-[[3-(trifluoromethyl)phenyl]sulfonyl]-tetrahydro-pyran-2-yl]-isonicotinonitrile Cis-rac 2-methoxy-5-[4-methyl-4-[[3-(trifluoromethyl)phenyl]sulfonyl]-tetrahydro-pyran-2-yl]-isonicotino-nitrile was subjected to preparative chiral-SFC (Lux Cellulose-2 column, MeOH, 20%) to give cis-EN1 SC-260 and cis-EN2 SC-261.

[cis-EN1] SC-260—analytical chiral SFC: Lux Cellulose-2 (250×4.6 mm 5μ), 0.5% DEA in MeOH 30%, 3 g/min, Ret. Time 2.33; ee >95%

[cis-EN2] SC-261—analytical chiral SFC: Lux Cellulose-2 (250×4.6 mm 5μ), 0.5% DEA in MeOH 30%, 3 g/min, Ret. Time 2.63; ee >95%

3-Methyl-5-methylsulfonyl-2-[4-methyl-4-[[3-(trifluoromethyl)phenyl]sulfonyl]-tetrahydro-pyran-2-yl]-pyridine (Example 56)

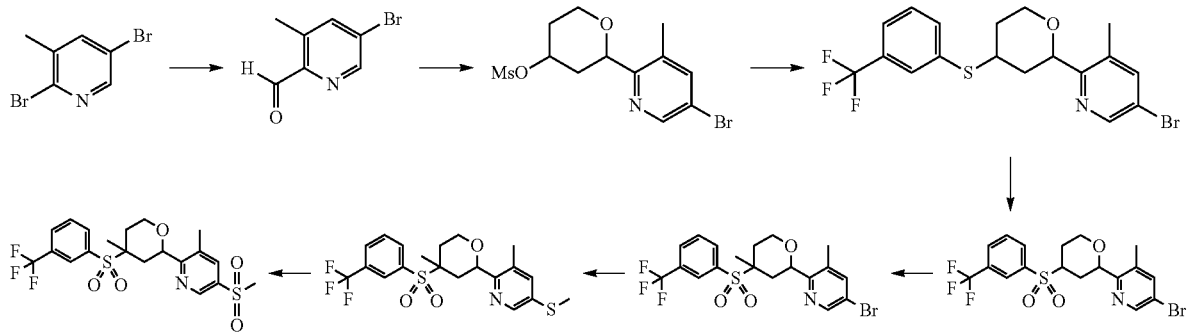

Step 1: 5-bromo-3methylpicolinaldehyde

A solution of BuLi (1.6 M in Hexane; 38 mL, 60 mmol) was added to 2,5-dibromo-3-methylpyridine (15.0 g, 60 mmol) in dry DCM (150 mL) under Ar at −78° C. over 20 min. The RM was stirred at −78° C. for 30 min and then dry DMF (5.7 mL, 72 mmol) was added slowly. The RM was slowly warmed to 0° C. and the RM was maintained at 0° C. for 20 min. After completion of the reaction, the RM was quenched with sat. NH$_4$Cl and extracted with DCM. The organic layer was washed with water followed by brine, dried over Na$_2$SO$_4$ and concentrated under reduced pressure to get crude compound. The crude compound was purified by CC (0-5% EtOAc in PE) to 5-bromo-3methylpicolinaldehyde (3.0 g, 28%) as a light yellow solid.

Step 2: 2-(5-bromo-3-methylpyridi-2yl)tetrahydro-2H-pyran-4-yl Methanesulfonate Methanesulphonic acid (20 mL, 303 mmol) was added to a solution of 5-bromo-3methylpicolinaldehyde (2.8 g, 0.018 mol) and 3-buten-1-ol (4.6 mL, 45.45 mmol) in DCM (120 mL) at 0° C., stirred at 0° C. for 1 h. The mixture was diluted with water and basified to pH-8.0 by using sat. NaHCO$_3$ solution. The mixture was extracted with DCM (300 mL) and washed with water (200 mL), and brine (200 mL), dried over Na2SO4 and concentrated under reduced pressure to get crude 2-(5-bromo-3-methylpyridi-2yl)tetra-hydro-2H-pyran-4-yl methanesulfonate (6.5 g, 62%) as a brown solid. The crude material was directly used for next step without further purification.

Step 3: 5-bromo-3-methyl-2-(4-(3-(trifluoromethyl)phenylthio)tetrahydro-2H-pyran-2-yl)pyridine 3-Trifluoromethyl thiophenol (4.5 mL, 34.38 mmol) was added to a suspension of 2-(5-bromo-3-methylpyridin-2-yl) tetrahydro-2H-pyran-4-yl methanesulfonate (6.0 g, 17.19 mmol) and K$_2$CO$_3$ (4.8 g, 34.38 mmol) in DMF (120 mL) and the RM was heated at 50° C. for 5 h and then stirred at RT for 16 h. After completion of reaction, the mixture was diluted with water (300 mL) and extracted with EtOAc (250 mL×2). The organic extract was washed with water (200 mL), brine (200 mL), dried (Na2SO4) and concentrated under reduced pressure to get crude compound. The crude compound was purified by CC (silica gel 100-200 mesh, 0-10% EtOAc in PE) to obtain 5-bromo-3-methyl-2-(4-(3-(trifluoromethyl)phenylthio)tetrahydro-2H-pyran-2-yl)pyridine (6.0 g, 81%) as a light brown gummy liquid.

Step 4: 5-bromo-3-methyl-2-(4-(3-(trifluoromethyl)phenylsulfonyl) tetrahydro-2H-pyran-2-yl) Pyridine 5-bromo-3-methyl-2-(4-(3-(trifluoromethyl)phenylthio) tetrahydro-2H-pyran-2-yl)pyridine (6.0 g, 13.92 mmol) was dissolved in MeOH (180 mL) and a solution of OXONE (17.0 g, 27.84 mmol) in water (150 mL) was added. The total reaction mass was stirred at RT for 18 h. The reaction mass was diluted with water (100 mL) and extracted with EtOAc (3×100 mL). The combined organic extract was washed with water (100 mL), brine (100 mL), dried over Na$_2$SO$_4$ and concentrated to get crude. The crude compound was purified by CC (0-30% EtOAc in PE) to obtain 5-bromo-3-methyl-2-(4-(3-(trifluoromethyl) phenylsulfonyl) tetrahydro-2H-pyran-2-yl) pyridine (3.5 g, 55%) as a white solid.

Step 5: 5-bromo-3-methyl-2-(4-methyl-4-(3-(trifluoromethyl)phenylsulfonyl)tetrahydro-2H-pyran-2-yl) pyridine A solution of 5-bromo-3-methyl-2-(4-(3-(trifluoromethyl) phenylsulfonyl) tetrahydro-2H-pyran-2-yl) pyridine (3.5 g, 7.55 mmol) in THF (30 mL) was cooled to −78° C. and t-BuOK (1M solution in THF) (15 mL, 15.11 mmol) was added drop-wise. The total reaction mass was stirred at −78° C. for 30 min, then MeI (1.2 mL, 18.89 mmol) was added and the resulting mixture was warmed to RT and stirred for 16 h. The reaction mass was diluted with EtOAc (150 mL) and washed with water (100 mL) and brine (100 mL), dried over Na2SO4 and concentrated under reduced pressure to get crude compound. The crude compound was purified by CC (0-20% EtOAc in PE) to get 5-bromo-3-methyl-2-(4-methyl-4-(3-(trifluoromethyl)phenylsulfonyl)-tetrahydro-2H-pyran-2-yl)pyridine (1.6 g, 45%) as a white solid.

Step 6: 3-methyl-2-(4-methyl-4-(3-(trifluoromethyl)phenylsulfonyl)tetrahydro-2H-pyran-2-yl)-5-(methylthio)pyridine Xantphos (126 mg, 0.22 mmol) followed by Pd$_2$(dba)$_3$ (201 mg, 0.22 mmol) were added to a degassed solution of 5-bromo-3-methyl-2-(4-methyl-4-(3-(trifluoromethyl)phenylsulfonyl)tetrahydro-2H-pyran-2-yl)pyridine (1.5 g, 3.14 mmol) and DIPEA (1.2 mL, 21.97 mmol) in toluene (50 mL) and further degassed for 10 min. Sodium thiomethoxide (1.1 g, 6.28 mmol) was added and further degassed for 5 min. The resulting mixture was heated at 120° C. for 16 h under Ar. Reaction mass was filtered through celite bed and washed the cake with EtOAc (50 mL). The filtrate concentrated to yield crude product. The crude product was purified by CC (0-30% EtOAc in PE) to obtain 3-methyl-2-(4-methyl-4-(3-(trifluoromethyl)phenylsulfonyl)tetrahydro-2H-pyran-2-yl)-5-(methylthio)pyridine (1.3 g, 93%) as off white solid.

Step 7: 3-methyl-2-(4-methyl-4-(3-(trifluoromethyl) phenylsulfonyl)tetrahydro-2H-pyran-2-yl)-5-(methylsulfonyl)pyridine 3-methyl-2-(4-methyl-4-(3-(trifluoromethyl)phenylsulfonyl)tetrahydro-2H-pyran-2-yl)-5-(methylthio)pyridine (1.5 g, 3.37 mmol) was dissolved in MeOH (45 mL) and a solution of OXONE (4.1 g, 6.74 mmol) in water (37.5 mL) was added and stirred at RT for 18 h. The reaction mass was diluted with water (50 mL) and extracted with EtOAc (3×100 mL). The organic extract was washed with brine (100 mL), dried over $Na_2SO_4$ and concentrated to get crude. The crude compound was purified by CC (0-50% EtOAc in PE) to obtain 3-methyl-5-methylsulfonyl-2-[4-methyl-4-[[3-(trifluoromethyl)phenyl]sulfonyl]-tetrahydro-pyran-2-yl]-pyridine (1.0 g, 63%) as a white solid.

$^1$H-NMR (600 MHz, [$d_6$]-DMSO): δ=8.86 (1H), 8.23-8.24 (1H), 8.20-8.21 (1H), 8.08 (1H), 7.97-8.00 (1H), 4.87-4.89 (1H), 3.98-4.01 (1H), 3.76-3.80 (1H), 3.30 (3H), 2.60-2.64 (1H), 2.46 (3H), 2.10-2.15 (1H), 1.69-1.72 (1H), 1.52 (3H), 1.45-1.48 (1H).

NOE: C-2 proton & methyl=cis

Chiral Resolution of 3-methyl-2-(4-methyl-4-(3-(trifluoromethyl)phenylsulfonyl)tetrahydro-2H-pyran-2-yl)-5-(methylsulfonyl)pyridine Cis-rac 3-Methyl-5-methylsulfonyl-2-[4-methyl-4-[[3-(trifluoromethyl)phenyl]sulfonyl]-tetrahydro-pyran-2-yl]-pyridine was subjected to preparative chiral-SFC (Chiralpak AS-H column, MeOH, 35%) to give cis-EN1 SC-262 and cis-EN2 SC-263.

[cis-EN1] SC-262—analytical chiral SFC: Chiralpak AS-H (250×4.6 mm 5μ), 0.5% DEA in MeOH 15%, 3 g/min, Ret. Time 4.3; ee >95%

[cis-EN2] SC-263—analytical chiral SFC: Chiralpak AS-H (250×4.6 mm 5μ), 0.5% DEA in MeOH 15%, 3 g/min, Ret. Time 6.7; ee >95%

The following compounds (Examples 35 to 45 and 57 to 60) were prepared from the aldehydes described above or from commercially available aldehydes or from intermediates described within this application in analogy to 3-methyl-5-methylsulfonyl-2-[4-methyl-4-[[3-(trifluoromethyl)phenyl]sulfonyl]-tetrahydro-pyran-2-yl]-pyridine (Example 56).

2-[4-[[3-(Difluoro-methyl)-phenyl]sulfonyl]-4-methyl-tetrahydro-pyran-2-yl]-3-methylsulfonyl-5-(trifluoromethyl)-pyridine (Example 35)

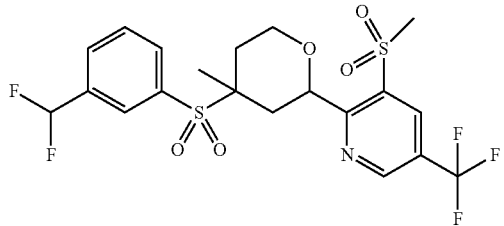 [SMILES: CC1(S(=O)(=O)c2cccc(C(F)F)c2)CCOC(c2ncc(C(F)(F)F)cc2S(C)(=O)=O)C1]

$^1$H-NMR (600 MHz, [$d_6$]-DMSO): δ=9.32 (1H), 8.55 (1H), 8.02-8.05 (3H), 7.86-7.89 (1H), 7.12-7.31 (1H), 5.40-5.42 (1H), 4.05-4.08 (1H), 3.74-3.79 (1H), 3.43 (3H), 2.53-2.57 (1H), 2.13-2.18 (1H), 1.83-1.86 (1H), 1.46-1.50 (4H).
NOE: C-2 proton & methyl=cis Chiral Resolution of 2-[4-[[3-(Difluoro-methyl)-phenyl]sulfonyl]-4-methyl-tetrahydro-pyran-2-yl]-3-methylsulfonyl-5-(trifluoromethyl)-pyridine Cis-rac 2-[4-[[3-(Difluoro-methyl)-phenyl]sulfonyl]-4-methyl-tetrahydro-pyran-2-yl]-3-methylsulfonyl-5-(trifluoromethyl)-pyridine was subjected to preparative chiral-SFC (Chiralpak OJ-H column, MeOH, 20%) to give cis-EN1 SC-212 and cis-EN2 SC-213.

[cis-EN1] SC-212—analytical chiral SFC: Chiralpak OJ-H (250×4.6 mm 5μ), MeOH, 10%, 3 g/min, Ret. Time 3.19; ee >95%

[cis-EN2] SC-213—analytical chiral SFC: Chiralpak OJ-H (250×4.6 mm 5μ), MeOH, 10%, 3 g/min, Ret. time 4.93; ee >95%

2-[4-Methyl-4-[(3-methylsulfonyl-phenyl)sulfonyl]-tetrahydro-pyran-2-yl]-3-methylsulfonyl-5-(trifluoromethyl)-pyridine

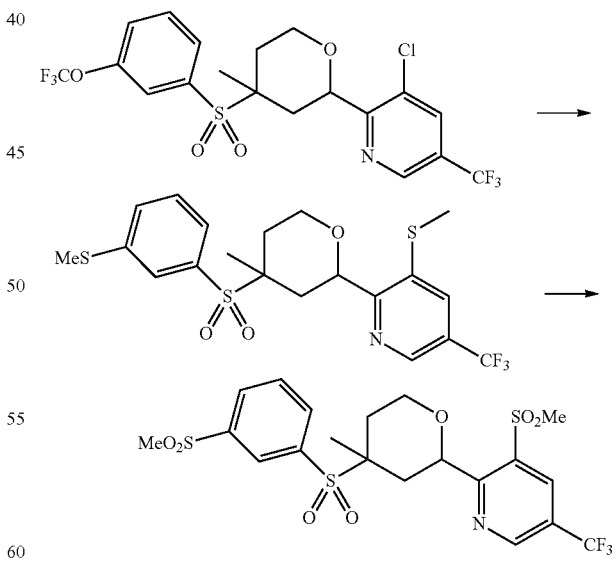

Step 1: 2-(4-methyl-4-((3-(methylthio)phenyl)sulfonyl)tetrahydro-2H-pyran-2-yl)-3-(methylthio)-5-(trifluoromethyl)pyridine A solution of 3-chloro-2-(4-methyl-4-((3-(trifluoromethoxy)phenyl)sulfonyl)tetrahydro-2H-pyran-2-yl)-5-

(trifluoromethyl)pyridine (2.1 g, 4.2 mmol) and NaSMe (1.51 g, 16.80 mmol) in pyridine (30 mL) was heated at 60° C. for 16 h under Ar. The RM was diluted with water (20 mL) and the organic product was extracted with EtOAc (3×50 mL). The combined organic layer was washed with brine, dried over anhydr. Na$_2$SO$_4$, filtered and evaporated the solvent under vacuo to give crude, which was purified by CC (0-15% EtOAc in PE as eluent) to get crude 2-(4-methyl-4-((3-(methylthio)phenyl)sulfonyl)tetra-hydro-2H-pyran-2-yl)-3-(methylthio)-5-(trifluoromethyl)pyridine (1.7 g). The crude was purified by SFC using the below condition and evaporating the fractions to get 2-(4-methyl-4-(3-(trifluoromethoxy)phenylsulfonyl)tetrahydro-2H-pyran-2-yl)-3-(methylthio)-5-(trifluoromethyl) pyridine (500 mg, 23%) as a white solid and 900 mg of 2-(4-methyl-4-((3-(methylthio)phenyl)sulfonyl)tetrahydro-2H-pyran-2-yl)-3-(methylthio)-5-(trifluoromethyl)-pyridine as a white solid.

$^1$H-NMR (600 MHz, [d$_6$]-DMSO): δ=8.70 (1H), 8.00 (1H), 7.67-7.69 (1H), 7.59-7.64 (3H), 4.81-4.83 (1H), 3.98-4.01 (1H), 3.69-3.74 (1H), 2.56 (6H), 2.07-2.12 (1H), 1.69-1.72 (1H), 1.45-1.50 (4H).

Step 2: 2-[4-Methyl-4-[(3-methylsulfonyl-phenyl)sulfonyl]-tetrahydro-pyran-2-yl]-3-methylsulfonyl-5-(trifluoromethyl)-pyridine 2-(4-methyl-4-((3-(methylthio)phenyl)sulfonyl)tetrahydro-2H-pyran-2-yl)-3-(methylthio)-5-(trifluoromethyl) pyridine (200 mg, 0.41 mmol) dissolved in CH3CN (20 mL)-THF (20 mL) and a solution of oxone (1.3 g, 2.09 mmol) in water (5 mL) was added. The RM was stirred at 40° C. for 16 h. The RM was concentrated in vacuo, the residue was diluted with water (50 mL) and the organic product was extracted with DCM (3×50 mL). The combined organic extract was washed with brine (2×50 mL), dried over anhydr. Na$_2$SO$_4$ and concentrated to get crude product. The crude compound was purified by CC (silica gel 60-120 mesh, 0-50% EtOAc in PE) to obtain 2-[4-methyl-4-[(3-methylsulfonyl-phenyl)sulfonyl]-tetrahydro-pyran-2-yl]-3-methylsulfonyl-5-(trifluoromethyl)-pyridine (135 mg) as a solid.

$^1$H-NMR (600 MHz, [d$_6$]-DMSO): δ=9.32 (1H), 8.56 (1H), 8.37-8.39 (1H), 8.28 (1H), 8.21-8.22 (1H), 7.99-8.02 (1H), 5.42-5.44 (1H), 4.06-4.09 (1H), 3.75-3.80 (1H), 3.44 (3H), 2.54-2.56 (1H), 2.13-2.19 (1H), 1.87-1.92 (1H), 1.48-1.52 (4H).

3-Chloro-2-[4-[[3-fluoro-5-(trifluoromethyl)-phenyl]sulfonyl]-4-methyl-tetrahydro-pyran-2-yl]-5-methylsulfonyl-pyridine (Example 36)

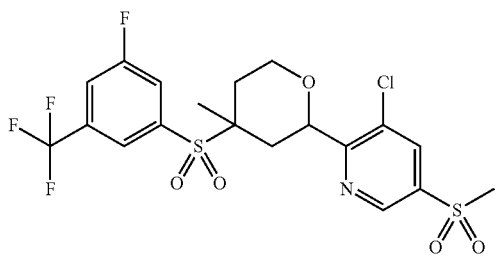 [SMILES: CC1(S(=O)(=O)c2cc(F)cc(C(F)(F)F)c2)CCOC(c2ncc(S(C)(=O)=O)cc2Cl)C1]

$^1$H-NMR (600 MHz, [d$_6$]-DMSO): δ=9.0-9.02 (1H), 8.46-8.47 (1H) 8.25-8.27 (1H), 8.07-8.09 1 (H), 7.93 (1H), 5.03-5.06 (1H), 4.02-4.05 (1H), 3.74-3.79 (1H), 3.38 (3H) 2.52-2.57 (1H), 2.14-2.20 (1H), 1.75-1.79 1 (H), 1.48-1.52 (4H).

NOE: C-2 proton & methyl=cis

Chiral Resolution of 3-Chloro-2-[4-[[3-fluoro-5-(trifluoromethyl)-phenyl]sulfonyl]-4-methyl-tetrahydro-pyran-2-yl]-5-methylsulfonyl-pyridine Cis-rac 3-Chloro-2-[4-[[3-fluoro-5-(trifluoromethyl)-phenyl]sulfonyl]-4-methyl-tetrahydro-pyran-2-yl]-5-methylsulfonyl-pyridine was subjected to preparative chiral-SFC (Chiralpak IC column, MeOH, 50%) to give cis-EN1 SC-214 and cis-EN2 SC-215.

[cis-EN1] SC-214—analytical chiral SFC: Chiralpak IC (250×4.6 mm 5μ), MeOH, 40%, 3 g/min, Ret. Time 2.02; ee >95%

[cis-EN2] SC-215—analytical chiral SFC: Chiralpak IC (250×4.6 mm 5μ), MeOH, 40%, 3 g/min, Ret. time 4.33; ee >95%

3-Chloro-2-[4-[[3-(difluoro-methyl)-5-fluoro-phenyl]sulfonyl]-4-methyl-tetrahydro-pyran-2-yl]-5-methylsulfonyl-pyridine (Example 37)

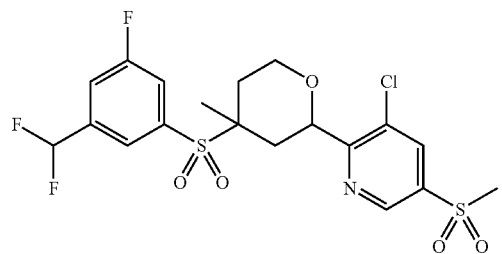 [SMILES: CC1(S(=O)(=O)c2cc(F)cc(C(F)F)c2)CCOC(c2ncc(S(C)(=O)=O)cc2Cl)C1]

$^1$H-NMR (600 MHz, [d$_6$]-DMSO): δ=9.02-9.03 (1H), 8.46-8.47 (1H), 7.95-7.97 (1H), 7.89-7.91 (2H), 7.12-7.31 (1H), 5.04-5.06 (1H), 4.02-4.05 (1H), 3.75-3.79 (1H), 3.39 (3H), 2.52-2.57 (1H), 2.13-2.19 (1H), 1.74-1.77 (1H), 1.48-1.52 (4H).

NOE: C-2 proton & methyl=cis

Chiral Resolution of 3-Chloro-2-[4-[[3-(difluoro-methyl)-5-fluoro-phenyl]sulfonyl]-4-methyl-tetrahydro-pyran-2-yl]-5-methylsulfonyl-pyridine Cis-rac 3-chloro-2-[4-[[3-(difluoro-methyl)-5-fluoro-phenyl]sulfonyl]-4-methyl-tetrahydro-pyran-2-yl]-5-methylsulfonyl-pyridine was subjected to preparative chiral-SFC (Chiralpak AS-H column, MeOH, 30%) to give cis-EN1 SC-216 and cis-EN2 SC-217.

[cis-EN1] SC-216—analytical chiral SFC: Chiralpak AS-H (250×4.6 mm 5μ), MeOH, 20%, 3 g/min, Ret. Time 3.15; ee >95%

[cis-EN2] SC-217—analytical chiral SFC: Chiralpak AS-H (250×4.6 mm 5μ), MeOH, 20%, 3 g/min, Ret. time 3.7; ee >95%

3-Chloro-5-methylsulfonyl-2-[4-methyl-4-[[3-(trifluoromethyloxy)-phenyl]sulfonyl]-tetrahydro-pyran-2-yl]-pyridine (Example 38)

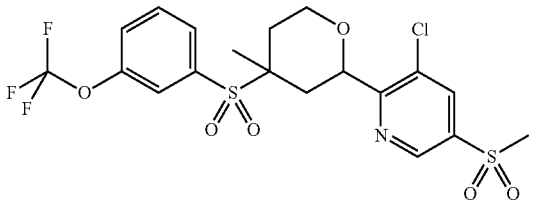 [SMILES: CC1(S(=O)(=O)c2cccc(OC(F)(F)F)c2)CCOC(c2ncc(S(C)(=O)=O)cc2Cl)C1]

¹H-NMR (600 MHz, [d₆]-DMSO): δ=9.00-9.01 (1H), 8.45 (1H), 7.90-7.92 (1H), 7.85-7.87 (2H), 7.76-7.77 (1H), 5.01-5.04 (1H), 4.01-4.04 (1H), 3.74-3.79 (1H), 3.38 (3H), 2.47-2.52 (1H), 2.10-2.15 (1H), 1.69-1.72 (1H), 147-1.50 (4H).
NOE: C-2 proton & methyl=cis

Chiral Resolution of 3-chloro-5-methylsulfonyl-2-[4-methyl-4-[[3-(trifluoromethyloxy)-phenyl]sulfonyl]-tetrahydro-pyran-2-yl]-pyridine Cis-rac 3-chloro-5-methylsulfonyl-2-[4-methyl-4-[[3-(trifluoromethyloxy)-phenyl]sulfonyl]-tetrahydro-pyran-2-yl]-pyridine was subjected to preparative chiral-SFC (Chiralpak AS-H column, MeOH, 35%) to give cis-EN1 SC-218 and cis-EN2 SC-219.

[cis-EN1] SC-218—analytical chiral SFC: Lux Cellulose-2 (250×4.6 mm 5μ), 0.5% DEA in MeOH, 35%, 3 g/min, Ret. Time 4.49; ee >95%

[cis-EN2] SC-219—analytical chiral SFC: Lux Cellulose-2 (250×4.6 mm 5μ), 0.5% DEA in MeOH, 35%, 3 g/min, Ret. time 5.12; ee >95%

3-Methylsulfonyl-2-[4-methyl-4-[[3-(trifluoromethyloxy)-phenyl]sulfonyl]-tetrahydro-pyran-2-yl]-5-(trifluoromethyl)-pyridine (Example 39)

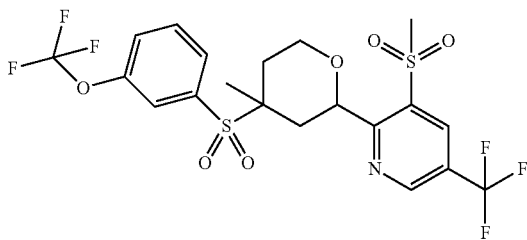 [SMILES: CC1(S(=O)(=O)c2cccc(OC(F)(F)F)c2)CCOC(c2ncc(C(F)(F)F)cc2S(C)(=O)=O)C1]

¹H-NMR (600 MHz, [d₆]-DMSO): δ=9.32 (1H), 8.56 (1H), 7.89-7.92 (1H), 7.84-7.87 (2H), 7.77 (1H), 5.40-5.42 (1H), 4.06-4.08 (1H), 3.75-3.79 (1H), 3.42 (3H), 2.50-2.54 (1H), 2.11-2.18 (1H), 1.83-1.86 (1H), 1.47-1.51 (4H).
NOE: C-2 proton & methyl=cis

Chiral Resolution of 3-Methylsulfonyl-2-[4-methyl-4-[[3-(trifluoromethyloxy)-phenyl]sulfonyl]-tetrahydro-pyran-2-yl]-5-(trifluoromethyl)-pyridine Cis-rac 3-methylsulfonyl-2-[4-methyl-4-[[3-(trifluoromethyloxy)-phenyl]sulfonyl]-tetrahydro-pyran-2-yl]-5-(trifluoromethyl)-pyridine was subjected to preparative chiral-SFC (Chiralpak IE column, 0.5% DEA in MeOH, 25%) to give cis-EN1 SC-220 and cis-EN2 SC-221.

[cis-EN1] SC-220—analytical chiral SFC: Chiralpak IE (250×4.6 mm 5μ), 0.5% DEA in MeOH, 25%, 3 g/min, Ret. Time 1.62; ee >95%

[cis-EN2] SC-221—analytical chiral SFC: Chiralpak IE (250×4.6 mm 5μ), 0.5% DEA in MeOH, 25%, 3 g/min, Ret. time 1.95; ee >95%

5-Methylsulfonyl-2-[4-methyl-4-[[3-(trifluoromethyl)phenyl]sulfonyl]-tetrahydro-pyran-2-yl]-3-(trifluoromethyl)-pyridine (Example 40)

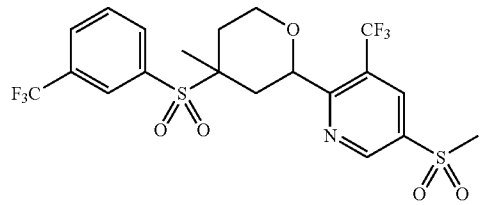 [SMILES: CC1(S(=O)(=O)c2cccc(C(F)(F)F)c2)CCOC(c2ncc(S(C)(=O)=O)cc2C(F)(F)F)C1]

¹H-NMR (600 MHz, [d₆]-DMSO): δ=9.35 (1H), 8.60-8.61 (1H), 8.22-8.24 (1H), 8.18-8.20 (1H), 8.07 (1H), 7.96-7.97 (1H), 4.90-4.92 (1H), 4.03-4.06 (1H), 3.73-3.76 (1H), 3.44 (3H), 2.57-2.61 (1H), 2.14-2.20 (1H), 1.72-1.75 (1H), 1.47-1.50 (4H).
NOE: C-2 proton & methyl=cis

Chiral Resolution of 5-Methylsulfonyl-2-[4-methyl-4-[[3-(trifluoromethyl)phenyl]sulfonyl]-tetrahydro-pyran-2-yl]-3-(trifluoromethyl)-pyridine Cis-rac 5-methylsulfonyl-2-[4-methyl-4-[[3-(trifluoromethyl)phenyl]sulfonyl]-tetrahydro-pyran-2-yl]-3-(trifluoromethyl)-pyridine was subjected to preparative chiral-SFC (Chiralpak AD-H column, MeOH, 35%) to give cis-EN1 SC-222 and cis-EN2 SC-223.

[cis-EN1] SC-222—analytical chiral SFC: Chiralpak AD-H (250×4.6 mm 5μ), MeOH, 30%, 3 g/min, Ret. Time 1.61; ee >95%

[cis-EN2] SC-223—analytical chiral SFC: Chiralpak AD-H (250×4.6 mm 5μ), MeOH, 30%, 3 g/min, Ret. time 2.08; ee >95%

3-Methoxy-5-methylsulfonyl-2-[4-methyl-4-[[3-(trifluoromethyl)phenyl]sulfonyl]-tetrahydro-pyran-2-yl]-pyridine (Example 41)

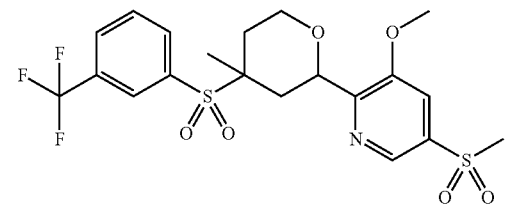 [SMILES: COc1cc(S(C)(=O)=O)cnc1C1CC(C)(S(=O)(=O)c2cccc(C(F)(F)F)c2)CCO1]

¹H-NMR (600 MHz, [d₆]-DMSO): δ=8.62 (1H), 8.21-8.23 (1H), 8.17-8.18 (1H), 8.05 (1H), 7.95-7.98 (1H), 7.86 (1H), 4.98-5.00 (1H), 3.97-4.00 (1H), 3.93 (3H), 3.68-3.72 (1H), 3.34 (3H), 2.50-2.54 (1H), 2.09-2.14 (1H), 1.57-1.60 (1H), 1.45-1.49 (4H).
NOE: C-2 proton & methyl=cis

Chiral Resolution of 3-Methoxy-5-methylsulfonyl-2-[4-methyl-4-[[3-(trifluoromethyl)phenyl]sulfonyl]-tetrahydro-pyran-2-yl]-pyridine Cis-rac 3-methoxy-5-methylsulfonyl-2-[4-methyl-4-[[3-(trifluoromethyl)phenyl]sulfonyl]-tetrahydro-pyran-2-yl]-pyridine was subjected to preparative chiral-SFC (Chiralpak IC column, MeOH, 40%) to give cis-EN1 SC-224 and cis-EN2 SC-225.

[cis-EN1] SC-224—analytical chiral SFC: Chiralpak IC (250×4.6 mm 5μ), MeOH, 40%, 4 g/min, Ret. Time 2.86; ee >95%

[cis-EN2] SC-225—analytical chiral SFC: Chiralpak IC (250×4.6 mm 5μ), MeOH, 40%, 4 g/min, Ret. time 9.47; ee >95%

5-Chloro-3-methylsulfonyl-2-[4-methyl-4-[[3-(trifluoromethyl)phenyl]sulfonyl]-tetrahydro-pyran-2-yl]-pyridine (Example 42)

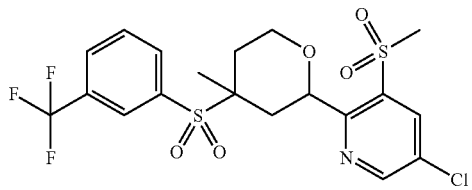 [SMILES: CC1(S(=O)(=O)c2cccc(C(F)(F)F)c2)CCOC(c2ncc(Cl)cc2S(C)(=O)=O)C1]

$^1$H-NMR (600 MHz, [d$_6$]-DMSO): δ=8.97 (1H), 8.35-8.36 (1H), 8.22-8.24 (1H), 8.18-8.20 (1H), 8.07 (1H), 7.96-7.99 (1H), 5.33-5.35 (1H), 4.03-4.06 (1H), 3.71-3.75 (1H), 3.39 (3H), 2.55-2.59 (1H), 1.13-2.18 (1H), 1.79-1.82 (1H), 1.46-1.49 (4H).

NOE: C-2 proton & methyl=cis

Chiral Resolution of 5-Chloro-3-methylsulfonyl-2-[4-methyl-4-[[3-(trifluoromethyl)phenyl]sulfonyl]-tetrahydro-pyran-2-yl]-pyridine Cis-rac 5-chloro-3-methylsulfonyl-2-[4-methyl-4-[[3-(trifluoromethyl)phenyl]sulfonyl]-tetrahydro-pyran-2-yl]-pyridine was subjected to preparative chiral-SFC (Chiralpak IC column, 0.5% DEA in MeOH, 30%) to give cis-EN1 SC-226 and cis-EN2 SC-227.

[cis-EN1] SC-226—analytical chiral SFC: Chiralpak IC (250×4.6 mm 5μ), 0.5% DEA in MeOH, 30%, 3 g/min, Ret. Time 3.45; ee >95%

[cis-EN2] SC-227—analytical chiral SFC: Chiralpak IC (250×4.6 mm 5μ), 0.5% DEA in MeOH, 30%, 3 g/min, Ret. time 5.01; ee >95%

3-(Methylsulfinyl)-2-[4-methyl-4-[[3-(trifluoromethyl)phenyl]sulfonyl]-tetrahydro-pyran-2-yl]-5-(trifluoromethyl)-pyridine (Example 43)

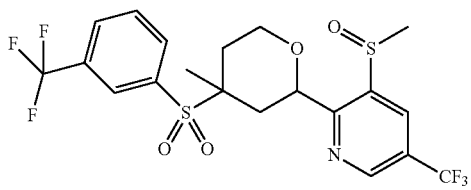 [SMILES: CS(=O)c1cc(C(F)(F)F)cnc1C1CC(C)(S(=O)(=O)c2cccc(C(F)(F)F)c2)CCO1]

Chiral Resolution of 2-(4-methyl-4-(3-(trifluoromethyl)phenylsulfonyl)tetrahydro-2H-pyran-2-yl)-3-(methylthio)-5-(trifluoromethyl)pyridine

[Cis-rac] 2-(4-methyl-4-(3-(trifluoromethyl)phenylsulfonyl)tetrahydro-2H-pyran-2-yl)-3-(methylthio)-5-(trifluoromethyl)pyridine was subjected to preparative chiral-SFC (Chiralpak-AD-H column, 0.5% DEA in MeOH, 40%)) to give [cis-EN1]-2-(4-methyl-4-(3-(trifluoromethyl)phenylsulfonyl)tetrahydro-2H-pyran-2-yl)-3-(methylthio)-5-(trifluoromethyl)pyridine and [cis-EN2]-2-(4-methyl-4-(3-(trifluoromethyl)phenyl-sulfonyl)tetrahydro-2H-pyran-2-yl)-3-(methylthio)-5-(trifluoromethyl)pyridine.

[cis-EN1]-2-(4-methyl-4-(3-(trifluoromethyl)phenylsulfonyl)tetrahydro-2H-pyran-2-yl)-3-(methylthio)-5-(trifluoromethyl)pyridine (900 mg, 1.80 mmol) dissolved in MeOH (36 mL), water (10 mL) and sodium periodate (770 mg, 3.60 mmol) was added. The RM was stirred at RT for 47 h. The RM was concentrated in vacuo; the resulting residue was diluted with water (10 mL) and the organic product was extracted with DCM (3×20 mL). The combined organic extract was washed with brine (2×25 mL), dried (anhydr. Na$_2$SO$_4$) and concentrated to get the crude product. The crude compound was purified by CC (0-30% EtOAc in PE) to obtain an epimeric mixture [Epi-Mix1] of 3-(Methylsulfinyl)-2-[4-methyl-4-[[3-(trifluoromethyl)phenyl]sulfonyl]-tetrahydro-pyran-2-yl]-5-(trifluoromethyl)-pyridine (750 mg, 80%) as a solid.

Purification of [Epi-Mix1]-3-(Methylsulfinyl)-2-[4-methyl-4-[[3-(trifluoromethyl)phenyl]sulfonyl]-tetrahydro-pyran-2-yl]-5-(trifluoromethyl)-pyridine

[Epi-Mix1]-3-(Methylsulfinyl)-2-[4-methyl-4-[[3-(trifluoromethyl)phenyl]sulfonyl]-tetrahydro-pyran-2-yl]-5-(trifluoromethyl)-pyridine was subjected to preparative HPLC (X-bridge C18, 10 mM ammonium acetate/MeCN)) to give [EN1] SC-229 and [EN2] SC-230.

[EN1] SC-229—analytical SFC: Chiralpak AS-H (250× 4.6 mm 5μ), 3 g/min, RT, 0.5% DEA in MeOH, 15%, Ret. Time 1.91; ee >95; [α]$_{25}^{589}$ (c=1.0, CHCl$_3$)=+97.4°; NOE: C-2 proton & methyl=cis; 1H-NMR (600 MHz, [d$_6$]-DMSO): δ=9.04 (1H), 8.64 (1H), 8.18-8.22 (2H, 8.08 (1H), 7.93-7.96 (1H), 4.96-4.98 (1H), 4.10-4.13 (1H), 3.73-3.78 (1H), 3.07 (3H), 2.28-2.32 (1H), 2.17-2.22 (1H), 1.85-1.89 (1H), 1.50-1.54 (4H).

[EN2] SC-230—analytical SFC: Chiralpak AS-H (250× 4.6 mm 5μ), 3 g/min, RT, 0.5% DEA in MeOH, 15%, Ret. Time 7.92; ee >95%; [α]$_{25}^{589}$ (c=1.0, CHCl$_3$)=−63.6°; 1H-NMR (600 MHz, [d6]-DMSO): δ=9.10-9.11 (1H), 8.61 (1H), 8.20-8.24 (1H), 8.08 (1H), 7.97-8.00 (1H), 4.93-4.95 (1H), 4.03-4.06 (1H), 3.75-3.79 (1H), 2.82 (3H), 2.42-2.46 (1H), 2.07-2.12 (2H), 1.47-1.49 (4H).

[cis-EN2]-2-(4-methyl-4-(3-(trifluoromethyl)phenylsulfonyl)tetrahydro-2H-pyran-2-yl)-3-(methylthio)-5-(trifluoromethyl)pyridine (850 mg, 1.75 mmol) dissolved in MeOH (36 mL), water (10 mL) and sodium periodate (750 mg, 3.50 mmol). The total reaction mass was stirred at RT for 47 h. The RM was concentrated in vacuo, the residue was diluted with water (10 mL) and extracted with DCM (3×20 mL). The combined organic extract was washed with brine (2×25 mL), dried (Na$_2$SO$_4$) and concentrated to get crude. The crude compound was purified by CC (0-30% EtOAc in PE) to obtain [Epi-Mix2]-3-(methylsulfinyl)-2-[4-methyl-4-[[3-

(trifluoromethyl)phenyl]sulfonyl]-tetrahydro-pyran-2-yl]-5-(trifluoromethyl)-pyridine (750 mg, 80%) as a solid.

Purification of [Epi-Mix2]-3-(Methylsulfinyl)-2-[4-methyl-4-[[3-(trifluoromethyl)phenyl]sulfonyl]-tetrahydro-pyran-2-yl]-5-(trifluoromethyl)-pyridine

[Epi-Mix2]-3-(Methylsulfinyl)-2-[4-methyl-4-[[3-(trifluoromethyl)phenyl]sulfonyl]-tetrahydro-pyran-2-yl]-5-(trifluoromethyl)-pyridine was subjected to preparative HPLC (X-bridge C18, 10 mM ammonium acetate/MeCN)) to give [EN3] SC-231 and [EN4] SC-228.

[EN3] SC-231—analytical SFC: Chiralpak AS-H (250× 4.6 mm 5μ), 3 g/min, RT, 0.5% DEA in MeOH, 15%, Ret. Time 4.24; ee >95; $[\alpha]_{25}^{589}$ (c=1.0, CHCl$_3$)=−137.7°; NOE: C-2 proton & methyl=cis; $^1$H-NMR (600 MHz, [d6]-DMSO): δ=9.04 (1H), 8.64 (1H), 8.18-8.22 (2H, 8.08 (1H), 7.93-7.96 (1H), 4.96-4.98 (1H), 4.10-4.13 (1H), 3.73-3.78 (1H), 3.07 (3H), 2.28-2.32 (1H), 2.17-2.22 (1H), 1.85-1.89 (1H), 1.50-1.54 (4H).

[EN4] SC-228—analytical SFC: Chiralpak AS-H (250× 4.6 mm 5μ), 3 g/min, RT, 0.5% DEA in MeOH, 15%, Ret. Time 2.3; ee >95%; $[\alpha]_{25}^{589}$ (c=1.0, CHCl$_3$)=+61.00; 1 H-NMR (600 MHz, [d6]-DMSO): δ=9.10-9.11 (1H), 8.61 (1H), 8.20-8.24 (1H), 8.08 (1H), 7.97-8.00 (1H), 4.93-4.95 (1H), 4.03-4.06 (1H), 3.75-3.79 (1H), 2.82 (3H), 2.42-2.46 (1H), 2.07-2.12 (2H), 1.47-1.49 (4H).

3-Chloro-5-(methylsulfinyl)-2-[4-methyl-4-[[3-(trifluoromethyl)phenyl]sulfonyl]-tetrahydro-pyran-2-yl]-pyridine (Example 44)

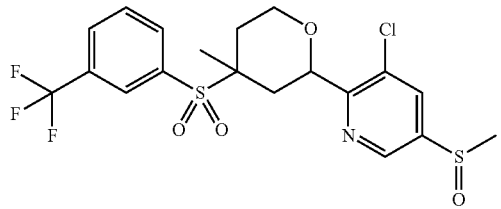 [SMILES: CS(=O)c1cnc(C2CC(C)(S(=O)(=O)c3cccc(C(F)(F)F)c3)CCO2)c(Cl)c1]

Chiral Resolution of 3-chloro-2-(4-methyl-4-((3-(trifluoromethyl)phenyl)sulfonyl)tetrahydro-2H-pyran-2-yl)-5-(methylsulfinyl)pyridine

[Cis-rac] 3-chloro-2-(4-methyl-4-((3-(trifluoromethyl)phenyl)sulfonyl)tetrahydro-2H-pyran-2-yl)-5-(methylsulfinyl)pyridine was subjected to preparative chiral-SFC (Chiralcel-OD-H column, MeOH, 40%)) to give [cis-EN1]-3-chloro-2-(4-methyl-4-((3-(trifluoromethyl)phenyl)sulfonyl)tetrahydro-2H-pyran-2-yl)-5-(methylsulfinyl)pyridine and [cis-EN2]-3-chloro-2-(4-methyl-4-((3-(trifluoromethyl)phenyl)sulfonyl)tetrahydro-2H-pyran-2-yl)-5-(methylsulfinyl)pyridine.

NOE: C-2 proton & methyl=cis

Sodium metaperiodate (0.45 g, 2.15 mmol) was added to a stirred solution of [cis-EN1]-3-chloro-2-(4-methyl-4-((3-(trifluoromethyl)phenyl)sulfonyl)tetrahydro-2H-pyran-2-yl)-5-(methylsulfinyl)pyridine (0.5 g, 1.07 mmol) in MeOH (50 mL), water (10 mL) and stirred for 24 h at RT. The RM was concentrated under reduced pressure to remove MeOH. The Aq. layer was diluted with water (100 mL), extracted with DCM (3×50 mL). The combined organic layer was washed with brine (50 mL), dried (Na$_2$SO$_4$), filtered and evaporated the solvent under vacuo to give crude, which was purified by CC (5% MeOH in dichloromethane) to give [Epi-Mix1]-3-chloro-2-(4-methyl-4-((3-(trifluoromethyl)phenyl)-sulfonyl)tetrahydro-2H-pyran-2-yl)-5-(methylsulfinyl)pyridine (0.35 g, 68%) as off white solid.

Chiral Resolution of [Epi-Mix1]-3-chloro-2-(4-methyl-4-((3-(trifluoromethyl)phenyl)sulfonyl)tetrahydro-2H-pyran-2-yl)-5-(methylsulfinyl)pyridine

[Epi-Mix1]-3-chloro-2-(4-methyl-4-((3-(trifluoromethyl)phenyl)sulfonyl)tetrahydro-2H-pyran-2-yl)-5-(methylsulfinyl)pyridine was subjected to preparative chiral SFC (Chiralcel OD-H, MeOH, 25%) to give [EN1] SC-232 and [EN2] SC-233.

[EN1] SC-232—analytical SFC: Chiralcel OD-H (250× 4.6 mm 5μ), 3 g/min, RT, 0.5% DEA in MeOH, 40%, Ret. Time 3.28; ee >95; $[\alpha]_{25}^{589}$ (c=1.0, CHCl$_3$)=−80.0°; $^1$H-NMR (600 MHz, [d$_6$]-DMSO): δ=8.80 (1H), 8.18-8.23 (3H), 8.07 (1H), 7.96-7.98 (1H), 4.98-5.00 (1H), 4.00-4.03 (1H), 3.72-3.77 (1H), 2.90 (3H), 2.53-2.60 (1H), 2.11-2.16 (1H), 1.69-1.72 (1H), 1.45-1.50 (4H).

[EN2] SC-233—analytical SFC: Chiralcel OD-H (250× 4.6 mm 5μ), 3 g/min, RT, 0.5% DEA in MeOH, 40%, Ret. Time 3.65; ee >95%; $[\alpha]_{25}^{589}$ (c=1.0, CHCl$_3$)=−23.6°; 1H-NMR (600 MHz, [d6]-DMSO): δ=8.79 (1H), 8.18-8.23 (3H), 8.07 (1H), 7.96-7.99 (1H), 4.98-5.00 (1H), 4.00-4.03 (1H), 3.72-3.77 (1H), 2.90 (3H), 2.56-2.60 (1H), 2.10-2.16 (1H), 1.69-1.72 (1H), 1.46-1.50 (4H).

Sodium metaperiodate (0.45 g, 2.15 mmol) was added to a stirred solution of [cis-EN2]-3-chloro-2-(4-methyl-4-((3-(trifluoromethyl)phenyl)sulfonyl)tetrahydro-2H-pyran-2-yl)-5-(methylsulfinyl)pyridine (0.5 g, 1.07 mmol) in MeOH (50 mL), Water (10 mL) and stirred for 24 h at RT. The RM was concentrated under reduced pressure to remove MeOH. The Aq. layer was diluted with water (100 mL), extracted with DCM (3×50 mL). The combined organic layer was washed with brine (50 mL), dried (Na$_2$SO$_4$), filtered and evaporated the solvent under vacuo to give crude, which was purified by CC (5% MeOH in DCM) to give [Epi-Mix2]-3-chloro-2-(4-methyl-4-((3-(trifluoromethyl)phenyl)sulfonyl)-tetrahydro-2H-pyran-2-yl)-5-(methylsulfinyl)pyridine (0.39 g, 76%) as an off white solid. Chiral resolution of [Epi-Mix2]-3-chloro-2-(4-methyl-4-((3-(trifluoromethyl)phenyl)sulfonyl)tetrahydro-2H-pyran-2-yl)-5-(methylsulfinyl)pyridine

[Epi-Mix2]-3-chloro-2-(4-methyl-4-((3-(trifluoromethyl)phenyl)sulfonyl)tetrahydro-2H-pyran-2-yl)-5-(methylsulfinyl)pyridine was subjected to preparative chiral SFC (Chiralcel OD-H, MeOH, 45%) to give [EN3] SC-234 and [EN4] SC-235.

[EN3] SC-234—analytical SFC: Chiralpak AS-H (250× 4.6 mm 5μ), 3 g/min, RT, 0.5% DEA in MeOH, 15%, Ret. Time 4.08; ee >95; $[\alpha]_{25}^{589}$ (c=1.0, CHCl$_3$)=+104°; $^1$H-NMR (600 MHz, [d6]-DMSO): δ=8.80 (1H), 8.18-8.23 (3H), 8.07 (1H), 7.96-7.98 (1H), 4.98-5.00 (1H), 4.00-4.03 (1H), 3.71-3.76 (1H), 2.86 (3H), 2.53-2.60 (1H), 2.11-2.16 (1H), 1.69-1.72 (1H), 1.45-1.52 (4H).

[EN4] SC-235—analytical SFC: Chiralpak AS-H (250× 4.6 mm 5μ), 3 g/min, RT, 0.5% DEA in MeOH, 15%, Ret. Time 5.23; ee >95%; $[\alpha]_{25}^{589}$ (c=1.0, CHCl$_3$)=+18.0°; 1H-NMR (600 MHz, [d6]-DMSO): δ=8.80 (1H), 8.18-8.23 (3H), 8.07 (1H), 7.96-7.99 (1H), 4.98-5.00 (1H), 4.00-4.03 (1H), 3.72-3.77 (1H), 2.90 (3H), 2.56-2.60 (1H), 2.10-2.15 (1H), 1.69-1.71 (1H), 1.46-1.50 (4H).

3-Chloro-5-(difluoro-methyl)-2-[4-methyl-4-[[3-(trifluoromethyl)phenyl]sulfonyl]-tetrahydro-pyran-2-yl]-pyridine (Example 45)

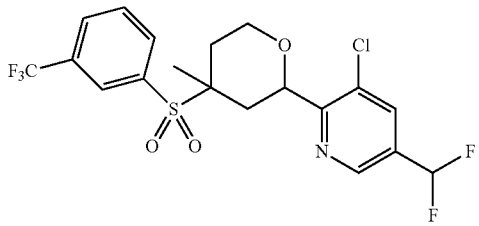 [SMILES: CC1(S(=O)(=O)c2cccc(C(F)(F)F)c2)CCOC(c2ncc(C(F)F)cc2Cl)C1]

$^1$H-NMR (600 MHz, [d$_6$]-DMSO): δ=8.76-8.77 (1H), 8.18-8.23 (3H), 8.07 (1H), 7.92-7.98 (1H), 7.06-7.26 (1H), 4.98-5.00 (1H), 4.00-4.09 (1H), 3.72-3.77 (1H), 3.41 (3H), 2.55-2.60 (1H), 2.11-2.16 (1H), 1.68-1.71 (1H), 1.46-1.50 (4H).
NOE: C-2 proton & methyl=cis

Chiral Resolution of 3-Chloro-5-(difluoro-methyl)-2-[4-methyl-4-[[3-(trifluoromethyl)phenyl]sulfonyl]-tetrahydro-pyran-2-yl]-pyridine Cis-rac 3-Chloro-5-(difluoro-methyl)-2-[4-methyl-4-[[3-(trifluoromethyl)phenyl]sulfonyl]-tetrahydro-pyran-2-yl]-pyridine was subjected to preparative chiral-SFC (Chiralpak IC column, 0.5% DEA in MeOH, 40%) to give cis-EN1 SC-236 and cis-EN2 SC-237.

[cis-EN1] SC-236—analytical chiral SFC: Chiralpak IC (250×4.6 mm 5µ), MeOH, 40%, 3 g/min, Ret. Time 1.73; ee >95%

[cis-EN2] SC-237—analytical chiral SFC: Chiralpak IC (250×4.6 mm 5µ), MeOH, 40%, 3 g/min, Ret. time 4.43; ee >95%

3-Chloro-2-[4-[[3-(difluoro-methyl)-phenyl]sulfonyl]-4-methyl-tetrahydro-pyran-2-yl]-5-methylsulfonyl-pyridine (Example 57)

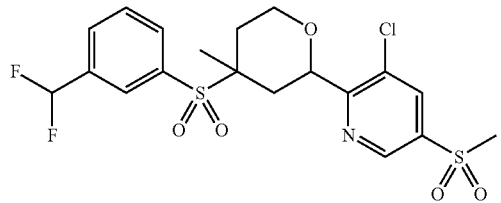 [SMILES: CC1(S(=O)(=O)c2cccc(C(F)F)c2)CCOC(c2ncc(S(C)(=O)=O)cc2Cl)C1]

$^1$H-NMR (600 MHz, [d$_6$]-DMSO): δ=9.01 (1H), 8.45 (1H), 8.02-8.05 (3H), 7.86-7.88 (1H), 7.12-7.31 (1H), 5.02-5.04 (1H), 4.01-4.04 (1H), 3.74-3.78 (1H), 3.39 (3H), 2.49-2.53 (1H), 2.06-2.15 (1H), 1.70-1.73 (1H), 1.41-1.56 (4H).
NOE: C-2 proton & methyl=cis

Chiral Resolution of 3-Chloro-2-[4-[[3-(difluoro-methyl)-phenyl]sulfonyl]-4-methyl-tetrahydro-pyran-2-yl]-5-methylsulfonyl-pyridine Cis-rac 3-chloro-2-[4-[[3-(difluoro-methyl)-phenyl]sulfonyl]-4-methyl-tetrahydro-pyran-2-yl]-5-methylsulfonyl-pyridine was subjected to preparative chiral-SFC (Lux Cellulose-2 column, MeOH, 45%) to give cis-EN1 SC-264 and cis-EN2 SC-265.

[cis-EN1] SC-264—analytical chiral SFC: Lux Cellulose-2 (250×4.6 mm 5µ), 0.5% DEA in MeOH, 40%, 3 g/min, Ret. Time 5.7; ee >95%

[cis-EN2] SC-265—analytical chiral SFC: Lux Cellulose-2 (250×4.6 mm 5µ), 0.5% DEA in MeOH, 40%, 3 g/min, Ret. time 7.02; ee >95%

5-(difluoromethoxy)-2-(4-methyl-4-((3-(trifluoromethyl)phenyl)sulfonyl)tetrahydro-2H-pyran-2-yl)-3-(methylsulfonyl)pyridine (Example 58)

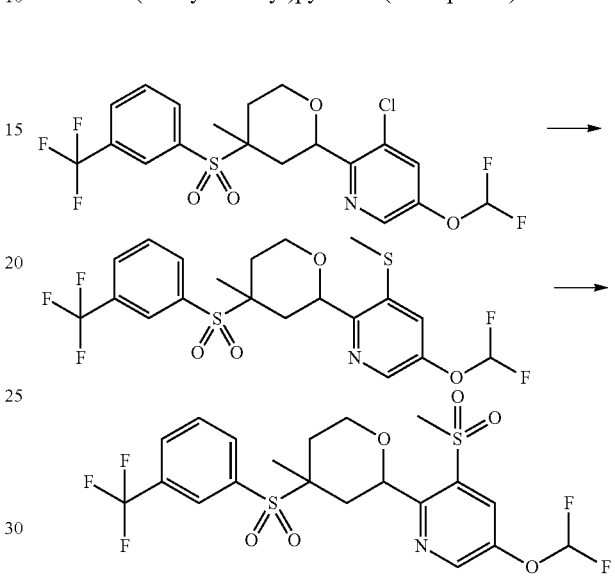

Step 1: 2-(4-methyl-4-((3-(trifluoromethyl)phenyl)sulfonyl)tetrahydro-2H-pyran-2-yl)-5-(methylsulfonyl)pyridin-3-ol A solution of 3-chloro-5-(difluoromethoxy)-2-(4-methyl-4-((3-(trifluoromethyl)phenyl)sulfonyl)tetrahydro-2H-pyran-2-yl)pyridine (3.7 g, 7.60 mmol) and NaSMe (0.64 g, 9.12 mmol) in pyridine (50 mL) was heated at 60° C. for 12 h under Ar. The RM was diluted with water (20 mL) and the organic product was extracted with EtOAc (3×50 mL). The combined organic layer was washed with brine, dried over anhydr. Na$_2$SO$_4$, filtered and evaporated the solvent under vacuo to get the crude. The crude product was submitted to SFC to get 1.2 g of a mixture of 5-(difluoromethoxy)-2-(4-methyl-4-(3-(trifluoromethyl)phenylsulfonyl)tetrahydro-2H-pyran-2-yl)-3-(methylthio)pyridine and 3-chloro-2-(4-methyl-4-((3-(trifluoromethyl)phenyl)-sulfonyl)tetrahydro-2H-pyran-2-yl)-5-(methylthio)pyridine. The mixture was directly taken for the next step without further purification.

Step 2: 5-(difluoromethoxy)-2-(4-methyl-4-((3-(trifluoromethyl)phenyl)sulfonyl)tetrahydro-2H-pyran-2-yl)-3-(methylsulfonyl)pyridine The mixture of 5-(difluoromethoxy)-2-(4-methyl-4-(3-(trifluoromethyl)phenylsulfonyl)tetrahydro-2H-pyran-2-yl)-3-(methylthio)pyridine and 3-chloro-2-(4-methyl-4-((3-(trifluoromethyl)phenyl)sulfonyl)tetrahydro-2H-pyran-2-yl)-5-(methylthio)pyridine (1.2 g, 2.41 mmol) was dissolved in MeOH (42 mL) and a solution of oxone (3.0 g, 4.82 mmol) in water (30 mL) was added. The RM was stirred at RT for 16 h. MeOH was concentrated in vacuo; the residue was diluted with water (150 mL) and the organic product was extracted with EtOAc (3×50 mL). The combined organic extract was washed with water, brine (100 mL), dried over anhydr. Na$_2$SO$_4$ and solvent was concentrated under reduced pressure to get crude product. The crude compound was purified by CC (0-30% EtOAc in PE) to obtain 5-(difluoromethoxy)-2-(4-methyl-4-((3-(trifluoromethyl)phenyl)sulfonyl)tetrahydro-2H-pyran-2-yl)-3-(methylsulfonyl)pyridine (0.4 g, 31%) as a white solid.

$^1$H-NMR (600 MHz, [d$_6$]-DMSO): δ=8.82 (1H), 8.23-8.24 (1H), 8.19-8.20 (1H), 8.10 (1H), 8.07 (1H), 7.96-7.99 (1H), 5.33-5.36 (1H), 4.03-4.06 (1H), 3.71-3.75 (1H), 3.34 (3H), 2.59-2.63 (1H), 2.13-2.18 (1H), 1.77-1.80 (1H), 1.47-1.50 (4H).

NOE: C-2 proton & methyl=cis

Chiral Resolution of 5-(difluoromethoxy)-2-(4-methyl-4-((3-(trifluoromethyl)phenyl)sulfonyl)tetrahydro-2H-pyran-2-yl)-3-(methylsulfonyl)pyridine Cis-rac 5-(difluoromethoxy)-2-(4-methyl-4-((3-(trifluoromethyl)phenyl)sulfonyl)tetrahydro-2H-pyran-2-yl)-3-(methylsulfonyl)pyridine was subjected to preparative chiral-SFC (Chiralcel OJ-H column, MeOH, 20%) to give cis-EN1 SC-266 and cis-EN2 SC-267.

[cis-EN1] SC-266—analytical chiral SFC: Chiralcel OJ-H (250×4.6 mm 5μ), MeOH, 20%, 3 g/min, Ret. Time 1.97; ee >95%

[cis-EN2] SC-267—analytical chiral SFC: Chiralcel OJ-H (250×4.6 mm 5μ), MeOH, 20%, 3 g/min, Ret. time 2.64; ee >95%

3-(difluoromethoxy)-2-(4-methyl-4-((3-(trifluoromethyl)phenyl)sulfonyl)tetrahydro-2H-pyran-2-yl)-5-(methylsulfonyl)pyridine (Example 59)

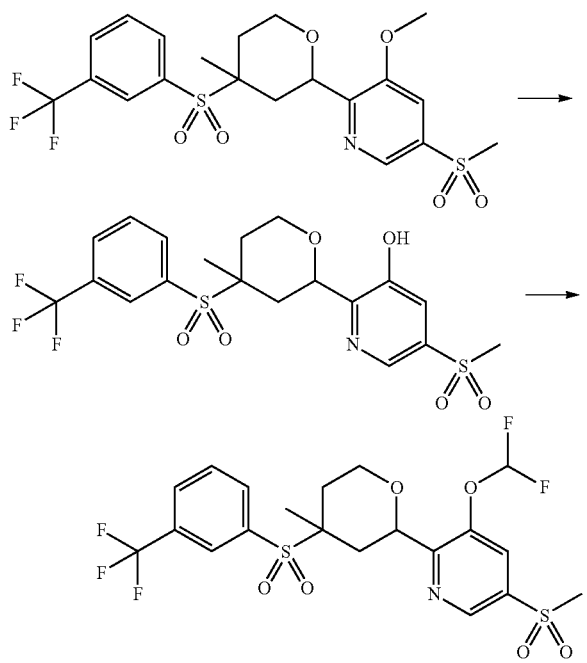

Step 1: 2-(4-methyl-4-((3-(trifluoromethyl)phenyl)sulfonyl)tetrahydro-2H-pyran-2-yl)-5-(methylsulfonyl)pyridin-3-ol Sodium thiomethoxide (0.283 g, 4.04 mmol) was added to a clear solution of 3-methoxy-2-(4-methyl-4-(3-(trifluoromethyl)phenylsulfonyl)tetrahydro-2H-pyran-2-yl)-5-(methylsulfonyl)pyridine (0.500 g, 1.01 mmol) in dry DMF (4 mL) at RT in microwave tube and the reaction mass was subjected to microwave irradiation at 120° C. for 90 min. The reaction mass was poured into cold water and acidified with dilute HCl solution up to pH-7.0. The solid product was precipitated out which was filtered, washed with water and dried in vacuo for 2 h to get 2-(4-methyl-4-((3-(trifluoromethyl)phenyl)sulfonyl)tetrahydro-2H-pyran-2-yl)-5-(methylsulfonyl)pyridin-3-ol (0.290 g, 60%) as a pale yellow solid.

Step 2: 3-(difluoromethoxy)-2-(4-methyl-4-((3-(trifluoromethyl)phenyl)sulfonyl)tetrahydro-2H-pyran-2-yl)-5-(methylsulfonyl)pyridine To stirred solution of 2-(4-methyl-4-((3-(trifluoromethyl)phenyl)sulfonyl)tetrahydro-2H-pyran-2-yl)-5-(methylsulfonyl)pyridin-3-ol (0.700 g, 1.46 mmol) in dry DMF (10 mL) was added K$_2$CO$_3$ (0.403 g, 2.92 mmol) at RT. The RM was heated to 90° C. and purged with freon gas (CF$_2$ClH) for 30 min. The RM was diluted with water (50 mL) and the organic product was extracted with EtOAc (50 mL×2). The organic extract was washed with water (2×50 mL), brine (100 mL), dried (anhydr. Na$_2$SO$_4$) and concentrated under reduced pressure to get crude compound. The crude compound was purified by CC (0-30% EtOAc in PE) to obtain racemic 3-(difluoromethoxy)-2-(4-methyl-4-((3-(trifluoromethyl)phenyl)sulfonyl)tetrahydro-2H-pyran-2-yl)-5-(methylsulfonyl)pyridine (0.360 g, 50%) as a white solid.

$^1$H-NMR (600 MHz, [d$_6$]-DMSO): δ=8.96 (1H), 8.22-8.24 (1H), 8.18-8.20 (1H), 8.13 (1H), 8.07 (1H), 7.96-7.98 (1H), 7.23-7.46 (1H), 4.95-4.98 (1H), 4.01-4.04 (1H), 3.71-3.76 (1H), 3.39 (3H), 2.50-2.52 (1H), 2.11-2.16 (1H), 1.66-1.69 (1H), 1.47-1.53 (4H).

NOE: C-2 proton & methyl=cis

Chiral Resolution of 3-(difluoromethoxy)-2-(4-methyl-4-((3-(trifluoromethyl)phenyl)sulfonyl)tetrahydro-2H-pyran-2-yl)-5-(methylsulfonyl)pyridine Cis-rac 3-(difluoromethoxy)-2-(4-methyl-4-((3-(trifluoromethyl)phenyl)sulfonyl)tetrahydro-2H-pyran-2-yl)-5-(methylsulfonyl)pyridine was subjected to preparative chiral-SFC (Chiralpak IC column, MeOH, 40%) to give cis-EN1 SC-268 and cis-EN2 SC-269.

[cis-EN1] SC-268—analytical chiral SFC: Chiralpak IC (250×4.6 mm 5μ), MeOH, 40%, 4 g/min, Ret. Time 1.48; ee >95%

[cis-EN2] SC-269—analytical chiral SFC: Chiralpak IC (250×4.6 mm 5μ), MeOH, 40%, 4 g/min, Ret. time 2.49; ee >95%

[cis-EN1]-3-cyclopropyl-2-(4-methyl-4-(3-(trifluoromethyl)phenylsulfonyl)tetrahydro-2H-pyran-2-yl)-5-(methylsulfonyl)pyridine (Example 60)

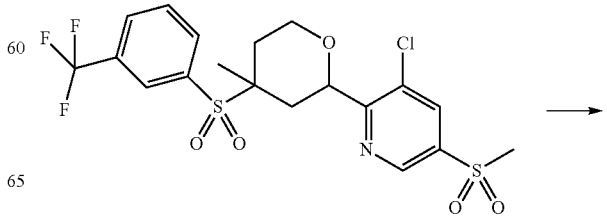

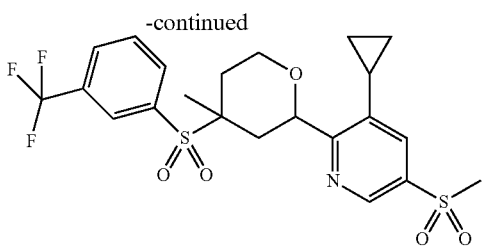

A solution of [cis-EN1]-3-chloro-2-(4-methyl-4-(3-(trifluoromethyl)phenylsulfonyl)tetrahydro-2H-pyran-2-yl)-5-(methylsulfonyl)pyridine (0.25 g, 0.50 mmol), K₃PO₄ (0.26 mL, 1.25 mmol) and 20% tricyclohexylphosphine in toluene (0.49 mL, 0.35 mmol) in toluene (18 mL)/water (2 mL) was degassed for 10 min. To the RM was added cycl propylboronic acid (98 mg, 1.15 mmol) and degassed again for 10 min. Catalytic Pd(OAc)₂ (23 mg, 0.035 mmol) was added and further degassed for 5 min. The resulting mixture was heated to reflux for 16 h under Ar. Reaction mass was filtered through celite and the filtrate was diluted with water (50 mL) and the organic product was extracted with EtOAc (3×50 mL). The combined organic extract was washed with brine (200 mL), dried (anhydr. Na₂SO₄) and concentrated to get crude. The crude product was purified by CC (0-35% EtOAc in PE) to give [cis-EN1]-3-cyclopropyl-2-(4-methyl-4-(3-(trifluoromethyl)phenylsulfonyl)tetrahydro-2H-pyran-2-yl)-5-(methylsulfonyl)pyridine (170 mg, 68%) as liquid.

¹H-NMR (600 MHz, [d₆]-DMSO): δ=8.82-8.84 (1H), 8.19-8.24 (2H), 8.08 (1H), 7.97-7.99 (1H), 7.79 (1H), 5.13-5.16 (1H), 4.00-4.04 (1H), 3.77-3.82 (1H), 3.31 (3H), 2.62-2.67 (1H), 2.26-2.31 (1H), 2.13-2.18 (1H), 1-70-1.73 (1H), 1.49-1.53 (4H), 1.00-1.07 (2H), 0.86-0.91 (1H), 0.72-0.76 (1H).

[cis-EN1] SC-270—analytical chiral SFC: Chiralcel OH—H (250×4.6 mm 5µ), 0.5% DEA in MeOH 10%, 3 g/min, Ret. Time 5.05; ee >95%

[cis-EN2]-3-cyclopropyl-2-(4-methyl-4-(3-(trifluoromethyl)phenylsulfonyl)tetrahydro-2H-pyran-2-yl)-5-(methylsulfonyl)pyridine (Example 60)

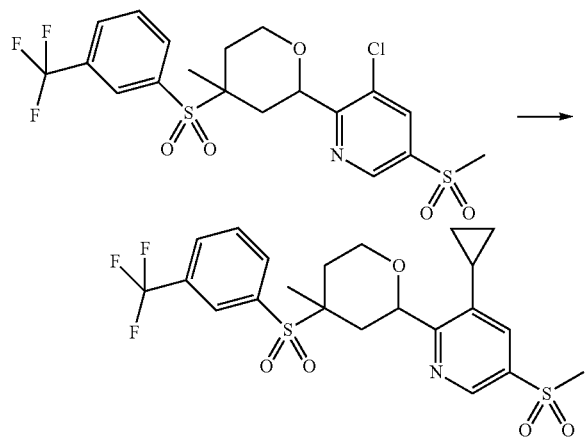

A solution of [cis-EN2]-3-chloro-2-(4-methyl-4-(3-(trifluoromethyl)phenylsulfonyl)tetrahydro-2H-pyran-2-yl)-5-(methylsulfonyl)pyridine (0.25 g, 0.50 mmol), K₃PO₄ (0.26 mL, 1.25 mmol) and 20% tricyclohexylphosphine in toluene (0.49 mL, 0.35 mmol) in toluene (18 mL)/water (2 mL) was degassed for 10 min. To the RM was added cyclopropylboronic acid (98 mg, 1.15 mmol) and degassed again for 10 min. Catalytic Pd(OAc)₂ (23 mg, 0.035 mmol) was added and further degassed for 5 min. The resulting mixture was heated to reflux for 16 h under Ar. Reaction mass was filtered through celite and the filtrate was diluted with water (50 mL) and the organic product was extracted with EtOAc (3×50 mL). The combined organic extract was washed with brine (200 mL), dried (anhydr. Na₂SO₄) and concentrated to get crude. The crude product was purified by CC (0-35% EtOAc in PE) to give [cis-EN2]-3-cyclopropyl-2-(4-methyl-4-(3-(trifluoromethyl)phenylsulfonyl)tetrahydro-2H-pyran-2-yl)-5-(methylsulfonyl)pyridine (180 mg, 72%) as liquid.

¹H-NMR (600 MHz, [d₆]-DMSO): δ=8.83-8.84 (1H), 8.19-8.24 (2H), 8.08 (1H), 7.97-7.99 (1H), 7.79 (1H), 5.13-5.16 (1H), 4.01-4.04 (1H), 3.78-3.82 (1H), 3.31 (3H), 2.62-2.67 (1H), 2.26-2.31 (1H), 2.13-2.18 (1H), 1-70-1.73 (1H), 1.48-1.53 (4H), 1.01-1.07 (2H), 0.86-0.91 (1H), 0.72-0.76 (1H).

[cis-EN2] SC-271—analytical chiral SFC: Chiralcel OH—H (250×4.6 mm 5µ), 0.5% DEA in MeOH 10%, 3 g/min, Ret. Time 5.6; ee >95%

Synthesis of Thiophenols 3-(difluoromethyl)benzenethiol

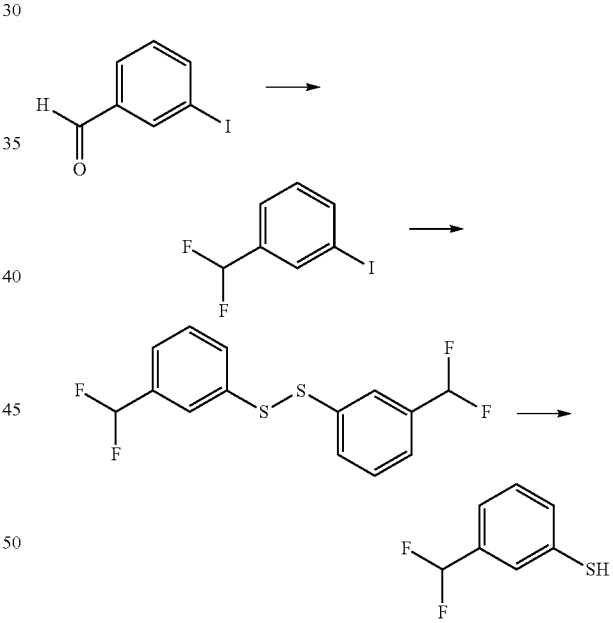

Step 1: 1-(difluoromethyl)-3-iodobenzene

DAST (27 mL, 172.41 mmol) was added to a solution of 3-Iodo benzaldehyde (10 g, 43.10 mmol) in DCM (150 mL) at 0° C. over a period of 10 min. The RM was warmed to RT and stirred for 19 h. The RM was carefully quenched into ice water and extracted with DCM (2×150 mL). The combined organic layer was washed with sat. NaHCO₃ solution, water (100 mL), brine (100 mL), dried over Na₂SO₄ and concentrated to get crude. The crude compound was purified by CC (0-5% EtOAc in PE) to obtain 9.0 g (82.5%) of 1-(difluoromethyl)-3-iodobenzene as yellow oil.

135

Step 2: 1,2-bis(3-(difluoromethyl)phenyl)disulfane

Sulphur powder (3.8 g, 118.11 mmol) was added to a suspension of 1-(difluoromethyl)-3-iodobenzene (10 g, 39.37 mmol), Copper (I) iodide (750 mg, 3.93 mmol) and $K_2CO_3$ (16.29 g, 118.11 m·mol) in DMF (100 mL) and stirred at 90° C. for 9 h. The RM was cooled to RT and filtered, washed the cake with EtOAc (100 mL). The filtrate was washed with water (100 mL), brine (100 mL), dried ($Na_2SO_4$) and concentrated to get 8 g 1,2-bis(3-(difluoromethyl)phenyl)disulfane of crude. The crude was used as such for the next step without purification.

Step 3: 3-(difluoromethyl)benzenethiol

Triphenylphosphine (17.36 g, 66.03 mmol) was added to a solution of 61-1-B (7 g, 22.01 mmol) in toluene (70 mL), added 5 mL of Conc. HCl and stirred for 12 h at 700 C-800 C. The RM was cooled to RT and taken for next step without isolation.

3-(difluoromethyl)benzenethiol

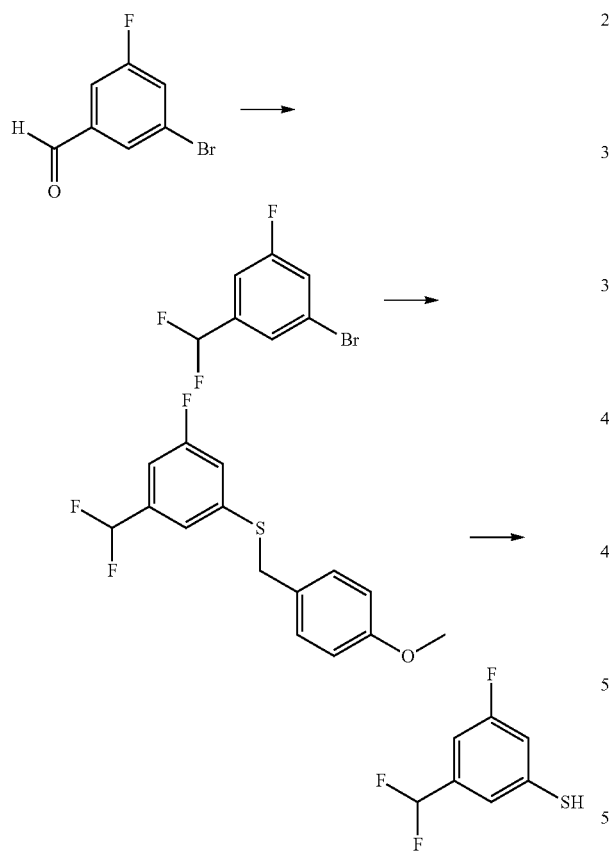

Step 1: 1-bromo-3-(difluoromethyl)-5-fluorobenzene

DAST (39 mL, 295.56 mmol) was added to a solution of 3-bromo-5-fluorobenzaldehyde (15 g, 73.89 mmol) in DCM (150 mL) at −78° C. over a period of 10 min. The RM was warmed to RT and stirred for 19 h. The RM was carefully quenched into ice water and extracted with DCM (2×250 mL). The combined organic layer was washed with sat. $NaHCO_3$ solution, water (150 mL), brine (150 mL), dried

136 over $Na_2SO_4$ and concentrated to get crude. The crude compound was purified by CC (0-5% EtOAc in PE) to obtain 10.0 g (60.6%) of 1-bromo-3-(difluoromethyl)-5-fluorobenzene as low boiling light yellow oil.

Step 2: (3-(difluoromethyl)-5-fluorophenyl)(4-methoxybenzyl)sulfan

To a Ar purged solution of DIPEA (15.2 mL, 85.20 mmol) in 1,4-dioxane (100 mL) was added $Pd_2(dba)_3$ (1.17 g, 1.27 mmol), Xantphos (1.7 g, 2.98 mmol), (4-methoxyphenyl)methanethiol (6.7 mL, 46.86 mmol) and 1-bromo-3-(difluoromethyl)-5-fluorobenzene (9.5 g, 42.60 mmol). The reaction was heated to 90° C. for 2 h. The RM was cooled to RT and filtered, washed the filter cake with EtOAc (100 mL). The filtrate was washed with water (100 mL), brine (100 mL), dried ($Na_2SO_4$) and concentrated to get the crude compound. The crude compound was purified by CC (0-5% EtOAc in PE) to obtain 9.0 g (74%) of (3-(difluoromethyl)-5-fluorophenyl)(4-methoxybenzyl)sulfan as a light yellow oil.

Step 3: 3-(difluoromethyl)-5-fluorobenzenethiol

Trifluoroacetic acid (36.0 mL) was added to a clear solution of (3-(difluoromethyl)-5-fluorophenyl)(4-methoxybenzyl)sulfan (9.0 g, 33.08 mmol) in anisole (18.0 mL) at RT. The reaction was heated to 80° C. for 1 h, then the RM was cooled to RT and quenched in ice water and extracted with EtOAc (2×150 mL). The combined organic layer was washed with 5N NaOH solution (3×300 mL). The combined aq. layer was acidified with 2NHCl solution up to pH=2.0 and extracted with dichloromethane (2×200 mL), the combine organic layer was washed with water (100 mL), sat. $NaHCO_3$ (100 mmL) followed by brine (100 mL), dried ($Na_2SO_4$) and concentrated to obtain 5.0 g (86.2%) of 3-(difluoro-methyl)-5-fluorobenzenethiol as a colorless oil.

Synthesis of Examples 61 to 77 (SC-330 to SC-356)

General Reaction Scheme for Examples SC-330, SC-331, SC-336 to SC-338, SC-353 & SC-354

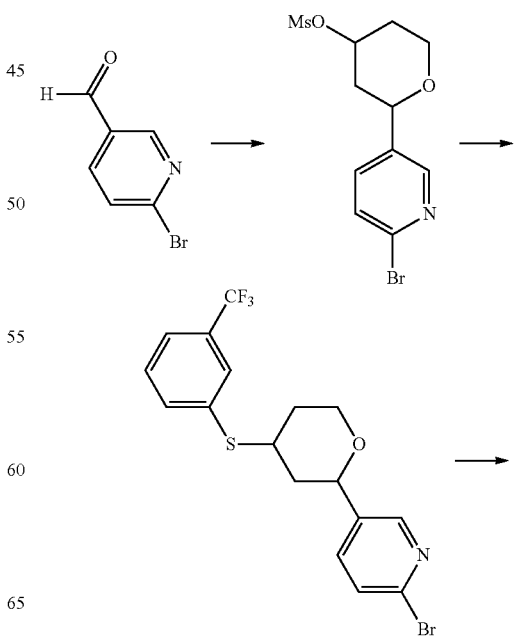

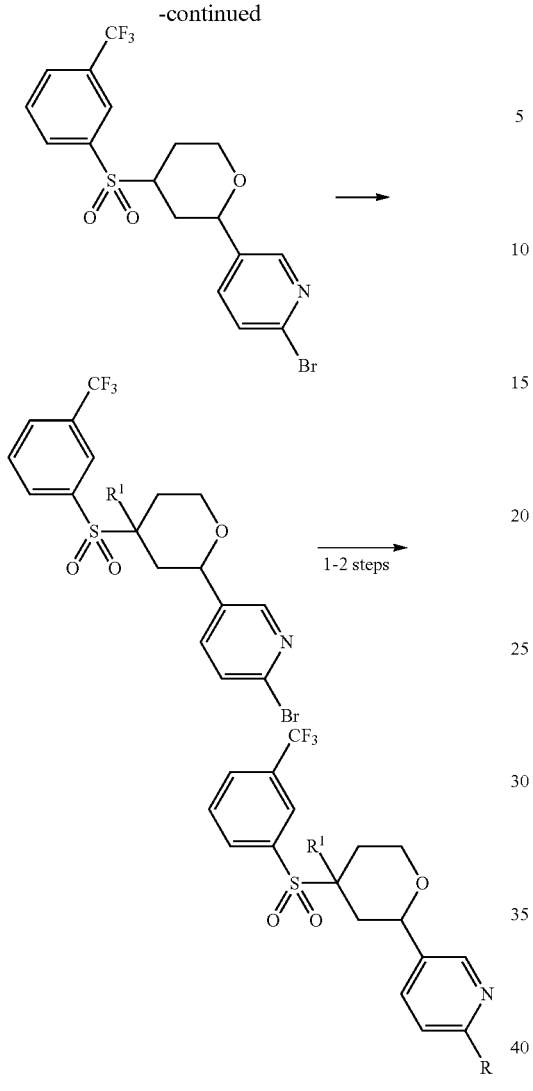

Dimethyl-[5-[4-methyl-4-[[3-(trifluoromethyl)phenyl]sulfonyl]-tetrahydro-pyran-2-yl]-pyridin-2-yl]-amine (Example 61)

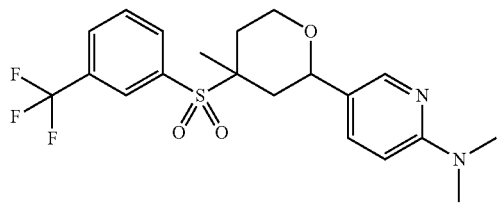 [SMILES: CN(C)c1ccc(C2CC(C)(S(=O)(=O)c3cccc(C(F)(F)F)c3)CCO2)cn1]

Step 5: Dimethyl-[5-[4-methyl-4-[[3-(trifluoromethyl)phenyl]sulfonyl]-tetrahydro-pyran-2-yl]-pyridin-2-yl]-amine A suspension of 2M HNMe$_2$ in THF (969 µL, 1.94 mmol) and [cis-rac] 2-bromo-5-[4-methyl-4-[[3-(trifluoromethyl)phenyl]sulfonyl]-tetrahydro-pyran-2-yl]-pyridine SC-337 (300 mg, 0.646 mmol) [see step 4 Example 64] was stirred in a closed vessel at 100° C. over the weekend. The RM was concentrated and sat. aq. Na$_2$CO$_3$ and EtOAc (75 mL) were added. The organic layer was separated, washed with brine, dried (Na$_2$SO$_4$) and concentrated. Purification by flash chromatography (silica, gradient heptane/EtOAc, 9:1 to 0:1) gave [cis-rac] dimethyl-[5-[4-methyl-4-[[3-(trifluoromethyl)phenyl]sulfonyl]-tetrahydro-pyran-2-yl]-pyridin-2-yl]-amine (125 mg, 45%). This reaction was repeated on the same scale and gave extra [cis-rac] dimethyl-[5-[4-methyl-4-[[3-(trifluoromethyl)phenyl]sulfonyl]-tetrahydro-pyran-2-yl]-pyridin-2-yl]-amine (45 mg, 16%). $^1$H-NMR (400 MHz, CDCl$_3$) of [cis-rac] dimethyl-[5-[4-methyl-4-[[3-(trifluoromethyl)phenyl]sulfonyl]-tetrahydro-pyran-2-yl]-pyridin-2-yl]-amine: δ 8.14 (s, 1H), 8.08-7.99 (m, 2H), 7.94 (d, J=7.8 Hz, 1H), 7.73 (t, J=7.8 Hz, 1H), 7.45 (dd, J=8.8, 2.4 Hz, 1H), 6.51 (d, J=8.8 Hz, 1H), 4.32 (dd, J=11.5, 2.0 Hz, 1H), 4.17-4.08 (m, 1H), 3.70 (td, J=12.3, 2.1 Hz, 1H), 3.08 (s, 6H), 2.34 (td, J=12.8, 5.4 Hz, 1H), 2.23 (t, J=12.3 Hz, 1H), 1.65 (dt, J=13.0, 2.2 Hz, 1H), 1.61-1.48 (m, 5H+H$_2$O).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] dimethyl-[5-[4-methyl-4-[[3-(trifluoromethyl)phenyl]sulfonyl]-tetrahydro-pyran-2-yl]-pyridin-2-yl]-amine

[Cis-rac] dimethyl-[5-[4-methyl-4-[[3-(trifluoromethyl)phenyl]sulfonyl]-tetrahydro-pyran-2-yl]-pyridin-2-yl]-amine (170 mg, 0.397 mmol) was subjected to preparative chiral-LC (IC-column, heptane/EtOH, 70:30). The products were dissolved in MeOH and slowly evaporated by air to form crystals, which were washed with pentane (2×) and dried on filter for 2 h to give [cis-EN1] SC-330 (62 mg, 36%) and [cis-EN2] SC-331 (73 mg, 42%).

[cis-EN1] SC-330—analytical chiral HPLC: chiralpak IC (250×4.6 mm 5µ), 1 ml/min, 35° C., heptane/EtOH 70/30, Ret. Time 9.739; ee >95%

[cis-EN2] SC-331—analytical chiral HPLC: chiralpak IC (250×4.6 mm 5µ), 1 ml/min, 35° C., heptane/EtOH 70/30, Ret. Time 20.471; ee >95%

2,6-Dimethyl-3-[4-[[3-(trifluoromethyl)phenyl]sulfonyl]-tetrahydro-pyran-2-yl]-pyridine (Example 63)

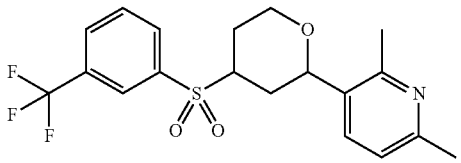 [SMILES: Cc1ccc(C2CC(S(=O)(=O)c3cccc(C(F)(F)F)c3)CCO2)c(C)n1]

See step 3 Example 15. Cis/trans mixture (1:4).

2-Methylsulfonyl-5-[4-methyl-4-[[3-(trifluoromethyl)phenyl]sulfonyl]-tetrahydro-pyran-2-yl]-pyridine (Example 64) and 2-Bromo-5-[4-methyl-4-[[3-(trifluoromethyl)phenyl]sulfonyl]-tetrahydro-pyran-2-yl]-pyridine (Example 65)

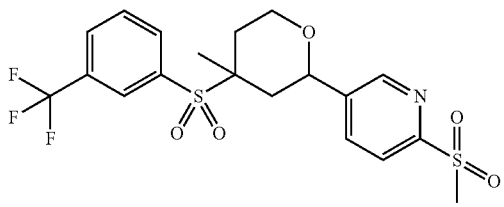 [SMILES: CC1(S(=O)(=O)c2cccc(C(F)(F)F)c2)CCOC(c2ccc(S(C)(=O)=O)nc2)C1]

Step 1: 2-(6-Bromopyridin-3-yl)tetrahydro-2H-pyran-4-yl Methanesulfonate

To an ice-cooled solution of 6-bromonicotinaldehyde (5.32 g, 28.6 mmol) in DCM (30 mL) was dropwise added MsOH (18.6 mL, 286 mmol), followed by the dropwise addition of 3-buten-1-ol (2.46 mL, 28.6 mmol). The reaction was stirred at 0° C. for 2 h and then basified with sat. aq. $Na_2CO_3$ and $H_2O$ (1/1, v/v). The RM was extracted with DCM, dried ($Na_2SO_4$) and concentrated. Crystallisation from EtOAc/heptane gave the first crop od the desired product (4.787 g). The mother liquor was concentrated and the resulting residue was crystallised from EtOAc/heptane to give the second crop of the desired product (2.575 g). All the crystals were combined to yield 2-(6-bromopyridin-3-yl) tetrahydro-2H-pyran-4-yl methanesulfonate (7.362 g, 77%).

Step 2: 2-Bromo-5-(4-((3-(trifluoromethyl)phenyl)thio)tetrahydro-2H-pyran-2-yl)pyridine A mixture of $Cs_2CO_3$ (6.92 g, 21.2 mmol), 3-(trifluoromethyl)benzenethiol (3.39 mL, 25.5 mmol) and 2-(6-bromopyridin-3-yl)tetrahydro-2H-pyran-4-yl methanesulfonate (7.14 g, 21.2 mmol) in anhydr. MeCN (70 mL) was stirred at 40° C. overnight. The RM was allowed to cool to RT, filtered over Celite and eluted with MeCN. The filtrate was concentrated and subjected to flash chromatography (silica, gradient heptane/EtOAc, 97:3 to 7:3) to give 5.0 g of impure title compound, which was used as such in the next step.

Step 3: 2-Bromo-5-(4-((3-(trifluoromethyl)phenyl)sulfonyl)tetrahydro-2H-pyran-2-yl)pyridine Oxone (12.56 g, min. 35.4 mmol) was added to a suspension of crude 2-bromo-5-(4-((3-(trifluoromethyl)phenyl)thio)tetrahydro-2H-pyran-2-yl)pyridine (4.93 g, max. 11.8 mmol) in MeCN (40 mL) and $H_2O$ (40 mL). The RM was stirred overnight at RT and then concentrated a bit. EtOAc (300 mL) was added and sat. aq. $NaHCO_3$ and sat. aq. $Na_2CO_3$ (1/1, v/v) was added until basic. The organic layer was separated, washed with brine, dried ($Na_2SO_4$) and concentrated. The residue was purified by flash chromatography (silica, gradient heptane/EtOAc, 85:15→1:1) to give the desired compound (4.56 g, 46% (corrected for residual solvent) over 2 steps).

Step 4: 2-Bromo-5-[4-methyl-4-[[3-(trifluoromethyl)phenyl]sulfonyl]-tetrahydro-pyran-2-yl]-pyridine

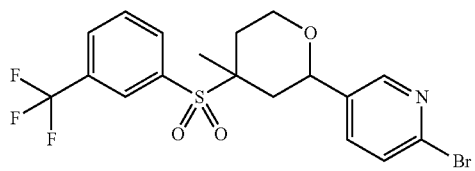 [SMILES: CC1(S(=O)(=O)c2cccc(C(F)(F)F)c2)CCOC(c2ccc(Br)nc2)C1]

A solution of 1.7M KOt-Bu in THF (6.63 mL, 11.3 mmol) was dropwise added to a solution of 2-bromo-5-(4-((3-(trifluoromethyl)phenyl)sulfonyl)tetrahydro-2H-pyran-2-yl)pyridine (4.23 g, 8.92 mmol (corrected for residual solvent)) in dry THF (40 mL) and dry DMF (20 mL) while cooling with an acetone/dry ice bath and the RM was stirred for 15 min. To the cooled solution was dropwise added MeI (1.76 mL, 28.2 mmol) and the RM was stirred for 1.5 h. The cooling bath was removed and ice-cold $H_2O$ (150 mL) was added. The resulting mixture was stirred for 15 min and filtered. The residue was washed with $H_2O$ and dried on the filter for 30 min. Crystallisation from MeOH gave desired [cis-rac] 2-bromo-5-[4-methyl-4-[[3-(trifluoromethyl)phenyl]sulfonyl]-tetrahydro-pyran-2-yl]-pyridine SC-337 (2.52 g, 61%).

Step 5: 5-(4-Methyl-4-((3-(trifluoromethyl)phenyl)sulfonyl)tetrahydro-2H-pyran-2-yl)-2-(methylthio) pyridine To a suspension of NaSMe (453 mg, 6.46 mmol) in pyridine (5.2 mL) was added [cis-rac] 2-bromo-5-(4-methyl-4-((3-(trifluoromethyl)phenyl)sulfonyl)tetrahydro-2H-pyran-2-yl)pyridine SC-337 (750 mg, 1.62 mmol) and the RM was stirred at 60° C. overnight. The RM was allowed to cool to RT, poured into ice-water (50 mL) and extracted with EtOAc (100 mL). The organic layer was washed with brine, dried ($Na_2SO_4$) and concentrated. Crystallisation from MeOH gave the first crop of the title compound (443 mg). The mother liquor was concentrated and crystallisation from MeOH of this residue gave the second crop of the title compound (127 mg). The crystals were combined to yield [cis-rac] 5-(4-methyl-4-((3-(trifluoromethyl)phenyl)sulfonyl)tetrahydro-2H-pyran-2-yl)-2-(methylthio)pyridine (570 mg, 82%).

Step 6: 2-Methylsulfonyl-5-[4-methyl-4-[[3-(trifluoromethyl)phenyl]sulfonyl]-tetrahydro-pyran-2-yl]-pyridine Oxone (742 mg, min. 2.09 mmol) was added to a solution of [cis-rac] 5-(4-methyl-4-((3-(trifluoromethyl)phenyl)sulfonyl)tetrahydro-2H-pyran-2-yl)-2-(methylthio)pyridine (300 mg, 0.695 mmol) in MeCN (3 mL), THF (1.5 mL) and $H_2O$ (1.5 mL) and the resulting RM was stirred overnight at RT and then concentrated a bit. $H_2O$ was added and the resulting precipitate was filtered off, washed with $H_2O$ (2×) and dried on a filter overnight. Purification by flash chromatography (silica, gradient heptane/EtOAc, 9:1→0:1) yielded [cis-rac] 2-methylsulfonyl-5-[4-methyl-4-[[3-(trifluoromethyl)phenyl]sulfonyl]-tetrahydro-pyran-2-yl]-pyridine (187 mg, 58%).

$^1$H NMR (400 MHz, $CDCl_3$) of [cis-rac] 2-methylsulfonyl-5-[4-methyl-4-[[3-(trifluoromethyl)phenyl]sulfonyl]-tetrahydro-pyran-2-yl]-pyridine: δ 8.64 (s, 1H), 8.13 (s, 1H), 8.09 (d, J=8.1 Hz, 1H), 8.04 (d, J=7.8 Hz, 1H), 8.00-7.91 (m, 2H), 7.76 (t, J=7.8 Hz, 1H), 4.60 (d, J=11.5 Hz, 1H), 4.22 (dd, J=12.1, 5.1 Hz, 1H), 4.12 (q, J=7.0 Hz, 0.2H, EtOAc), 3.73 (td, J=12.5, 2.0 Hz, 1H), 3.24 (s, 3H), 2.39 (td, J=12.9, 5.4 Hz, 1H), 2.14 (t, J=12.3 Hz, 1H), 2.05 (s, 0.3H, EtOAc), 1.81 (d, J=13.0 Hz, 1H), 1.59 (s, 3H), 1.59-1.56 (m, 3H+$H_2O$), 1.26 (t, J=7.1 Hz, 0.3H, EtOAc).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 2-methylsulfonyl-5-[4-methyl-4-[[3-(trifluoromethyl)phenyl]sulfonyl]-tetrahydro-pyran-2-yl]-pyridine

[Cis-rac] 2-methylsulfonyl-5-[4-methyl-4-[[3-(trifluoromethyl)phenyl]sulfonyl]-tetrahydro-pyran-2-yl]-pyridine (187 mg, 0.403 mmol) was subjected to preparative chiral-LC (IC-column, heptane/EtOH, 70:30). The products were dissolved in MeOH and slowly evaporated by air to form crystals, which were washed with MeOH (2×) and dried on filter for 2 h to give [cis-EN1] SC-336 (62 mg, 33%) and [cis-EN2] SC-338 (60 mg, 32%).

[cis-EN1] SC-336—analytical chiral HPLC: chiralpak IC (250×4.6 mm 5µ), 1 ml/min, 35° C., heptane/EtOH 70/30, Ret. Time 38.834; ee >95%

[cis-EN2] SC-338—analytical chiral HPLC: chiralpak IC (250×4.6 mm 5µ), 1 ml/min, 35° C., heptane/EtOH 70/30, Ret. Time 44.234; ee >95%

2-Isopropoxy-5-[4-[[3-(trifluoromethyl)phenyl]sulfonyl]-tetrahydro-pyran-2-yl]-pyridine (Example 67)

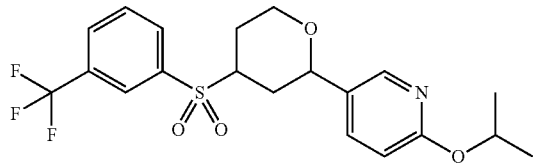 [SMILES: CC(C)Oc1ccc(C2CC(S(=O)(=O)c3cccc(C(F)(F)F)c3)CCO2)cn1]

See step 3 Example 9. Cis/trans mixture (1:9).

[Trans-rac] 2-methyl-6-[4-[[3-(trifluoromethyl)phenyl]sulfonyl]-tetrahydro-pyran-2-yl]-pyridine (Example 69)

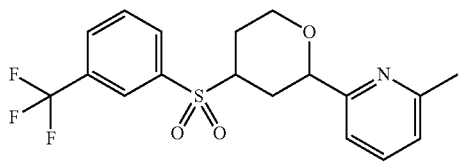 [SMILES: Cc1cccc(C2CC(S(=O)(=O)c3cccc(C(F)(F)F)c3)CCO2)n1]

See step 3 Example 15.

2-(Trifluoromethyl)-5-[4-[[3-(trifluoromethyl)phenyl]sulfonyl]-tetrahydro-pyran-2-yl]-pyridine (Example 70)

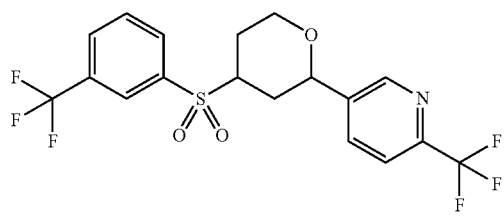 [SMILES: O=S(=O)(c1cccc(C(F)(F)F)c1)C1CCOC(c2ccc(C(F)(F)F)nc2)C1]

See step 3 Example 14. Cis/trans mixture (3:7).

General Reaction Scheme for Examples 62, 71 to 75 (SC-332 to SC-334, SC-343 to SC-348 to SC-352)

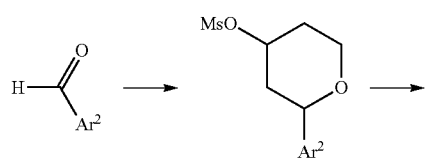

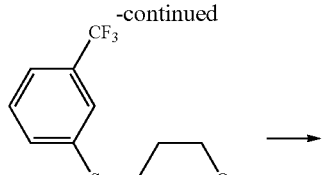

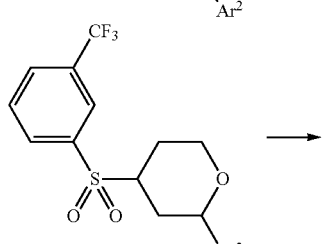

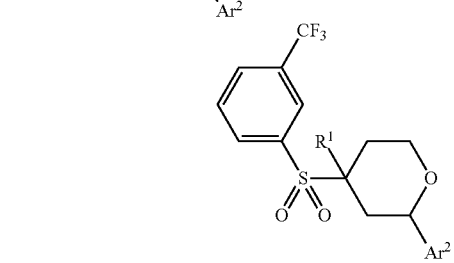

2-Cyclopropyl-5-[4-ethyl-4-[[3-(trifluoromethyl)phenyl]sulfonyl]-tetrahydro-pyran-2-yl]-pyrazine (Example 62)

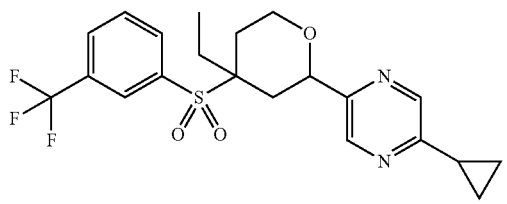 [SMILES: CCC1(S(=O)(=O)c2cccc(C(F)(F)F)c2)CCOC(c2cnc(C3CC3)cn2)C1]

Step 4: 2-Cyclopropyl-5-[4-ethyl-4-[[3-(trifluoromethyl)phenyl]sulfonyl]-tetrahydro-pyran-2-yl]-pyrazine A solution of 2-cyclopropyl-5-(4-((3-(trifluoromethyl)phenyl)sulfonyl)tetrahydro-2H-pyran-2-yl)pyrazine (step 3, Example 18) (3.00 g, 7.27 mmol) in dry THF (35 mL) was prepared, the temperature was lowered to −78° C., 1 M KOtBu in THF (21.82 mL, 21.82 mmol) was added dropwise and the RM was stirred for 10 min. Dropwise addition of EtI (2.91 mL, 36.4 mmol) was followed by stirring the RM at −78° C. for 1 h. The flask was left in the cooling bath. Consequently, the temperature was kept at −78° C. for a few hours, followed by slow raise of temperature to RT and stirring overnight at RT. The RM was combined with aq. 1 M KHSO$_4$ (200 mL), H$_2$O (50 mL) and EtOAc (250 mL) to result in a two phase system. The layers were separated, the aq. layer was extracted with EtOAc (50 mL). The combination of organic layers was washed with aq. 1 M Na$_2$S$_2$O$_3$ (2×50 mL), sat. aq. NaHCO$_3$ (50 mL) and dried (brine and Na₂SO₄), followed by concentration. The residue was dissolved in DCM (5 mL), addition of i-PrOH (50 mL) was followed by concentration. The residue was used for a few crystallisation-cycles from hot i-PrOH. The crystals were filtered off, washed with i-PrOH and dried by suction to provide [cis-rac] 2-cyclopropyl-5-[4-ethyl-4-[[3-(trifluoromethyl)phenyl]sulfonyl]-tetrahydro-pyran-2-yl]-pyrazine (1.01 g, 31%).

¹H-NMR (400 MHz, CDCl₃) of [cis-rac] 2-cyclopropyl-5-[4-ethyl-4-[[3-(trifluoromethyl)phenyl]sulfonyl]-tetrahydro-pyran-2-yl]-pyrazine: δ 8.45 (m, 1H), 8.37 (d, J=1.3 Hz, 1H), 8.12 (s, 1H), 8.04 (d, J=7.9 Hz, 1H), 7.94 (d, J=7.8 Hz, 1H), 7.73 (t, J=7.8 Hz, 1H), 4.54 (dd, J=11.3, 2.2 Hz, 1H), 4.17 (dd, J=12.0, 4.0 Hz, 1H), 3.72 (td, J=12.3, 2.0 Hz, 1H), 2.28-1.99 (m, 6H), 1.83-1.74 (m, 1H), 1.19 (t, J=7.5 Hz, 3H), 1.11-1.02 (m, 4H).

A filtrate from a crystallisation cycle described above was concentrated, dissolved in DCM (0.5 mL) and used for flash chromatography (silica, gradient heptane/EtOAc, 95:5 to 9:1). The product was dissolved in MeCN (5 mL) and concentrated. The residue was dissolved in MeCN (2 mL), addition of H₂O (2 mL) was followed by freeze drying to result in [trans-rac] 2-cyclopropyl-5-[4-ethyl-4-[[3-(trifluoromethyl)phenyl]sulfonyl]-tetrahydro-pyran-2-yl]-pyrazine SC-333 (45 mg, 1%).

¹H-NMR (400 MHz, CDCl₃) of [trans-rac] 2-cyclopropyl-5-[4-ethyl-4-[[3-(trifluoromethyl)phenyl]sulfonyl]-tetrahydro-pyran-2-yl]-pyrazine SC-333: δ 8.52 (s, 1H), 8.42 (d, J=1.4 Hz, 1H), 8.19 (s, 1H), 8.13 (d, J=7.9 Hz, 1H), 7.96 (d, J=7.6 Hz, 1H), 7.77 (t, J=7.8 Hz, 1H), 5.42 (dd, J=11.7, 2.4 Hz, 1H), 4.51 (td, J=12.2, 2.7 Hz, 1H), 4.11 (dd, J=11.7, 5.5 Hz, 1H), 2.34 (d, J=15.4 Hz, 1H), 2.17 (d, J=15.1 Hz, 1H), 2.12-1.90 (m, 3H), 1.67-1.54 (m, 6H+H₂O), 1.53-1.43 (m, 1H), 1.25 (s, 0.1H (impurity)), 1.23-1.17 (m, 0.2H (impurity)), 1.13-1.03 (m, 4H), 0.95 (t, J=7.4 Hz, 3H).

The relative stereochemistry was assigned by comparing the central ring signals in the ¹H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 2-cyclopropyl-5-[4-ethyl-4-[[3-(trifluoromethyl)phenyl]sulfonyl]-tetrahydro-pyran-2-yl]-pyrazine

[Cis-rac] 2-cyclopropyl-5-[4-ethyl-4-[[3-(trifluoromethyl)phenyl]sulfonyl]-tetrahydro-pyran-2-yl]-pyrazine (500 mg, 1.135 mmol) was subjected to preparative chiral-HPLC (IC-column, heptane/EtOH, 85:15). The two products were dissolved in EtOAc (20 mL), followed by concentration. The residues were dissolved in DCM (4 mL), followed by addition of silica (1 g) and concentration. The residues were brought on plugs of silica (3 g) and eluted with heptane (30 mL), the filtrates were discarded. Subsequently, elution with EtOAc (30 mL) provided two filtrates, which were concentrated. The products were dissolved in MeCN (5 mL) and concentrated. The residues were dissolved in MeCN (2 mL), addition of H₂O (2 mL) was followed by freeze drying to result in 206 mg (41%) of [cis-EN1] SC-332 and 204 mg (40%) of [cis-EN2] SC-334.

[cis-EN1] SC-332—analytical chiral HPLC: chiralpak IC (250×4.6 mm 5μ), 1 ml/min, 35° C., heptane/EtOH 80/20, Ret. Time 10.706; ee >95%

[cis-EN2] SC-334—analytical chiral HPLC: chiralpak IC (250×4.6 mm 5μ), 1 ml/min, 35° C., heptane/EtOH 80/20, Ret. Time 17.743; ee >95%

1-Methyl-5-[4-methyl-4-[[3-(trifluoromethyl)phenyl] sulfonyl]-tetrahydro-pyran-2-yl]-3-(trifluoromethyl)-1H-pyrazole (Example 71)

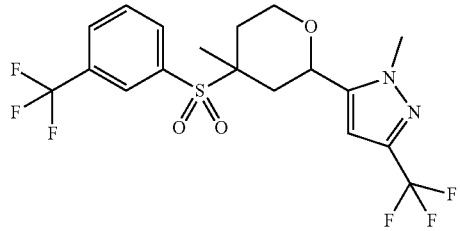 [SMILES: Cn1nc(C(F)(F)F)cc1C1CC(C)(S(=O)(=O)c2cccc(C(F)(F)F)c2)CCO1]

Step 1: 2-(1-Methyl-3-(trifluoromethyl)-1H-pyrazol-5-yl)tetrahydro-2H-pyran-4-yl Methanesulfonate A solution of 1-methyl-3-(trifluoromethyl)-1H-pyrazole-5-carbaldehyde (2 g, 10.67 mmol, purity 95%) and but-3-en-1-ol (0.936 mL, 10.88 mmol) in DCM (25 mL) was cooled to −16° C. using a NaCl/ice bath. MsOH (6.93 mL, 107 mmol) was added at a slow rate, keeping the temperature below −10° C. The mixture was stirred at −16° C. for 30 min. The RM was slowly poured out in a cooled solution of Na₂CO₃ (5.77 g, 54.4 mmol) in H₂O (100 mL). EtOAc/i-Pr₂O (1/1, v/v, 150 mL) was added and the mixture was stirred vigorously for 30 min. The layers were separated and the organic layer was washed with sat. aq. NaHCO₃ (2×50 mL) and brine (2×50 mL) before drying on Na₂SO₄ and concentration in vacuo. The product was purified using flash chromatography (silica, gradient heptane/EtOAc, 1:1 to 0:1) to give a colorless oil. The product was triturated with Et₂O to give the desired product (1.67 g, 47%) as a white solid. The mother liquor was concentrated in vacuo to give another batch of the desired product (1.08 g, 30%) as a colorless oil; totaled yield 2.75 g (78%).

Step 2: 1-Methyl-3-(trifluoromethyl)-5-(4-((3-(trifluoromethyl)phenyl)thio)tetrahydro-2H-pyran-2-yl)-1H-pyrazole A solution of 2-(1-methyl-3-(trifluoromethyl)-1H-pyrazol-5-yl)tetrahydro-2H-pyran-4-yl methanesulfonate (2.75 g, 8.38 mmol) in dry DMF (60 mL) was degassed by alternating vacuum and Ar 5 times with 1 min intervals. Cs₂CO₃ (6.82 g, 20.94 mmol) and 3-(trifluoromethyl)benzenethiol (2.78 mL, 20.94 mmol) were added and the degassing sequence was repeated 3 times. The mixture was stirred at 80° C. in a pre-heated oil bath under Ar for 2 h. The heating was stopped and the mixture was stirred at RT for 16 h. The RM was poured out in sat. aq. NaHCO₃ (50 mL) and the product was extracted with EtOAc/i-Pr₂O (1/1, v/v, 2×125 mL). The combined organic layers were washed with sat. aq. NaHCO₃ (2×50 mL) and brine (2×50 mL) before drying on Na₂SO₄ and concentration in vacuo. The product was purified using flash chromatography (silica, gradient heptane/EtOAc, 9:1→6:4) to give the desired product (2.95 g, 85%).

Step 3: 1-Methyl-3-(trifluoromethyl)-5-(4-((3-(trifluoromethyl)phenyl)sulfonyl)tetrahydro-2H-pyran-2-yl)-1H-pyrazole To a solution of 1-methyl-3-(trifluoromethyl)-5-(4-((3-(trifluoromethyl)phenyl)thio)tetrahydro-2H-pyran-2-yl)-

1H-pyrazole (2.85 g, 6.94 mmol) in MeOH (110 mL) was added a solution of oxone (6.40 g, min. 18 mmol) in H$_2$O (80 mL) and the resulting white suspension was stirred at RT for 2 h. The MeOH was distilled off in vacuo and the residue was basified with sat. aq. NaHCO$_3$. The product was extracted with i-Pr$_2$O/EtOAc (1/1, v/v, 250 mL). The organic layer was washed with sat. aq. NaHCO$_3$ (2×50 mL) and brine (2×50 mL) before drying on Na$_2$SO$_4$ and concentration in vacuo. The product was purified using flash chromatography (silica, gradient heptane/EtOAc, 9:1 to 1:1, then flush with EtOAc) to give the desired product (1.4 g, 45%) as a colorless oil. Also an impure batch (1.47 g) was obtained which was dissolved in MeOH (70 mL), cooled in an ice bath and a solution of oxone (229 mg, min. 0.644 mmol) in H$_2$O (15 mL) was added, giving a white suspension. The mixture was stirred at RT for 3 h. More oxone (500 mg, min. 1.40 mmol) was added and the stirring was continued for 16 h. The MeOH was removed in vacuo and the residue was poured out in sat. aq. NaHCO$_3$ (50 mL). The product was extracted with EtOAc (2×50 mL). The combined organic layers were washed with sat. aq. NaHCO$_3$ (2×25 mL) and brine (2×25 mL) before drying on Na$_2$SO$_4$ and concentration in vacuo to give another batch of the desired product (1.33 g, 43%) as a waxy solid; totaled yield 2.73 g (89%).

Step 4: 1-Methyl-5-[4-methyl-4-[[3-(trifluoromethyl)phenyl]sulfonyl]-tetrahydro-pyran-2-yl]-3-(trifluoromethyl)-1H-pyrazole To a solution of 1-methyl-3-(trifluoromethyl)-5-(4-((3-(trifluoromethyl)phenyl)sulfonyl)tetrahydro-2H-pyran-2-yl)-1H-pyrazole (2.72 g, 6.15 mmol) in dry THF (40 mL) under Ar at −78° C. was added 1.7 M KOtBu in THF (7.96 mL, 13.53 mmol) in a dropwise manner, keeping the temperature below −70° C. The mixture was stirred at −78° C. for 10 min. MeI (1.531 mL, 24.59 mmol) was added dropwise, keeping the temperature below −70° C. The mixture was stirred at −78° C. for 1 h. The cooling bath was removed and sat. aq. NaHCO$_3$ (50 mL) was added while still cold. The mixture was left to thaw and H$_2$O (50 mL) and EtOAc (100 mL) were added. The layers were separated and the aq. layer was extracted with EtOAc (50 mL). The combined organic layers were washed with sat. aq. NaHCO$_3$ (2×25 mL), aq. 1M Na$_2$S$_2$O$_3$ (2×25 mL) and brine (2×25 mL) before drying on Na$_2$SO$_4$ and concentration in vacuo. The product was dissolved in DCM and left at RT for 16 h. The solid was filtered off and dried on air to give [cis-rac] 1-methyl-5-[4-methyl-4-[[3-(trifluoromethyl)phenyl]sulfonyl]-tetrahydro-pyran-2-yl]-3-(trifluoromethyl)-1H-pyrazole (1.65 g, 58%).

$^1$H-NMR (400 MHz, CDCl$_3$) of [cis-rac] 1-methyl-5-[4-methyl-4-[[3-(trifluoromethyl)phenyl]sulfonyl]-tetrahydro-pyran-2-yl]-3-(trifluoromethyl)-1H-pyrazole: δ 8.17 (s, 1H), 8.11 (d, J=7.9 Hz, 1H), 7.98 (d, J=7.8 Hz, 1H), 7.79 (t, J=7.8 Hz, 1H), 6.45 (s, 1H), 4.52 (dd, J=11.8, 2.0 Hz, 1H), 4.13 (dd, J=12.1, 4.2 Hz, 1H), 3.93 (s, 3H), 3.70 (td, J=12.4, 2.1 Hz, 1H), 2.44 (t, J=12.3 Hz, 1H), 2.34 (td, J=12.9, 5.4 Hz, 1H), 1.92 (d, J=12.9 Hz, 1H), 1.58-1.51 (m, 4.5H+H$_2$O).

The mother liquor was concentrated and purified using flash chromatography (silica, gradient heptane/EtOAc, 9:1 to 1:1) to give [trans-rac] 1-methyl-5-[4-methyl-4-[[3-(trifluoromethyl)phenyl]sulfonyl]-tetrahydro-pyran-2-yl]-3-(trifluoromethyl)-1H-pyrazole SC-344 (197 mg, 7%) after trituration with pentane and drying in vacuo.

$^1$H-NMR (400 MHz, CDCl$_3$) of [trans-rac] 1-methyl-5-[4-methyl-4-[[3-(trifluoromethyl)phenyl]sulfonyl]-tetrahydro-pyran-2-yl]-3-(trifluoromethyl)-1H-pyrazole SC-344: δ 8.14 (s, 1H), 8.07 (d, J=7.9 Hz, 1H), 7.99 (d, J=7.8 Hz, 1H), 7.79 (t, J=7.8 Hz, 1H), 6.44 (s, 1H), 5.35 (dd, J=11.9, 2.1 Hz, 1H), 4.44 (td, J=12.7, 2.3 Hz, 1H), 4.08-3.96 (m, 4H), 2.62 (d, J=15.1 Hz, 1H), 2.25 (d, J=15.4 Hz, 1H), 1.97-1.77 (m, 2H), 1.29 (s, 3H).

Another batch of [cis-rac] 1-methyl-5-[4-methyl-4-[[3-(trifluoromethyl)phenyl]sulfonyl]-tetrahydro-pyran-2-yl]-3-(trifluoromethyl)-1H-pyrazole (340 mg, 12%) was also obtained. The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 1-methyl-5-[4-methyl-4-[[3-(trifluoromethyl)phenyl]sulfonyl]-tetrahydro-pyran-2-yl]-3-(trifluoromethyl)-1H-pyrazole-

[Cis-rac] 1-methyl-5-[4-methyl-4-[[3-(trifluoromethyl)phenyl]sulfonyl]-tetrahydro-pyran-2-yl]-3-(trifluoromethyl)-1H-pyrazole (500 mg, 1.096 mmol) was subjected to preparative chiral LC (IC-column, heptane/EtOH, 95:5) to give 112 mg (22%) of [cis-EN1] SC-343 and 132 mg (26%) of [cis-EN2] SC-345.

[cis-EN1] SC-343—analytical chiral HPLC: chiralpak IC (250×4.6 mm 5μ), 1 ml/min, 35° C., heptane/iPrOH 95/5, Ret. Time 12.420; ee >95%

[cis-EN2] SC-345—analytical chiral HPLC: chiralpak IC (250×4.6 mm 5μ), 1 ml/min, 35° C., heptane/iPrOH 95/5, Ret. Time 15.937; ee >95%

2-Cyclopropyl-5-[4-methyl-4-[[3-(trifluoromethyl)phenyl]sulfonyl]-tetrahydro-pyran-2-yl]-pyridine (Example 72)

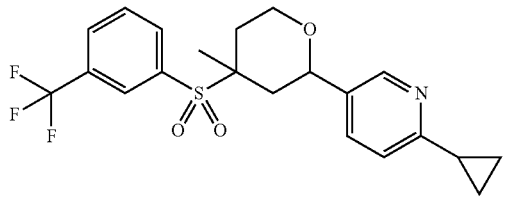 [SMILES: CC1(S(=O)(=O)c2cccc(C(F)(F)F)c2)CCOC(c2ccc(C3CC3)nc2)C1]

Step 1: 2-(6-Cyclopropylpyridin-3-yl)tetrahydro-2H-pyran-4-yl Methanesulfonate

To a cooled (0° C.) solution of 6-cyclopropylnicotinaldehyde (0.98 g, 6.66 mmol) and but-3-en-1-ol (0.573 mL, 6.66 mmol) in DCM (10 mL), MsOH (4.32 mL, 66.6 mmol) was added and the RM was stirred at RT for 72 h. The RM was combined with a RM which was prepared in the same manner from 20 mg (0.14 mmol) of 6-cyclopropylnicotinaldehyde. The combined RMs were diluted with DCM (50 mL) and basified using sat. aq. NaHCO$_3$ (~100 mL) until basic. The aq. phase was extracted with DCM (50 mL) and the combined organics were dried over Na$_2$SO$_4$. The solvent was removed under reduced pressure and the product was purified using flash chromatography (silica, gradient DCM/(10% MeOH in DCM), 1:0 to 1:1) to give 2.6 g ('129%') of the desired product.

Step 2: 2-Cyclopropyl-5-(4-((3-(trifluoromethyl)phenyl)thio)tetrahydro-2H-pyran-2-yl)pyridine K$_2$CO$_3$ (2.417 g, 17.49 mmol) was added to a solution of 2-(6-yclopropylpyridin-3-yl)tetrahydro-2H-pyran-4-yl methanesulfonate (2.6 g, max. 6.66 mmol) and 3-(trifluoromethyl)benzenethiol (2.325 mL, 17.49 mmol) in MeCN (80 mL) under N$_2$. The RM was stirred at 50° C. for 18 h. More 3-(trifluoromethyl)benzenethiol (2.325 mL, 17.49 mmol) and K$_2$CO$_3$ (2.417 g, 17.49 mmol) were added and the RM was stirred for 5 h at 50° C. The RM was concentrated under reduced pressure and the residue was partitioned between DCM (50 mL) and H$_2$O (50 mL). The aq. phase was extracted with DCM (2×50 mL). The combined organics were dried over Na$_2$SO$_4$ and concentrated under reduced pressure to give a brown oil. The product was coated on silica and purified using flash chromatography (silica, gradient heptane/i-Pr$_2$O, 1:0 to 0:1) to give a pure and an impure batch of the desired product. The impure batch was purified further using flash chromatography (silica, gradient heptane/acetone, 1:0 to 7:3). Both batches were combined to afford the title compound (1.03 g, 40% over two steps).

Step 3: 2-Cyclopropyl-5-(4-((3-(trifluoromethyl)phenyl)sulfonyl)tetrahydro-2H-pyran-2-yl)pyridine A solution of oxone (1.57 g, min. 4.4 mmol) in H$_2$O (20 mL) was added dropwise to a cooled (0° C.) solution of 2-cyclopropyl-5-(4-((3-(trifluoromethyl)phenyl)thio)tetrahydro-2H-pyran-2-yl)pyridine (970 mg, 2.56 mmol) in MeOH (25 mL). The pale yellow suspension was stirred for 2 h at RT. More oxone (236 mg, min. 0.66 mmol) was added and the RM was stirred at RT for 18 h. The RM was combined with a RM which was prepared in the same manner from 61 mg (0.16 mmol) of 2-cyclopropyl-5-(4-((3-(trifluoromethyl)phenyl)thio)tetrahydro-2H-pyran-2-yl)pyridine and the solvent, with the exception of H$_2$O, was removed under reduced pressure. The residue was partitioned between H$_2$O (50 mL), sat. aq. NaHCO$_3$ (50 mL) and EtOAc (100 mL). The aq. phase was extracted with EtOAc (50 mL). The combined organics were washed with brine and dried over Na$_2$SO$_4$. The solvent was removed under reduced pressure. The product was purified using flash chromatography (silica, gradient heptane/EtOAc, 1:0 to 1:1) and co-evaporated with heptane (50 mL) to give 0.95 g (85%) of the desired product.

Step 4: 2-Cyclopropyl-5-[4-methyl-4-[[3-(trifluoromethyl)phenyl]sulfonyl]-tetrahydro-pyran-2-yl]-pyridine 1.7 M KOtBu in THF (1.930 mL, 3.28 mmol) was added dropwise via a syringe to a cooled (−78° C., acetone/dry ice) solution of 2-cyclopropyl-5-(4-((3-(trifluoromethyl)phenyl)sulfonyl)tetrahydro-2H-pyran-2-yl)pyridine (900 mg, 2.187 mmol) in dry THF (15 mL) under N$_2$ resulting in an orange solution. After stirring for 30 min at −78° C., MeI (0.684 mL, 10.94 mmol) was added dropwise by syringe and the RM was stirred for 30 min. The RM was quenched with half sat. aq. NH$_4$Cl (10 mL) and combined with a RM which was prepared in the same manner starting from 50 mg (0.12 mmol) of 2-cyclopropyl-5-(4-((3-(trifluoromethyl)phenyl)sulfonyl)tetrahydro-2H-pyran-2-yl)pyridine. The RM was partitioned between sat. aq. NaHCO$_3$ (50 mL) and EtOAc (50 mL). The aq. layer was extracted with EtOAc (50 mL) and the combined organics were washed with aq. 1 M Na$_2$S$_2$O$_3$ (50 mL), brine (50 mL), dried (Na$_2$SO$_4$) and evaporated to dryness. The product was purified using flash chromatography (silica, gradient heptane/EtOAc, 1:0 to 1:1) to afford 0.82 g (83%) of [cis-rac] 2-cyclopropyl-5-[4-methyl-4-[[3-(trifluoromethyl)phenyl]sulfonyl]-tetrahydropyran-2-yl]-pyridine and 94 mg (10%) of [trans-rac] 2-cyclopropyl-5-[4-methyl-4-[[3-(trifluoromethyl)phenyl]sulfonyl]-tetrahydro-pyran-2-yl]-pyridine SC-347.

$^1$H-NMR (400 MHz, CDCl$_3$) of [cis-rac] 2-cyclopropyl-5-[4-methyl-4-[[3-(trifluoromethyl)phenyl]sulfonyl]-tetrahydro-pyran-2-yl]-pyridine: δ 8.31 (d, J=2.1 Hz, 1H), 8.13 (s, 1H), 8.04 (d, J=7.9 Hz, 1H), 7.95 (d, J=7.8 Hz, 1H), 7.74 (t, J=7.8 Hz, 1H), 7.53 (dd, J=8.1, 2.3 Hz, 1H), 7.12 (d, J=8.1 Hz, 1H), 4.42 (dd, J=11.5, 2.0 Hz, 1H), 4.21-4.11 (m, 1H), 3.70 (td, J=12.4, 2.1 Hz, 1H), 2.36 (td, J=12.8, 5.3 Hz, 1H), 2.19 (t, J=12.3 Hz, 1H), 2.03 (p, J=6.4 Hz, 1H), 1.75-1.50 (m, 5H), 1.30-1.23 (m, 0.3H (heptane)), 0.99 (d, J=6.6 Hz, 4H), 0.88 (t, J=6.8 Hz, 0.1H (heptane)).

[Trans-rac] 2-cyclopropyl-5-[4-methyl-4-[[3-(trifluoromethyl)phenyl]sulfonyl]-tetrahydro-pyran-2-yl]-pyridine SC-347 was lyophilised using MeCN/H$_2$O (3/1, v/v, 2 mL) to remove residual solvent.

$^1$H-NMR (400 MHz, CDCl$_3$) of [trans-rac] 2-cyclopropyl-5-[4-methyl-4-[[3-(trifluoromethyl)phenyl]sulfonyl]-tetrahydro-pyran-2-yl]-pyridine SC-347: δ 8.43 (d, J=2.1 Hz, 1H), 8.19-8.06 (m, 2H), 7.96 (d, J=7.8 Hz, 1H), 7.77 (t, J=7.8 Hz, 1H), 7.54 (dd, J=8.1, 2.2 Hz, 1H), 7.11 (d, J=8.1 Hz, 1H), 5.21 (dd, J=11.7, 2.3 Hz, 1H), 4.41 (td, J=12.4, 2.5 Hz, 1H), 4.08-4.00 (m, 1H), 2.43-2.35 (m, 1H), 2.34-2.25 (m, 1H), 2.07-1.98 (m, 1H), 1.84 (ddd, J=15.4, 12.7, 5.7 Hz, 1H), 1.63 (dd, J=15.3, 11.8 Hz, 1H), 1.23 (s, 3H), 1.03-0.94 (m, 4H).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 2-cyclopropyl-5-[4-methyl-4-[[3-(trifluoromethyl)phenyl]sulfonyl]-tetrahydro-pyran-2-yl]-pyridine

[Cis-rac] 2-cyclopropyl-5-[4-methyl-4-[[3-(trifluoromethyl)phenyl]sulfonyl]-tetrahydro-pyran-2-yl]-pyridine (300 mg, 0.705 mmol) was subjected to preparative chiral-LC (IC-column, heptane/EtOH 9:1). The products was transferred to shipment vials using EtOH (5 mL) and co-evaporated with heptane (3×2 mL) to afford 135 mg (45%) of [cis-EN1] SC-346 and 135 mg (45%) of [cis-EN2] SC-348

[cis-EN1] SC-346—analytical chiral HPLC: chiralpak IC (250×4.6 mm 5µ), 1 ml/min, 35° C., heptane/EtOH 90/10, Ret. Time 16.511; ee >95%

[cis-EN2] SC-348—analytical chiral HPLC: chiralpak IC (250×4.6 mm 5µ), 1 ml/min, 35° C., heptane/EtOH 90/10, Ret. Time 23.574; ee >95%

2-(Trifluoromethyl)-6-[4-[[3-(trifluoromethyl)phenyl]sulfonyl]-tetrahydro-pyran-2-yl]-pyridine (Example 74) and 2-[4-Methyl-4-[[3-(trifluoromethyl)phenyl]sulfonyl]-tetrahydro-pyran-2-yl]-6-(trifluoromethyl)-pyridine (Example 75)

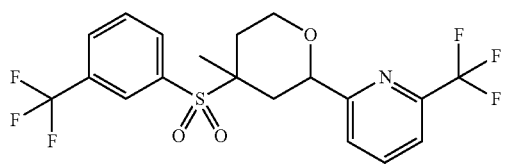 [SMILES: CC1(S(=O)(=O)c2cccc(C(F)(F)F)c2)CCOC(c2cccc(C(F)(F)F)n2)C1]

Step 1: 2-(6-(Trifluoromethyl)pyridin-2-yl)tetrahydro-2H-pyran-4-yl Methanesulfonate A solution of 6-(trifluoromethyl)picolinaldehyde (5.26 g, 30.0 mmol) and but-3-en-1-ol (2.58 mL, 30.0 mmol) in DCM (50 mL) was cooled to 0° C. MsOH (19.51 mL, 300 mmol) was added dropwise and the RM was stirred at RT for 30 min. DCM (250 mL) was added followed by the careful addition of sat. aq. NaHCO$_3$ (500 mL). The organic layer was dried (Na$_2$SO$_4$) and evaporated under reduced pressure, to give 9.13 g (93%) of the desired product.

Step 2: 2-(Trifluoromethyl)-6-(4-((3-(trifluoromethyl)phenyl)thio)tetrahydro-2H-pyran-2-yl)pyridine A solution of 2-(6-(trifluoromethyl)pyridin-2-yl)tetrahydro-2H-pyran-4-yl methanesulfonate (5.04 g, 15.49 mmol) in dry MeCN (50 mL) was flushed with N$_2$ for 30 min. K$_2$CO$_3$ (5.35 g, 38.7 mmol) was added followed by 3-trifluoromethyl)benzenethiol (5.25 mL, 38.7 mmol). The RM was stirred at 50° C. overnight under N$_2$. The suspension was filtered over Celite and the residue washed with EtOAc. The combined filtrate was evaporated under reduced pressure. The product was coated on silica and purified by flash chromatography (silica, gradient heptane/EtOAc, 1:0 to 3:1) to afford 4.58 g (73%) of pure title compound and 1.58 g of impure title compound. The impure batch was purified further by flash chromatography (silica, gradient heptane/EtOAc, 1:0 to 4:1), to afford another 0.82 g (13%) of pure title compound. Total yield: 5.40 g (86%).

Step 3: 2-(Trifluoromethyl)-6-[4-[[3-(trifluoromethyl)phenyl]sulfonyl]-tetrahydro-pyran-2-yl]-pyridine

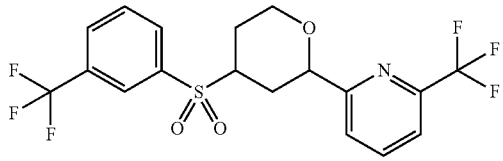 [SMILES: O=S(=O)(c1cccc(C(F)(F)F)c1)C1CCOC(c2cccc(C(F)(F)F)n2)C1]

H$_2$O (25 mL) was added to oxone (11.56 g, 32.5 mmol) and the mixture was stirred at RT for 15 min. The resulting suspension was added to a solution of 2-(trifluoromethyl)-6-(4-((3-(trifluoromethyl)phenyl)thio)tetrahydro-2H-pyran-2-yl)pyridine (5.30 g, 13.01 mmol) in MeOH (25 mL). The RM was stirred at RT overnight. More MeOH (5 mL) was added followed by oxone (2.313 g, 6.51 mmol) in H$_2$O (5 mL). Stirring was continued at RT overnight. Most of the MeOH was removed under reduced pressure. DCM (300 mL) and H$_2$O (200 mL) were added. The aq. layer was extracted with DCM (200 mL). Organic layers were combined, dried (Na$_2$SO$_4$) and evaporated under reduced pressure. The product was purified by flash chromatography (silica, gradient heptane/EtOAc, 1:0 to 2:1), to afford 5.37 g (94%) of the desired product SC-350 (cis/trans mixture (1:4)).

Step 4: 2-[4-Methyl-4-[[3-(trifluoromethyl)phenyl]sulfonyl]-tetrahydro-pyran-2-yl]-6-(trifluoromethyl)-pyridine This reaction was carried out under Ar. The reaction vial was dried (heat-gun) before use. A solution of 2-(Trifluoromethyl)-6-[4-[[3-(trifluoromethyl)phenyl]sulfonyl]-tetrahydro-pyran-2-yl]-pyridine SC-350 (1.19 g, 2.71 mmol) in dry THF (15 mL) was cooled to −78° C., 1 M LiHMDS in THF (4.06 mL, 4.06 mmol) was added dropwise, 10 min later MeI (0.339 mL, 5.42 mmol) was added dropwise and stirring was continued at −78° C. for 6 h and the RM was allowed to very slowly warm to RT overnight. Half sat. aq. NH$_4$Cl (50 mL) and DCM (50 mL) were added. The aq. layer was extracted with DCM (50 mL). Organic layers were combined, washed with aq. 1 M Na$_2$S$_2$O$_3$, dried (Na$_2$SO$_4$) and evaporated to dryness. The product was purified by flash chromatography (silica, gradient heptane/EtOAc, 9:1 to 2:1) to give 0.79 g (64%) of [cis-rac] 2-[4-methyl-4-[[3-(trifluoromethyl)phenyl]sulfonyl]-tetrahydro-pyran-2-yl]-6-(trifluoromethyl)-pyridine SC-351 and 156 mg (13%) of [trans-rac] 2-[4-methyl-4-[[3-(trifluoromethyl)phenyl]sulfonyl]-tetrahydro-pyran-2-yl]-6-(trifluoromethyl)-pyridine SC-352.

$^1$H-NMR (400 MHz, CDCl$_3$) of [cis-rac] 2-[4-methyl-4-[[3-(trifluoromethyl)phenyl]sulfonyl]-tetrahydro-pyran-2-yl]-6-(trifluoromethyl)-pyridine SC-351: δ 8.12 (s, 1H), 8.06 (d, J=7.9 Hz, 1H), 7.95 (d, J=7.8 Hz, 1H), 7.90 (t, J=7.9 Hz, 1H), 7.78-7.69 (m, 2H), 7.60 (d, J=7.7 Hz, 1H), 4.60 (dd, J=9.1, 5.0 Hz, 1H), 4.23 (dd, J=12.1, 4.3 Hz, 1H), 3.76 (td, J=12.3, 2.1 Hz, 1H), 2.40 (td, J=12.9, 5.5 Hz, 1H), 2.15-2.03 (m, 2H), 1.64-1.52 (m, 7.6H+H$_2$O).

$^1$H-NMR (400 MHz, CDCl$_3$) of [trans-rac] 2-[4-methyl-4-[[3-(trifluoromethyl)phenyl]sulfonyl]-tetrahydro-pyran-2-yl]-6-(trifluoromethyl)-pyridine SC-352: δ 8.24-8.20 (m, 2H), 7.97 (d, J=7.7 Hz, 1H), 7.88 (t, J=7.8 Hz, 1H), 7.80 (t, J=8.1 Hz, 1H), 7.70 (d, J=7.9 Hz, 1H), 7.57 (d, J=7.7 Hz, 1H), 5.43 (dd, J=11.4, 2.3 Hz, 1H), 4.47 (td, J=12.2, 2.6 Hz, 1H), 4.15-4.04 (m, 1.1H+EtOAc), 2.67-2.47 (m, 2H), 2.05 (s, 0.1H (EtOAc)), 1.85 (ddd, J=15.3, 12.5, 5.7 Hz, 1H), 1.66 (dd, J=15.4, 11.4 Hz, 1H), 1.28-1.25 (m, 0.4H (impurity)), 1.23 (s, 3H), 0.88 (t, J=6.7 Hz, 0.1H (EtOAc)).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

2-Methoxy-5-[4-methyl-4-[[3-(trifluoromethyl)phenyl]sulfonyl]-tetrahydro-pyran-2-yl]-pyridine (Example 76)

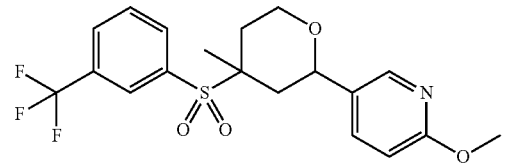

Step 5: 2-Methoxy-5-[4-methyl-4-[[3-(trifluoromethyl)phenyl]sulfonyl]-tetrahydro-pyran-2-yl]-pyridine

[Cis-rac] 2-bromo-5-(4-methyl-4-((3-(trifluoromethyl)phenyl)sulfonyl)tetrahydro-2H-pyran-2-yl)pyridine SC-337 (300 mg, 0.646 mmol) [see step 4, Example 64] was added to a solution of 5.4 M NaOMe in MeOH (239 μL, 1.29 mmol) and pyridine (1.05 mL). The RM was stirred at 60° C. over the weekend, allowed to cool to RT and poured into ice-water (50 mL). After the addition of EtOAc (75 mL), the organic layer was separated. The organic layer was washed with brine, dried (Na$_2$SO$_4$) and concentrated. Crystallisation from MeOH gave the title compound (154 mg). The mother liquor was concentrated and crystallisation (MeOH) of this residue gave extra title compound (18 mg). The crystals were combined to give a total amount of 172 mg (64%) of [cis-rac] 2-methoxy-5-[4-methyl-4-[[3-(trifluoromethyl)phenyl]sulfonyl]-tetrahydro-pyran-2-yl]-pyridine.

$^1$H-NMR (400 MHz, CDCl$_3$) of [cis-rac] 2-methoxy-5-[4-methyl-4-[[3-(trifluoromethyl)phenyl]sulfonyl]-tetrahydro-pyran-2-yl]-pyridine: δ 8.14 (s, 1H), 8.08-8.02 (m, 2H), 7.95 (d, J=7.8 Hz, 1H), 7.74 (t, J=7.9 Hz, 1H), 7.58 (dd, J=8.6, 2.4 Hz, 1H), 6.75 (d, J=8.6 Hz, 1H), 4.40 (dd, J=11.6, 2.0 Hz, 1H), 4.15 (dd, J=12.0, 4.1 Hz, 1H), 3.93 (s, 3H), 3.71 (td, J=12.4, 2.2 Hz, 1H), 3.49 (d, J=5.4 Hz, 0.1H (MeOH)), 2.36 (td, J=12.8, 5.4 Hz, 1H), 2.21 (t, J=12.3 Hz, 1H), 1.74-1.66 (m, 1H), 1.59-1.50 (m, 5.3H+H$_2$O).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 2-methoxy-5-[4-methyl-4-[[3-(trifluoromethyl)phenyl]sulfonyl]-tetrahydro-pyran-2-yl]-pyridine

[Cis-rac] 2-methoxy-5-[4-methyl-4-[[3-(trifluoromethyl)phenyl]sulfonyl]-tetrahydro-pyran-2-yl]-pyridine (170 mg, 0.409 mmol) was subjected to preparative chiral-LC (IC-column, heptane/EtOH, 90:10). The products were dissolved in MeOH and slowly evaporated by air to form crystals, which were washed with MeOH (2×) and dried on filter for 2 h to give [cis-EN1] SC-353 (61 mg, 35%) and [cis-EN2] SC-354 (56 mg, 33%).

[cis-EN1] SC-353—analytical chiral HPLC: chiralpak IC (250×4.6 mm 5µ), 1 ml/min, 35° C., heptane/EtOH 90/10, Ret. Time 12.878; ee >95%

[cis-EN2] SC-354—analytical chiral HPLC: chiralpak IC (250×4.6 mm 5µ), 1 ml/min, 35° C., heptane/EtOH 70/30, Ret. Time 17.389; ee >95%

General Reaction Scheme for Examples 68 and 77 (SC-340, SC-355 & 356)

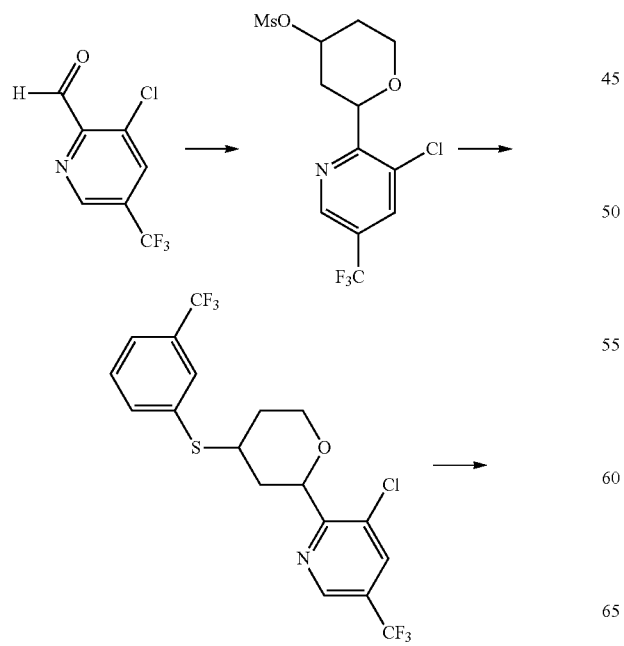

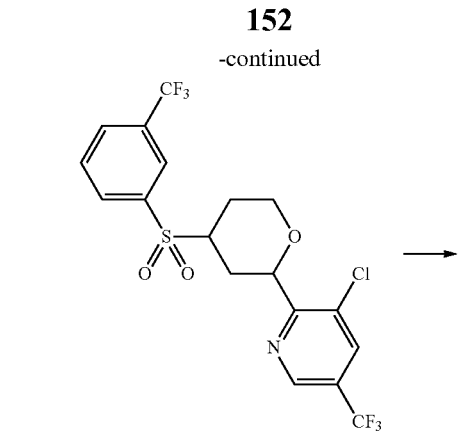

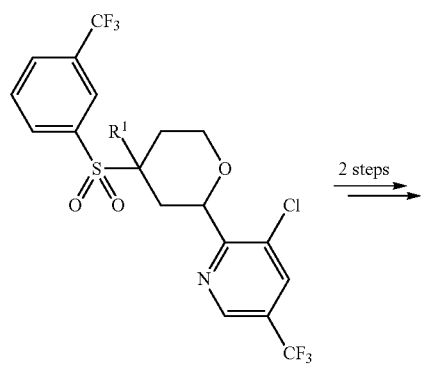

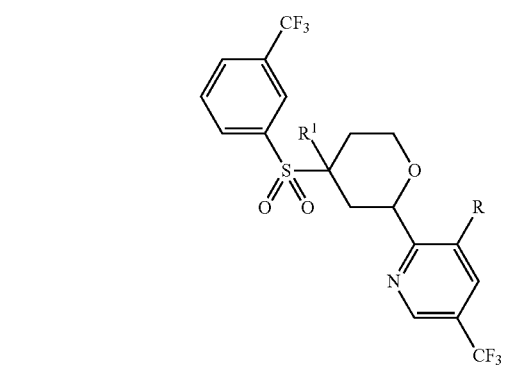

3-Chloro-2-(4-methyl-4-((3-(trifluoromethyl)phenyl)sulfonyl)tetrahydro-2H-pyran-2-yl)-5-(trifluoromethyl)pyridine (Example 68) and 3-Methylsulfonyl-2-[4-methyl-4-[[3-(trifluoromethyl)phenyl]sulfonyl]-tetrahydro-pyran-2-yl]-5-(trifluoromethyl)-pyridine (Example 77)

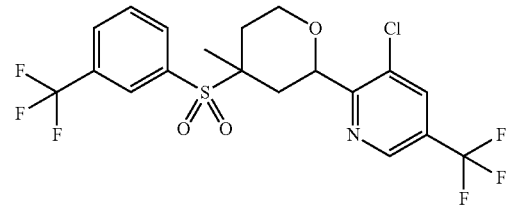

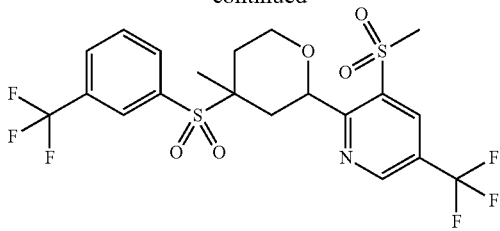

Step 1: 2-(3-Chloro-5-(trifluoromethyl)pyridin-2-yl)tetrahydro-2H-pyran-4-yl Methanesulfonate To a solution of 3-chloro-5-(trifluoromethyl)picolinaldehyde (4.64 g, 22.1 mmol) and MsOH (14.4 mL, 221 mmol) in DCM (25 mL) was added 3-buten-1-ol (1.91 mL, 22.1 mmol). The RM was stirred at 40° C. overnight. The RM was allowed to cool to RT, quenched with sat. aq. $Na_2CO_3$, extracted with DCM and concentrated. The residue was purified by flash chromatography (silica, gradient heptane/EtOAc, 97:3 to 3:7) resulting in the title compound (5.27 g, 66%).

Step 2: 3-Chloro-5-(trifluoromethyl)-2-(4-((3-(trifluoromethyl)phenyl)thio)tetrahydro-2H-pyran-2-yl)pyridine A suspension of $Cs_2CO_3$ (4.77 g, 14.7 mmol) and 2-(3-chloro-5-(trifluoromethyl)pyridin-2-yl)tetrahydro-2H-pyran-4-yl methanesulfonate (5.27 g, 14.8 mmol) in dry MeCN (50 mL) was bubbled through with $N_2$ for 5 min and 3-trifluoromethyl)benzenethiol (2.34 mL, 17.6 mmol) was added. The RM was stirred at 40° C. overnight. The RM was allowed to reach RT, filtered over Celite, eluted with MeCN and concentrated. The residue was dissolved in EtOAc (400 mL), washed with sat. aq. $Na_2CO_3$, brine, dried ($Na_2SO_4$) and concentrated. The residue was purified by flash chromatography (silica, gradient heptane/EtOAc, 97:3 to 70:30) to yield the desired product (4.97 g, 77%).

Step 3: 3-Chloro-5-(trifluoromethyl)-2-(4-((3-(trifluoromethyl)phenyl)sulfonyl)tetrahydro-2H-pyran-2-yl)pyridine Oxone (9.60 g, 27.0 mmol) was added to a milky suspension of 3-chloro-5-(trifluoromethyl)-2-(4-((3-(trifluoromethyl)phenyl)thio)tetrahydro-2H-pyran-2-yl)pyridine (4.97 g, 11.3 mmol) in MeCN (30 mL) and $H_2O$ (30.0 mL). The RM was stirred at RT overnight and concentrated a bit. EtOAc (250 mL) and a solution of sat. aq. $NaHCO_3$ and sat. aq. $Na_2CO_3$ (1/1, v/v) was added to the RM. The organic layer was separated, washed with brine, dried ($Na_2SO_4$), concentrated and co-evaporated with $Et_2O$ (twice) to give the desired product (4.84 g, 91%).

Step 4: 3-Chloro-2-(4-methyl-4-((3-(trifluoromethyl)phenyl)sulfonyl)tetrahydro-2H-pyran-2-yl)-5-(trifluoromethyl)pyridine A solution of 1M LiHMDS in THF (15 mL, 15 mmol) was dropwise added to a solution of 3-chloro-5-(trifluoromethyl)-2-(4-((3-(trifluoromethyl)phenyl)sulfonyl)tetrahydro-2H-pyran-2-yl)pyridine (4.11 g, 8.67 mmol) in dry THF (50 mL) while cooling with an acetone/dry ice bath. The RM was stirred at −78° C. for 15 min and MeI (1.1 mL, 18 mmol) was dropwise added. The RM was allowed to very slowly warm to RT overnight. The RM was poured into ice-water and stirred for 15 min. The precipitate was filtered and washed with $H_2O$ (2×). The residue was dissolved in DCM and the organic layer was separated with a phase separator and concentrated. Crystallization of the residue from MeOH gave [cis-rac] 3-chloro-2-(4-methyl-4-((3-(trifluoromethyl)phenyl)sulfonyl)tetrahydro-2H-pyran-2-yl)-5-(trifluoromethyl)pyridine SC-340 (Example 68, 1.623 g, 35%).

Step 5: 2-(4-Methyl-4-((3-(trifluoromethyl)phenyl)sulfonyl)tetrahydro-2H-pyran-2-yl)-3-(methylthio)-5-(trifluoromethyl)pyridine

[Cis-rac] 3-chloro-2-(4-methyl-4-((3-(trifluoromethyl)phenyl)sulfonyl)tetrahydro-2H-pyran-2-yl)-5-(trifluoromethyl)pyridine SC-340 (750 mg, 1.41 mmol) was added to a suspension of MeSNa (431 mg, 6.15 mmol) in pyridine (5 mL). The RM was stirred at 60° C. overnight and then allowed to reach RT. The RM was poured into ice-water (50 mL) and extracted with EtOAc (75 mL). The organic layer was washed with brine, dried ($Na_2SO_4$) and concentrated. Crystallization of the residue from MeOH gave the desired product (609 mg, 80%).

Step 6: 3-Methylsulfonyl-2-[4-methyl-4-[[3-(trifluoromethyl)phenyl]sulfonyl]-tetrahydro-pyran-2-yl]-5-(trifluoromethyl)-pyridine Oxone (641 mg, 1.80 mmol) was added to a solution of 2-(4-methyl-4-((3-(trifluoromethyl)phenyl)sulfonyl)tetrahydro-2H-pyran-2-yl)-3-(methylthio)-5-(trifluoromethyl)pyridine (300 mg, 0.559 mmol) in MeCN (3 mL), THF (1.5 mL) and $H_2O$ (1.5 mL) and the resulting RM was stirred at 40° C. overnight and then concentrated a bit. To the RM was added $H_2O$ and the resulting precipitate was filtrated, washed with $H_2O$ (2×) and dried on a filter overnight. Purification by flash chromatography (silica, gradient heptane/EtOAc, 9:1 to 0:1) yielded [cis-rac] 3-methylsulfonyl-2-[4-methyl-4-[[3-(trifluoromethyl)phenyl]sulfonyl]-tetrahydro-pyran-2-yl]-5-(trifluoromethyl)-pyridine (207 mg, 70%).

$^1$H NMR (400 MHz, $CDCl_3$) of [cis-rac] 3-methylsulfonyl-2-[4-methyl-4-[[3-(trifluoromethyl)phenyl]sulfonyl]-tetrahydro-pyran-2-yl]-5-(trifluoromethyl)-pyridine: δ 9.06 (s, 1H), 8.61 (d, J=1.7 Hz, 1H), 8.20 (s, 1H), 8.13 (d, J=7.9 Hz, 1H), 7.96 (d, J=7.8 Hz, 1H), 7.77 (t, J=7.8 Hz, 1H), 5.46 (dd, J=11.3, 1.8 Hz, 1H), 4.16 (dd, J=11.3, 4.9 Hz, 1H), 3.86 (td, J=12.5, 2.1 Hz, 1H), 3.26 (s, 3H), 2.83-2.73 (m, 1H), 2.38 (td, J=13.0, 5.3 Hz, 1H), 2.05 (s, 0.1H (impurity)), 1.96 (d, J=13.3 Hz, 1H), 1.66 (d, J=13.2 Hz, 1H), 1.59 (s, 3H), 1.29-1.20 (m, 0.2H (aliphatic impurity).

The relative stereochemistry was assigned by comparing the central ring signals in the $^1$H-NMRs with the spectra of [cis-rac] and [trans-rac] 2-[4-methyl-4-[[3-(trifluoromethyl)phenyl]sulfonyl]-tetrahydro-pyran-2-yl]-5-(trifluoromethyl)-pyridine.

Chiral Resolution of [Cis-rac] 3-methylsulfonyl-2-[4-methyl-4-[[3-(trifluoromethyl)phenyl]sulfonyl]-tetrahydro-pyran-2-yl]-5-(trifluoromethyl)-pyridine

[Cis-rac] 3-methylsulfonyl-2-[4-methyl-4-[[3-(trifluoromethyl)phenyl]sulfonyl]-tetrahydro-pyran-2-yl]-5-(trifluoromethyl)-pyridine (202 mg, 0.380 mmol) was subjected to preparative chiral-LC (IC-column, heptane/EtOH, 80:20).

The products were dissolved in MeOH and slowly evaporated by air to form crystals, which were washed with MeOH (2×) and dried on filter for 2 h to give [cis-EN1] SC-355 (68 mg, 34%) and [cis-EN2] SC-356 (73 mg, 36%).

[cis-EN1] SC-355—analytical chiral HPLC: chiralpak IC (250×4.6 mm 5μ), 1 ml/min, 35° C., heptane/EtOH 80/20, Ret. Time 9.705; ee >95%/specific rotation $[\alpha]_D^{27.3}$ −0.26° (c 0.78; DCM).

the relative stereochemistry was confirmed by 2D-NMR. A NOE was observed for the sulfone aromate with H1$_{ax}$ en H5$_{ax}$ and also a NOE was observed for the Me-group with H4$_{ax}$. Ent1

[cis-EN2] SC-356—analytical chiral HPLC: chiralpak IC (250×4.6 mm 5μ), 1 ml/min, 35° C., heptane/EtOH 80/20, Ret. Time 15.643; ee >95%/specific rotation $[\alpha]_D^{27.6}$ +1.34° (c 0.82; DCM).

Synthesis of Examples 78 to 96 (SC-400 to SC-454)

Cis/Trans Assignment of SC-400 to SC-454

The cis racemic [cis-rac] and trans racemic [trans-rac] compounds were separated after the methylation step using CC or prep-HPLC. The assignment of cis racemic [cis-rac] versus trans racemic [trans-rac] was carried out by NOE studies. In some cases only the cis racemic [cis-rac] compound was assigned by NOE studies at this stage (after the methylation step). In these cases the trans racemic [trans-rac] compound was confirmed by NOE studies on the final trans racemic [trans-rac] target molecule. Formation of the cis racemic [cis-rac] isomer is generally favoured over formation of the trans racemic [trans-rac] isomer (generally yield <10%).

5-[4-Methyl-4-[[3-(trifluoromethyl)phenyl]sulfonyl]-tetrahydro-pyran-2-yl]-2-pyrrolidin-1-yl-pyridine (Example 78)

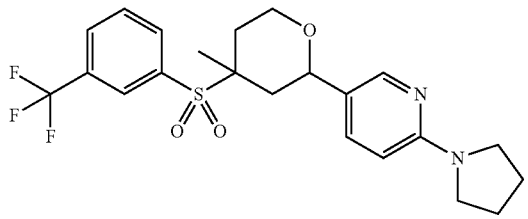 [SMILES: CC1(S(=O)(=O)c2cccc(C(F)(F)F)c2)CCOC(c2ccc(N3CCCC3)nc2)C1]

Step 1:
2-(6-Chloropyridin-3-yl)tetrahydro-2H-pyran-4-yl Methanesulfonate

To a solution of 6-chloronicotinaldehyde (8 g, 56.7 mmol, 1 eq) in DCM (80 ml) was added methane sulfonic acid (36.7 ml, 567 mmol, 10 eq) at 0° C. and the RM was stirred for 10 min. Then 3-buten-1-ol (4.0 g, 56.7 mmol, 1 eq) was added and the RM was stirred at RT for 2 h. The RM was quenched with ice-water (100 ml) and basified to pH=10 using sat. NaHCO$_3$ solution. The aq. layer was extracted with DCM (2×250 ml). The combined organic layers were washed with brine (100 ml), dried (Na$_2$SO$_4$) and concentrated afforded the desired product (12 g, 72%).

Step 2: 2-Chloro-5-(4-((3-(trifluoromethyl)phenyl)thio)tetrahydro-2H-pyran-2-yl)pyridine To a solution of 3-(trifluoromethyl)benzenethiol (8.8 g, 49.48 mmol, 1.2 eq) in DMF (150 ml), was added K$_2$CO$_3$ (17.06 g, 123.6 mmol, 3 eq) and 2-(6-chloropyridin-3-yl)tetrahydro-2H-pyran-4-yl methanesulfonate in DMF (12 g, 41.23 mmol, 1 eq) and the RM was heated to 50° C. and stirred for 18 h. After completion of the reaction, the mixture was diluted with EtOAc (2×250 ml), washed with water (2×250 ml) and brine (200 ml), dried (Na$_2$SO$_4$) and concentrated in vacuum to provide the crude compound which was purified by CC (silica-gel; 15-20% EtOAc in PE) to afford the desired product (10 g, 65%).

Step 3: 2-Chloro-5-(4-((3-(trifluoromethyl)phenyl)sulfonyl)tetrahydro-2H-pyran-2-yl)pyridine Oxone (49.38 g, 80.42 mmol, 3 eq) in water (50 ml) was added to a solution of 2-chloro-5-(4-((3-(trifluoromethyl)phenyl)thio)tetrahydro-2H-pyran-2-yl)pyridine (10 g, 26.80 mmol, 1 eq) in EtOH (100 mL) at RT and the RM was stirred for 14 h. After completion of the reaction, EtOH was distilled off under reduced pressure. The residue was diluted with water (100 ml) and extracted with EtOAc (2×250 ml). The organic layer was washed with brine (200 ml), dried (Na$_2$SO$_4$) and concentrated to give the crude compound which was purified by flash chromatography to afford the desired product (7.5 g, 71%).

Step 4: 2-Chloro-5-(4-methyl-4-((3-(trifluoromethyl)phenyl)sulfonyl)tetrahydro-2H-pyran-2-yl)pyridine A solution of 2-chloro-5-(4-((3-(trifluoromethyl)phenyl)sulfonyl)tetrahydro-2H-pyran-2-yl)pyridine (7.5 g, 18.5 mmol, 1 eq) in THF (150 ml) was cooled to −78° C. and KOtBu (1M solution in THF), (37.0 ml, 37.0 mmol, 2 eq) was added dropwise. The mixture was stirred for 30 min then MeI (1.7 ml, 27.75 mmol, 1.5 eq) was added and the resulting RM allowed to warm to RT and stirred for 14 h. The RM was quenched with cold water (200 ml) and extracted with EtOAc (2×250 ml). The combined organic layers were washed with brine (200 ml), dried (Na$_2$SO$_4$) and concentrated. The residue upon purification by CC (silica gel; EtOAc-PE) afforded [cis rac] 2-chloro-5-(4-methyl-4-((3-(trifluoromethyl)phenyl)sulfonyl)tetrahydro-2H-pyran-2-yl)pyridine (3.5 g, 46%) [TLC system: EtOAc/PE; 4:6; Rf: 0.50].

Step 5: 5-[4-Methyl-4-[[3-(trifluoromethyl)phenyl]sulfonyl]-tetrahydro-pyran-2-yl]-2-pyrrolidin-1-yl-pyridine To a solution of [cis rac] 2-chloro-5-(4-methyl-4-((3-(trifluoromethyl)phenyl)sulfonyl)tetrahydro-2H-pyran-2-yl)pyridine (2 g, 4.7 mmol, 1 eq) and K$_2$CO$_3$ (1.94 g, 14.1 mmol, 3 eq) in DMF (30 ml) was added pyrrolidine (0.67 g, 9.5 mmol, 2 eq). The resulting mixture was heated to 100° C. for 24 h. The RM was filtered through celite and the filtrate concentrated to yield the crude product which was purified by flash chromatography to afford [cis rac] 5-[4-methyl-4-[[3-(trifluoromethyl)phenyl]sulfonyl]-tetrahydro-pyran-2-yl]-2-pyrrolidin-1-yl-pyridine (0.5 g, 24%) [TLC system: EtOAc-100%; Rf: 0.4].

Chiral Resolution of [Cis rac] 5-[4-methyl-4-[[3-(trifluoromethyl)phenyl]sulfonyl]-tetrahydro-pyran-2-yl]-2-pyrrolidin-1-yl-pyridine

[Cis rac] 5-[4-methyl-4-[[3-(trifluoromethyl)phenyl]sulfonyl]-tetrahydro-pyran-2-yl]-2-pyrrolidin-1-yl-pyridine was subjected to chiral prep-SFC purification to give 102 mg of [cis-EN1] SC-400 and 105 mg of [cis-EN2] SC-401. Preparative SFC Conditions: Column/dimensions: Chiralcel OJ-H (250×30)mm; CO2: 70%; Co solvent: 30% MeOH; Total Flow: 100 g/min; Back Pressure: 100 bar; UV: 253 nm.

[cis-EN1] SC-400—analytical SFC: Chiralcel OJ-H (250×4.6 mm 5µ), 26° C., 3 g/min, 100 bar, 40% of 0.5% DEA in MeOH, Ret. Time 1.94 min/specific rotation $[\alpha]_D^{24.4}$ −10.3° (c 0.77; DCM)

[cis-EN2] SC-401—analytical SFC: Chiralcel OJ-H (250×4.6 mm 5µ), 26° C., 3 g/min, 100 bar, 40% of 0.5% DEA in MeOH, Ret. Time 2.40 min/specific rotation $[\alpha]_D^{24.5}$ +10.2° (c 0.78; DCM)

[Trans rac] 5-[4-methyl-4-[[3-(trifluoromethyl)phenyl]sulfonyl]-tetrahydro-pyran-2-yl]-2-pyrrolidin-1-yl-pyridine The corresponding [trans rac] isomer was prepared in analogy to step 5 starting from [trans rac] 2-bromo-5-(4-methyl-4-((3-(trifluoromethyl)phenyl)sulfonyl)tetrahydro-2H-pyran-2-yl)pyridine (see step 4 Example 80) to yield [trans-rac] 5-[4-methyl-4-[[3-(trifluoromethyl)phenyl]sulfonyl]-tetrahydro-pyran-2-yl]-2-pyrrolidin-1-yl-pyridine SC-406 (40 mg) [TLC system: EtOAc-100%; Rf: 0.4].

5-[4-Methyl-4-[[3-(trifluoromethyl)phenyl]sulfonyl]-tetrahydro-pyran-2-yl]-2-(1H-[1,2,4]triazol-1-yl)-pyridine (Example 79)

Step 5: 5-[4-Methyl-4-[[3-(trifluoromethyl)phenyl]sulfonyl]-tetrahydro-pyran-2-yl]-2-(1H-[1,2,4]triazol-1-yl)-pyridine A mixture of [cis rac] 2-bromo-5-(4-methyl-4-((3-(trifluoromethyl)phenyl)sulfonyl)tetrahydro-2H-pyran-2-yl) pyridine (see step 4, Example 80) (0.95 g, 2.04 mmol, 1 eq), Cs₂CO₃ (1.78 g, 4.08 mmol, 2 eq) in DMSO (15 ml), CuI (193 mg, 1.02 mmol, 0.5 eq), and 1,2,4-triazole (423 mg, 6.142 mmol, 3 eq) in a sealed tube, was heated to 120° C. for 14 h. The RM was filtered through celite and the filtrate concentrated to give the crude product which was purified by flash chromatography to afford [cis-rac] 5-[4-methyl-4-[[3-(trifluoromethyl)phenyl]sulfonyl]-tetrahydro-pyran-2-yl]-2-(1H-[1,2,4]triazol-1-yl)-pyridine (0.5 g, 37%) [TLC system: EtOAc-PE; 4:6; Rf: 0.2].

Chiral Resolution of [Cis-rac] 5-[4-methyl-4-[[3-(trifluoromethyl)phenyl]sulfonyl]-tetrahydro-pyran-2-yl]-2-(1H-[1,2,4]triazol-1-yl)-pyridine

[Cis-rac] 5-[4-methyl-4-[[3-(trifluoromethyl)phenyl]sulfonyl]-tetrahydro-pyran-2-yl]-2-(1H-[1,2,4]triazol-1-yl)-pyridine was subjected to chiral prep-SFC purification to give 114 mg of [cis-EN1] SC-402 and 99 mg of [cis-EN2] SC-403. Preparative SFC Conditions: Column/dimensions: Chiralpak AS-H (250×30) mm; CO2: 50%; Co solvent: 50% MeOH; Total Flow: 60 g/min; Back Pressure: 100 bar; UV: 238 nm.

[cis-EN1] SC-402—analytical SFC: Chiralpak AS-H (250×4.6 mm 5µ), 26° C., 3 g/min, 100 bar, 30% of 0.5% DEA in MeOH, Ret. Time 2.69 min

[cis-EN2] SC-403—analytical SFC: Chiralpak AS-H (250×4.6 mm 5µ), 26° C., 3 g/min, 100 bar, 30% of 0.5% DEA in MeOH, Ret. Time 4.73 min

[Trans rac] 5-[4-methyl-4-[[3-(trifluoromethyl)phenyl]sulfonyl]-tetrahydro-pyran-2-yl]-2-(1H-[1,2,4]triazol-1-yl)-pyridine The corresponding [trans rac] isomer was prepared in analogy to step 5 starting from [trans rac] 2-bromo-5-(4-methyl-4-((3-(trifluoromethyl)phenyl)sulfonyl)tetrahydro-2H-pyran-2-yl)pyridine (see step 4, Example 80) to yield [trans-rac] 5-[4-methyl-4-[[3-(trifluoromethyl)phenyl]sulfonyl]-tetrahydro-pyran-2-yl]-2-(1H-[1,2,4]triazol-1-yl)-pyridine SC-407 (40 mg) [TLC system: EtOAc-PE; 3:6; Rf: 0.2].

2-(2-Methoxy-ethoxy)-5-[4-methyl-4-[[3-(trifluoromethyl)phenyl]sulfonyl]-tetrahydro-pyran-2-yl]-pyridine (Example 80)

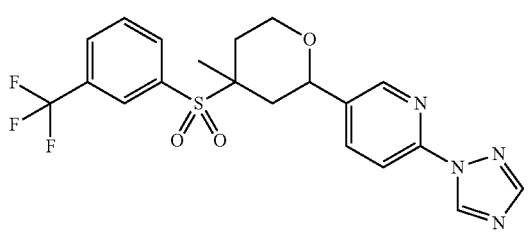 [SMILES: CC1(S(=O)(=O)c2cccc(C(F)(F)F)c2)CCOC(c2ccc(-n3cncn3)nc2)C1]

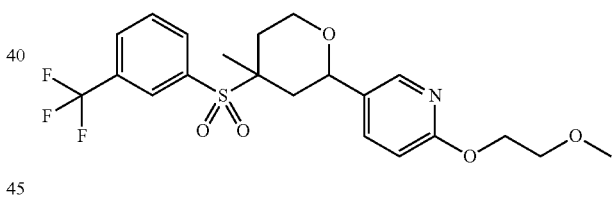

Step 1: 2-(6-Bromopyridin-3-yl)tetrahydro-2H-pyran-4-yl Methanesulfonate

To a stirred solution of 6-bromonicotinaldehyde (10 g, 53.763 mmol, 1.0 eq) in DCM (100 ml), methane sulfonic acid (34.87 ml, 537.63 mmol, 10 eq) was added dropwise at 0° C., followed by 3-buten-1-ol (4.6 ml, 53.763, 1 eq). The RM was allowed to warm to RT and stir for 4 h. Reaction progress was monitored by TLC. The RM was neutralized to pH 7 with aq. NaHCO₃ and extracted with DCM (2×300 ml). The organic layer was washed with brine solution (100 ml)), dried (Na₂SO₄), filtered and concentrated to afford the desired product (16 g, 88%).

Step 2: 2-Bromo-5-(4-((3-(trifluoromethyl)phenyl)thio)tetrahydro-2H-pyran-2-yl)pyridine To a stirred solution of 3-triflouromethyl thiophenol (15.9 g, 89.285 mmol, 2.0 eq) in DMF (100 ml), K₂CO₃ (12.32 g, 89.285 mmol, 2.0 eq) was added at 0° C., followed by 2-(6-bromopyridin-3-yl)tetrahydro-2H-pyran-4-yl methanesulfonate (15 g, 44.642 mmol, 1 eq). The RM was then heated to 50° C. and stirred for 12 h. Reaction progress was monitored by TLC. The RM was quenched with ice water (50 ml) and diluted with Et$_2$O (200 ml). It was then washed with water (3×300 ml) and brine solution (300 ml), dried (Na$_2$SO$_4$), filtered and concentrated. This afforded a residue, which was purified by CC (silica gel, 25% EtOAc in PE) to give the desired product (16.7 g, 90%).

Step 3: 2-Bromo-5-(4-((3-(trifluoromethyl)phenyl)sulfonyl)tetrahydro-2H-pyran-2-yl)pyridine To a stirred solution of 2-bromo-5-(4-((3-(trifluoromethyl)phenyl)thio)tetrahydro-2H-pyran-2-yl)pyridine (16.7 g, 40.047 mmol, 1.0 eq) in EtOH (300 ml) and water (200 ml), Oxone (36.884 g, 120.14 mmol, 3.0 eq) was added at RT and the mixture was stirred for 12 h. Reaction progress was monitored by TLC. The RM was basified with aq. NaHCO$_3$ and extracted with DCM (300 ml). The organic layer was washed with water (300 ml) and brine solution (300 ml), dried (Na$_2$SO$_4$), filtered and concentrated to afford the crude product, which was purified by CC (silica gel, 30% EtOAc in PE) to afford the desired product (15.7 g, 88%).

Step 4: 2-Bromo-5-(4-methyl-4-((3-(trifluoromethyl)phenyl)sulfonyl)tetrahydro-2H-pyran-2-yl)pyridine To a stirred solution of 2-bromo-5-(4-((3-(trifluoromethyl)phenyl)sulfonyl)tetrahydro-2H-pyran-2-yl)pyridine (16 g, 35.634 mmol, 1.0 eq) in THF (100 ml), 1 M KOtBu in THF (71 ml, 71.26 mmol, 2.0 eq) was added at −78° C. followed by MeI (3.3 ml, 53.451 mmol, 1.5 eq). The RM was allowed to slowly warm to RT and then stirred for 12 h. Reaction progress was monitored by TLC. The RM was poured into ice-water and extracted with EtOAc (500 ml). The organic layer was washed with water (2×300 ml) and brine solution (300 ml), dried (Na$_2$SO$_4$), filtered and concentrated to afford the crude product, which was purified by prep HPLC to give [cis rac] 2-bromo-5-(4-methyl-4-((3-(trifluoromethyl)phenyl)sulfonyl)tetrahydro-2H-pyran-2-yl)pyridine (6.8 g, 41%) and [trans rac] 2-bromo-5-(4-methyl-4-((3-(trifluoromethyl)phenyl)sulfonyl)tetrahydro-2H-pyran-2-yl)pyridine (205 mg).

Step 5: 2-(2-Methoxy-ethoxy)-5-[4-methyl-4-[[3-(trifluoromethyl)phenyl]sulfonyl]-tetrahydro-pyran-2-yl]-pyridine To a stirred solution of [cis rac] 2-bromo-5-(4-methyl-4-((3-(trifluoromethyl)phenyl)sulfonyl)tetrahydro-2H-pyran-2-yl)pyridine (1 g, 2.159 mmol, 1.0 eq) in DMF (20 ml), NaH (0.259 g, 6.477 mmol, 3.0 eq) was added at 0° C. The mixture was then stirred at RT for 30 min, followed by addition of 2-methoxy-ethanol. Subsequently the mixture was heated to 90° C. for 12 h. Reaction progress was monitored by TLC. The RM was cooled to RT and quenched with ice-water. It was then diluted with EtOAc (300 ml), washed with water (3×300 ml) and brine solution (300 ml), dried (Na$_2$SO$_4$), filtered and concentrated to afford the crude product, which was purified by prep HPLC to afford [cis rac] 2-(2-methoxy-ethoxy)-5-[4-methyl-4-[[3-(trifluoromethyl)phenyl]sulfonyl]-tetrahydro-pyran-2-yl]-pyridine (500 mg, 50%) [TLC system: EtOAc-PE; 3:7; Rf: 0.35].

Chiral Resolution of [Cis rac] 2-(2-methoxy-ethoxy)-5-[4-methyl-4-[[3-(trifluoromethyl)phenyl]sulfonyl]-tetrahydro-pyran-2-yl]-pyridine

[Cis rac] 2-(2-methoxy-ethoxy)-5-[4-methyl-4-[[3-(trifluoromethyl)phenyl]sulfonyl]-tetrahydro-pyran-2-yl]-pyridine pyridine was subjected to chiral prep-SFC purification to give 95 mg of [cis-EN1] SC-404 and 155 mg of [cis-EN2] SC-405. Preparative SFC Conditions: Column/dimensions: Chiralcel OX-H (250×30)mm; CO2: 70%; Co solvent: 30% MeOH; Total Flow: 100 g/min; Back Pressure: 100 bar; UV: 215 nm.

[cis-EN1] SC-404—analytical SFC: Chiralcel OX-H (250×4.6 mm 5µ), 26° C., 5 g/min, 100 bar, 40% of 0.5% DEA in MeOH, Ret. Time 1.55 min

[cis-EN2] SC-405—analytical SFC: Chiralcel OX-H (250×4.6 mm 5µ), 26° C., 5 g/min, 100 bar, 40% of 0.5% DEA in MeOH, Ret. Time 1.89 min

[Trans rac] 2-(2-methoxy-ethoxy)-5-[4-methyl-4-[[3-(trifluoromethyl)phenyl]sulfonyl]-tetrahydro-pyran-2-yl]-pyridine The corresponding [trans rac] isomer was prepared in analogy to step 5 starting from [trans rac] 2-bromo-5-(4-methyl-4-((3-(trifluoromethyl)phenyl)sulfonyl)tetrahydro-2H-pyran-2-yl)pyridine (see step 4) to yield [trans-rac] 2-(2-methoxy-ethoxy)-5-[4-methyl-4-[[3-(trifluoromethyl)phenyl]sulfonyl]-tetrahydro-pyran-2-yl]-pyridine SC-420 (30 mg) [TLC system: EtOAc-PE; 3:7; Rf: 0.45].

Methyl-[5-[4-methyl-4-[[3-(trifluoromethyl)phenyl]sulfonyl]-tetrahydro-pyran-2-yl]-pyridin-2-yl]-amine (Example 81)

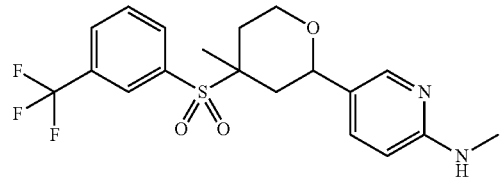 [SMILES: CNc1ccc(C2CC(C)(S(=O)(=O)c3cccc(C(F)(F)F)c3)CCO2)cn1]

Step 5: Methyl-[5-[4-methyl-4-[[3-(trifluoromethyl)phenyl]sulfonyl]-tetrahydro-pyran-2-yl]-pyridin-2-yl]-amine A mixture of [cis rac] 2-bromo-5-(4-methyl-4-((3-(trifluoromethyl)phenyl)sulfonyl)tetrahydro-2H-pyran-2-yl)pyridine (see step 4, Example 80) (1.5 g, 4.319 mmol, 1 eq), K$_2$CO$_3$ (1.78 g, 12.9 mmol, 3 eq) in DMF (20 ml), CuI (410 mg, 2.15 mmol, 0.5 eq) and methylamine solution in MeOH (10 ml, 21.59 mmol, 10 eq) in a sealed tube, was heated to 120° C. for 24 h. The RM was filtered through celite and the filtrate concentrated to yield the crude product which was purified by flash chromatography to afford [cis rac] methyl-[5-[4-methyl-4-[[3-(trifluoromethyl)phenyl]sulfonyl]-tetrahydro-pyran-2-yl]-pyridin-2-yl]-amine (0.5 g, 37%) [TLC system: EtOAc-PE; 4:6; Rf: 0.2].

Chiral Resolution of [Cis-rac] methyl-[5-[4-methyl-4-[[3-(trifluoromethyl)phenyl]sulfonyl]-tetrahydro-pyran-2-yl]-pyridin-2-yl]-amine

[Cis-rac] methyl-[5-[4-methyl-4-[[3-(trifluoromethyl)phenyl]sulfonyl]-tetrahydro-pyran-2-yl]-pyridin-2-yl]- amine was subjected to chiral prep-SFC purification to give 106 mg of [cis-EN1] SC-408 and 97 mg of [cis-EN2] SC-409. Preparative SFC Conditions: Column/dimensions: Chiralpak AD-H (250×21) mm; CO2: 70%; Co solvent: 30% MeOH; Total Flow: 60 g/min; Back Pressure: 100 bar; UV: 245 nm.

[cis-EN1] SC-408—analytical SFC: Chiralpak AD-H (250×4.6 mm 5µ), 26° C., 3 g/min, 100 bar, 40% of 0.5% DEA in MeOH, Ret. Time 3.22 min

[cis-EN2] SC-409—analytical SFC: Chiralpak AD-H (250×4.6 mm 5µ), 26° C., 3 g/min, 100 bar, 40% of 0.5% DEA in MeOH, Ret. Time 3.95 min

[Trans rac] methyl-[5-[4-methyl-4-[[3-(trifluoromethyl)phenyl]sulfonyl]-tetrahydro-pyran-2-yl]-pyridin-2-yl]-amine The corresponding [trans rac] isomer was prepared in analogy to step 5 starting from [trans rac] 2-bromo-5-(4-methyl-4-((3-(trifluoromethyl)phenyl)sulfonyl)tetrahydro-2H-pyran-2-yl)pyridine (see step 4 Example 80) to yield [trans-rac] methyl-[5-[4-methyl-4-[[3-(trifluoromethyl)phenyl]sulfonyl]-tetrahydro-pyran-2-yl]-pyridin-2-yl]-amine SC-412 (50 mg) [TLC system: EtOAc-PE; 4:6; Rf: 0.3].

2-(Difluoro-methoxy)-5-[4-methyl-4-[[3-(trifluoromethyl)phenyl]sulfonyl]-tetrahydro-pyran-2-yl]-pyridine (Example 85)

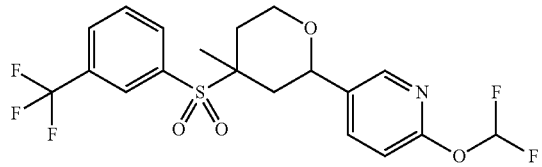 [SMILES: CC1(S(=O)(=O)c2cccc(C(F)(F)F)c2)CCOC(c2ccc(OC(F)F)nc2)C1]

Steps 1 to 4 were carried out in analogy to Example 78 (steps 1 to 4) to give, after purification by prep HPLC [cis rac] 2-methoxy-5-(4-methyl-4-((3-(trifluoromethyl)phenyl)sulfonyl)tetrahydro-2H-pyran-2-yl)pyridine (6.1 g, step 4: 42%) and [trans rac] 2-methoxy-5-(4-methyl-4-((3-(trifluoromethyl)phenyl)sulfonyl)tetrahydro-2H-pyran-2-yl)pyridine (600 mg). [TLC system: EtOAc-PE (3:7); $R_f$: 0.45].

Step 5: 5-((4-Methyl-4-((3-(trifluoromethyl)phenyl)sulfonyl)tetrahydro-2H-pyran-2-yl)pyridin-2-ol A stirred solution of [cis rac] 2-methoxy-5-(4-methyl-4-((3-(trifluoromethyl)phenyl)sulfonyl)tetrahydro-2H-pyran-2-yl)pyridine (3.5 g, 8.43 mmol, 1.0 eq) in HBr (47% aq) was heated to 150° C. for 2 h. Reaction progress was monitored by TLC. The RM was cooled to RT and basified to pH 8 with sat. NaHCO$_3$ solution. The mixture was extracted with EtOAc (2×200 ml), the collected organic layer was dried over Na$_2$SO$_4$, filtered and concentrated to afford the crude product. Purification by trituration with Et$_2$O afforded [cis rac] 5-((4-methyl-4-((3-(trifluoromethyl)phenyl)sulfonyl)tetrahydro-2H-pyran-2-yl)pyridin-2-ol (1.9 g, 56%).

Step 6: 2-(Difluoro-methoxy)-5-[4-methyl-4-[[3-(trifluoromethyl)phenyl]sulfonyl]-tetrahydro-pyran-2-yl]-pyridine To a stirred solution of [cis rac] 5-((4-methyl-4-((3-(trifluoromethyl)phenyl)sulfonyl)tetrahydro-2H-pyran-2-yl)pyridin-2-ol (1.9 g, 4.738 mmol, 1.0 eq) in DMF (20 ml), K$_2$CO$_3$ (1.3 g, 9.47 mmol, 2.0 eq) was added at RT. The mixture was heated to 90° C. and purged with Freon gas for 2 h. Reaction progress was monitored by TLC. The RM was cooled to RT, quenched with ice water and diluted with Et$_2$O (100 ml). The organic layer was washed with water (3×300 ml) and brine solution (300 ml), dried (Na$_2$SO$_4$), filtered and concentrated to afford the crude product, which was triturated with Et$_2$O (10 ml) to afford [cis rac] 2-(difluoro-methoxy)-5-[4-methyl-4-[[3-(trifluoromethyl)phenyl]sulfonyl]-tetrahydro-pyran-2-yl]-pyridine (1 g, 46%) [TLC system: EtOAc-PE (3:7); $R_F$: 0.35].

Chiral Resolution of [Cis rac] 2-(difluoro-methoxy)-5-[4-methyl-4-[[3-(trifluoromethyl)phenyl]sulfonyl]-tetrahydro-pyran-2-yl]-pyridine

[Cis-rac] 2-(difluoro-methoxy)-5-[4-methyl-4-[[3-(trifluoromethyl)phenyl]sulfonyl]-tetrahydro-pyran-2-yl]-pyridine was subjected to chiral prep-SFC purification to give 135 mg of [cis-EN1] SC-418 and 195 mg [cis-EN2] SC-419. Preparative SFC Conditions: Column/dimensions: Chiralcel OJ-H (250×21) mm; CO2: 85%; Co solvent: 15% MeOH; Total Flow: 60 g/min; Back Pressure: 100 bar; UV: 212 nm.

[cis-EN1] SC-418—analytical SFC: Chiralcel OJ-H (250×4.6 mm 5µ), 26° C., 3 g/min, 100 bar, 15% of 0.5% DEA in MeOH, Ret. Time 2.12 min/specific rotation $[\alpha]_D^{24.7}$ −20.1° (c 0.85; DCM)

[cis-EN2] SC-419—analytical SFC: Chiralcel OJ-H (250×4.6 mm 5µ), 26° C., 3 g/min, 100 bar, 15% of 0.5% DEA in MeOH, Ret. Time 2.63 min/specific rotation $[\alpha]_D^{24.7}$ +21.3° (c 0.81; DCM)

[Trans rac] 2-(difluoro-methoxy)-5-[4-methyl-4-[[3-(trifluoromethyl)phenyl]sulfonyl]-tetrahydro-pyran-2-yl]-pyridine The corresponding [trans rac] isomer was prepared in analogy to steps 5 & 6 starting from [trans rac] 2-methoxy-5-(4-methyl-4-((3-(trifluoromethyl)phenyl)sulfonyl)tetrahydro-2H-pyran-2-yl)pyridine to yield [trans-rac] 2-(difluoro-methoxy)-5-[4-methyl-4-[[3-(trifluoromethyl)phenyl]sulfonyl]-tetrahydro-pyran-2-yl]-pyridine SC-417 (60 mg) [TLC system: EtOAc-PE; 3:7; Rf: 0.45].

The starting material 6-methoxynicotinaldehyde was prepared as follows:

(A) To a stirred solution of methyl 6-methoxynicotinate (14 g, 83.83 mmol, 1.0 eq) in THF (300 ml), NaBH$_4$ (47.7 g, 1.257 mol, 15 eq) was added at RT, followed by MeOH (300 ml). The RM was stirred at RT for 12 h. Reaction progress was monitored by TLC. The RM was quenched with sat. NH$_4$Cl (100 ml), diluted with water (100 ml) and extracted with EtOAc (3×200 ml). The organic layer was washed with brine solution (100 ml), dried (Na$_2$SO$_4$), filtered and concentrated to afford the crude product, which upon CC (silica gel, 40% EtOAc in PE afforded (6-methoxypyridin-3-yl)methanol (10 g, 86%).

(B) To a stirred solution of (6-methoxypyridin-3-yl)methanol (9.3 g, 66.906 mmol, 1.0 eq) in DCM (300 ml), DMP (42.55 g, 100.35 mmol, 1.5 eq) was added at 0° C. The mixture was allowed to warm to RT and stir for 12 h. Reaction progress was monitored by TLC. The RM was quenched with ice water (150 ml) and extracted with DCM (2×200 ml). The organic layer was washed with brine solution (100 ml), dried (Na$_2$SO$_4$), filtered and concentrated to afford the crude product, which was purified by CC (silica gel, 25% EtOAc in PE) to afford 6-methoxynicotinaldehyde (6 g, 61%).

General Reaction Scheme for Examples 82, 83, 84, 86, 87, 89 (SC-410, SC-411, SC-413 to SC-416, SC-421 to SC-424, SC-427, SC-428 & SC-438)

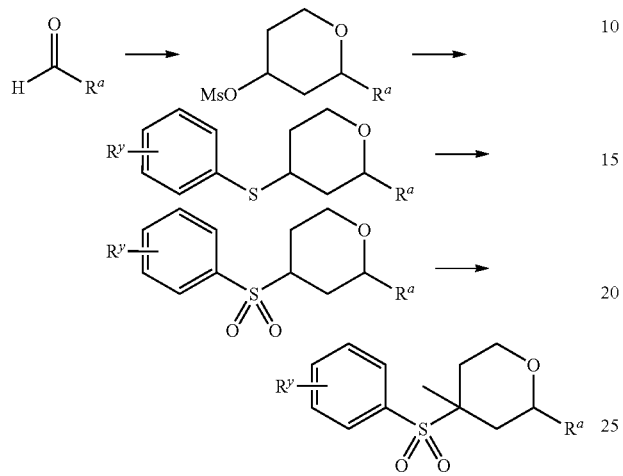

2-Methoxy-5-[4-methyl-4-[[3-(trifluoromethyl)phenyl]sulfonyl]-tetrahydro-pyran-2-yl]-pyrimidine (Example 82)

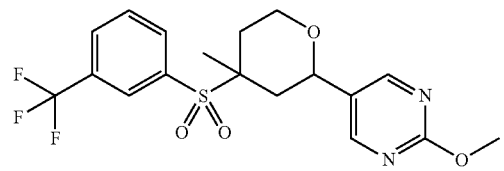 [SMILES: COc1ncc(C2CC(C)(S(=O)(=O)c3cccc(C(F)(F)F)c3)CCO2)cn1]

The synthesis was carried out in analogy to Example 78 (steps 1 to 4) to give [cis rac] 2-methoxy-5-[4-methyl-4-[[3-(trifluoromethyl)phenyl]sulfonyl]-tetrahydro-pyran-2-yl]-pyrimidine [TLC system: EtOAc-PE; 2:3; Rf: 0.26].

Chiral Resolution of [Cis-rac] 2-methoxy-5-[4-methyl-4-[[3-(trifluoromethyl)phenyl]sulfonyl]-tetra-hydro-pyran-2-yl]-pyrimidine

[Cis-rac] 2-methoxy-5-[4-methyl-4-[[3-(trifluoromethyl) phenyl]sulfonyl]-tetrahydro-pyran-2-yl]-pyrimidine was subjected to chiral prep-SFC purification to give of [cis-EN1] SC-410 and [cis-EN2] SC-411. Preparative SFC Conditions: Column/dimensions: Lux-Amylose-2 (250×30) mm; CO2: 70%; Co solvent: 30% MeOH; Total Flow: 60 g/min; Back Pressure: 100 bar; UV: 210 nm.

[cis-EN1] SC-410—analytical SFC: Lux-Amylose-2 (250×4.6 mm 5μ), 26° C., 3 g/min, 100 bar, 40% of 0.5% DEA in MeOH, Ret. Time 2.69 min

[cis-EN2] SC-411—analytical SFC: Lux-Amylose-2 (250×4.6 mm 5μ), 26° C., 3 g/min, 100 bar, 40% of 0.5% DEA in MeOH, Ret. Time 4.36 min The starting material 2-methoxypyrimidine-5-carbaldehyde was prepared as follows:

(A) To a solution of 2-bromoacetic acid (40 g, 289.55 mmol, 1 eq) in DMF (125 ml) was added $POCl_3$ (106 ml) dropwise at 0° C. and the RM was stirred at 105° C. for 8 h. The RM was quenched with EtOH (160 ml) dropwise at 0° C., followed by THF (800 ml). The RM was stirred at 0° C. for 2 h. The precipitated crystals were filtered off, washed with (20% EtOH-THF) and dried under vacuum.

(B) To a solution of methyl carbamimidate sulfate (10 g, 81.3 mmol, 1 eq) and the product from step (A) (41.30 g, 162.6 mmol, 2 eq) in $^i$PrOAc (200 ml) was added a solution of $KHCO_3$ (24.39 g, 243.9 mmol, 3 eq) in water (100 ml) in one portion at RT. The RM was stirred at RT for 48 h. It was diluted with water (100 ml) and the aq. layer was extracted with EtOAc (3×100 ml). The organics were dried ($Na_2SO_4$) and concentrated to afford 2-methoxypyrimidine-5-carbaldehyde (10 g, 88%; over 2 steps).

Dimethyl-[5-[4-methyl-4-[[3-(trifluoromethyl)phenyl]sulfonyl]-tetrahydro-pyran-2-yl]-pyrimidin-2-yl]-amine (Example 83)

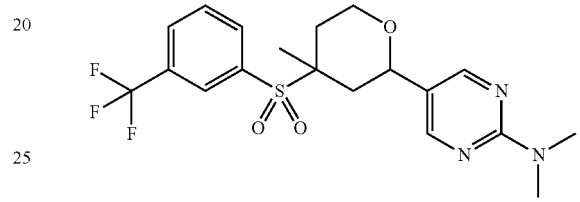

The synthesis was carried out in analogy to Example 78 (steps 1 to 4) to give [cis rac]dimethyl-[5-[4-methyl-4-[[3-(trifluoromethyl)phenyl]sulfonyl]-tetrahydro-pyran-2-yl]-pyrimidin-2-yl]-amine [TLC system: EtOAc-PE; 1:1; Rf: 0.24].

Chiral Resolution of [Cis-rac] dimethyl-[5-[4-methyl-4-[[3-(trifluoromethyl)phenyl]sulfonyl]-tetra-hydro-pyran-2-yl]-pyrimidin-2-yl]-amine

[Cis-rac] dimethyl-[5-[4-methyl-4-[[3-(trifluoromethyl) phenyl]sulfonyl]-tetrahydro-pyran-2-yl]-pyrimidin-2-yl]-amine was subjected to chiral prep-SFC purification (Chiralpak AD-H) to give of [cis-EN1] SC-413 and [cis-EN2] SC-414.

[cis-EN1] SC-413—analytical SFC: Chiralpak AD-H (250×4.6 mm 5μ), 26° C., 3 g/min, 100 bar, 40% of 0.5% DEA in MeOH, Ret. Time 3.52 min

[cis-EN2] SC-414—analytical SFC: Chiralpak AD-H (250×4.6 mm 5μ), 26° C., 3 g/min, 100 bar, 40% of 0.5% DEA in MeOH, Ret. Time 5.15 min The starting material 2-(dimethylamino)pyrimidine-5-carbaldehyde was prepared as follows:

(A) To a solution of 2-bromoacetic acid (40 g, 289.55 mmol, 1 eq) in DMF (125 ml) was added $POCl_3$ (106 ml) dropwise at 0° C. and the RM was stirred at 105° C. for 8 h. The RM was quenched with EtOH (160 ml) dropwise at 0° C., followed by THF (800 ml). The RM was stirred at 0° C. for 2 h. The precipitated crystals were filtered off, washed with (20% EtOH-THF) and dried under vacuum.

(B) To a solution of 1,1-dimethylguanidine hydrochloride (10 g, 81.3 mmol, 1 eq) and the product from (A) (41.30 g, 162.6 mmol, 2 eq) in i-PrOAc (200 ml) was added a solution of $KHCO_3$ (24.39 g, 243.9 mmol, 3 eq) in water (100 ml) in one portion at RT. The RM was stirred at RT for 48 h. The RM was diluted with water (100 ml), and the aq. layer was extracted with EtOAc (3×100 ml), dried ($Na_2SO_4$) and 2-Methoxy-5-[4-methyl-4-[[3-(trifluoromethyl)phenyl]sulfonyl]-tetrahydro-pyran-2-yl]-pyrazine (Example 84)

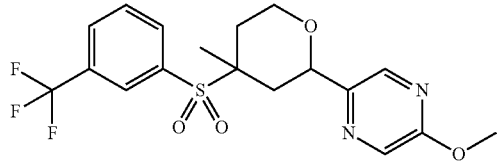

The synthesis was carried out in analogy to Example 78 (steps 1 to 4) to give [cis rac] 2-methoxy-5-[4-methyl-4-[[3-(trifluoromethyl)phenyl]sulfonyl]-tetrahydro-pyran-2-yl]-pyrazine [TLC system: EtOAc-PE; 4:6; Rf: 0.48].

Chiral Resolution of [Cis rac] 2-methoxy-5-[4-methyl-4-[[3-(trifluoromethyl)phenyl]sulfonyl]-tetrahydro-pyran-2-yl]-pyrazine

[Cis-rac] 2-methoxy-5-[4-methyl-4-[[3-(trifluoromethyl)phenyl]sulfonyl]-tetrahydro-pyran-2-yl]-pyrazine was subjected to chiral prep-SFC purification to give 110 mg of [cis-EN1] SC-415 and 70 mg [cis-EN2] SC-416. Preparative SFC Conditions: Column/dimensions: Chiralpak AD-H (250×30) mm; CO2: 75%; Co solvent: 25% MeOH; Total Flow: 60 g/min; Back Pressure: 100 bar; UV: 216 nm.

[cis-EN1] SC-415—analytical SFC: Chiralpak AD-H (250×4.6 mm 5μ), 26° C., 3 g/min, 100 bar, 25% of 0.5% DEA in MeOH, Ret. Time 2.79 min

[cis-EN2] SC-416—analytical SFC: Chiralpak AD-H (250×4.6 mm 5μ), 26° C., 3 g/min, 100 bar, 25% of 0.5% DEA in MeOH, Ret. Time 3.23 min The starting material 5-methoxypyrazine-2-carbaldehyde was prepared as follows:
(A) To a solution of methyl 5-chloropyrazine-2-carboxylate (3×5 g, 28.98 mmol, 1 eq) in MeOH (50 ml), was added NaOMe (4 g, 72.45 mmol, 2.5 eq) and the RM was stirred at 60° C. for 18 h. Reaction progress was monitored by TLC. The RM was diluted with water (300 ml) and extracted with EtOAc (3×200 ml). The combined organic layers were washed with brine solution (200 ml), dried over Na2SO4 and concentrated to afford methyl 5-methoxypyrazine-2-carboxylate (12 g, 82%).
(B) To a solution of methyl 5-methoxypyrazine-2-carboxylate (5 g, 29.73 mmol, 1 eq) in THF (100 ml) at 0° C., was added NaBH4 (17 g, 446.03 mmol, 15 eq) portionwise, followed by dropwise addition of MeOH (100 ml). The RM was stirred at RT for 3 h. Reaction progress was monitored by TLC. The RM was quenched with sat. NH4Cl solution at 0° C. The solvent was distilled off and the residue was diluted with EtOAc (3×100 ml). The organic layer was washed with water (100 ml) and brine (100 ml), dried over Na2SO4 and concentrated to afford (5-methoxypyrazin-2-yl)methanol (4.5 g, 54%).
(C) To a solution of (5-methoxypyrazin-2-yl)methanol (2 g, 10.703 mmol, 1 eq) in CHCl3 (50 ml), was added MnO2 (9.3 g, 107.03 mmol, 10 eq) at RT. The RM was refluxed for 18 h. Reaction progress was monitored by TLC. The RM was cooled to RT, filtered through celite and washed with DCM (200 ml). The filtrate was concentrated to afford 5-methoxy-pyrazine-2-carbaldehyde (1 g, 51%).

concentrated to afford 2-(dimethylamino)pyrimidine-5-carbaldehyde (4.8 g, 39%; over 2 steps).

Dimethyl-[5-[4-methyl-4-[[3-(trifluoromethyl)phenyl]sulfonyl]-tetrahydro-pyran-2-yl]-pyrazin-2-yl]-amine (Example 86)

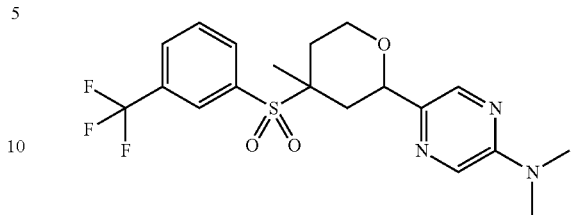

The synthesis was carried out in analogy to Example 78 (steps 1 to 4) to give [cis rac]dimethyl-[5-[4-methyl-4-[[3-(trifluoromethyl)phenyl]sulfonyl]-tetrahydro-pyran-2-yl]-pyrazin-2-yl]-amine [TLC system: EtOAc-PE; 4:6; Rf: 0.38].

Chiral Resolution of [Cis rac] dimethyl-[5-[4-methyl-4-[[3-(trifluoromethyl)phenyl]sulfonyl]-tetrahydro-pyran-2-yl]-pyrazin-2-yl]-amine

[Cis-rac] dimethyl-[5-[4-methyl-4-[[3-(trifluoromethyl)phenyl]sulfonyl]-tetrahydro-pyran-2-yl]-pyrazin-2-yl]-amine was subjected to chiral prep-SFC purification to give 120 mg of [cis-EN1] SC-421 and 92 mg [cis-EN2] SC-422. Preparative SFC Conditions: Column/dimensions: Chiralpak AD-H (250×30) mm; CO2: 60%; Co solvent: 40% of 0.5% DEA in MeOH; Total Flow: 100 g/min; Back Pressure: 100 bar; UV: 254 nm.

[cis-EN1] SC-421—analytical SFC: Chiralpak AD-H (250×4.6 mm 5μ), 26° C., 3 g/min, 100 bar, 40% of 0.5% DEA in MeOH, Ret. Time 2.91 min

[cis-EN2] SC-422—analytical SFC: Chiralpak AD-H (250×4.6 mm 5μ), 26° C., 3 g/min, 100 bar, 40% of 0.5% DEA in MeOH, Ret. Time 3.75 min The starting material 5-(dimethylamino)pyrazine-2-carbaldehyde was prepared as follows:
(A) To a solution of methyl 5-chloropyrazine-2-carboxylate (5 g, 28.98 mmol, 1 eq) in DMF (30 ml), was added K2CO3 (12 g, 86.94 mmol, 3 eq) followed by Me2NH.HCl. The RM mixture was stirred at 60° C. for 18 h. Reaction progress was monitored by TLC. The RM was diluted with water (200 ml) and extracted with EtOAc (2×200 ml). The combined organic layers were washed with water (2×150 ml) and brine solution (100 ml), dried over Na2SO4 and concentrated to afford methyl 5-(dimethylamino)pyrazine-2-carboxylate (3 g, 57%).
(B) (5-(Dimethylamino)pyrazin-2-yl)methanol was prepared in analogy to step (B) Example 84.
(C) 5-(Dimethylamino)pyrazine-2-carbaldehyde was prepared in analogy to step (C) Example 84.

5-Methoxy-2-[4-methyl-4-[[3-(trifluoromethyl)phenyl]sulfonyl]-tetrahydro-pyran-2-yl]-pyrimidine (Example 87)

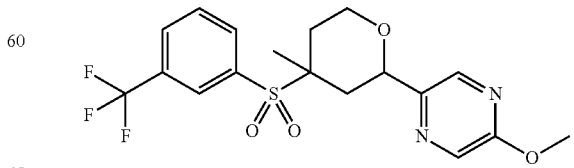

The synthesis was carried out in analogy to Example 78 (steps 1 to 4) to give [cis rac] 5-methoxy-2-[4-methyl-4-[[3-

(trifluoromethyl)phenyl]sulfonyl]-tetrahydro-pyran-2-yl]-pyrimidine [TLC system: EtOAc-PE; 1:1; Rf: 0.26].

Chiral Resolution of [Cis rac] 5-methoxy-2-[4-methyl-4-[[3-(trifluoromethyl)phenyl]sulfonyl]-tetrahydro-pyran-2-yl]-pyrimidine

[Cis-rac] 5-methoxy-2-[4-methyl-4-[[3-(trifluoromethyl)phenyl]sulfonyl]-tetrahydro-pyran-2-yl]-pyrimidine was subjected to chiral prep-SFC purification to give 100 mg of [cis-EN1] SC-423 and 60 mg [cis-EN2] SC-424. Preparative SFC Conditions: Column/dimensions: LuxCellulose-2 (250×30) mm; CO2: 60%; Co solvent: 40% MeOH; Total Flow: 100 g/min; Back Pressure: 100 bar; UV: 217 nm.

[cis-EN1] SC-423—analytical SFC: LuxCellulose-2 (250×4.6 mm 5μ), 30° C., 3 g/min, 100 bar, 30% of 0.5% DEA in MeOH, Ret. Time 2.97 min

[cis-EN2] SC-424—analytical SFC: LuxCellulose-2 (250×4.6 mm 5μ), 30° C., 3 g/min, 100 bar, 30% of 0.5% DEA in MeOH, Ret. Time 5.28 min The starting material 5-methoxypyrimidine-2-carbaldehyde was prepared as follows:

(A) A mixture of 2-chloro-5-methoxypyrimidine (10 g, 69.44 mmol, 1 eq) MeOH—$CH_3CN$ 4:1 (160 ml-40 ml), TEA (20 ml) and Pd(dppf)$Cl_2$ DCM (6 g, 7.34 mmol, 0.1 eq) in an autoclave, was stirred at 100° C. for 18 h under CO gas atmosphere. The RM was cooled to RT, filtered through celite, washed with MeOH (100 ml), and the filtrate was concentrated. The residue upon purification by CC (silica gel; EtOAc-PE; 3:7) afforded methyl 5-methoxypyrimidine-2-carboxylate (6 g, 52%).

(B) (5-Methoxypyrimidin-2-yl)methanol was prepared in analogy to step (B) Example 84.

(C) 5-Methoxypyrimidine-2-carbaldehyde was prepared in analogy to step (C) Example 84. This filtered $CHCl_3$ solution of the product was used next step without further purification.

3-Chloro-5-(difluoro-methoxy)-2-[4-methyl-4-[[3-(trifluoromethyl)phenyl]sulfonyl]-tetrahydro-pyran-2-yl]-pyridine (Example 89)

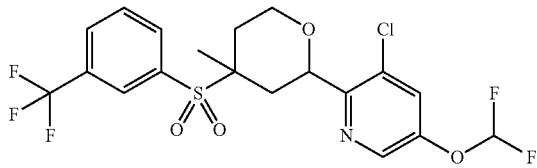 [SMILES: CC1(S(=O)(=O)c2cccc(C(F)(F)F)c2)CCOC(c2ncc(OC(F)F)cc2Cl)C1]

The synthesis was carried out in analogy to example 78 (steps 1 to 4) to give, upon purification by flash chromatography (silica-gel; 15-20% EtOAc in PE) [cis rac] 3-chloro-5-(difluoro-methoxy)-2-[4-methyl-4-[[3-(trifluoromethyl)phenyl]sulfonyl]-tetrahydro-pyran-2-yl]-pyridine (0.6 g, step 4: 20%) [TLC system: EtOAc-PE; 3:7; Rf: 0.4] and [trans rac]3-chloro-5-(difluoro-methoxy)-2-[4-methyl-4-[[3-(trifluoromethyl)phenyl]sulfonyl]-tetrahydro-pyran-2-yl]-pyridine SC-438 (26 mg) [TLC system: EtOAc-PE; 3:7; Rf: 0.5].

Chiral Resolution of [Cis-rac]3-chloro-5-(difluoro-methoxy)-2-[4-methyl-4-[[3-(trifluoromethyl)phenyl]sulfonyl]-tetrahydro-pyran-2-yl]-pyridine

[Cis-rac] 3-chloro-5-(difluoro-methoxy)-2-[4-methyl-4-[[3-(trifluoromethyl)phenyl]sulfonyl]-tetrahydro-pyran-2-yl]-pyridine was subjected to chiral prep-SFC purification to give of [cis-EN1] SC-427 and [cis-EN2] SC-428. Preparative SFC Conditions: Column/dimensions: Chiralpak AS-H (250×30) mm; CO2: 85%; Co solvent: 15% MeOH; Total Flow: 100 g/min; Back Pressure: 100 bar; UV: 212 nm.

[cis-EN1] SC-410—analytical SFC: Chiralpak AS-H (250×4.6 mm 5μ), 30° C., 3 g/min, 100 bar, 15% of 0.5% DEA in MeOH, Ret. Time 1.92 min

[cis-EN2] SC-411—analytical SFC: Chiralpak AS-H (250×4.6 mm 5μ), 30° C., 3 g/min, 100 bar, 15% of 0.5% DEA in MeOH, Ret. Time 2.35 min The starting material 3-chloro-5-(difluoromethoxy)picolinaldehyde was prepared as follows:

(A) To a solution of 5,6-dichloropyridin-3-ol (8.5 g, 52.14 mmol, 1 eq) in EtOH (60 ml) was added Pd(dppf)$C_2$ (4.25 g, 5.21 mmol, 0.1 eq), Pd(OAc)$_2$ (1.16 g, 5.21 mmol, 0.1 eq) and $CH_3COONa$ (4.27 g, 52.14 mmol, 1 eq). The RM was stirred in a steel bomb filled with CO gas (250 psi) at 90° C. for 14 h. After completion (monitored by TLC), the RM was filtered through celite. The filtrate was concentrated to give the crude product, which was purified by CC (silica-gel, 30-40% EtOAc in PE) to afford ethyl 3-chloro-5-hydroxypicolinate (8.5 g, 81%).

(B) To a solution of ethyl 3-chloro-5-hydroxypicolinate (7.5 g, 37.3 mmol, 1 eq) in DMF (70 ml), was added $K_2CO_3$ (10.2 g, 74.6 mmol, 2 eq). The mixture was stirred at 90° C., then Freon gas was bubbled through for 1 h. After completion (monitored by TLC), the RM was diluted with ice-cold water and extracted with EtOAc (3×100 ml). The organics were washed with water (100 ml) and brine (100 ml), dried ($Na_2SO_4$) and concentrated to give the crude product, which was purified by CC (silica-gel, 20-25% EtOAc in PE) to afford ethyl 3-chloro-5-(difluoromethoxy)picolinate (5.6 g, 62%).

(C) To a solution of ethyl 3-chloro-5-(difluoromethoxy)picolinate (5.6 g, 22.3 mmol, 1 eq) in MeOH (50 ml), was added $NaBH_4$ (4.2 g, 11.5 mmol, 5 eq) at 0° C. and the RM was stirred at RT for 4 h. After completion (monitored by TLC), the RM was quenched with ice-water (200 ml), MeOH was distilled off and the mixture was extracted with EtOAc (3×200 ml). The combined organic layers were washed with brine (300 ml), dried ($Na_2SO_4$) and concentrated to afford (3-chloro-5-(difluoromethoxy)pyridin-2-yl)methanol (4.3 g).

(D) To a solution of (3-chloro-5-(difluoromethoxy)pyridin-2-yl)methanol (4.3 g, 20.57 mmol, 1 eq) in DCM (50 ml) was added, DMP (13 g, 30.08 mmol, 1.5 eq) at 0° C. and the mixture was stirred for 16 h at RT. After completion (monitored by TLC), the mixture was filtered through a bed of celite. The filtrate was diluted with water (200 ml) and extracted EtOAc (3×200 ml). The organics were washed with with water (200 ml), sat $NaHCO_3$ (200 ml) and brine (200 ml), dried ($Na_2SO_4$) and the solvent was distilled off under reduced pressure. The crude product was purified by CC (silica-gel, 15-20% EtOAc in PE) to afford 3-chloro-5-(difluoromethoxy)picolinaldehyde (3.1 g, 67%, over 2 steps).

General Reaction Scheme for Examples 88, 93-99
(SC-425, SC-426, SC-435, SC-439 to SC-450,
SC-452 to SC-454)

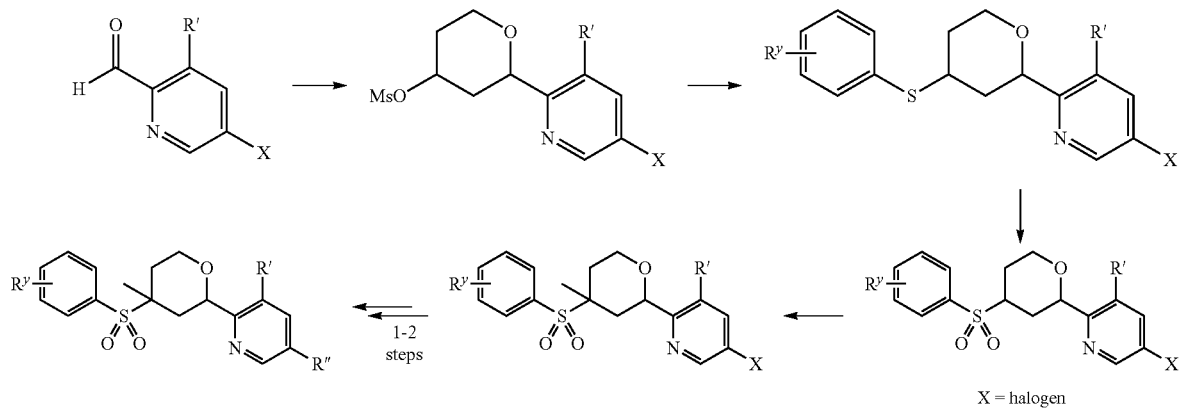

X = halogen

3-Chloro-5-cyclopropyl-2-[4-methyl-4-[[3-(trifluoromethyl)phenyl]sulfonyl]-tetrahydro-pyran-2-yl]-pyridine (Example 88)

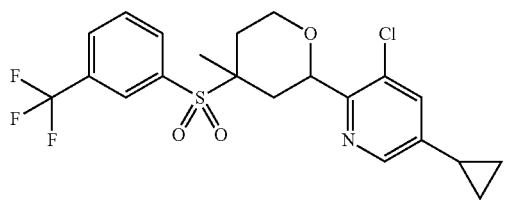 [SMILES: CC1(S(=O)(=O)c2cccc(C(F)(F)F)c2)CCOC(c2ncc(C3CC3)cc2Cl)C1]

Steps 1 to 4 were carried out in analogy to Example 78 (steps 1 to 4) to give, after trituration with 50% ether in PE, [cis rac] 5-bromo-3-chloro-2-(4-methyl-4-((3-(trifluoromethyl)phenyl)sulfonyl)tetrahydro-2H-pyran-2-yl)pyridine (3 g, step 4: 73%). The filtrate was purified further by prep-HPLC to give [trans rac] 5-bromo-3-chloro-2-(4-methyl-4-((3-(trifluoromethyl)phenyl)sulfonyl)tetrahydro-2H-pyran-2-yl)pyridine (0.25 g). [TLC system: EtOAc-PE (2:8); $R_f$: 0.37]

Step 5: 3-Chloro-5-cyclopropyl-2-(4-methyl-4-((3-(trifluoromethyl)phenyl)sulfonyl)tetrahydro-2H-pyran-2-yl)pyridine To a stirred solution of [cis rac] 5-bromo-3-chloro-2-(4-methyl-4-((3-(trifluoromethyl)phenyl)sulfonyl)tetrahydro-2H-pyran-2-yl)pyridine (2 g, 4.02 mmol, 1.0 eq) and cyclopropylboronic acid (0.52 g, 6.03 mmol, 1.5 eq) in toluene (50 ml) and water (1 ml), $Cs_2CO_3$ (2.61 g, 8.04 mmol, 2 eq) was added. The mixture was purged with Ar for 10 min, then Pd(dppf)Cl$_2$ was added and it was again purged with Ar for 10 min. The RM was heated to 90° C. for 12 h. The mixture was was cooled to RT and passed through celite. The filtrate was concentrated to give the crude product, which was purified by CC (silica gel) to afford [cis rac] 3-chloro-5-cyclopropyl-2-(4-methyl-4-((3-(trifluoromethyl)phenyl)sulfonyl)tetrahydro-2H-pyran-2-yl)pyridine (0.6 g, 33%) [TLC system: EtOAc-PE, 3:7; $R_F$: 0.12].

Chiral Resolution of [Cis rac] 3-chloro-5-cyclopropyl-2-(4-methyl-4-((3-(trifluoromethyl)phenyl)sulfonyl)tetrahydro-2H-pyran-2-yl)pyridine

[Cis-rac] 3-chloro-5-cyclopropyl-2-(4-methyl-4-((3-(trifluoromethyl)phenyl)sulfonyl)tetrahydro-2H-pyran-2-yl) pyridine was subjected to chiral prep-SFC purification to give 160 mg of [cis-EN1] SC-425 and 175 mg [cis-EN2] SC-426. Preparative SFC Conditions: Column/dimensions: Lux-Cellulose-2 (250×30) mm; CO2: 60%; Co solvent: 40% MeOH; Total Flow: 90 g/min; Back Pressure: 100 bar; UV: 220 nm.

[cis-EN1] SC-425—analytical SFC: Lux-Cellulose-2 (250×4.6 mm 5µ), 30° C., 3 g/min, 100 bar, 40% of 0.5% DEA in MeOH, Ret. Time 2.62 min

[cis-EN2] SC-426—analytical SFC: Lux-Cellulose-2 (250×4.6 mm 5µ), 30° C., 3 g/min, 100 bar, 40% of 0.5% DEA in MeOH, Ret. Time 3.77 min

[Trans rac] 3-chloro-5-cyclopropyl-2-(4-methyl-4-((3-(trifluoromethyl)phenyl)sulfonyl)tetrahydro-2H-pyran-2-yl)pyridine The corresponding [trans rac] isomer was prepared in analogy to step 5 starting from [trans rac] 5-bromo-3-chloro-2-(4-methyl-4-((3-(trifluoromethyl)phenyl)sulfonyl)tetrahydro-2H-pyran-2-yl)pyridine to yield [trans-rac] 3-chloro-5-cyclopropyl-2-(4-methyl-4-((3-(trifluoromethyl)phenyl) sulfonyl)tetrahydro-2H-pyran-2-yl)pyridine SC-435 (45 mg) [TLC system: EtOAc-PE; 3:7; Rf: 0.45].

The starting material 5-bromo-3-chloropicolinaldehyde was prepared as follows:

5-Bromo-3-chloropicolinaldehyde was prepared in 2 steps from methyl 5-bromo-3-chloropicolinate. The synthesis was carried out in analogy to the methods described for the preparation of 6-methoxynicotinaldehyde, the starting material for Example 85.

3-Chloro-2-[4-[(3-chlorophenyl)sulfonyl]-4-methyl-tetrahydro-pyran-2-yl]-5-methylsulfonyl-pyridine (Example 93)

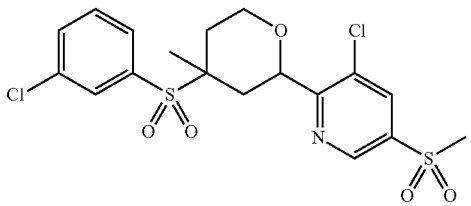 [SMILES: CC1(S(=O)(=O)c2cccc(Cl)c2)CCOC(c2ncc(S(C)(=O)=O)cc2Cl)C1]

Steps 1 to 4 were carried out in analogy to Example 78 (steps 1 to 4) to give, after purification by Prep-HPLC, [cis rac] 5-bromo-3-chloro-2-(4-((3-chlorophenyl)sulfonyl)-4-methyltetrahydro-2H-pyran-2-yl)pyridine (750 mg, step 4: 14%). [TLC system: EtOAc-PE (4:6); $R_f$: 0.68].

Step 5: 3-Chloro-2-(4-((3-chlorophenyl)sulfonyl)-4-methyltetrahydro-2H-pyran-2-yl)-5-(methylthio)pyridine To a solution of [cis rac] 5-bromo-3-chloro-2-(4-((3-chlorophenyl)sulfonyl)-4-methyltetrahydro-2H-pyran-2-yl)pyridine (750 mg, 1.619 mmol, 1 eq) and DIPEA (0.8 ml, 4.859 mmol, 3 eq) in toluene (50 ml) was added NaSMe (170 mg, 2.429 mmol, 1.5 eq). The mixture was degassed for 10 min and Xantphos (66 mg, 0.113 mmol, 0.07 eq), followed by Pd$_2$(dba)$_3$ (104 mg, 0.113 mmol, 0.07 eq) was added. The mixture was again degassed for 10 min. The RM was heated to 110° C. for 18 h under Ar. The reaction was monitored by TLC, and after completion filtered through celite. The filtrate was concentrated to yield the crude product which was purified by flash chromatography to afford [cis rac] 3-chloro-2-(4-((3-chlorophenyl)sulfonyl)-4-methyltetrahydro-2H-pyran-2-yl)-5-(methylthio)pyridine (400 mg, 57%).

Step 6: 3-Chloro-2-[4-[(3-chlorophenyl)sulfonyl]-4-methyl-tetrahydro-pyran-2-yl]-5-methylsulfonyl-pyridine Oxone (1.7 g, 2.784 mmol, 3 eq) in water (15 ml) was added to a solution of [cis rac] 3-chloro-2-(4-((3-chlorophenyl)sulfonyl)-4-methyltetrahydro-2H-pyran-2-yl)-5-(methylthio)pyridine (400 mg, 0.928 mmol, 1 eq) in EtOH (25 ml) at RT and stirred for 18 h. The reaction was monitored by TLC. EtOH was distilled off under reduced pressure and the residue was diluted with H$_2$O (50 ml) and extracted with EtOAc (2×50 ml). The organics were washed with aq NaHCO$_3$ (100 ml), water (100 ml) and brine (50 ml), dried (Na$_2$SO$_4$) and concentrated to give the crude product which was purified by flash chromatography to afford [cis rac] 3-chloro-2-[4-[(3-chlorophenyl)sulfonyl]-4-methyl-tetrahydro-pyran-2-yl]-5-methylsulfonyl-pyridine (300 mg, 70%) [TLC system: EtOAc-PE; 7:3; RF: 0.48].

Chiral Resolution of [Cis rac] 3-chloro-2-[4-[(3-chlorophenyl)sulfonyl]-4-methyl-tetrahydro-pyran-2-yl]-5-methylsulfonyl-pyridine

[Cis-rac] 3-chloro-2-[4-[(3-chlorophenyl)sulfonyl]-4-methyl-tetrahydro-pyran-2-yl]-5-methylsulfonyl-pyridine was subjected to chiral prep-SFC purification to give 130 mg of [cis-EN1] SC-439 and 160 mg [cis-EN2] SC-440. Preparative SFC Conditions: Column/dimensions: Chiralcel OJ-H (250×30) mm; CO2: 70%; Co solvent: 30% MeOH; Total Flow: 90 g/min; Back Pressure: 100 bar; UV: 217 nm.

[cis-EN1] SC-439—analytical SFC: Chiralcel OJ-H (250×4.6 mm 5µ), 30° C., 3 g/min, 100 bar, 30% MeOH, Ret. Time 3.4 min

[cis-EN2] SC-440—analytical SFC: Chiralcel OJ-H (250×4.6 mm 5µ), 30° C., 3 g/min, 100 bar, 30% MeOH, Ret. Time 4.2 min The starting material 5-bromo-3-chloropicolinaldehyde was prepared as follows:

5-Bromo-3-chloropicolinaldehyde was prepared in 2 steps from methyl 5-bromo-3-chloropicolinate. The synthesis was carried out in analogy to the methods described for the preparation of 6-methoxynicotinaldehyde, the starting material for Example 85.

3-Methyl-5-methylsulfonyl-2-[4-methyl-4-[[3-(trifluoromethyl)phenyl]sulfonyl]-tetrahydro-pyran-2-yl]-pyridine (Example 94)

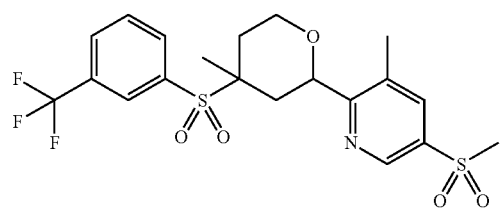 [SMILES: Cc1cc(S(C)(=O)=O)cnc1C1CC(C)(S(=O)(=O)c2cccc(C(F)(F)F)c2)CCO1]

The synthesis was carried out in analogy to Example 95 to afford [trans rac] 3-methyl-5-methylsulfonyl-2-[4-methyl-4-[[3-(trifluoromethyl)phenyl]sulfonyl]-tetrahydro-pyran-2-yl]-pyridine (105 mg) [TLC system: EtOAc-PE; 3:2; RF: 0.34].

2-[4-[[3-(Difluoro-methyl)-5-fluoro-phenyl]sulfonyl]-4-methyl-tetrahydro-pyran-2-yl]-3-methyl-5-methylsulfonyl-pyridine (Example 95)

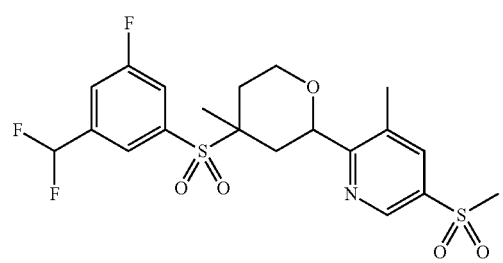 [SMILES: Cc1cc(S(C)(=O)=O)cnc1C1CC(C)(S(=O)(=O)c2cc(F)cc(C(F)F)c2)CCO1]

Steps 1 to 4 were carried out in analogy to Example 78 (steps 1 to 4). The crude product after work-up was washed with 50% Et$_2$O-PE, filtered and dried under vacuum to afford [cis rac] 5-bromo-2-(4-((3-(difluoromethyl)-5-fluorophenyl)sulfonyl)-4-methyltetrahydro-2H-pyran-2-yl)-3-methylpyridine (1.3 g; step 4: 70%) [TLC system: EtOAc-PE; 3:7; Rf: 0.53]. The filtrate upon concentration and purification by flash chromatography afforded [trans rac] 5-bromo-2-(4-((3-(difluoromethyl)-5-fluorophenyl)-sulfonyl)-4-methyltetrahydro-2H-pyran-2-yl)-3-methylpyridine (140 mg) [TLC system: EtOAc-PE; 3:7; Rf: 0.54].

Steps 5 & 6 were carried out in analogy to Example 93 to afford [cis rac] 2-[4-[[3-(difluoro-methyl)-5-fluoro-phenyl]sulfonyl]-4-methyl-tetrahydro-pyran-2-yl]-3-methyl-5-methylsulfonyl-pyridine (700 mg, 70%) [TLC system: EtOAc-PE; 6:4; RF: 0.38].

Chiral Resolution of [Cis rac] 2-[4-[[3-(difluoro-methyl)-5-fluoro-phenyl]sulfonyl]-4-methyl-tetrahydro-pyran-2-yl]-3-methyl-5-methylsulfonyl-pyridine

[Cis-rac] 2-[4-[[3-(difluoro-methyl)-5-fluoro-phenyl]sulfonyl]-4-methyl-tetrahydro-pyran-2-yl]-3-methyl-5-methylsulfonyl-pyridine was subjected to chiral prep-SFC purification to give 235 mg of [cis-EN1] SC-442 and 230 mg [cis-EN2] SC-443. Preparative SFC Conditions: Column/dimensions: Chiralpak AS-H (250×30) mm; CO2: 70%; Co solvent: 30% MeOH; Total Flow: 90 g/min; Back Pressure: 100 bar; UV: 213 nm.

[cis-EN1] SC-442—analytical SFC: Chiralpak AS-H (250×4.6 mm 5µ), 30° C., 3 g/min, 100 bar, 20% MeOH, Ret. Time 3.18 min

[cis-EN2] SC-443—analytical SFC: Chiralpak AS-H (250×4.6 mm 5µ), 30° C., 3 g/min, 100 bar, 20% MeOH, Ret. Time 4.32 min

[Trans rac] 2-[4-[[3-(difluoro-methyl)-5-fluoro-phenyl]sulfonyl]-4-methyl-tetrahydro-pyran-2-yl]-3-methyl-5-methylsulfonyl-pyridine The corresponding [trans rac] isomer was prepared in analogy to step 5 & 6 starting from [trans rac] 5-bromo-2-(4-((3-(difluoromethyl)-5-fluorophenyl)sulfonyl)-4-methyl-tetrahydro-2H-pyran-2-yl)-3-methylpyridine to yield [trans-rac] 2-[4-[[3-(difluoro-methyl)-5-fluoro-phenyl]sulfonyl]-4-methyl-tetrahydro-pyran-2-yl]-3-methyl-5-methylsulfonyl-pyridine SC-448 (20 mg) [TLC system: EtOAc-PE; 6:4; Rf: 0.41].

The starting material 5-bromo-3-methylpicolinaldehyde was prepared as follows:

To a solution of 2,5-dibromo-3-methylpyridine (30 g, 119.52 mmol, 1 eq) in DCM (300 ml) was added n-BuLi (2.5 M in THF, 47.8 ml, 119.52 mmol, 1 eq) dropwise at −78° C. After 30 min DMF (11.1 ml, 143.42 mmol, 1.2 eq) was added at the same temperature. The RM was stirred at RT for 1.5 h. The mixture was quenched with sat. NH$_4$Cl solution (300 ml) and extracted with DCM (3×300 ml). The combined organic layers were washed with brine (300 ml), dried (Na$_2$SO$_4$) and concentrated. Purification by flash chromatography afforded 5-bromo-3-methylpicolinaldehyde (9.5 g, 40%).

The starting material 3-(difluoromethyl)-5-fluorobenzenethiol was prepared as follows:
(A) To a solution of 3-bromo-5-fluorobenzaldehyde (15 g, 73.89 mmol, 1 eq) in DCM (150 ml) was added DAST (39 ml, 295.5 mmol 4 eq) dropwise at −78° C. and the mixture was stirred at RT for 16 h. After completion of the reaction, the mixture was poured into ice-cold water and basified with sat. NaHCO$_3$ solution. The mixture was then extracted with DCM (3×200 ml), washed with water (200 ml) and brine (200 ml), dried (Na$_2$SO$_4$), and concentrated in vacuum to give the crude product, which was purified by flash chromatography to afford 1-bromo-3-(difluoromethyl)-5-fluorobenzene (10 g, 60%).
(B) To a solution of 1-bromo-3-(difluoromethyl)-5-fluorobenzene (8.6 g, 38.56 mmol, 1 eq) and DIPEA (13.44 ml, 77.12 mmol, 2 eq) in 1,4-dioxane (150 ml) was added PMB-SH (5.89 ml, 42.42 mmol, 1.1 eq). The mixture was degassed for 10 min, and Xantphos (1.56 g, 2.69 mmol, 0.07 eq), followed by Pd$_2$(dba)$_3$ (1.0 g, 1.15 mmol, 0.03 eq) were added. The mixture was again degassed for 10 min. The resulting RM was heated to 90° C. and stirred for 2 h under Ar. The RM was filtered through celite and the filtrate concentrated to yield the crude product, which upon flash chromatography afforded 1-bromo-3-(difluoromethyl)-5-fluorobenzene (10 g, 87%).
(C) To a solution of 1-bromo-3-(difluoromethyl)-5-fluorobenzene (10 g, 33.55 mmol, 1 eq) in anisole (10 ml) was added TFA (20 ml) at RT. The RM was stirred at 80° C. for 2 h. After completion of the reaction, the mixture was diluted with water (200 ml) and extracted with EtOAc (3×200 ml). The organics were washed with water (200 ml) and brine (200 ml), dried (Na$_2$SO$_4$), and concentrated in vacuum to afford 3-(difluoromethyl)-5-fluorobenzenethiol (3.3 g, 55%).

2-[4-[[3-Fluoro-5-(trifluoromethyl)-phenyl]sulfonyl]-4-methyl-tetrahydro-pyran-2-yl]-3-methyl-5-methylsulfonyl-pyridine (Example 96)

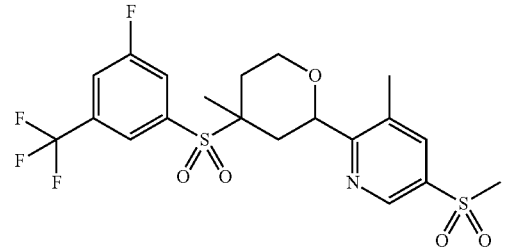 [SMILES: Cc1cc(S(C)(=O)=O)cnc1C1CC(C)(S(=O)(=O)c2cc(F)cc(C(F)(F)F)c2)CCO1]

Steps 1 to 4 were carried out in analogy to Example 78 (steps 1 to 4). The crude product after work-up was purified by flash CC (0-15% EtOAc in PE) to afford [cis rac] 5-bromo-2-(4-((3-fluoro-5-(trifluoromethyl)phenyl)sulfonyl)-4-methyltetrahydro-2H-pyran-2-yl)-3-methylpyridine (800 mg; step 4: 82%) and [trans rac] 5-bromo-2-(4-((3-fluoro-5-(trifluoromethyl)phenyl)sulfonyl)-4-methyltetrahydro-2H-pyran-2-yl)-3-methylpyridine (400 mg). [TLC system: EtOAc-PE; 2:3; Rf: 0.28].

Steps 5 & 6 were carried out in analogy to Example 93 to afford [cis rac] 2-[4-[[3-fluoro-5-(trifluoromethyl)-phenyl]sulfonyl]-4-methyl-tetrahydro-pyran-2-yl]-3-methyl-5-methylsulfonyl-pyridine (280 mg, 75%) [TLC system: EtOAc-PE; 3:7; RF: 0.26].

Chiral Resolution of [Cis rac] 2-[4-[[3-fluoro-5-(trifluoromethyl)-phenyl]sulfonyl]-4-methyl-tetrahydro-pyran-2-yl]-3-methyl-5-methylsulfonyl-pyridine

[Cis-rac] 2-[4-[[3-fluoro-5-(trifluoromethyl)-phenyl]sulfonyl]-4-methyl-tetrahydro-pyran-2-yl]-3-methyl-5-methylsulfonyl-pyridine was subjected to chiral prep-SFC purification to give 100 mg of [cis-EN1] SC-444 and 112 mg [cis-EN2] SC-445. Preparative SFC Conditions: Column/dimensions: Chiralpak AS-H (250×30) mm; CO2: 80%; Co solvent: 20% MeOH; Total Flow: 60 g/min; Back Pressure: 100 bar; UV: 213 nm.

[cis-EN1] SC-444—analytical SFC: Chiralpak AS-H (250×4.6 mm 5µ), 30° C., 3 g/min, 100 bar, 10% MeOH, Ret. Time 3.31 min

[cis-EN2] SC-445—analytical SFC: Chiralpak AS-H (250×4.6 mm 5µ), 30° C., 3 g/min, 100 bar, 10% MeOH, Ret. Time 4.72 min

[Trans rac] 2-[4-[[3-fluoro-5-(trifluoromethyl)-phenyl]sulfonyl]-4-methyl-tetrahydro-pyran-2-yl]-3-methyl-5-methylsulfonyl-pyridine The corresponding [trans rac] isomer was prepared in analogy to step 5 & 6 starting from [trans rac] 5-bromo-2-(4-((3-fluoro-5-(trifluoromethyl)phenyl)sulfonyl)-4-methyl-tetrahydro-2H-pyran-2-yl)-3-methylpyridine to yield [trans-rac] 2-[4-[[3-fluoro-5-(trifluoromethyl)-phenyl]sulfonyl]-4-methyl-tetrahydro-pyran-2-yl]-3-methyl-5-methylsulfonyl-pyridine SC-454 (28 mg) [TLC system: EtOAc-PE; 3:7; Rf: 0.27].

The starting material 5-bromo-3-methylpicolinaldehyde was prepared as follows:

The synthesis is described above (see Example 95).

3-Chloro-2-[4-[(3-isopropyl-phenyl)sulfonyl]-4-methyl-tetrahydro-pyran-2-yl]-5-methylsulfonyl-pyridine (Example 97)

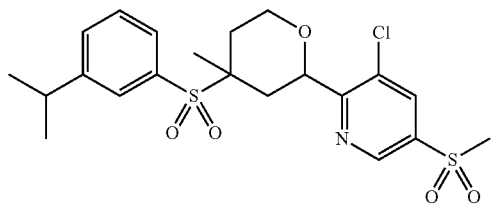 [SMILES: CC(C)c1cccc(S(=O)(=O)C2(C)CCOC(c3ncc(S(C)(=O)=O)cc3Cl)C2)c1]

The synthesis was carried out in analogy to Example 93 to afford [cis rac] 3-chloro-2-[4-[(3-isopropyl-phenyl)sulfonyl]-4-methyl-tetrahydro-pyran-2-yl]-5-methylsulfonyl-pyridine (600 mg, step 6: 56%) [TLC system: EtOAc-PE; 2:3; RF: 0.40].

Chiral Resolution of [Cis rac] 3-chloro-2-[4-[(3-isopropyl-phenyl)sulfonyl]-4-methyl-tetrahydro-pyran-2-yl]-5-methylsulfonyl-pyridine

[Cis-rac] 3-chloro-2-[4-[(3-isopropyl-phenyl)sulfonyl]-4-methyl-tetrahydro-pyran-2-yl]-5-methylsulfonyl-pyridine was subjected to chiral prep-SFC purification to give 190 mg of [cis-EN1] SC-446 and 195 mg [cis-EN2] SC-447. Preparative SFC Conditions: Column/dimensions: Chiralpak AD-H (250×30) mm; CO2: 50%; Co solvent: 50% MeOH; Total Flow: 70 g/min; Back Pressure: 100 bar; UV: 216 nm.

[cis-EN1] SC-446—analytical SFC: Chiralpak AD-H (250×4.6 mm 5µ), 30° C., 4 g/min, 100 bar, 40% MeOH, Ret. Time 3.57 min

[cis-EN2] SC-447—analytical SFC: Chiralpak AD-H (250×4.6 mm 5µ), 30° C., 4 g/min, 100 bar, 40% MeOH, Ret. Time 4.48 min 3-Methyl-5-methylsulfonyl-2-[4-methyl-4-[[3-(trifluoromethyloxy)-phenyl]sulfonyl]-tetrahydro-pyran-2-yl]-pyridine (Example 98)

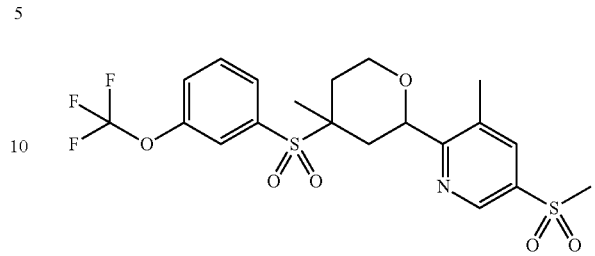

The synthesis was carried out in analogy to Example 95 to afford [cis rac] 3-methyl-5-methylsulfonyl-2-[4-methyl-4-[[3-(trifluoromethyloxy)-phenyl]sulfonyl]-tetrahydro-pyran-2-yl]-pyridine (690 mg, step 6: 65%) [TLC system: EtOAc-PE; 2:3; RF: 0.20].

Chiral Resolution of [Cis rac] 3-methyl-5-methylsulfonyl-2-[4-methyl-4-[[3-(trifluoromethyloxy)-phenyl]sulfonyl]-tetrahydro-pyran-2-yl]-pyridine

[Cis-rac] 3-methyl-5-methylsulfonyl-2-[4-methyl-4-[[3-(trifluoromethyloxy)-phenyl]sulfonyl]-tetrahydro-pyran-2-yl]-pyridine was subjected to chiral prep-SFC purification to give 190 mg of [cis-EN1] SC-449 and 220 mg [cis-EN2] SC-450. Preparative SFC Conditions: Column/dimensions: Chiralpak AS-H (250×21) mm; CO2: 50%; Co solvent: 50% MeOH; Total Flow: 60 g/min; Back Pressure: 100 bar; UV: 214 nm.

[cis-EN1] SC-449—analytical SFC: Chiralpak AS-H (250×4.6 mm 5µ), 30° C., 3 g/min, 100 bar, 30% MeOH, Ret. Time 2.06 min

[cis-EN2] SC-450—analytical SFC: Chiralpak AS-H (250×4.6 mm 5µ), 30° C., 3 g/min, 100 bar, 30% MeOH, Ret. Time 2.65 min

[Trans rac] 3-methyl-5-methylsulfonyl-2-[4-methyl-4-[[3-(trifluoromethyloxy)-phenyl]sulfonyl]-tetrahydro-pyran-2-yl]-pyridine The synthesis was carried out in analogy to Example 95 to afford [trans rac] 3-methyl-5-methylsulfonyl-2-[4-methyl-4-[[3-(trifluoromethyloxy)-phenyl]sulfonyl]-tetrahydro-pyran-2-yl]-pyridine (80 mg) [TLC system: EtOAc-PE; 2:3; RF: 0.21].

3-[[2-(3-Chloro-5-methylsulfonyl-pyridin-2-yl)-4-methyl-tetrahydro-pyran-4-yl]sulfonyl]-benzonitrile (Example 99)

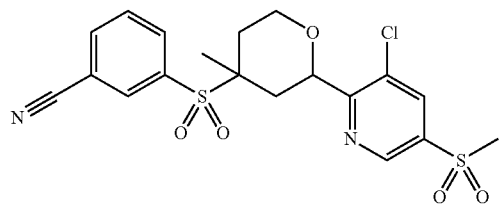 [SMILES: CC1(S(=O)(=O)c2cccc(C#N)c2)CCOC(c2ncc(S(C)(=O)=O)cc2Cl)C1]

The synthesis was carried out in analogy to Example 93 to afford [cis rac] 3-[[2-(3-chloro-5-methylsulfonyl-pyridin- 2-yl)-4-methyl-tetrahydro-pyran-4-yl]sulfonyl]-benzonitrile (770 mg, step 6: 80%) [TLC system: EtOAc-PE; 7:3; RF: 0.38].

Chiral Resolution of [Cis rac] 3-[[2-(3-chloro-5-methylsulfonyl-pyridin-2-yl)-4-methyl-tetrahydro-pyran-4-yl]sulfonyl]-benzonitrile

[Cis-rac] 3-[[2-(3-chloro-5-methylsulfonyl-pyridin-2-yl)-4-methyl-tetrahydro-pyran-4-yl]sulfonyl]-benzonitrile was subjected to chiral prep-SFC purification to give 149 mg of [cis-EN1] SC-452 and 135 mg [cis-EN2] SC-453. Preparative SFC Conditions: Column/dimensions: Chiralcel OJ-H (250×30) mm; CO2: 60%; Co solvent: 40% MeOH; Total Flow: 60 g/min; Back Pressure: 100 bar; UV: 218 nm.

[cis-EN1] SC-452—analytical SFC: Chiralcel OJ-H (250×4.6 mm 5μ), 30° C., 3 g/min, 100 bar, 30% MeOH, Ret. Time 3.84 min

[cis-EN2] SC-453—analytical SFC: Chiralcel OJ-H (250×4.6 mm 5μ), 30° C., 3 g/min, 100 bar, 30% MeOH, Ret. Time 4.77 min The starting material 3-mercaptobenzonitrile was prepared as follows:

To a stirred solution of 3-iodobenzonitrile (20 g, 87.33 mmol, 1.0 eq) in DMF (300 ml), was added sequentially $K_2CO_3$ (24 g, 174.66 mmol, 2.0 eq), CuI (1.65 g, 8.73 mmol, 0.1 eq) and sulfur powder (8.38 g, 261.9 mmol, 3.0 eq). The resulting RM was heated to 90° C. and stirred for 14 h. The RM was cooled to 0° C. and flushed with Ar. Triphenyl phosphine (13.1 g, 50.37 mmol, 1.5 eq) was added, followed by conc. HCl (1.5 ml). The RM was heated to 110° C. and stirred at this temperature for 14 h. 3-mercaptobenzonitrile was used as such in the next step reaction without any further purification.

Reaction Scheme for Example 92 (SC-436 & SC-437)

3-Chloro-2-[4-[[3-(difluoro-methoxy)-phenyl]sulfonyl]-4-methyl-tetrahydro-pyran-2-yl]-5-methylsulfonyl-pyridine (Example 92)

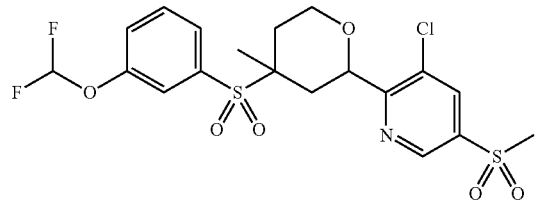 [SMILES: CC1(S(=O)(=O)c2cccc(OC(F)F)c2)CCOC(c2ncc(S(C)(=O)=O)cc2Cl)C1]

Step 1: 2-(5-Bromo-3-chloropyridin-2-yl)tetrahydro-2H-pyran-4-yl Methanesulfonate Methane sulfonic acid (35.7 ml, 550.45 mmol, 10 eq) was added to a solution of 5-bromo-3-chloropicolinaldehyde (see Example 88) (12 g, 55.04 mmol, 1 eq) in DCM (200 ml) at 0° C. But-3-en-1-ol (4.5 ml, 55.04 mmol, 1 eq) was added and the mixture stirred for 16 h at RT. The RM was quenched with sat. $Na_2CO_3$ solution and extracted with DCM (3×150 ml). The organics were washed with water (150 ml) and brine (150 ml), dried ($Na_2SO_4$) and the the solvent was distilled-off under reduced pressure to afford the desired product (18 g).

Step 2: 3-((2-(5-Bromo-3-chloropyridin-2-yl)tetrahydro-2H-pyran-4-yl)thio)phenol To a solution of 3-Hydroxythiophenol (4.46 ml, 43.47 mmol, 2 eq) in DMF (200 ml) was added $K_2CO_3$ (5.99 g, 43.47 mmol 2 eq) and 2-(5-bromo-3-chloropyridin-2-yl) tetrahydro-2H-pyran-4-yl methanesulfonate (8 g, 21.73 mmol, 1 eq). The RM was heated to 50° C. for 6 h and was then stirred at RT for 10 h. The RM was diluted with cold water (300 ml) and extracted with EtOAc (200 ml). The

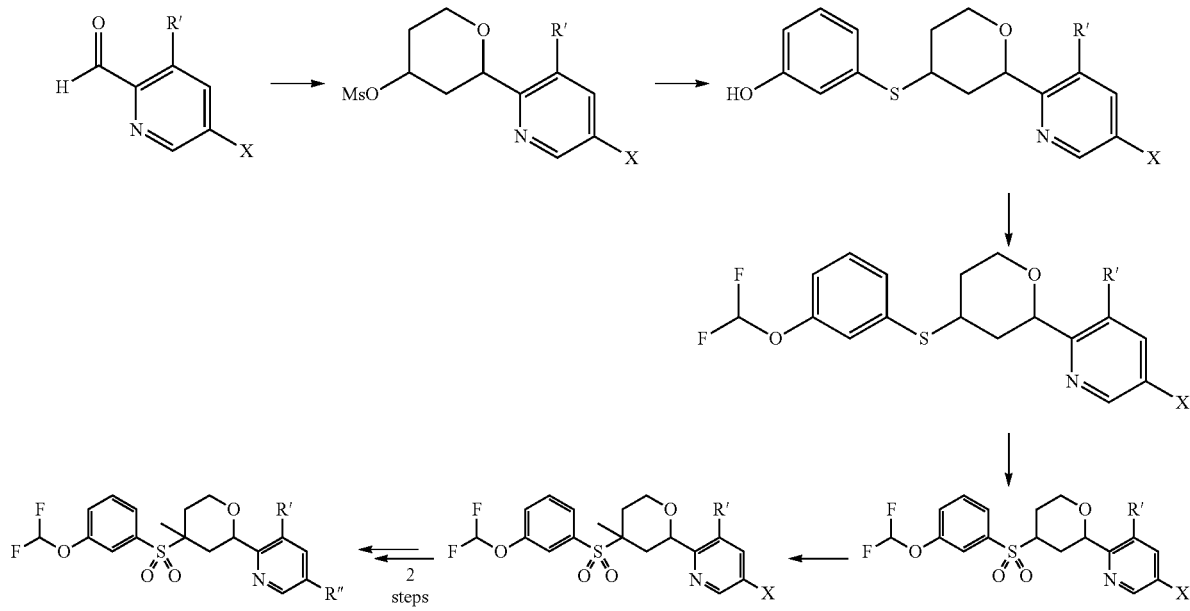

X = halogen organics were washed with water (200 ml) and brine (200 ml), dried ($Na_2SO_4$) and concentrated under reduced pressure. The crude product was purified by flash chromatography (silica gel; EtOAc-PE; 0:100 to 15:85) to afford the desired product (5 g, 45%).

Step 3: 5-Bromo-3-chloro-2-(4-((3-(difluoromethoxy)phenyl)thio)tetrahydro-2H-pyran-2-yl)pyridine To a solution of 3-((2-(5-bromo-3-chloropyridin-2-yl)tetrahydro-2H-pyran-4-yl)thio)phenol (5.0 g, 12.53 mmol, 1 eq) in DMF (150 ml), was added $K_2CO_3$ (3.45 g, 25.06 mmol, 2 eq) and the RM was heated to 90° C. The mixture was purged with Freon gas for 2 h at the same temperature. The RM was diluted with cold water and extracted with EtOAc (3×100 ml). The combined organic layers were washed with water (100 ml) and brine (100 ml), dried ($Na_2SO_4$) and concentrated to give the crude product, which upon purification by flash chromatography (silica gel; EtOAc: PE; 0:100 to 4:96) afforded the desired product (1.3 g, 12% over 3 steps).

Step 4: 5-Bromo-3-chloro-2-(4-((3-(difluoromethoxy)phenyl)sulfonyl)tetrahydro-2H-pyran-2-yl)pyridine Oxone (2.6 g, 8.68 mmol, 3 eq) in water (25 ml) was added to a solution of 5-bromo-3-chloro-2-(4-((3-(difluoromethoxy)phenyl)thio)tetrahydro-2H-pyran-2-yl)pyridine (1.3 g, 2.89 mmol, 1 eq) in MeOH (50 ml) at RT and the mixture was stirred for 18 h. MeOH was removed under reduced pressure, and the residue was diluted with $H_2O$ (50 ml) and extracted with EtOAc (3×50 ml). The organics were washed with water (50 ml) and brine (50 ml), dried ($Na_2SO_4$) and concentrated to give the crude product which upon purification by flash chromatography (silica gel; EtOAc: PE; 0:100 to 17:83) afforded the desired product (1.0 g, 71%).

Step 5: 5-Bromo-3-chloro-2-((2R,4S)-4-((3-(difluoromethoxy)phenyl)sulfonyl)-4-methyltetrahydro-2H-pyran-2-yl)pyridine A solution of 5-bromo-3-chloro-2-(4-((3-(difluoromethoxy)phenyl)sulfonyl)tetrahydro-2H-pyran-2-yl)pyridine (1.0 g, 2.07 mmol, 1 eq) in THF (40 ml) was cooled to −78° C. and t-BuOK (1M in THF; 4.15 ml, 4.15 mmol, 2 eq) was added dropwise. The mixture was stirred for 30 min, then MeI (0.19 ml, 3.11 mmol, 1.5 eq) was added and the resulting mixture was allowed to warm to RT and stir for 16 h. The RM was quenched with water (50 ml) and extracted with EtOAc (3×50 ml). The combined organic layers were washed with water (50 ml) and brine (50 ml), dried ($Na_2SO_4$) and concentrated. The residue upon purification by flash chromatography (silica gel, EtOAc: PE, 0:100 to 14:86) afforded [cis rac] 5-bromo-3-chloro-2-((2R,4S)-4-((3-(difluoromethoxy)phenyl)sulfonyl)-4-methyltetrahydro-2H-pyran-2-yl)pyridine (840 mg, 84%) [TLC system: EtOAc-PE; 3:7; Rf: 0.51].

Step 5: 3-Chloro-2-(4-((3-(difluoromethoxy)phenyl)sulfonyl)-4-methyltetrahydro-2H-pyran-2-yl)-5-(methylthio)pyridine A solution of [cis rac] 5-bromo-3-chloro-2-((2R,4S)-4-((3-(difluoromethoxy)phenyl)sulfonyl)-4-methyltetrahydro-2H-pyran-2-yl)pyridine (950 mg, 1.91 mmol, 1 eq) and DIPEA (1 ml, 5.75 mmol, 3 eq) in toluene (30 ml) was treated with NaSMe (201 mg, 2.87 mmol, 1.5 eq). The mixture was degassed with Ar for 10 min, and Xantphos (110 mg, 0.191 mmol, 0.1 eq), followed by $Pd_2(dba)_3$ (123 mg, 0.131 mmol, 0.07 eq) were added. The RM was again degassed for 10 min. The resulting mixture was heated to 100° C. and stirred for 18 h. The RM was filtered through celite and the filtrate concentrated to yield the crude product which upon purification by flash chromatography (silica gel; EtOAc: PE; 0:100 to 18:82) afforded [cis rac] 3-chloro-2-(4-((3-(difluoromethoxy)phenyl)sulfonyl)-4-methyltetrahydro-2H-pyran-2-yl)-5-(methylthio)pyridine (600 mg, 67%).

Step 6: 3-Chloro-2-[4-[[3-(difluoro-methoxy)-phenyl]sulfonyl]-4-methyl-tetrahydro-pyran-2-yl]-5-methylsulfonyl-pyridine A solution of Oxone (1.19 g, 3.88 mmol, 3 eq) in water (10 ml) was added to a solution of [cis rac] 3-chloro-2-(4-((3-(difluoromethoxy)phenyl)sulfonyl)-4-methyltetrahydro-2H-pyran-2-yl)-5-(methylthio)pyridine (600 mg, 1.29 mmol, 1 eq) in MeOH (20 ml) at RT and the mixture was stirred for 18 h. MeOH was distilled-off under reduced pressure and the residue was diluted with $H_2O$ (50 ml) and extracted with EtOAc (3×50 ml). The organics were washed with water (50 ml) and brine (50 ml), dried ($Na_2SO_4$) and concentrated to give the crude product, which was purified flash chromatography (silica gel; EtOAc: PE; 0:100 to 28:72) to afford [cis rac] 3-chloro-2-[4-[[3-(difluoro-methoxy)-phenyl]sulfonyl]-4-methyl-tetrahydro-pyran-2-yl]-5-methylsulfonyl-pyridine (500 mg, 78%) [TLC system: EtOAc-PE; 1:1; Rf: 0.38].

Chiral Resolution of [Cis rac] 3-chloro-2-[4-[[3-(difluoro-methoxy)-phenyl]sulfonyl]-4-methyl-tetrahydro-pyran-2-yl]-5-methylsulfonyl-pyridine

[Cis-rac] 3-chloro-2-[4-[[3-(difluoro-methoxy)-phenyl]sulfonyl]-4-methyl-tetrahydro-pyran-2-yl]-5-methylsulfonyl-pyridine was subjected to chiral prep-SFC purification to give 180 mg of [cis-EN1] SC-436 and 160 mg [cis-EN2] SC-437. Preparative SFC Conditions: Column/dimensions: Chiralcel OJ-H (250×21) mm; CO2: 70%; Co solvent: 30% MeOH; Total Flow: 90 g/min; Back Pressure: 100 bar; UV: 215 nm.

[cis-EN1] SC-436—$1^{st}$ eluting enantiomer

[cis-EN2] SC-437—$2^{nd}$ eluting enantiomer

General Reaction Scheme for Examples 90-91
(SC-429 to SC-434)+New Compounds

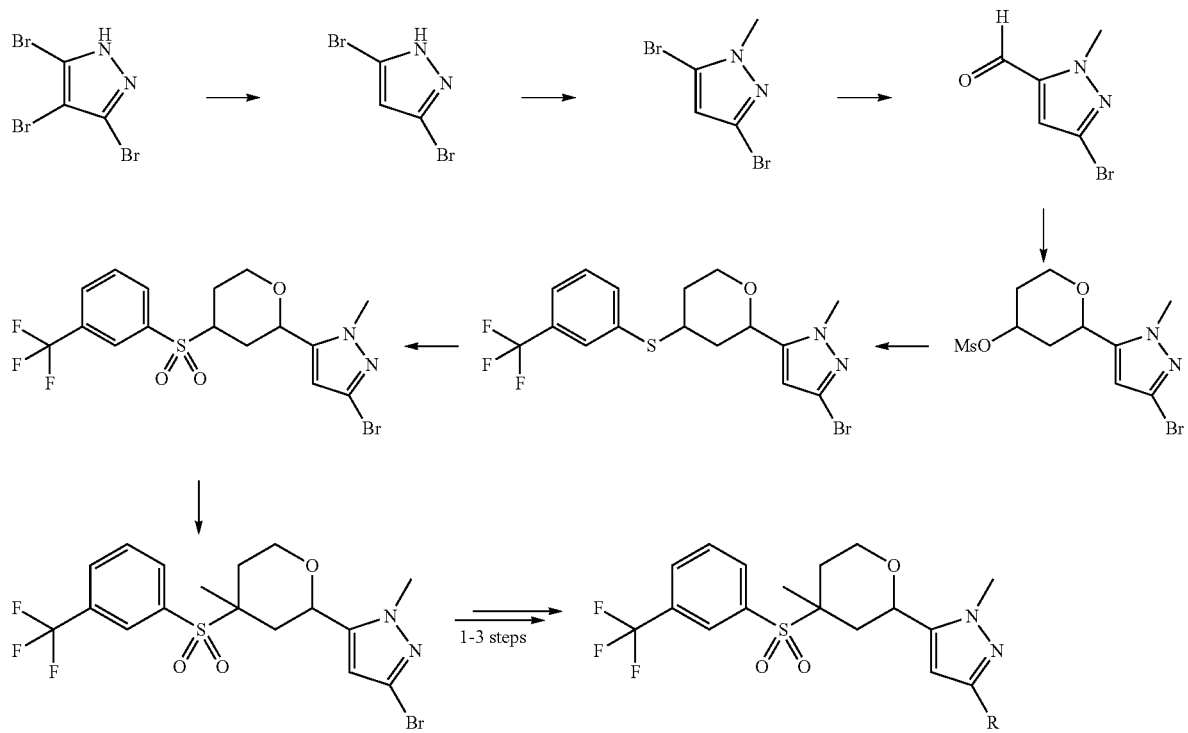

1-Methyl-3-methylsulfonyl-5-[4-methyl-4-[[3-(trif-luoromethyl)phenyl]sulfonyl]-tetrahydro-pyran-2-yl]-1H-pyrazole (Example 90)

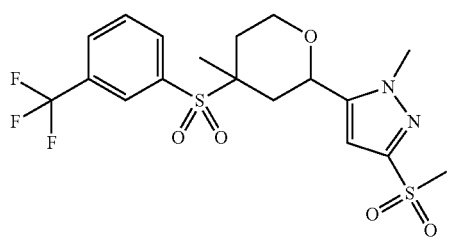 [SMILES: Cn1nc(S(C)(=O)=O)cc1C1CC(C)(S(=O)(=O)c2cccc(C(F)(F)F)c2)CCO1]

Step 1: 3,5-Bibromo-1H-pyrazole

To a solution of 3,4,5-tribromo-1H-pyrazole (25 g, 82 mmol, 1.0 eq) in THF (300 ml), was added n-BuLi (2.5 M in hexanes, 82.0 ml, 205 mmol, 2.5 eq) over 30 min at −78° C. and the RM was stirred at this temperature for 1 h. The RM was quenched by dropwise addition of MeOH-THF (2:3; 150 ml) at −78° C., and the mixture was stirred for an additional 2 h allowing to warm RT gradually. The solvent was removed under reduced pressure. The residue was diluted with Et$_2$O (600 ml), washed with dil. HCl (0.5N, 60 ml) and brine (75 ml), dried (Na$_2$SO$_4$), filtered and concentrated under reduced pressure to afford the desired product (12.5 g, 67%).

Step 2: 3,5-Bibromo-1-methyl-1H-pyrazole

A solution of 3,5-dibromo-1H-pyrazole (25 g, 111.60 mmol, 1.0 eq) in THF (150 ml) was added to a suspension of NaH (60%; 13.30 g, 334.8 mmol, 3.0 eq) in THF (150 ml) at 0° C. The mixture was stirred for 1 h before adding MeI (18.0 ml, 279.0 mmol, 2.5 eq). The RM was stirred at 0° C. for 3 h and then allowed to RT, and stirred for a further 12 h. The RM was quenched with cold water (500 ml) and extracted with EtOAc (3×200 ml). The combined organic layers were washed with water (2×200 ml) and brine solution (200 ml), dried (Na$_2$SO$_4$), filtered and concentrated under reduced pressure to afford the desired product (15 g, 57%).

Step 3:
3-Bromo-1-methyl-1H-pyrazole-5-carbaldehyde

A stirred solution of 3,5-dibromo-1-methyl-1H-pyrazole (15 g, 62.5 mmol, 1.0 eq) in THF (300 ml) was treated with iPrMgCl (2.0M, 56.5 ml, 112.5 mmol, 1.8 eq) at −78° C. The mixture was stirred for 30 min, and DMF (14.7 ml, 187.5 mmol, 3.0 eq) was added. The RM was allowed to gradually warm to RT, and stirred for 5 h. The RM was quenched with aq. NH$_4$Cl (300 ml) and extracted with EtOAc (3×150 ml). The combined organic layers were washed with water (2×150 ml) and brine (150 ml), dried (Na$_2$SO$_4$), filtered and concentrated under reduced pressure to afford the desired product (11.0 g).

Step 4: 2-(3-Bromo-1-methyl-1H-pyrazol-5-yl)tetrahydro-2H-pyran-4-yl Methanesulfonate A stirred solution of 3-bromo-1-methyl-1H-pyrazole-5-carbaldehyde (11.0 g, 58.5 mmol, 1.0 eq) in DCM (250 ml)

was treated with MsOH (36.4 ml, 585.1 mmol, 10.0 eq) at 0° C. The mixture was stirred for 10 min and but-3-en-1-ol (4.8 ml, 58.5 mmol, 1.0 eq) was added. The RM was allowed to warm to RT and stir for 18 h. The RM was quenched with sat. aq. $Na_2CO_3$ (150 ml) and extracted with DCM (2×200 ml). The combined organic layers were washed with water (2×150 ml) and brine (150 ml), dried ($Na_2SO_4$), filtered and concentrated under reduced pressure. The residue upon purification by flash chromatography (silica-gel; EtOAc-PE; 20:80 to 50:50) afforded the desired product (13.5 g, 78% over 2 steps).

Step 5: 3-Bromo-1-methyl-5-(4-((3-(trifluoromethyl)phenyl)thio)tetrahydro-2H-pyran-2-yl)-1H-pyrazole A stirred solution of 3-(trifluoromethyl)benzenethiol (27.3 g, 199.70 mmol, 2.5 eq) in DMF (250 ml) was treated with $K_2CO_3$ (33.0 g, 239.65 mmol, 3.0 eq). The mixture was stirred for 10 min at RT and a solution of 2-(3-bromo-1-methyl-1H-pyrazol-5-yl)tetrahydro-2H-pyran-4-yl methanesulfonate (37.0 g, 80.0 mmol, 1.0 eq) in DMF (150 ml) was added. The resulting RM was heated to 50° C., stirred for 6 h, then brought to RT and stirred for additional 10 h. The RM was concentrated under reduced pressure, and the residue was diluted with water (500 ml) and extracted with EtOAc (3×200 ml). The combined organic layers were washed with water (2×200 ml) and brine (200 ml), dried ($Na_2SO_4$) filtered and concentrated under reduced pressure. The crude product upon purification by flash chromatography (silica-gel; EtOAc-PE; 10:90 to 20:80) afforded the desired product (27.0 g, 80%).

Step 6: 3-Bromo-1-methyl-5-(4-((3-(trifluoromethyl)phenyl)sulfonyl)tetrahydro-2H-pyran-2-yl)-1H-pyrazole Oxone (49.33 g, 160.7 mmol, 5.0 eq) in water (150 ml) was added to a solution of 3-bromo-1-methyl-5-(4-((3-(trifluoromethyl)phenyl)thio)tetrahydro-2H-pyran-2-yl)-1H-pyrazole (13.5 g, 32.15 mmol, 1.0 eq) in MeOH (350 ml) at RT and stirred for 18 h. After completion of the reaction, MeOH was distilled-off under reduced pressure. The residue was made alkaline by addition of sat. aq. $NaHCO_3$ (200 ml) and extracted with EtOAc (3×150 ml). The organic layer was washed with water (2×150 ml) and brine (100 ml), dried ($Na_2SO_4$), filtered and concentrated under reduced pressure. The residue upon purification by flash chromatography (silica-gel; EtOAc-PE; 10:90 to 30:70) afforded the desired product (9.0 g, 71%).

Step 7: 3-Bromo-1-methyl-5-(4-methyl-4-((3-(trifluoromethyl)phenyl)sulfonyl)tetrahydro-2H-pyran-2-yl)-1H-pyrazole A solution of 3-bromo-1-methyl-5-(4-((3-(trifluoromethyl)phenyl)sulfonyl)tetrahydro-2H-pyran-2-yl)-1H-pyrazole (18.0 g, 39.82 mmol, 1.0 eq) in THF (400 ml) was cooled to −78° C. and t-BuOK (1M in THF, 80.0 ml, 79.65 mmol, 2.0 eq) was added dropwise. The mixture was stirred for 30 min and MeI (6.45 ml, 99.60 mmol, 2.5 eq) was added. The resulting RM was allowed to warm to RT and stir for 18 h. The RM was quenched with sat. aq. $NH_4Cl$ (200 ml) and water (200 ml), and extracted with EtOAc (3×200 ml). The combined organic layers were washed with water (2×200 ml) and brine (200 ml), dried ($Na_2SO_4$), filtered and concentrated under reduced pressure. The residue upon purification flash chromatography (silica gel; EtOAc-PE; 15:85 to 30:70) afforded [cis rac] 3-bromo-1-methyl-5-(4-methyl-4-((3-(trifluoromethyl)phenyl)sulfonyl)tetrahydro-2H-pyran-2-yl)-1H-pyrazole (8.5 g, 45%) [TLC system: EtOAc-PE; 1:1; Rf: 0.50] and [trans rac] 3-bromo-1-methyl-5-(4-methyl-4-((3-(trifluoromethyl)phenyl)-sulfonyl)tetrahydro-2H-pyran-2-yl)-1H-pyrazole (1.0 g) [TLC system: EtOAc-PE; 1:1; Rf: 0.60].

Step 8: 1-Methyl-5-(4-methyl-4-((3-(trifluoromethyl)phenyl)sulfonyl)tetrahydro-2H-pyran-2-yl)-3-(methylthio)-1H-pyrazole A stirred solution of [cis rac] 3-bromo-1-methyl-5-(4-methyl-4-((3-(trifluoromethyl)phenyl)sulfonyl)tetrahydro-2H-pyran-2-yl)-1H-pyrazole (100 mg, 0.214 mmol, 1.0 eq), DIPEA (1.15 ml, 0.642 mmol, 3.0 eq) and sodium thiomethoxide (30 mg, 0.642 mmol, 3.0 eq) in toluene (15 ml) was degassed for 10 min, and Xantphos (14 mg, 0.0214 mmol, 0.1 eq) followed by $Pd_2(dba)_3$ (14 mg, 0.15 mmol, 0.07 eq) were added. The mixture was again degassed for 5 min. The resulting mixture was heated to 110° C. and stirred for 16 h under Ar. The RM was diluted with water (25 ml) and extracted with EtOAc (2×20 ml). The combined organic extracts were washed with water (2×20 ml) and brine (25 ml), dried ($Na_2SO_4$) and concentrated under reduced pressure. The residue upon purification by flash chromatography (silica gel; EtOAc in PE; 50:50 to 60:40) afforded [cis rac] 1-methyl-5-(4-methyl-4-((3-(trifluoromethyl)-phenyl)sulfonyl)tetrahydro-2H-pyran-2-yl)-3-(methylthio)-1H-pyrazole (60 mg, 64%). In another batch [cis rac] 3-bromo-1-methyl-5-(4-methyl-4-((3-(trifluoromethyl)-phenyl)sulfonyl)tetrahydro-2H-pyran-2-yl)-1H-pyrazole (1.5 g) was transformed into [cis rac] 1-methyl-5-(4-methyl-4-((3-(trifluoromethyl)phenyl)sulfonyl)tetrahydro-2H-pyran-2-yl)-3-(methylthio)-1H-pyrazole (900 mg; 64%).

Step 9: 1-Methyl-3-methylsulfonyl-5-[4-methyl-4-[[3-(trifluoromethyl)phenyl]sulfonyl]-tetrahydro-pyran-2-yl]-1H-pyrazole Oxone (3.20 g, 10.37 mmol, 5.0 eq) in water (20 ml) was added to a solution of [cis rac]1-methyl-5-(4-methyl-4-((3-(trifluoromethyl)phenyl)sulfonyl)tetrahydro-2H-pyran-2-yl)-3-(methylthio)-1H-pyrazole (900 mg, 2.07 mmol, 1.0 eq) in MeOH (60 ml) at RT and the mixture was stirred for 18 h. The RM was concentrated under reduced pressure, and the residue made alkaline by addition of sat. aq. $NaHCO_3$ (70 ml) and extracted with EtOAc (3×50 ml). The organic layer was washed with water (2×75 ml) and brine (75 ml), dried ($Na_2SO_4$), filtered and concentrated under reduced pressure. The residue upon purification by flash chromatography (silica-gel; EtOAc-PE; 60:70 to 70:30) afforded [cis rac] 1-methyl-3-methylsulfonyl-5-[4-methyl-4-[[3-(trifluoromethyl)phenyl]-sulfonyl]-tetrahydro-pyran-2-yl]-1H-pyrazole (700 mg, 72%) [TLC system: EtOAc-PE; 1:1, Rf: 0.30].

Chiral Resolution of [Cis rac] 1-methyl-3-methylsulfonyl-5-[4-methyl-4-[[3-(trifluoromethyl)phenyl]sulfonyl]-tetrahydro-pyran-2-yl]-1H-pyrazole

[Cis-rac] 1-methyl-3-methylsulfonyl-5-[4-methyl-4-[[3-(trifluoromethyl)phenyl]sulfonyl]-tetrahydro-pyran-2-yl]-1H-pyrazole was subjected to chiral prep-SFC purification to give 180 mg of [cis-EN1] SC-429 and 190 mg [cis-EN2] SC-430. Preparative SFC Conditions: Column/dimensions:

Chiralpak AD-H (250×30) mm; CO2: 50%; Co solvent: 450% MeOH; Total Flow: 100 g/min; Back Pressure: 100 bar; UV: 214 nm.

[cis-EN1] SC-429—analytical SFC: Chiralpak AD-H (250×4.6 mm 5µ), 30° C., 4 g/min, 100 bar, 40% MeOH, Ret. Time 1.46 min

[cis-EN2] SC-430—analytical SFC: Chiralcel OJ-H (250×4.6 mm 5µ), 30° C., 3 g/min, 100 bar, 30% MeOH, Ret. Time 3.65 min

[Trans rac] 1-methyl-3-methylsulfonyl-5-[4-methyl-4-[[3-(trifluoromethyl)phenyl]sulfonyl]-tetrahydro-pyran-2-yl]-1H-pyrazole The corresponding [trans rac] isomer was prepared in analogy to steps 8 & 9 starting from [trans rac] 3-bromo-1-methyl-5-(4-methyl-4-((3-(trifluoromethyl)phenyl)sulfonyl)tetrahydro-2H-pyran-2-yl)-1H-pyrazole to yield [trans-rac] 1-methyl-3-methylsulfonyl-5-[4-methyl-4-[[3-(trifluoromethyl)phenyl]sulfonyl]-tetrahydro-pyran-2-yl]-1H-pyrazole SC-433 (48 mg) [TLC system: EtOAc-PE; 2:3; Rf: 0.40].

3-Cyclopropyl-1-methyl-5-[4-methyl-4-[[3-(trifluoromethyl)phenyl]sulfonyl]-tetrahydro-pyran-2-yl]-1H-pyrazole (Example 91)

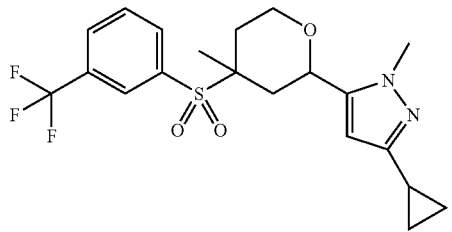 [SMILES: Cn1nc(C2CC2)cc1C1CC(C)(S(=O)(=O)c2cccc(C(F)(F)F)c2)CCO1]

For steps 1 to 7 see Example 90.

Step 8: 3-Cyclopropyl-1-methyl-5-[4-methyl-4-[[3-(trifluoromethyl)phenyl]sulfonyl]-tetrahydro-pyran-2-yl]-1H-pyrazole To a stirred solution of [cis rac] 3-bromo-1-methyl-5-(4-methyl-4-((3-(trifluoromethyl)phenyl)sulfonyl)tetrahydro-2H-pyran-2-yl)-1H-pyrazole (1.5 g, 3.21 mmol, 1.0 eq) and cyclopropyl boronic acid (830 mg, 9.63 mmol, 3.0 eq) in toluene (100 ml) was added $Cs_2CO_3$ (3.14 g, 9.63 mmol, 3.0 eq). The mixture was degassed for 15 min, and Pd(dppf)$Cl_2.CH_2Cl_2$ (176 mg, 0.193 mmol, 0.06 eq) was added. It was again degassed for 10 min. The resulting mixture was heated to 110° C. and stirred for 16 h under Ar. The RM was diluted with EtOAc (60 ml) and filtered. The filtrate was washed with washed with water (60 ml) and brine (60 ml), dried ($Na_2SO_4$) and concentrated under reduced pressure. The residue upon purification by flash chromatography (silica gel; EtOAc in PE; 50:50 to 60:40) afforded [cis rac] 3-cyclopropyl-1-methyl-5-[4-methyl-4-[[3-(trifluoromethyl)phenyl]sulfonyl]-tetrahydro-pyran-2-yl]-1H-pyrazole (600 mg, 43%) [TLC system: EtOAc-PE; 1:1; Rf: 0.40].

Chiral Resolution of [Cis rac] 3-cyclopropyl-1-methyl-5-[4-methyl-4-[[3-(trifluoromethyl)phenyl]sulfonyl]-tetrahydro-pyran-2-yl]-1H-pyrazole

[Cis rac] 3-cyclopropyl-1-methyl-5-[4-methyl-4-[[3-(trifluoromethyl)phenyl]sulfonyl]-tetrahydro-pyran-2-yl]-1H-pyrazole was subjected to chiral prep-SFC purification to give 170 mg of [cis-EN1] SC-431 and 170 mg [cis-EN2] SC-432. Preparative SFC Conditions: Column/dimensions: Chiralpak IC (250×30) mm; CO2: 55%; Co solvent: 45% MeOH; Total Flow: 60 g/min; Back Pressure: 100 bar.

[cis-EN1] SC-431—analytical SFC: Chiralpak IC (250×4.6 mm 5µ), 30° C., 3 g/min, 100 bar, 35% of 0.5% DEA in MeOH, Ret. Time 2.09 min

[cis-EN2] SC-432—analytical SFC: Chiralpak IC (250×4.6 mm 5µ), 30° C., 3 g/min, 100 bar, 35% of 0.5% DEA in MeOH, Ret. Time 3.03 min

[Trans rac] 3-cyclopropyl-1-methyl-5-[4-methyl-4-[[3-(trifluoromethyl)phenyl]sulfonyl]-tetrahydro-pyran-2-yl]-1H-pyrazole The corresponding [trans rac] isomer was prepared in analogy to step 8 starting from [trans rac] 3-bromo-1-methyl-5-(4-methyl-4-((3-(trifluoromethyl)phenyl)sulfonyl)tetrahydro-2H-pyran-2-yl)-1H-pyrazole to yield [trans-rac] 3-cyclopropyl-1-methyl-5-[4-methyl-4-[[3-(trifluoromethyl)phenyl]sulfonyl]-tetrahydro-pyran-2-yl]-1H-pyrazole SC-434 (50 mg) [TLC system: EtOAc-PE; 2:3; Rf: 0.40].

General Reaction Scheme for the Preparation of Examples 100 to 107 (SC-500 to SC-508)

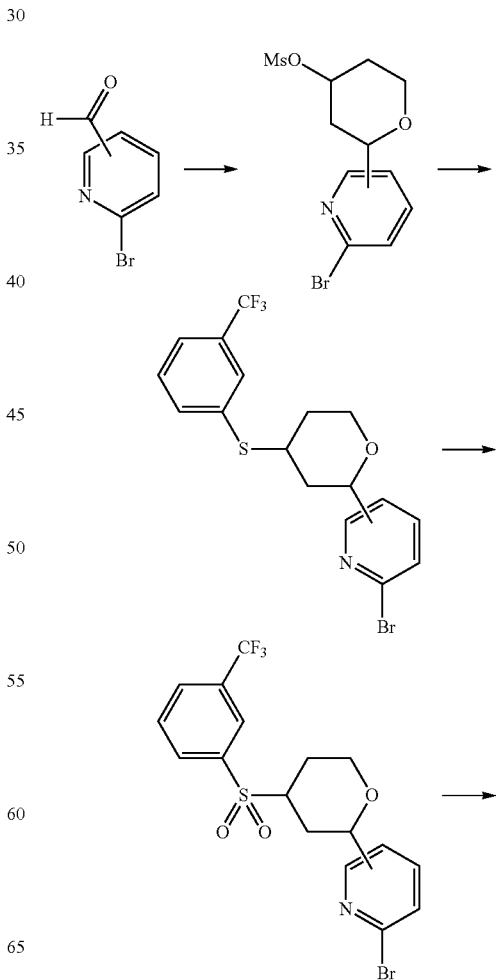

-continued

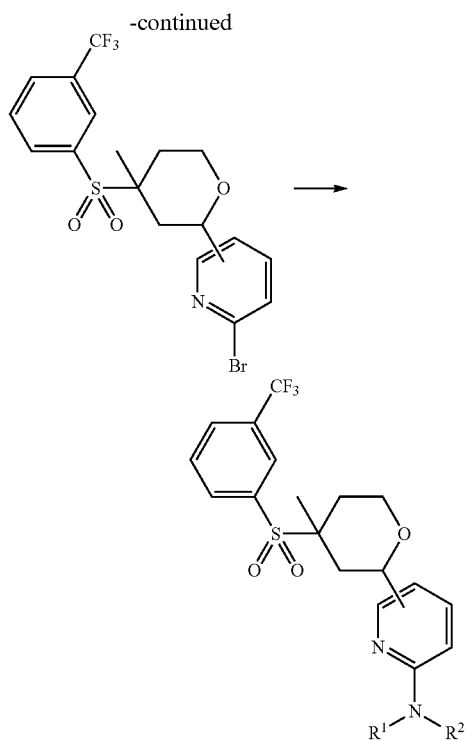

2-Bromo-6-(4-methyl-4-((3-(trifluoromethyl)phenyl)
sulfonyl)tetrahydro-2H-pyran-2-yl)pyridine

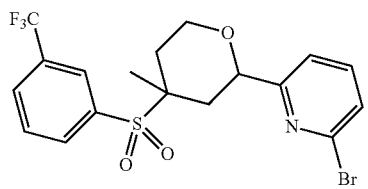 [SMILES: CC1(S(=O)(=O)c2cccc(C(F)(F)F)c2)CCOC(c2cccc(Br)n2)C1]

Step 1:
2-(6-Bromopyridin-2-yl)tetrahydro-2H-pyran-4-yl
Methanesulfonate

The first step was carried out in analogy to the synthesis of 2-isopropoxy-5-[4-methyl-4-[[3-(trifluoromethyl)phenyl]sulfonyl]-tetrahydro-pyran-2-yl]-pyridine.

Step 2: 2-Bromo-6-(4-((3-(trifluoromethyl)phenyl)thio)tetrahydro-2H-pyran-2-yl)pyridine To a stirred solution of 2-(6-bromopyridin-2-yl)tetrahydro-2H-pyran-4-yl methanesulfonate (15 g, 44.77 mmol) in DMF (100 mL) was added $Cs_2CO_3$ (14.5 g, 44.77 mmol), 3-(trifluoromethyl)benzenethiol (6.8 mL, 53.73 mmol) at RT and stirred for 16 h at 40° C. The RM was diluted with water (30 mL), and extracted into EtOAc (2×50 mL), washed could water (2×20 mL), and brine (30 mL), dried over anhydr. $Na_2SO_4$ and evaporated under vacuum. The crude was purified by silica gel (100-200 mesh) CC using 5% EtOAc in PE as eluent to get the product (12 g, ~53% over 2 steps) as a liquid.

Step 3: 2-Bromo-6-(4-((3-(trifluoromethyl)phenyl)sulfonyl)tetrahydro-2H-pyran-2-yl)pyridine To a stirred solution of 2-Bromo-6-(4-((3-(trifluoromethyl)phenyl)thio)tetrahydro-2H-pyran-2-yl)pyridine (12 g, 28.7 mmol) in EtOH (200 mL) was added oxone (26.5 g, 86.33 mmol) in water (100 mL) and stirred at RT for 16 h. The RM was evaporated under vacuum, extracted with EtOAc (2×50 mL), washed with brine (30 mL), dried over anhydr. $Na_2SO_4$ and evaporated vacuum. The crude was purified by silica gel (100-200 mesh) CC using 10% EtOAc in PE as eluent to get compound 4 (12 g, ~93%) as a liquid.

Step 4: 2-bromo-6-(4-methyl-4-((3-(trifluoromethyl)phenyl)sulfonyl)tetrahydro-2H-pyran-2-yl)pyridine To a stirred solution of 2-Bromo-6-(4-((3-(trifluoromethyl)phenyl)sulfonyl)tetrahydro-2H-pyran-2-yl)pyridine (5 g, 11.13 mmol) in THF (50 mL) at −78° C. under dry atmosphere was added 1M KOt-Bu (22.26 mL, 22.26 mmol), stirred for 15 min then added MeI (1.7 mL, 27.82 mmol) after addition slowly allowed to RT stirred for 16 h. The RM was cool to 0° C. quenched with ice water (20 mL), and extracted into EtOAc (2×50 mL), dried over anhydr. $Na_2SO_4$ and evaporated under vacuum. The crude product was purified by silica gel (100-200 mesh) CC using 20% EtOAc in PE as eluent to get the product (5.0 g, ~98%) as white solid.

$^1$H NMR (400 MHz, DMSO-$d_6$) of [cis-rac] 2-bromo-6-(4-methyl-4-((3-(trifluoromethyl)phenyl)sulfonyl)tetrahydro-2H-pyran-2-yl)pyridine: δ 8.22 (d, J=7.6 Hz, 1H), 8.18 (d, J=7.6 Hz, 1H), 8.04 (s, 1H), 7.95 (t, J=8.0 Hz, 1H), 7.77 (t, J=7.8 Hz, 1H), 7.57 (d, J=8.0 Hz, 1H), 7.47 (d, J=7.6 Hz, 1H), 4.61 (dd, J=11.2, 2.4 Hz, 1H), 4.10-4.03 (m, 1H), 3.78-3.68 (m, 1H), 2.13-2.08 (m, 1H), 1.95-1.91 (m, 1H), 1.86-1.83 (m, 1H), 1.50 (s, 3H), 1.47-1.43 (m, 1H).

2-Bromo-5-(4-methyl-4-((3-(trifluoromethyl)phenyl)
sulfonyl)tetrahydro-2H-pyran-2-yl)pyridine

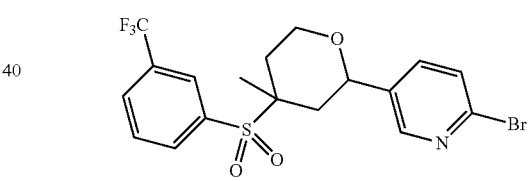

The steps 1 to 4 were carried out in analogy to the synthesis of 2-Bromo-6-(4-methyl-4-((3-(trifluoromethyl)phenyl)sulfonyl)tetrahydro-2H-pyran-2-yl)pyridine $^1$H NMR (400 MHz, DMSO-$d_6$) of [cis-rac] 2-Bromo-5-(4-methyl-4-((3-(trifluoromethyl)phenyl)sulfonyl)tetrahydro-2H-pyran-2-yl)pyridine: δ 8.35 (d, J=2.4 Hz, 1H), 8.22-8.15 (m, 2H), 8.05 (s, 1H), 7.94 (t, J=7.8 Hz, 1H), 7.71 (dd, J=8.2, 2.6 Hz, 1H), 7.63 (d, J=8.4 Hz, 1H), 4.64 (dd, J=11.2, 2.0 Hz, 1H), 4.07 (dd, J=11.8, 4.2 Hz, 1H), 3.74-3.68 (m, 1H), 2.14-2.10 (m, 1H), 1.92-1.85 (m, 1H), 1.79-1.75 (m, 1H), 1.49 (s, 3H), 1.48-1.47 (m, 1H).

General Procedure for the Coupling of 2-Bromo-6-(4-methyl-4-((3-(trifluoromethyl)phenyl)sulfonyl)
tetrahydro-2H-pyran-2-yl)pyridine (A) and
2-Bromo-5-(4-methyl-4-((3-(trifluoromethyl)phenyl)
sulfonyl)tetrahydro-2H-pyran-2-yl)pyridine (B) with
Amines The amine (0.1 mmol), $K_3PO_4$ (0.02 g, 0.4 mmol), CuI (0.01 g, 0.05 mmol) were mixed in a capped glass vessel. 2-Bromo-6-(4-methyl-4-((3-(trifluoromethyl)phenyl)sulfonyl)tetrahydro-2H-pyran-2-yl)pyridine (A) or 2-Bromo-5-(4-methyl-4-((3-(trifluoromethyl)phenyl)sulfonyl)tetrahydro-2H-pyran-2-yl)pyridine (B) (0.46 g, 0.1 mmol) and N,N'-Dimethylethylenediamine (0.2 mL, 1.8 mmol) were added and the mixture was stirred at 120° C. for 16 h. The RM was quenched with water (3 mL) and extracted into DCM (3×3 mL). The crude product was purified by HPLC.

Chiralcel OJ-H (250×30) mm; CO2: 75%; Co solvent: 25% MeOH; Total Flow: 100 g/min; Back Pressure: 100 bar, UV: 216 nm.

[cis-EN1] SC-509—analytical SFC: Chiralcel OJ-H (250×4.6 mm 5μ), 30° C., 3 g/min, 100 bar, 15% of MeOH, Ret. Time 2.83 min

| Cpd No. | A/B | Amine | cis/trans | Product |
|---|---|---|---|---|
| SC-500/Example 100 | B | (5-Methyl-3-isoxazolyl)-methylamine | cis | [(5-Methyl-isoxazol-3-yl)-methyl]-[5-[4-methyl-4-[[3-(trifluoromethyl)phenyl]sulfonyl]-tetrahydro-pyran-2-yl]-pyridin-2-yl]-amine |
| SC-501/Example 101 | B | 2-oxa-7-aza-spiro[3.5]-nonane | cis | 7-[5-[4-Methyl-4-[[3-(trifluoromethyl)phenyl]-sulfonyl]-tetrahydro-pyran-2-yl]-pyridin-2-yl]-2-oxa-7-azaspiro[3.5]nonane |
| SC-502/Example 102 | B | 2-(methyl-amino)-ethanol | cis | 2-[Methyl-[5-[4-methyl-4-[[3-(trifluoromethyl)-phenyl]sulfonyl]-tetrahydro-pyran-2-yl]-pyridin-2-yl]-amino]-ethanol |
| SC-503/Example 103 | A | (5-Methyl-3-isoxazolyl)-methylamine | cis | [(5-Methyl-isoxazol-3-yl)-methyl]-[6-[4-methyl-4-[[3-(trifluoromethyl)phenyl]sulfonyl]-tetrahydro-pyran-2-yl]-pyridin-2-yl]-amine |
| SC-504/Example 104 | A | 2-oxa-7-aza-spiro[3.5]-nonane | cis | 7-[6-[4-Methyl-4-[[3-(trifluoromethyl)-phenyl]sulfonyl]-tetrahydro-pyran-2-yl]-pyridin-2-yl]-2-oxa-7-azaspiro[3.5]nonane |
| SC-505/Example 105 | A | tetrahydro-2H-pyran-4-amine | cis | [6-[4-Methyl-4-[[3-(trifluoromethyl)phenyl]-sulfonyl]-tetrahydro-pyran-2-yl]-pyridin-2-yl]-tetrahydro-pyran-4-yl-amine |
| SC-506/Example 106 | A | 2-(methyl-amino)-ethanol | cis | 2-[Methyl-[6-[4-methyl-4-[[3-(trifluoromethyl)-phenyl]sulfonyl]-tetrahydro-pyran-2-yl]-pyridin-2-yl]-amino]-ethanol |
| SC-508/Example 108 | A | Cyclopropyl amine | cis | Cyclopropyl-[6-[4-methyl-4-[[3-(trifluoromethyl)phenyl]sulfonyl]-tetrahydro-pyran-2-yl]-pyridin-2-yl]-amine |

1-Ethyl-3-methylsulfonyl-5-[4-methyl-4-[[3-(trifluoromethyl)phenyl]sulfonyl]-tetrahydro-pyran-2-yl]-1H-pyrazole (Example 109)

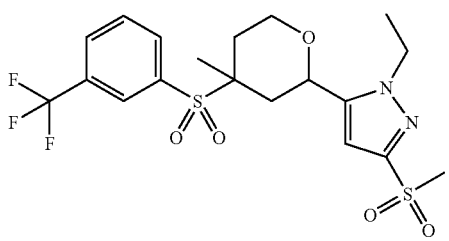 [SMILES: CCn1nc(S(C)(=O)=O)cc1C1CC(C)(S(=O)(=O)c2cccc(C(F)(F)F)c2)CCO1]

The synthesis was carried out in analogy to the method described for Example 90 to yield [cis rac] 1-ethyl-3-methylsulfonyl-5-[4-methyl-4-[[3-(trifluoromethyl)phenyl] sulfonyl]-tetrahydro-pyran-2-yl]-1H-pyrazole (800 mg, step 9: 74%) [TLC system: EtOAc-pet-ether; 1:1; Rf: 0.30].

Chiral Resolution of [Cis rac] 1-ethyl-3-methylsulfonyl-5-[4-methyl-4-[[3-(trifluoromethyl)phenyl] sulfonyl]-tetrahydro-pyran-2-yl]-1H-pyrazole

[Cis rac] 1-ethyl-3-methylsulfonyl-5-[4-methyl-4-[[3-(trifluoromethyl)phenyl]sulfonyl]-tetrahydro-pyran-2-yl]-1H-pyrazole was subjected to chiral prep-SFC purification to give 2000 mg of [cis-EN1] SC-509 and 205 mg [cis-EN2] SC-510. Preparative SFC Conditions: Column/dimensions:

[cis-EN2] SC-510—analytical SFC: Chiralcel OJ-H (250×4.6 mm 5μ), 30° C., 3 g/min, 100 bar, 15% of MeOH, Ret. Time 3.85 min

[Trans rac] 1-ethyl-3-methylsulfonyl-5-[4-methyl-4-[[3-(trifluoromethyl)phenyl]sulfonyl]-tetrahydro-pyran-2-yl]-1H-pyrazole

[Trans rac] 1-ethyl-3-methylsulfonyl-5-[4-methyl-4-[[3-(trifluoromethyl)phenyl]sulfonyl]-tetrahydro-pyran-2-yl]-1H-pyrazole SC-511 (55 mg) [TLC system: EtOAc-pet-ether; 1:1; Rf: 0.35] was prepared according to the method described for SC-433.

3-(Difluoro-methoxy)-1-methyl-5-[4-methyl-4-[[3-(trifluoromethyl)phenyl]sulfonyl]-tetrahydro-pyran-2-yl]-1H-pyrazole (Example 110)

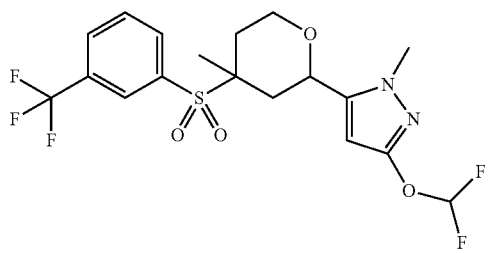 [SMILES: Cn1nc(OC(F)F)cc1C1CC(C)(S(=O)(=O)c2cccc(C(F)(F)F)c2)CCO1]

For steps 1 to 7 see Example 90.

Step 8 & 9: 1-Methyl-5-(4-methyl-4-((3-(trifluoromethyl)phenyl)sulfonyl)tetrahydro-2H-pyran-2-yl)-1H-pyrazol-3-ol A stirred solution of 3-bromo-1-methyl-5-(4-methyl-4-((3-(trifluoromethyl)phenyl)sulfonyl)tetrahydro-2H-pyran-2-yl)-1H-pyrazole (2 g, 4.282 mmol, 1.0 eq), Bis-pinacolato diboron (4.35 g, 17.13 mmol, 4.0 eq) and KOAc (1.25 g, 12.85 mmol, 3.0 eq) in DMF (100 ml) was degassed for 15 min. PdCl$_2$(dppf)$_2$ CH$_2$Cl$_2$ (244 mg, 0.30 mmol, 0.07 eq) was added and it was again degassed again for 10 min. The resulting mixture was heated to 120° C. and stirred for 36 h under Ar. The RM was concentrated under reduced pressure. The residue was diluted with water (100 ml) and extracted with EtOAc (2×100 ml). The combined organic extracts were washed with water (2×100 ml) and brine (100 ml), dried (Na$_2$SO$_4$) and concentrated under reduced pressure. To the crude product (4.0 g), dissolved in THF (100 ml), was added NaOH (1.55 g, 38.91 mmol, 5.0 eq) in water (20 ml) at 10° C. This was followed by dropwise addition of 30% aq. hydrogen peroxide solution (4.5 ml, 38.91 mmol, 5.0 eq). The RM was stirred at RT for 16 h. The RM was diluted with water (100 ml) and acidified to pH ~3-4 with 1 N aq. HCl. It was extracted with EtOAc (3×100 ml) and the combined organic layers were washed with water (2×100 ml) and brine (100 ml), dried over anhydr. Na$_2$SO$_4$, filtered and concentrated under reduced pressure. The residue upon purification by flash chromatography (silica gel, MeOH-DCM; 0:100 to 5:95), followed by trituration and filtration with Et$_2$O (50 ml) afforded [cis rac] 1-methyl-5-(4-methyl-4-((3-(trifluoromethyl)phenyl)sulfonyl)tetrahydro-2H-pyran-2-yl)-1H-pyrazol-3-ol (850 mg, 49%; over 2 steps).

Step 10: 3-(Difluoro-methoxy)-1-methyl-5-[4-methyl-4-[[3-(trifluoromethyl)phenyl]sulfonyl]-tetrahydro-pyran-2-yl]-1H-pyrazole To a stirred solution of [cis rac] 1-methyl-5-(4-methyl-4-((3-(trifluoromethyl)phenyl)sulfonyl)tetrahydro-2H-pyran-2-yl)-1H-pyrazol-3-ol (1.7 g, 4.21 mmol, 1.0 eq) in DMF (80 ml) was added K$_2$CO$_3$ (1.70 g, 12.62 mmol, 3.0 eq). The RM was heated to 90° C. and at this temperature treated with Freon gas (balloon pressure) over a period of 2 h. The RM was then stirred at 90° C. for another 4 h. The RM was concentrated under reduced pressure. The residue was diluted with water (100 ml) and extracted with EtOAc (3×75 ml). The combined organic layers were washed with water (2×75 ml) and brine (75 ml), dried over anhydr. Na$_2$SO$_4$, filtered and concentrated under reduced pressure. The residue upon purification by flash chromatography (silica gel, EtOAc-PE; 40:60 to 60:40), afforded [cis rac] 3-(difluoromethoxy)-1-methyl-5-[4-methyl-4-[[3-(trifluoromethyl)phenyl]sulfonyl]-tetrahydro-pyran-2-yl]-1H-pyrazole (550 mg, 28%) [TLC system: EtOAc-PE; 7:3; Rf: 0.60].

Chiral Resolution of [Cis rac] 3-(difluoromethoxy)-1-methyl-5-[4-methyl-4-[[3-(trifluoromethyl)phenyl]sulfonyl]-tetrahydro-pyran-2-yl]-1H-pyrazole

[Cis rac] 3-(difluoro-methoxy)-1-methyl-5-[4-methyl-4-[[3-(trifluoromethyl)phenyl]sulfonyl]-tetrahydro-pyran-2-yl]-1H-pyrazole was subjected to chiral prep-SFC purification to give 170 mg of [cis-EN1] SC-512 and 175 mg [cis-EN2] SC-513. Preparative SFC Conditions: Column/dimensions: Chiralpak AD-H (250×30) mm; CO2: 50%; Co solvent: 50% MeOH; Total Flow: 90 g/min; Back Pressure: 100 bar, UV: 271 nm.

[cis-EN1] SC-512—analytical SFC: Chiralpak AD-H (250×4.6 mm 5µ), 30° C., 5 g/min, 100 bar, 40% of MeOH, Ret. Time 1.31 min

[cis-EN2] SC-513—analytical SFC: Chiralpak AD-H (250×4.6 mm 5µ), 30° C., 5 g/min, 100 bar, 40% of MeOH, Ret. Time 5.52 min

[Trans rac] 3-(difluoro-methoxy)-1-methyl-5-[4-methyl-4-[[3-(trifluoromethyl)phenyl]sulfonyl]-tetrahydro-pyran-2-yl]-1H-pyrazole The corresponding [trans rac] isomer was prepared in analogy to steps 8 to 10 starting from [trans rac] 3-bromo-1-methyl-5-(4-methyl-4-((3-(trifluoromethyl)phenyl)sulfonyl)tetrahydro-2H-pyran-2-yl)-1H-pyrazole to yield [trans rac] 3-(difluoro-methoxy)-1-methyl-5-[4-methyl-4-[[3-(trifluoromethyl)phenyl]sulfonyl]-tetrahydro-pyran-2-yl]-1H-pyrazole SC-514 (20 mg) [TLC system: EtOAc-PE; 7:3; Rf: 0.65].

Analytical Data:

Material and Methods for LC/MS Analytics:

Hardware: Coupled Agilent 1290 Infinity UHPLC-TOF System; LC-Module: MTP-Handler: Agilent, Model Bench-Cel 2R; Thermostatic Control Autoinjector: Agilent, Modell G4226A; Column oven: Agilent, Model G1316C; DAD: Agilent, Model G4212A; Binary Pump: Agilent, Model G4220A; Time Of Flight Mass Spectrometer: Agilent 6224; Ion source: Dual ESI; Column: Supplier: Waters; Type: Acquity UPLC HSS T3 1.8 µm (Part No. 186003538); Dimensions: 2.1×50 mm; Eluents: Eluent A: Water from Millipore Ultrapure water System: Milli-Q Integral 3+0.1% Formic acid; Eluent B: Acetonitrile, Merck KGaA: LiChrosolv Hypergrade for LC-MS (1.00029.9010)+0.1% Formic acid; Formic acid: Merck KGaA: Suprapure 98-100% (1.11670.1000); LC-Method: Flow: 2.5 mL/min; Runtime: 1.2 min; Gradient: Start 2% B, 1 min 100% B, 1.09 min 100% B, 1.11 min 2% B, 1.2 min 2% B Stop; Column temperature: 80° C.; UV: 190-400 nm; MS-Method: Ion Polarity: Positive; Gas Temperature: 325° C.; Gas Flow: 10 mL/min The following tables summarize the LC-MS analytical data

| Ex. No. | cis/ trans | Cpd No. | Target Mass | Mass Found | UV$_{254}$-purity | Ex. No. | cis/ trans | Cpd No. | Target Mass | Mass Found | UV$_{254}$-purity |
|---|---|---|---|---|---|---|---|---|---|---|---|
| 1 | cis | SC-100 | 463.073 | Yes | 100 | 11 | cis | SC-305 | 454.079 | Yes | 99 |
| 1 | cis | SC-101 | 463.073 | Yes | 100 | 14 | cis | SC-306 | 453.083 | Yes | 100 |
| 2 | cis | SC-102 | 425.127 | Yes | 100 | 14 | trans | SC-307 | 453.083 | Yes | 100 |
| 2 | cis | SC-103 | 425.127 | Yes | 100 | 12 | cis | SC-308 | 453.083 | Yes | 100 |

-continued

| Ex. No. | cis/ trans | Cpd No. | Target Mass | Mass Found | UV$_{254}$- purity | Ex. No. | cis/ trans | Cpd No. | Target Mass | Mass Found | UV$_{254}$- purity |
|---|---|---|---|---|---|---|---|---|---|---|---|
| 3 | cis | SC-104 | 463.073 | Yes | 100 | 12 | cis | SC-309 | 453.083 | Yes | 100 |
| 3 | cis | SC-105 | 463.073 | Yes | 100 | 12 | trans | SC-310 | 453.083 | Yes | 100 |
| 4 | cis | SC-106 | 467.099 | Yes | 100 | 12 | trans | SC-311 | 453.083 | Yes | 100 |
| 4 | trans | SC-107 | 467.099 | Yes | 100 | 13 | cis | SC-312 | 413.127 | Yes | 100 |
| 4 | cis | SC-108 | 467.099 | Yes | 100 | 13 | cis | SC-313 | 413.127 | Yes | 100 |
| 4 | trans | SC-109 | 467.099 | Yes | 100 | 13 | trans | SC-314 | 413.127 | Yes | 99 |
| 5 | cis | SC-200 | 458.073 | Yes | 100 | 14 | cis | SC-315 | 453.083 | Yes | 100 |
| 5 | cis | SC-201 | 458.073 | Yes | 95 | 14 | cis | SC-316 | 453.083 | Yes | 100 |
| 6 | cis | SC-202 | 430.117 | Yes | 100 | 15 | cis | SC-317 | 427.143 | Yes | 100 |
| 6 | cis | SC-203 | 430.117 | Yes | 100 | 15 | cis | SC-318 | 427.143 | Yes | 100 |
| 7 | cis | SC-204 | 426.122 | Yes | 100 | 15 | trans | SC-319 | 427.143 | Yes | 100 |
| 7 | cis | SC-205 | 426.122 | Yes | 100 | 16 | cis | SC-323 | 413.127 | Yes | 100 |
| 8 | cis | SC-206 | 430.117 | Yes | 100 | 16 | cis | SC-324 | 413.127 | Yes | 100 |
| 8 | cis | SC-207 | 430.117 | Yes | 100 | 17 | cis | SC-325 | 425.127 | Yes | 100 |
| 9 | cis | SC-300 | 443.138 | Yes | 100 | 17 | cis | SC-326 | 425.127 | Yes | 100 |
| 9 | cis | SC-301 | 443.138 | Yes | 98 | 18 | cis | SC-327 | 426.122 | Yes | 100 |
| 9 | trans | SC-302 | 443.138 | Yes | 100 | 18 | cis | SC-328 | 426.122 | Yes | 100 |
| 10 | trans | SC-303 | 413.127 | Yes | 100 | 18 | trans | SC-329 | 426.122 | Yes | 100 |
| 11 | cis | SC-304 | 454.079 | Yes | 97 | | | | | | |
| 19 | cis | SC-110 | 416.102 | Yes | 100 | 35 | cis | SC-213 | 513.070 | Yes | 100 |
| 19 | cis | SC-111 | 416.102 | Yes | 100 | 36 | cis | SC-214 | 515.025 | Yes | 100 |
| 20 | cis | SC-112 | 429.122 | Yes | 100 | 36 | cis | SC-215 | 515.025 | Yes | 100 |
| 20 | cis | SC-113 | 429.122 | Yes | 100 | 37 | cis | SC-216 | 497.034 | Yes | 100 |
| 20 | trans | SC-114 | 429.122 | Yes | 100 | 37 | cis | SC-217 | 497.034 | Yes | 100 |
| 21 | cis | SC-115 | 453.083 | Yes | 100 | 38 | cis | SC-218 | 513.029 | Yes | 100 |
| 21 | cis | SC-116 | 453.083 | Yes | 100 | 38 | cis | SC-219 | 513.029 | Yes | 100 |
| 22 | cis | SC-117 | 455.138 | Yes | 100 | 39 | cis | SC-220 | 547.056 | Yes | 100 |
| 22 | cis | SC-118 | 455.138 | Yes | 100 | 39 | cis | SC-221 | 547.056 | Yes | 96 |
| 23 | cis | SC-119 | 481.064 | Yes | 100 | 40 | cis | SC-222 | 531.061 | Yes | 100 |
| 23 | cis | SC-120 | 481.064 | Yes | 100 | 40 | cis | SC-223 | 531.061 | Yes | 100 |
| 24 | cis | SC-121 | 444.058 | Yes | 100 | 41 | cis | SC-224 | 493.084 | Yes | 100 |
| 24 | cis | SC-122 | 444.058 | Yes | 100 | 41 | cis | SC-225 | 493.084 | Yes | 100 |
| 25 | cis | SC-123 | 426.067 | Yes | 100 | 42 | cis | SC-226 | 497.034 | Yes | 100 |
| 25 | cis | SC-124 | 426.067 | Yes | 100 | 42 | cis | SC-227 | 497.034 | Yes | 100 |
| 26 | cis | SC-125 | 418.117 | Yes | 100 | 43 | cis | SC-228 | 515.066 | Yes | 100 |
| 26 | cis | SC-126 | 418.117 | Yes | 100 | 43 | cis | SC-229 | 515.066 | Yes | 100 |
| 27 | trans | SC-127 | 416.102 | Yes | 100 | 43 | cis | SC-230 | 515.066 | Yes | 100 |
| 27 | cis | SC-128 | 416.102 | Yes | 100 | 43 | cis | SC-231 | 515.066 | Yes | 100 |

-continued

| Ex. No. | cis/trans | Cpd No. | Target Mass | Mass Found | UV$_{254}$-purity | Ex. No. | cis/trans | Cpd No. | Target Mass | Mass Found | UV$_{254}$-purity |
|---|---|---|---|---|---|---|---|---|---|---|---|
| 27 | cis | SC-129 | 416.102 | Yes | 100 | 44 | cis | SC-232 | 481.040 | Yes | 100 |
| 28 | cis | SC-130 | 497.034 | Yes | 100 | 44 | cis | SC-233 | 481.040 | Yes | 100 |
| 28 | cis | SC-131 | 497.034 | Yes | 100 | 44 | cis | SC-234 | 481.040 | Yes | 100 |
| 29 | cis | SC-132 | 456.133 | Yes | 100 | 44 | cis | SC-235 | 481.040 | Yes | 100 |
| 29 | cis | SC-133 | 456.133 | Yes | 100 | 45 | cis | SC-236 | 469.054 | Yes | 100 |
| 30 | cis | SC-150 | 483.019 | Yes | 100 | 45 | cis | SC-237 | 469.054 | Yes | 100 |
| 30 | cis | SC-151 | 483.019 | Yes | 100 | 46 | cis | SC-238 | 430.117 | Yes | 100 |
| 30 | trans | SC-152 | 483.019 | Yes | 100 | 46 | cis | SC-239 | 430.117 | Yes | 100 |
| 30 | trans | SC-153 | 483.019 | Yes | 100 | 47 | cis | SC-240 | 458.073 | Yes | 100 |
| 31 | cis | SC-154 | 463.073 | Yes | 100 | 47 | cis | SC-241 | 458.073 | Yes | 100 |
| 31 | cis | SC-155 | 463.073 | Yes | 100 | 47 | cis | SC-242 | 458.073 | Yes | 100 |
| 31 | trans | SC-156 | 463.073 | Yes | 100 | 48 | cis | SC-243 | 419.057 | Yes | 100 |
| 31 | trans | SC-157 | 463.073 | Yes | 100 | 48 | cis | SC-244 | 419.057 | Yes | 100 |
| 32 |  | SC-158 | 415.106 | Yes | 100 | 49 | cis | SC-245 | 445.117 | Yes | 100 |
| 33 | cis | SC-208 | 483.094 | Yes | 100 | 49 | cis | SC-246 | 445.117 | Yes | 100 |
| 33 | cis | SC-209 | 483.094 | Yes | 100 | 49 | trans | SC-247 | 445.117 | Yes | 100 |
| 34 | cis | SC-210 | 477.071 | Yes | 98 | 50 | cis | SC-248 | 429.122 | Yes | 100 |
| 34 | cis | SC-211 | 541.051 | Yes | 94 | 50 | cis | SC-249 | 429.122 | Yes | 100 |
| 35 | cis | SC-212 | 513.070 | Yes | 100 | 51 | cis | SC-250 | 431.101 | Yes | 100 |
| 51 | cis | SC-251 | 431.101 | Yes | 100 | 72 | trans | SC-347 | 425.127 | Yes | 100 |
| 50 | trans | SC-252 | 429.122 | Yes | 100 | 72 | cis | SC-348 | 425.127 | Yes | 100 |
| 52 | cis | SC-253 | 481.098 | Yes | 100 | 74 |  | SC-350 | 439.068 | Yes | 100 |
| 52 | cis | SC-254 | 481.098 | Yes | 100 | 75 | cis | SC-351 | 453.083 | Yes | 100 |
| 53 | cis | SC-255 | 433.097 | Yes | 100 | 75 | trans | SC-352 | 453.083 | Yes | 100 |
| 53 | cis | SC-256 | 433.097 | Yes | 100 | 76 | cis | SC-353 | 415.106 | Yes | 100 |
| 54 | cis | SC-257 | 433.097 | Yes | 100 | 76 | cis | SC-354 | 415.106 | Yes | 100 |
| 54 | cis | SC-258 | 433.097 | Yes | 100 | 77 | cis | SC-355 | 531.061 | Yes | 100 |
| 54 | trans | SC-259 | 433.097 | Yes | 100 | 77 | cis | SC-356 | 531.061 | Yes | 100 |
| 55 | cis | SC-260 | 440.102 | Yes | 100 | 78 | cis | SC-400 | 454.154 | Yes | 100 |
| 55 | cis | SC-261 | 440.102 | Yes | 100 | 78 | cis | SC-401 | 454.154 | Yes | 100 |
| 56 | cis | SC-262 | 477.089 | Yes | 100 | 79 | cis | SC-402 | 452.113 | Yes | 100 |
| 56 | cis | SC-263 | 477.089 | Yes | 100 | 79 | cis | SC-403 | 452.113 | Yes | 100 |
| 57 | cis | SC-264 | 479.044 | Yes | 100 | 80 | cis | SC-404 | 459.133 | Yes | 100 |
| 57 | cis | SC-265 | 479.044 | Yes | 100 | 80 | cis | SC-405 | 459.133 | Yes | 100 |
| 58 | cis | SC-266 | 529.065 | Yes | 100 | 78 | trans | SC-406 | 454.154 | Yes | 100 |
| 58 | cis | SC-267 | 529.065 | Yes | 100 | 79 | trans | SC-407 | 452.113 | Yes | 100 |
| 59 | cis | SC-268 | 529.065 | Yes | 100 | 81 | cis | SC-408 | 414.122 | Yes | 100 |
| 59 | cis | SC-269 | 529.065 | Yes | 100 | 81 | cis | SC-409 | 414.122 | Yes | 100 |

-continued

| Ex. No. | cis/ trans | Cpd No. | Target Mass | Mass Found | UV$_{254}$-purity | Ex. No. | cis/ trans | Cpd No. | Target Mass | Mass Found | UV$_{254}$-purity |
|---|---|---|---|---|---|---|---|---|---|---|---|
| 60 | cis | SC-270 | 503.105 | Yes | 100 | 82 | cis | SC-410 | 416.102 | Yes | 100 |
| 60 | cis | SC-271 | 503.105 | Yes | 100 | 82 | cis | SC-411 | 416.102 | Yes | 100 |
| 61 | cis | SC-330 | 428.138 | Yes | 100 | 81 | trans | SC-412 | 414.122 | Yes | 100 |
| 61 | cis | SC-331 | 428.138 | Yes | 100 | 83 | cis | SC-413 | 429.133 | Yes | 100 |
| 62 | cis | SC-332 | 440.138 | Yes | 100 | 83 | cis | SC-414 | 429.133 | Yes | 100 |
| 62 | trans | SC-333 | 440.138 | Yes | 100 | 84 | cis | SC-415 | 416.102 | Yes | 100 |
| 62 | cis | SC-334 | 440.138 | Yes | 100 | 84 | cis | SC-416 | 416.102 | Yes | 100 |
| 63 |  | SC-335 | 399.112 | Yes | 100 | 85 | trans | SC-417 | 451.088 | Yes | 100 |
| 64 | cis | SC-336 | 463.073 | Yes | 100 | 85 | cis | SC-418 | 451.088 | Yes | 100 |
| 65 | cis | SC-337 | 463.006 | Yes | 100 | 85 | cis | SC-419 | 451.088 | Yes | 100 |
| 64 | cis | SC-338 | 463.073 | Yes | 100 | 80 | trans | SC-420 | 459.133 | Yes | 59 |
| 67 |  | SC-339 | 429.122 | Yes | 100 | 86 | cis | SC-421 | 429.133 | Yes | 100 |
| 68 | cis | SC-340 | 487.044 | Yes | 100 | 86 | cis | SC-422 | 429.133 | Yes | 98 |
| 69 | trans | SC-341 | 385.096 | Yes | 100 | 87 | cis | SC-423 | 416.102 | Yes | 100 |
| 70 |  | SC-342 | 439.068 | Yes | 100 | 87 | cis | SC-424 | 416.102 | Yes | 100 |
| 71 | cis | SC-343 | 456.094 | Yes | 100 | 88 | cis | SC-425 | 459.088 | Yes | 100 |
| 71 | trans | SC-344 | 456.094 | Yes | 100 | 88 | cis | SC-426 | 459.088 | Yes | 100 |
| 71 | cis | SC-345 | 456.094 | Yes | 100 | 89 | cis | SC-427 | 485.049 | Yes | 100 |
| 72 | cis | SC-346 | 425.127 | Yes | 100 | 89 | cis | SC-428 | 485.049 | Yes | 100 |
| 90 | cis | SC-429 | 466.084 | Yes | 100 | 98 | cis | SC-450 | 493.084 | Yes | 100 |
| 90 | cis | SC-430 | 466.084 | Yes | 100 | 98 | trans | SC-451 | 493.084 | Yes | 100 |
| 91 | cis | SC-431 | 428.138 | Yes | 100 | 99 | cis | SC-452 | 454.042 | Yes | 100 |
| 91 | cis | SC-432 | 428.138 | Yes | 100 | 99 | cis | SC-453 | 454.042 | Yes | 100 |
| 90 | trans | SC-433 | 466.084 | Yes | 100 | 96 | trans | SC-454 | 495.080 | Yes | 100 |
| 91 | trans | SC-434 | 428.138 | Yes | 100 | 100 | cis | SC-500 | 495.144 | Yes | 100 |
| 88 | trans | SC-435 | 459.088 | Yes | 100 | 101 | cis | SC-501 | 510.180 | Yes | 100 |
| 92 | cis | SC-436 | 495.039 | Yes | 100 | 102 | cis | SC-502 | 458.149 | Yes | 100 |
| 92 | cis | SC-437 | 495.039 | Yes | 100 | 103 | cis | SC-503 | 495.144 | Yes | 100 |
| 89 | trans | SC-438 | 485.049 | Yes | 86 | 104 | cis | SC-504 | 510.180 | Yes | 100 |
| 93 | cis | SC-439 | 463.008 | Yes | 90 | 105 | cis | SC-505 | 484.164 | Yes | 100 |
| 93 | cis | SC-440 | 463.008 | Yes | 100 | 106 | cis | SC-506 | 458.149 | Yes | 100 |
| 94 | trans | SC-441 | 477.089 | Yes | 100 | 107 | cis | SC-507 | 458.149 | Yes | 98 |
| 95 | cis | SC-442 | 477.089 | Yes | 100 | 108 | cis | SC-508 | 440.138 | Yes | 99 |
| 95 | cis | SC-443 | 477.089 | Yes | 100 | 109 | cis | SC-509 | 480.100 | Yes | 100 |
| 96 | cis | SC-444 | 495.080 | Yes | 100 | 109 | cis | SC-510 | 480.100 | Yes | 100 |
| 96 | cis | SC-445 | 495.080 | Yes | 100 | 109 | trans | SC-511 | 480.100 | Yes | 72.97 |
| 97 | cis | SC-446 | 471.094 | Yes | 100 | 110 | cis | SC-512 | 454.099 | Yes | 95.34 |
| 97 | cis | SC-447 | 471.094 | Yes | 100 | 110 | cis | SC-513 | 454.099 | Yes | 100 |

-continued

| Ex. No. | cis/trans | Cpd No. | Target Mass | Mass Found | UV$_{254}$-purity | Ex. No. | cis/trans | Cpd No. | Target Mass | Mass Found | UV$_{254}$-purity |
|---|---|---|---|---|---|---|---|---|---|---|---|
| 95 | trans | SC-448 | 477.089 | Yes | 100 | 110 | trans | SC-514 | 454.099 | Yes | 100 |
| 98 | cis | SC-449 | 493.084 | Yes | 100 | 100 | cis | SC-500 | 495.144 | Yes | 100 |

2. Assay Descriptions and Biological Data:

2.1 Fluorescence Assay for CaV2.2 Channels Using Potassium Depolarization to Induce Channel Opening Human CaV2.2 channels were stably expressed in HEK293 cells together with alpha2-delta and beta subunits of voltage gated calcium channels. In addition, an inwardly rectifying potassium channel (Kir2.3) was stably expressed in these cells to augment control of the cell membrane potential by the concentration of extracellular potassium ions. Raise of the extracellular potassium concentration leads to depolarization of the membrane potential and thus regulates the voltage dependent state of CaV2.2 channels. For preparation, cells were seeded in black poly-D-lysine coated 96-well plates (Becton Dickinson, Biocoat 4640) in 100 µL medium [500 mL DMEM/F-12 plus Glutamax (Invitrogen 31331-093) plus 5.5 mL MEM NEAA 100× (Invitrogen 11140-035) plus 50 mL FBS decomplemented (Invitrogen 10270-106) plus 200 µg/mL Geneticin (Invitrogen 10131-027) plus 50 µg/mL Hygromycin B (Invitrogen 10687-010) plus 2 µg/mL Blasticidin (anti-bl5b Invivo-Gen) plus 0.2 µg/mL Puromycin (A 11138-03)] at a cell density of 30.000 cells per well. Plates were incubated at 37° C. (5% CO$_2$) for 20 to 23 h. On the day of experiment medium was discarded and cells were loaded with Fluo 4 by addition of 100 µL of basic assay buffer (10 mM HEPES, 1 mM KCl, 149 mM NaCl, 0.8 mM CaCl$_2$, 1.7 mM MgCl$_2$, 10 mM Glucose, 0.1% BSA. pH 7.4) containing 2 µM Fluo 4 (Molecular Probes; F-14201), 0.01% pluronic acid (Molecular Probes; P-6866) and 2.5 mM probenecid (Molecular Probes; P36400). Cells were incubated in the dark at 25° C. for 60 min. Then dye containing buffer was discarded and 100 µL basic (1 mM KCl) or alternative (30 mM KCl) assay buffer was added. The alternative assay buffer contained altered concentrations of KCl (30 mM) and NaCl (120 mM) and was used in order to promote the inactivated channel state. After that 25 µL of basic or alternative assay buffer with or without test compound were added and cells were incubated again in the dark at 25° C. for 15 min. Fluorescence intensity was measured on a FLIPR 3 instrument (Molecular Devices Corp., Sunnyvale, Calif.) with excitation at 480 nm and emission at 535 nm. After continuously reading fluorescence for 30 sec, 50 µL of basic assay buffer containing 210 mM KCl (NaCl omitted) were added for depolarization. Peak fluorescent signal intensity was determined and the amplitude of the peak signal, normalized to base line, was used to measure channel inhibition by test compounds.

The following tables summarize the inhibitory activity of exemplified compounds according to the present invention.

| Cpd No. | Activity Category | Cpd No. | Activity Category | Cpd No. | Activity Category | Cpd No. | Activity Category |
|---|---|---|---|---|---|---|---|
| SC-100 | C | SC-202 | B | SC-306 | A | SC-318 | B |
| SC-101 | B | SC-203 | B | SC-307 | A | SC-319 | C |
| SC-102 | A | SC-204 | B | SC-308 | A | SC-323 | B |
| SC-103 | A | SC-205 | A | SC-309 | A | SC-324 | B |
| SC-104 | B | SC-206 | C | SC-310 | A | SC-325 | A |
| SC-105 | B | SC-207 | C | SC-311 | A | SC-326 | A |
| SC-106 | A | SC-300 | A | SC-312 | C | SC-327 | B |
| SC-107 | A | SC-301 | A | SC-313 | C | SC-328 | A |
| SC-108 | A | SC-302 | A | SC-314 | C | SC-329 | A |
| SC-109 | B | SC-303 | B | SC-315 | A | | |
| SC-200 | B | SC-304 | B | SC-316 | A | | |
| SC-201 | B | SC-305 | A | SC-317 | C | | |
| SC-110 | B | SC-118 | A | SC-126 | B | SC-158 | A |
| SC-111 | B | SC-119 | B | SC-127 | C | SC-208 | B |
| SC-112 | C | SC-120 | B | SC-128 | B | SC-209 | A |
| SC-113 | B | SC-121 | C | SC-129 | C | SC-210 | A |
| SC-114 | B | SC-122 | B | SC-130 | B | SC-212 | B |
| SC-115 | B | SC-123 | B | SC-131 | B | SC-213 | B |
| SC-116 | A | SC-124 | C | SC-132 | B | SC-214 | C |
| SC-117 | B | SC-125 | C | SC-133 | A | SC-215 | B |
| SC-216 | C | SC-253 | B | SC-347 | A | SC-425 | A |
| SC-217 | C | SC-254 | A | SC-348 | A | SC-426 | A |
| SC-218 | B | SC-255 | A | SC-349 | A | SC-427 | A |
| SC-219 | A | SC-256 | B | SC-350 | A | SC-428 | A |
| SC-220 | A | SC-257 | B | SC-351 | A | SC-429 | C |
| SC-221 | B | SC-258 | A | SC-352 | A | SC-430 | B |
| SC-222 | B | SC-259 | A | SC-353 | B | SC-431 | B |
| SC-223 | B | SC-260 | A | SC-354 | A | SC-432 | A |
| SC-224 | B | SC-261 | C | SC-355 | B | SC-433 | C |
| SC-225 | B | SC-262 | B | SC-356 | A | SC-434 | B |
| SC-226 | B | SC-263 | B | SC-400 | A | SC-435 | A |
| SC-227 | B | SC-265 | C | SC-401 | A | SC-436 | C |

-continued

| Cpd No. | Activity Category | Cpd No. | Activity Category | Cpd No. | Activity Category | Cpd No. | Activity Category |
|---|---|---|---|---|---|---|---|
| SC-228 | A | SC-266 | A | SC-402 | B | SC-437 | B |
| SC-229 | B | SC-267 | A | SC-403 | B | SC-438 | A |
| SC-230 | B | SC-268 | B | SC-404 | B | SC-439 | C |
| SC-231 | B | SC-269 | A | SC-405 | B | SC-440 | B |
| SC-233 | C | SC-270 | B | SC-406 | A | SC-441 | B |
| SC-234 | C | SC-271 | B | SC-407 | B | SC-442 | C |
| SC-235 | C | SC-330 | B | SC-408 | B | SC-444 | B |
| SC-236 | B | SC-331 | A | SC-409 | B | SC-445 | C |
| SC-237 | B | SC-332 | B | SC-410 | C | SC-446 | B |
| SC-238 | B | SC-333 | A | SC-411 | C | SC-447 | A |
| SC-239 | B | SC-334 | B | SC-412 | B | SC-449 | B |
| SC-240 | C | SC-335 | C | SC-413 | B | SC-450 | C |
| SC-241 | B | SC-336 | C | SC-414 | B | SC-451 | C |
| SC-242 | C | SC-337 | A | SC-415 | B | | |
| SC-243 | A | SC-338 | B | SC-416 | B | | |
| SC-244 | B | SC-339 | A | SC-417 | A | | |
| SC-245 | B | SC-340 | A | SC-418 | A | | |
| SC-246 | A | SC-341 | C | SC-419 | A | | |
| SC-247 | B | SC-342 | B | SC-420 | B | | |
| SC-248 | B | SC-343 | B | SC-421 | B | | |
| SC-249 | B | SC-344 | B | SC-422 | B | | |
| SC-251 | C | SC-345 | A | SC-423 | C | | |
| SC-252 | B | SC-346 | B | SC-424 | B | | |

* %-Inhib (CaV2.2) @3 µM @30 mM KCl: "A": %-Inhibition >95%; "B": %-Inhibition >75% up to ≤95%; "C": %-Inhibition >40% up to ≤75%; "D": %-Inhibition >30% up to ≤40%.

2.2 Electrophysiological Assessment of Calcium Channel Activity

Patch-clamp recordings were performed using HEK293 cells stably expressing human Cav2.2. Cells were plated in T150 flasks and grown a humidified incubator at 37° C. and under 5% $CO_2$ to approximately 50-60% confluency. Cells were maintained at 30° C. for 48 hrs prior to recording. On the day of the experiment, cells were harvested with TrypLE cell detachment solution (Invitrogen) diluted to 25% with phosphate buffered saline and maintained in 50% cell culture media, 50% NaCl based external saline (in mM, 140 NaCl, 4 KCl, 1 $MgCl_2$, 2 $CaCl_2$, 5 Glucose, 10 HEPES, pH 7.4) up to several hours prior to experiment.

Currents were recorded at RT (21-23° C.) using the Patchliner planar array technology (Nanion). Patchliner is a multi-well whole-cell automated patch clamp device that operates asynchronously with fully integrated fluidics. Capacitance and series resistance compensation was automated and no correction for liquid junction potential was employed. Leak was subtracted on-line. Whole-cell patch-clamp recordings were obtained using extracellular saline consisting of (mM): 145 TEA-Cl, 10 $BaCl_2$, 10 HEPES, 10 Glucose. The pH was adjusted to 7.35 with NaOH and the osmolarity was adjusted to 310 mOsm with sucrose. Intracellular solution consisted of (mM): 50 CsCl, 60 CsF, 10 NaCl, 20 EGTA, 5 BAPTA, 10 HEPES. Prior to an experiment, 5 mM MgATP and 0.3 NaGTP were added, the pH was adjusted to 7.2 with CsOH and the osmolarity was adjusted to 290 mOsm with sucrose.

A voltage pulse protocol was utilised to assess compound inhibition. Cells were held at a holding potential of −60 mV and channels were activated using a 10 ms test pulse to +30 mV activated every 10 seconds (0.1 Hz). Increasing concentrations of compound were applied to individual cells with 5 minutes at each test concentration. Compounds were prepared in DMSO as 10 mM stock solutions and subsequent 1:3 serial dilutions performed. Final dilution of 1:1000 in external solution resulted in a final DMSO concentration of 0.1%. For each cell, current responses were normalised to dimethyl sulfoxide vehicle control to generate concentration-response curves. When multiple doses were achieved per cell, $IC_{50}$ values were calculated from the fits of the Hill equation to the data. The form of the Hill equation used was: Relative current=$(100/(1+(IC_{50}/conc)^{Slope}))$. A selection of the foregoing exemplified compounds was tested under these conditions: Several compounds are potent inhibitors ($IC_{50}$<5 µM) or even very potent inhibitors ($IC_{50}$<2 µM).

The invention claimed is:
1. A method for the treatment and/or prophylaxis of one or more disorders selected from the group consisting of pain; stroke; mood disorders; epilepsy; and schizophrenia, said method comprising administering to a subject in need thereof of an effective amount therefor of at least one compound of formula (I),

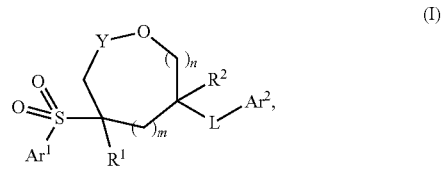

(I)

wherein
m represents 1 or 2;
n denotes 0 or 1;
Y is selected from the group consisting of bond and —$C(R^3)_2$—;
  wherein each $R^3$ is independently selected from the group consisting of H and $C_{1-6}$-alkyl, or two $R^3$ form together with the C-atom connecting them a $C_{3-10}$-cycloalkyl or a 3 to 7 membered heterocyclyl;
L is —$[C(R^4)_2]_x$—$(X)_y$—$[C(R^4)_2]_z$—,
  wherein x is 0, 1 or 2, y is 0 or 1 and z is 0 or 1, with the proviso that x≥y;
  each $R^4$ is independently selected from the group consisting of H and $C_{1-6}$-alkyl, or two $R^4$ form together with the C-atom connecting them a $C_{3-10}$-cycloalkyl or a 3 to 7 membered heterocyclyl or two $R^4$ form together with two adjacent C-atoms connecting them a $C_{3-10}$-cycloalkyl or a 3 to 7 membered heterocyclyl,
X is selected from the group consisting of O, S, $S(O)_2$, N(H) or N($C_{1-6}$-alkyl);
$R^1$ is selected from the group consisting of H; F; Cl; CN; $C_{1-6}$-alkyl; $C_{1-6}$-alkyl-O($R^5$) and $C_{1-6}$-alkyl-N($R^5$)$_2$;

wherein each R⁵ is independently selected from H or C₁₋₆-alkyl or two R⁵ form together with the N-atom connecting them a 3 to 7 membered heterocyclyl;

R² is selected from the group consisting of H; F; Cl; CN; C₁₋₆-alkyl; C₁₋₆-alkyl-O(R⁶) and C₁₋₆-alkyl-N(R⁶)₂;
wherein each R⁶ is independently selected from H or C₁₋₆-alkyl or two R⁶ form together with the N-atom connecting them a 3 to 7 membered heterocyclyl;

Ar¹ represents aryl or heteroaryl, wherein said aryl or said heteroaryl is substituted by zero or one or two or three substituents R⁷, Ar² represents heteroaryl, substituted by zero or one or two or three substituents R⁸, wherein each R⁷ and each R⁸ is independently selected from the group consisting of F; Cl; Br; I; NO₂; CN; C₁₋₆-alkyl; CF₃; CF₂H; CFH₂; CF₂Cl; CFCl₂; C(=O)—H; C(=O)—C₁₋₆-alkyl; C(=O)—OH; C(=O)—O—C₁₋₆-alkyl; C(=O)—N(H)(OH); C(=O)—NH₂; C(=O)—N(H)(C₁₋₆-alkyl); C(=O)—N(C₁₋₆-alkyl)₂; C(=N—OH)—H; C(=N—OH)—C₁₋₆-alkyl; C(=N—O—C₁₋₆-alkyl)-H; C(=N—O—C₁₋₆-alkyl)-C₁₋₆-alkyl; OH; OCF₃; OCF₂H; OCFH₂; OCF₂Cl; OCFCl₂; O—C₁₋₆-alkyl; O—C(=O)—C₁₋₆-alkyl; O—C(=O)—O—C₁₋₆-alkyl; O—(C=O)—N(H)(C₁₋₆-alkyl); O—C(=O)—N(C₁₋₆-alkyl)₂; O—S(=O)₂—C₁₋₆-alkyl; O—S(=O)₂—OH; O—S(=O)₂—O—C₁₋₆-alkyl; O—S(=O)₂—NH₂; O—S(=O)₂—N(H)(C₁₋₆-alkyl); O—S(=O)₂—N(C₁₋₆-alkyl)₂; NH₂; N(H)(C₁₋₆-alkyl); N(C₁₋₆-alkyl)₂; N(H)—C(=O)—C₁₋₆-alkyl; N(H)—C(=O)—O—C₁₋₆-alkyl; N(H)—C(=O)—NH₂; N(H)—C(=O)—N(H)(C₁₋₆-alkyl); N(H)—C(=O)—N(C₁₋₆-alkyl)₂; N(C₁₋₆-alkyl)-C(=O)—C₁₋₆-alkyl; N(C₁₋₆-alkyl)-C(=O)—O—C₁₋₆-alkyl; N(C₁₋₆-alkyl)-C(=O)—NH₂; N(C₁₋₆-alkyl)-C(=O)—N(H)(C₁₋₆-alkyl); N(C₁₋₆-alkyl)-C(=O)—N(C₁₋₆-alkyl)₂; N(H)—S(=O)₂OH; N(H)—S(=O)₂—C₁₋₆-alkyl; N(H)—S(=O)₂—O—C₁₋₆-alkyl; N(H)—S(=O)₂—NH₂; N(H)—S(=O)₂—N(H)(C₁₋₆-alkyl); N(H)—S(=O)₂N(C₁₋₆-alkyl)₂; N(C₁₋₆-alkyl)-S(=O)₂—OH; N(C₁₋₆-alkyl)-S(=O)₂—C₁₋₆-alkyl; N(C₁₋₆-alkyl)-S(=O)₂—O—C₁₋₆-alkyl; N(C₁₋₆-alkyl)-S(=O)₂—NH₂; N(C₁₋₆-alkyl)-S(=O)₂—N(H)(C₁₋₆-alkyl); N(C₁₋₆-alkyl)-S(=O)₂—N(C₁₋₆-alkyl)₂; SH; SCF₃; SCF₂H; SCFH₂; SCF₂Cl; SCFCl₂; S—C₁₋₆-alkyl; S(=O)—C₁₋₆-alkyl; S(=O)₂—C₁₋₆-alkyl; S(=O)₂—OH; S(=O)₂—O—C₁₋₆-alkyl; S(=O)₂—NH₂; S(=O)₂—N(H)(C₁₋₆-alkyl); S(=O)₂—N(C₁₋₆-alkyl)₂; C₃₋₁₀-cycloalkyl; 3 to 7 membered heterocyclyl; aryl; heteroaryl; O—C₃₋₁₀-cycloalkyl; O-(3 to 7 membered heterocyclyl); O-aryl; O-heteroaryl; N(H)—C₃₋₁₀-cycloalkyl; N(H)-(3 to 7 membered heterocyclyl); N(H)-aryl; N(H)-heteroaryl; N(C₁₋₆-alkyl)-C₃₋₁₀-cycloalkyl; N(C₁₋₆-alkyl)-(3 to 7 membered heterocyclyl); N(C₁₋₆-alkyl)-aryl; N(C₁₋₆-alkyl)-heteroaryl; C(=O)—C₃₋₁₀-cycloalkyl; C(=O)-(3 to 7 membered heterocyclyl); C(=O)-aryl; C(=O)-heteroaryl; S(=O)₂—C₃₋₁₀-cycloalkyl; S(=O)₂-(3 to 7 membered heterocyclyl); S(=O)₂-aryl; S(=O)₂-heteroaryl; S(=O)(=NR¹³)—C₃₋₁₀-cycloalkyl; S(=O)(=NR¹³)-(3 to 7 membered heterocyclyl); S(=O)(=NR¹³)-aryl and S(=O)(=NR¹³)-heteroaryl, wherein R¹³ represents H or C₁₋₆-alkyl;

wherein in each case said C₁₋₆-alkyl may be branched or unbranched; unsubstituted or mono- or polysubstituted; and wherein in each case said C₃₋₁₀-cycloalkyl, 3 to 7 membered heterocyclyl aryl and heteroaryl may be unsubstituted or mono- or polysubstituted;

optionally in the form of a single stereoisomer or a mixture of stereoisomers, in form of the free compound and/or a physiologically acceptable salt.

2. The method according to claim 1, wherein the compound of formula (I) is a compound according to formula (II),

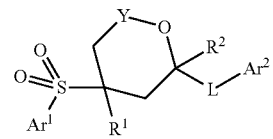

or formula (IIa) or (IIb),

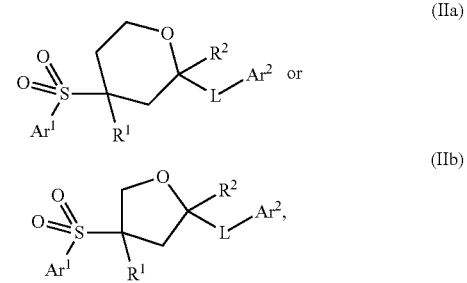

wherein each Ar¹, Ar², R¹, R², Y and L are defined according to claim 1.

3. The method according to claim 1, wherein the compound of formula (I) is one diastereomer.

4. The method according to claim 3, wherein the compound of formula (I) is one enantiomer.

5. The method according to claim 1, wherein in the compound of formula (I)
R² represents H, CH₃, C₂H₅, CH₂CH₂CH₃, CH(CH₃)₂, CH₂OH, CH₂OCH₃, CH₂NH₂, CH₂N(H)CH₃ or CH₂N(CH₃)₂.

6. The method according to claim 1, wherein in the compound of formula (I)
R¹ represents H, CH₃, C₂H₅, CH₂CH₂CH₃, CH(CH₃)₂, CH₂OH, CH₂OCH₃, CH₂NH₂, CH₂N(H)CH₃ or CH₂N(CH₃)₂.

7. The method according to claim 1, wherein in the compound of formula (I) Ar¹ represents phenyl or pyridinyl, substituted by zero or one or two or three substituents R⁷,
wherein each R⁷ is independently selected from the group consisting of F; Cl; CN; C₁₋₆-alkyl; CF₃; CF₂H; CFH₂; C(=O)—C₁₋₆-alkyl; C(=O)—OH; C(=O)—O—C₁₋₆-alkyl; C(=O)—N(H)(OH); C(=O)—NH₂; C(=O)—N(H)(C₁₋₆-alkyl); C(=O)—N(C₁₋₆-alkyl)₂; OH; OCF₃; OCF₂H; OCFH₂; OCF₂Cl; OCFCl₂; O—C₁₋₆-alkyl; NH₂; N(H)(C₁₋₆-alkyl); N(C₁₋₆-alkyl)₂; N(H)—C(=O)—C₁₋₆-alkyl; N(C₁₋₆-alkyl)-C(=O)—C₁₋₆-alkyl; N(H)—S(=O)₂—C₁₋₆-alkyl; SCF₃; S—C₁₋₆-alkyl; S(=O)—C₁₋₆-alkyl; S(=O)₂—C₁₋₆-alkyl; S(=O)₂—NH₂; S(=O)₂—N(H)(C₁₋₆-alkyl); S(=O)₂—N(C₁₋₆-alkyl)₂; C₃₋₁₀-cycloalkyl; 3 to 7 membered heterocyclyl; O—C$_{3-10}$-cycloalkyl and O-(3 to 7 membered heterocyclyl).

8. The method according to claim 1, wherein in the compound of formula (I) Ar$^1$ is represented by subformula SF-I

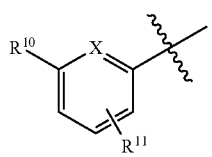

(SF-I)

wherein

X is CH or N,

R$^{10}$ is selected from the group consisting of CF$_3$; CF$_2$H; CFH$_2$; OCF$_3$; OCF$_2$H and OCFH$_2$; and R$^{11}$ is selected from the group consisting of H; F; Cl; CN; CH$_3$; CH$_2$CH$_3$; CH$_2$CH$_2$CH$_3$; CH(CH$_3$)$_2$; CH(CH$_3$)CH$_2$CH$_3$; CH$_2$CH$_2$CH$_2$CH$_3$; CH$_2$CH(CH$_3$)$_2$; C(CH$_3$)$_3$; CF$_3$; CF$_2$H; CFH$_2$; OCF$_3$; OCH$_3$; OCH$_2$CH$_3$; OCH(CH$_3$)$_2$; S(=O)—CH$_3$ and S(=O)$_2$—CH$_3$.

9. The method according to claim 1, wherein in the compound of formula (I) L is bond, CH$_2$; C(CH$_3$)$_2$; CH(CH$_3$); CH$_2$CH$_2$; CH$_2$C(CH$_3$)$_2$; C(CH$_3$)$_2$CH$_2$; CH$_2$O; C(CH$_3$)$_2$O; CH(CH$_3$)O;

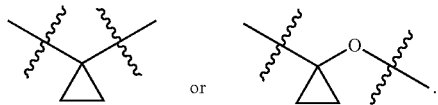 [SMILES: *C1(*)CC1 ; *OC1(*)CC1]

10. The method according to claim 1, wherein in the compound of formula (I) Ar$^2$ represents pyridinyl, pyrazinyl, pyridazinyl, pyrimidinyl, oxazolyl, isoxazolyl and oxadiazolyl, each substituted by zero, one or two substituents R$^8$, wherein each R$^8$ is independently selected from the group consisting of F; Cl; CN; C$_{1-6}$-alkyl; CF$_3$; CF$_2$H; CFH$_2$; OCF$_3$; OCF$_2$H; OCFH$_2$; O—C$_{1-6}$-alkyl; S—C$_{1-6}$-alkyl; S(=O)—C$_{1-6}$-alkyl; S(=O)$_2$—C$_{1-6}$-alkyl; C$_{3-10}$-cycloalkyl; 3 to 7 membered heterocyclyl; aryl; heteroaryl; O—C$_{3-10}$-cycloalkyl; O-(3 to 7 membered heterocyclyl); O-aryl; O-heteroaryl; C(=O)—C$_{3-10}$-cycloalkyl; C(=O)-(3 to 7 membered heterocyclyl); C(=O)-aryl; C(=O)-heteroaryl; S(=O)$_2$—C$_{3-10}$-cycloalkyl; S(=O)$_2$-(3 to 7 membered heterocyclyl); S(=O)$_2$-aryl; S(=O)$_2$-heteroaryl; S(=O)(=NR$^{13}$)—C$_{3-10}$-cycloalkyl; S(=O)(=NR$^{13}$)-(3 to 7 membered heterocyclyl); S(=O)(=NR$^{13}$)-aryl and S(=O)(=NR$^{13}$)-heteroaryl, wherein R$^{13}$ represents H or C$_{1-6}$-alkyl.

11. The method according to claim 1, wherein in the compound of formula (I) Ar$^2$ is selected from the group consisting of pyridinyl, pyrazinyl, pyrimidinyl, pyrazolyl, oxazolyl, isoxazolyl and oxadiazolyl, each substituted by zero, one or two substituents R$^8$, wherein each R$^8$ is selected from the group consisting of F; Cl; CN; CH$_3$; CH$_2$CH$_3$; CH$_2$CH$_2$CH$_3$; CH(CH$_3$)$_2$; CF$_3$; CF$_2$H; CFH$_2$; OCF$_3$; OCF$_2$H; OCFH$_2$; OCH$_3$; OCH$_2$CH$_3$; OCH(CH$_3$)$_2$; S(=O)CH$_3$; S(=O)$_2$CH$_3$; S(=O)$_2$CH$_2$CH$_3$; S(=O)$_2$CH$_2$CH$_3$; cyclopropyl and O-cyclopropyl.

12. The method according to claim 1, the compound of formula (I) is selected from the group consisting of:

1  3-Methylsulfonyl-5-[4-methyl-4-[[3-(trifluoromethyl)phenyl]sulfonyl]-tetrahydro-pyran-2-yl]-pyridine
2  5-Cyclopropyl-2-[4-methyl-4-[[3-(trifluoromethyl)phenyl]sulfonyl]-tetrahydro-pyran-2-yl]-pyridine
3  5-Methylsulfonyl-2-[4-methyl-4-[[3-(trifluoromethyl)phenyl]sulfonyl]-tetrahydro-pyran-2-yl]-pyridine
4  2-[4-Ethyl-4-[[3-(trifluoromethyl)phenyl]sulfonyl]-tetrahydro-pyran-2-yl]-5-(trifluoromethyl)-pyridine
5  5-[4-Ethyl-4-[[3-(trifluoromethyl)phenyl]sulfonyl]-tetrahydro-pyran-2-yl]-3-(trifluoromethyl)-[1,2,4]oxadiazole
6  3-Cyclopropyl-5-[4-ethyl-4-[[3-(trifluoromethyl)phenyl]sulfonyl]-tetrahydro-pyran-2-yl]-[1,2,4]oxadiazole
7  2-Cyclopropyl-5-[4-methyl-4-[[3-(trifluoromethyl)phenyl]sulfonyl]-tetrahydro-pyran-2-yl]-pyrimidine
8  2-Cyclopropyl-5-[4-ethyl-4-[[3-(trifluoromethyl)phenyl]sulfonyl]-tetrahydro-pyran-2-yl]-[1,3,4]oxadiazole
9  2-Isopropoxy-5-[4-methyl-4-[[3-(trifluoromethyl)phenyl]sulfonyl]-tetrahydro-pyran-2-yl]-pyridine
10  2-[4-Ethyl-4-[[3-(trifluoromethyl)phenyl]sulfonyl]-tetrahydro-pyran-2-yl]-6-methyl-pyridine
11  5-[4-Methyl-4-[[3-(trifluoromethyl)phenyl]sulfonyl]-tetrahydro-pyran-2-yl]-2-(trifluoromethyl)-pyrimidine
12  2-[4-Methyl-4-[[3-(trifluoromethyl)phenyl]sulfonyl]-tetrahydro-pyran-2-yl]-5-(trifluoromethyl)-pyridine
13  3-[4-Ethyl-4-[[3-(trifluoromethyl)phenyl]sulfonyl]-tetrahydro-pyran-2-yl]-2-methyl-pyridine
14  5-[4-Methyl-4-[[3-(trifluoromethyl)phenyl]sulfonyl]-tetrahydro-pyran-2-yl]-2-(trifluoromethyl)-pyridine
15  3-[4-Ethyl-4-[[3-(trifluoromethyl)phenyl]sulfonyl]-tetrahydro-pyran-2-yl]-2,6-dimethyl-pyridine
16  2-[4-Ethyl-4-[[3-(trifluoromethyl)phenyl]sulfonyl]-tetrahydro-pyran-2-yl]-6-methyl-pyridine
17  3-Cyclopropyl-5-[4-methyl-4-[[3-(trifluoromethyl)phenyl]sulfonyl]-tetrahydro-pyran-2-yl]-pyridine
18  2-Cyclopropyl-5-[4-methyl-4-[[3-(trifluoromethyl)phenyl]sulfonyl]-tetrahydro-pyran-2-yl]-pyrazine
19  5-Cyclopropyl-3-[4-methyl-4-[[3-(trifluoromethyl)phenyl]sulfonyl]-tetrahydro-pyran-2-yl]-[1,2,4]oxadiazole
20 2-Methyl-5-[[4-methyl-4-[[3-(trifluoromethyl)phenyl]sulfonyl]-tetrahydro-pyran-2-yl]-methoxy]-pyridine
21  3-[4-Methyl-4-[[3-(trifluoromethyl)phenyl]sulfonyl]-tetrahydro-pyran-2-yl]-5-(trifluoromethyl)-pyridine
22  2-Cyclopropyl-5-[[4-methyl-4-[[3-(trifluoromethyl)phenyl]sulfonyl]-tetrahydro-pyran-2-yl]-methoxy]-pyridine
23 3-Fluoro-5-methylsulfonyl-2-[4-methyl-4-[[3-(trifluoromethyl)phenyl]sulfonyl]-tetrahydro-pyran-2-yl]-pyridine
24  2-[4-Methyl-4-[[3-(trifluoromethyl)phenyl]sulfonyl]-tetrahydro-pyran-2-yl]-5-(trifluoromethyl)-[1,3,4]oxadiazole
25  2-(Difluoro-methyl)-5-[4-methyl-4-[[3-(trifluoromethyl)phenyl]sulfonyl]-tetrahydro-pyran-2-yl]-[1,3,4]oxadiazole
26  2-Isopropyl-5-[4-methyl-4-[[3-(trifluoromethyl)phenyl]sulfonyl]-tetrahydro-pyran-2-yl]-[1,3,4]oxadiazole
27  2-Cyclopropyl-5-[4-methyl-4-[[3-(trifluoromethyl)phenyl]sulfonyl]-tetrahydro-pyran-2-yl]-[1,3,4]oxadiazole
28 3-Chloro-5-methylsulfonyl-2-[4-methyl-4-[[3-(trifluoromethyl)phenyl]sulfonyl]-tetrahydro-pyran-2-yl]-pyridine 29  2-Cyclopropyl-5-[[4-methyl-4-[[3-(trifluoromethyl)phenyl]sulfonyl]-tetrahydro-pyran-2-yl]-methoxy]-pyrazine
30  3-Chloro-2-(4-methyl-4-((3-(trifluoromethyl)phenyl)sulfonyl)tetrahydrofuran-2-yl)-5-(methylsulfonyl)pyridine
31  3-Methyl-2-(4-methyl-4-((3-(trifluoromethyl)phenyl)sulfonyl)tetrahydrofuran-2-yl)-5-(methylsulfonyl)pyridine
32  4-Cyclopropyl-2-[4-methyl-4-[[3-(trifluoromethyl)phenyl]sulfonyl]-tetrahydro-pyran-2-yl]-oxazole
33  5-[[4-Methyl-4-[[3-(trifluoromethyl)phenyl]sulfonyl]-tetrahydro-pyran-2-yl]-methoxy]-2-(trifluoromethyl)-pyridine
34  2-[4-Methyl-4-[(3-methylsulfonyl-phenyl)sulfonyl]-tetrahydro-pyran-2-yl]-3-methylsulfonyl-5-(trifluoromethyl)-pyridine
35  2-[4-[[3-(Difluoro-methyl)-phenyl]sulfonyl]-4-methyl-tetrahydro-pyran-2-yl]-3-methylsulfonyl-5-(trifluoromethyl)-pyridine
36  3-Chloro-2-[4-[[3-fluoro-5-(trifluoromethyl)-phenyl]sulfonyl]-4-methyl-tetrahydro-pyran-2-yl]-5-methylsulfonyl-pyridine
37  3-Chloro-2-[4-[[3-(difluoro-methyl)-5-fluoro-phenyl]sulfonyl]-4-methyl-tetrahydro-pyran-2-yl]-5-methylsulfonyl-pyridine
38  3-Chloro-5-methylsulfonyl-2-[4-methyl-4-[[3-(trifluoromethyloxy)-phenyl]sulfonyl]-tetrahydro-pyran-2-yl]-pyridine
39  3-Methylsulfonyl-2-[4-methyl-4-[[3-(trifluoromethyloxy)-phenyl]sulfonyl]-tetrahydro-pyran-2-yl]-5-(trifluoromethyl)-pyridine
40  5-Methylsulfonyl-2-[4-methyl-4-[[3-(trifluoromethyl)phenyl]sulfonyl]-tetrahydro-pyran-2-yl]-3-(trifluoromethyl)-pyridine
41  3-Methoxy-5-methylsulfonyl-2-[4-methyl-4-[[3-(trifluoromethyl)phenyl]sulfonyl]-tetrahydro-pyran-2-yl]-pyridine
42  5-Chloro-3-methylsulfonyl-2-[4-methyl-4-[[3-(trifluoromethyl)phenyl]sulfonyl]-tetrahydro-pyran-2-yl]-pyridine
43  3-(Methylsulfinyl)-2-[4-methyl-4-[[3-(trifluoromethyl)phenyl]sulfonyl]-tetrahydro-pyran-2-yl]-5-(trifluoromethyl)-pyridine
44  3-Chloro-5-(methylsulfinyl)-2-[4-methyl-4-[[3-(trifluoromethyl)phenyl]sulfonyl]-tetrahydro-pyran-2-yl]-pyridine
45  3-Chloro-5-(difluoro-methyl)-2-[4-methyl-4-[[3-(trifluoromethyl)phenyl]sulfonyl]-tetrahydro-pyran-2-yl]-pyridine
46  5-Cyclopropyl-3-[4-ethyl-4-[[3-(trifluoromethyl)phenyl]sulfonyl]-tetrahydro-pyran-2-yl]-[1,2,4]oxadiazole
47  2-[4-Ethyl-4-[[3-(trifluoromethyl)phenyl]sulfonyl]-tetrahydro-pyran-2-yl]-5-(trifluoromethyl)-[1,3,4]oxadiazole
48  5-Chloro-2-[4-methyl-4-[[3-(trifluoromethyl)phenyl]sulfonyl]-tetrahydro-pyran-2-yl]-pyridine
49  2,4-Dimethoxy-5-[4-methyl-4-[[3-(trifluoromethyl)phenyl]sulfonyl]-tetrahydro-pyran-2-yl]-pyridine
50  2-Methoxy-4-methyl-5-[4-methyl-4-[[3-(trifluoromethyl)phenyl]sulfonyl]-tetrahydro-pyran-2-yl]-pyridine
51  2-Methoxy-5-[4-methyl-4-[[3-(trifluoromethyl)phenyl]sulfonyl]-tetrahydro-pyran-2-yl]-pyridin-4-ol
52  4-(Difluoro-methoxy)-2-methoxy-5-[4-methyl-4-[[3-(trifluoromethyl)phenyl]sulfonyl]-tetrahydro-pyran-2-yl]-pyridine
53  3-Fluoro-2-methoxy-5-[4-methyl-4-[[3-(trifluoromethyl)phenyl]sulfonyl]-tetrahydro-pyran-2-yl]-pyridine
54  4-Fluoro-2-methoxy-5-[4-methyl-4-[[3-(trifluoromethyl)phenyl]sulfonyl]-tetrahydro-pyran-2-yl]-pyridine
55  2-Methoxy-5-[4-methyl-4-[[3-(trifluoromethyl)phenyl]sulfonyl]-tetrahydro-pyran-2-yl]-isonicotinonitrile
56  3-Methyl-5-methylsulfonyl-2-[4-methyl-4-[[3-(trifluoromethyl)phenyl]sulfonyl]-tetrahydro-pyran-2-yl]-pyridine
57  3-Chloro-2-[4-[[3-(difluoro-methyl)-phenyl]sulfonyl]-4-methyl-tetrahydro-pyran-2-yl]-5-methylsulfonyl-pyridine
58  5-(difluoromethoxy)-2-(4-methyl-4-((3-(trifluoromethyl)phenyl)sulfonyl)tetrahydro-2H-pyran-2-yl)-3-(methylsulfonyl)pyridine
59  3-(difluoromethoxy)-2-(4-methyl-4-((3-(trifluoromethyl)phenyl)sulfonyl)tetrahydro-2H-pyran-2-yl)-5-(methylsulfonyl)pyridine
60  3-cyclopropyl-2-(4-methyl-4-(3-(trifluoromethyl)phenylsulfonyl)tetrahydro-2H-pyran-2-yl)-5-(methylsulfonyl)pyridine
61  Dimethyl-[5-[4-methyl-4-[[3-(trifluoromethyl)phenyl]sulfonyl]-tetrahydro-pyran-2-yl]-pyridin-2-yl]-amine
62  2-Cyclopropyl-5-[4-ethyl-4-[[3-(trifluoromethyl)phenyl]sulfonyl]-tetrahydro-pyran-2-yl]-pyrazine
63  2,6-Dimethyl-3-[4-[[3-(trifluoromethyl)phenyl]sulfonyl]-tetrahydro-pyran-2-yl]-pyridine
64  2-Methylsulfonyl-5-[4-methyl-4-[[3-(trifluoromethyl)phenyl]sulfonyl]-tetrahydro-pyran-2-yl]-pyridine
65  2-Bromo-5-[4-methyl-4-[[3-(trifluoromethyl)phenyl]sulfonyl]-tetrahydro-pyran-2-yl]-pyridine
67  2-Isopropoxy-5-[4-[[3-(trifluoromethyl)phenyl]sulfonyl]-tetrahydro-pyran-2-yl]-pyridine
68  3-Chloro-2-[4-methyl-4-[[3-(trifluoromethyl)phenyl]sulfonyl]-tetrahydro-pyran-2-yl]-5-(trifluoromethyl)-pyridine
69  2-Methyl-6-[4-[[3-(trifluoromethyl)phenyl]sulfonyl]-tetrahydro-pyran-2-yl]-pyridine
70  2-(Trifluoromethyl)-5-[4-[[3-(trifluoromethyl)phenyl]sulfonyl]-tetrahydro-pyran-2-yl]-pyridine
71  1-Methyl-5-[4-methyl-4-[[3-(trifluoromethyl)phenyl]sulfonyl]-tetrahydro-pyran-2-yl]-3-(trifluoromethyl)-1H-pyrazole
72  2-Cyclopropyl-5-[4-methyl-4-[[3-(trifluoromethyl)phenyl]sulfonyl]-tetrahydro-pyran-2-yl]-pyridine
74  2-(Trifluoromethyl)-6-[4-[[3-(trifluoromethyl)phenyl]sulfonyl]-tetrahydro-pyran-2-yl]-pyridine
75  2-[4-Methyl-4-[[3-(trifluoromethyl)phenyl]sulfonyl]-tetrahydro-pyran-2-yl]-6-(trifluoromethyl)-pyridine
76  2-Methoxy-5-[4-methyl-4-[[3-(trifluoromethyl)phenyl]sulfonyl]-tetrahydro-pyran-2-yl]-pyridine
77  3-Methylsulfonyl-2-[4-methyl-4-[[3-(trifluoromethyl)phenyl]sulfonyl]-tetrahydro-pyran-2-yl]-5-(trifluoromethyl)-pyridine
78  5-[4-Methyl-4-[[3-(trifluoromethyl)phenyl]sulfonyl]-tetrahydro-pyran-2-yl]-2-pyrrolidin-1-yl-pyridine
79  5-[4-Methyl-4-[[3-(trifluoromethyl)phenyl]sulfonyl]-tetrahydro-pyran-2-yl]-2-(1H-[1,2,4]triazol-1-yl)-pyridine
80  2-(2-Methoxy-ethoxy)-5-[4-methyl-4-[[3-(trifluoromethyl)phenyl]sulfonyl]-tetrahydro-pyran-2-yl]-pyridine
81  Methyl-[5-[4-methyl-4-[[3-(trifluoromethyl)phenyl]sulfonyl]-tetrahydro-pyran-2-yl]-pyridin-2-yl]-amine
82  2-Methoxy-5-[4-methyl-4-[[3-(trifluoromethyl)phenyl]sulfonyl]-tetrahydro-pyran-2-yl]-pyrimidine 83 Dimethyl-[5-[4-methyl-4-[[3-(trifluoromethyl)phenyl]sulfonyl]-tetrahydro-pyran-2-yl]-pyrimidin-2-yl]-amine
84 2-Methoxy-5-[4-methyl-4-[[3-(trifluoromethyl)phenyl]sulfonyl]-tetrahydro-pyran-2-yl]-pyrazine
85 2-(Difluoro-methoxy)-5-[4-methyl-4-[[3-(trifluoromethyl)phenyl]sulfonyl]-tetrahydro-pyran-2-yl]-pyridine
86 Dimethyl-[5-[4-methyl-4-[[3-(trifluoromethyl)phenyl]sulfonyl]-tetrahydro-pyran-2-yl]-pyrazin-2-yl]-amine
87 5-Methoxy-2-[4-methyl-4-[[3-(trifluoromethyl)phenyl]sulfonyl]-tetrahydro-pyran-2-yl]-pyrimidine
88 3-Chloro-5-cyclopropyl-2-[4-methyl-4-[[3-(trifluoromethyl)phenyl]sulfonyl]-tetrahydro-pyran-2-yl]-pyridine
89 3-Chloro-5-(difluoro-methoxy)-2-[4-methyl-4-[[3-(trifluoromethyl)phenyl]sulfonyl]-tetrahydro-pyran-2-yl]-pyridine
90 1-Methyl-3-methylsulfonyl-5-[4-methyl-4-[[3-(trifluoromethyl)phenyl]sulfonyl]-tetrahydro-pyran-2-yl]-1H-pyrazole
91 3-Cyclopropyl-1-methyl-5-[4-methyl-4-[[3-(trifluoromethyl)phenyl]sulfonyl]-tetrahydro-pyran-2-yl]-1H-pyrazole
92 3-Chloro-2-[4-[[3-(difluoro-methoxy)-phenyl]sulfonyl]-4-methyl-tetrahydro-pyran-2-yl]-5-methylsulfonyl-pyridine
93 3-Chloro-2-[4-[(3-chlorophenyl)sulfonyl]-4-methyl-tetrahydro-pyran-2-yl]-5-methylsulfonyl-pyridine
94 3-Methyl-5-methylsulfonyl-2-[4-methyl-4-[[3-(trifluoromethyl)phenyl]sulfonyl]-tetrahydro-pyran-2-yl]-pyridine
95 2-[4-[[3-(Difluoro-methyl)-5-fluoro-phenyl]sulfonyl]-4-methyl-tetrahydro-pyran-2-yl]-3-methyl-5-methylsulfonyl-pyridine
96 2-[4-[[3-Fluoro-5-(trifluoromethyl)-phenyl]sulfonyl]-4-methyl-tetrahydro-pyran-2-yl]-3-methyl-5-methylsulfonyl-pyridine
97 3-Chloro-2-[4-[(3-isopropyl-phenyl)sulfonyl]-4-methyl-tetrahydro-pyran-2-yl]-5-methylsulfonyl-pyridine
98 3-Methyl-5-methylsulfonyl-2-[4-methyl-4-[[3-(trifluoromethyloxy)-phenyl]sulfonyl]-tetrahydro-pyran-2-yl]-pyridine
99 3-[[2-(3-Chloro-5-methylsulfonyl-pyridin-2-yl)-4-methyl-tetrahydro-pyran-4-yl]sulfonyl]-benzonitrile
100 [(5-Methyl-isoxazol-3-yl)-methyl]-[5-[4-methyl-4-[[3-(trifluoromethyl)phenyl]sulfonyl]-tetrahydro-pyran-2-yl]-pyridin-2-yl]-amine
101 7-[5-[4-Methyl-4-[[3-(trifluoromethyl)phenyl]sulfonyl]-tetrahydro-pyran-2-yl]-pyridin-2-yl]-2-oxa-7-azaspiro[3.5]nonane
102 2-[Methyl-[5-[4-methyl-4-[[3-(trifluoromethyl)phenyl]sulfonyl]-tetrahydro-pyran-2-yl]-pyridin-2-yl]-amino]-ethanol
103 [(5-Methyl-isoxazol-3-yl)-methyl]-[6-[4-methyl-4-[[3-(trifluoromethyl)phenyl]sulfonyl]-tetrahydro-pyran-2-yl]-pyridin-2-yl]-amine
104 7-[6-[4-Methyl-4-[[3-(trifluoromethyl)phenyl]sulfonyl]-tetrahydro-pyran-2-yl]-pyridin-2-yl]-2-oxa-7-azaspiro[3.5]nonane
105 [6-[4-Methyl-4-[[3-(trifluoromethyl)phenyl]sulfonyl]-tetrahydro-pyran-2-yl]-pyridin-2-yl]-tetrahydro-pyran-4-yl-amine
106 2-[Methyl-[6-[4-methyl-4-[[3-(trifluoromethyl)phenyl]sulfonyl]-tetrahydro-pyran-2-yl]-pyridin-2-yl]-amino]-ethanol
107 2-[Methyl-[5-[4-methyl-4-[[3-(trifluoromethyl)phenyl]sulfonyl]-tetrahydro-pyran-2-yl]-pyridin-2-yl]-amino]-ethanol
108 Cyclopropyl-[6-[4-methyl-4-[[3-(trifluoromethyl)phenyl]sulfonyl]-tetrahydro-pyran-2-yl]-pyridin-2-yl]-amine
109 1-Ethyl-3-methylsulfonyl-5-[4-methyl-4-[[3-(trifluoromethyl)phenyl]sulfonyl]-tetrahydro-pyran-2-yl]-1H-pyrazole
110 3-(Difluoro-methoxy)-1-methyl-5-[4-methyl-4-[[3-(trifluoromethyl)phenyl]sulfonyl]-tetrahydro-pyran-2-yl]-1H-pyrazole optionally in the form of a single stereoisomer or a mixture of stereoisomers, in the form of the free compound and/or a physiologically acceptable salt.

13. The method according to claim 1, which is conducted for the treatment and/or prophylaxis of pain, wherein the pain is at least one member selected from the group consisting of acute pain, chronic pain, visceral pain, headache pain, inflammatory pain, and mixed pain.

\* \* \* \* \*